(12) United States Patent
Zucherman et al.

(10) Patent No.: US 8,828,017 B2
(45) Date of Patent: Sep. 9, 2014

(54) SPINE DISTRACTION IMPLANT AND METHOD

(75) Inventors: James F. Zucherman, San Francisco, CA (US); Ken Y. Hsu, San Francisco, CA (US); Charles J. Winslow, Walnut Creek, CA (US); Henry A. Klyce, Piedmont, CA (US); John J. Flynn, West Milford, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1340 days.

(21) Appl. No.: 11/770,312

(22) Filed: Jun. 28, 2007

(65) Prior Publication Data

US 2008/0027553 A1    Jan. 31, 2008

Related U.S. Application Data

(60) Continuation of application No. 11/806,529, filed on May 31, 2007, now abandoned, which is a
(Continued)

(51) Int. Cl.
    *A61B 17/56*    (2006.01)
(52) U.S. Cl.
    USPC .......................................................... 606/99

(58) Field of Classification Search
    USPC ................. 606/247–249, 99, 104, 86 A, 86 B
    See application file for complete search history.

(56) References Cited

U.S. PATENT DOCUMENTS

| 2,248,054 | A | 7/1941 | Becker |
| 2,472,103 | A | 6/1949 | Giesen |

(Continued)

FOREIGN PATENT DOCUMENTS

| DE | 2821678 A1 | 11/1979 |
| DE | 4217660 A1 | 12/1993 |

(Continued)

OTHER PUBLICATIONS

"Dispositivo Intervertebrale Ammortizzante DIAM," date unknown, p. 1.

(Continued)

*Primary Examiner* — Mary Hoffman

(57) ABSTRACT

A tool for inserting an interspinous-process implant during surgery includes first and second elongate members. A post extending from the first elongate member may extend transverse to and cross the first elongate member's longitudinal axis. The second elongate member may be moveable longitudinally relative to the first elongate member, and a biasing member may bias the second elongate member toward a deployed position. The tool may further include an actuator to assist in moving the second elongate member.

8 Claims, 138 Drawing Sheets

Related U.S. Application Data continuation-in-part of application No. 11/092,862, filed on Mar. 29, 2005, now Pat. No. 7,621,939, which is a division of application No. 09/842,819, filed on Apr. 26, 2001, now Pat. No. 7,201,751, which is a continuation-in-part of application No. 09/579,039, filed on May 26, 2000, now Pat. No. 6,451,019, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 08/958,281, filed on Oct. 27, 1997, now Pat. No. 5,860,977, which is a continuation-in-part of application No. 08/778,093, filed on Jan. 2, 1997, now Pat. No. 5,836,948, said application No. 11/806,529 is a continuation-in-part of application No. 10/747,534, filed on Dec. 29, 2003, now abandoned, which is a continuation of application No. 10/014,118, filed on Oct. 26, 2001, now Pat. No. 6,695,842, which is a continuation-in-part of application No. 09/799,215, filed on Mar. 5, 2001, now Pat. No. 7,101,375, which is a continuation-in-part of application No. 09/473,173, which is a continuation of application No. 09/179,570, which is a continuation-in-part of application No. 08/958,281, which is a continuation-in-part of application No. 08/778,093, said application No. 11/806,529 is a continuation-in-part of application No. 10/037,236, filed on Nov. 9, 2001, now abandoned, which is a continuation-in-part of application No. 09/799,215, which is a continuation-in-part of application No. 09/473,173, which is a continuation of application No. 09/179,570, which is a continuation-in-part of application No. 08/958,281, which is a continuation-in-part of application No. 08/778,093, said application No. 11/806,529 is a continuation-in-part of application No. 10/770,372, filed on Feb. 2, 2004, now Pat. No. 7,473,268, which is a division of application No. 09/981,859, filed on Oct. 18, 2001, now Pat. No. 6,712,819, which is a continuation-in-part of application No. 09/799,470, filed on Mar. 5, 2001, now Pat. No. 6,902,566, which is a continuation-in-part of application No. 09/474,037, filed on Dec. 28, 1999, now Pat. No. 6,190,387, which is a division of application No. 09/175,645, filed on Oct. 20, 1998, now Pat. No. 6,068,630, which is a continuation-in-part of application No. 08/958,281, which is a continuation-in-part of application No. 08/778,093, said application No. 09/799,470 is a continuation-in-part of application No. 09/473,173, which is a continuation of application No. 09/179,570, which is a continuation-in-part of application No. 08/958,281, which is a continuation-in-part of application No. 08/778,093, said application No. 09/799,470 is a continuation-in-part of application No. 09/200,266, filed on Nov. 25, 1998, now Pat. No. 6,183,471, which is a continuation of application No. 09/139,333, filed on Aug. 25, 1998, now Pat. No. 5,876,404, which is a continuation-in-part of application No. 08/958,281, which is a continuation-in-part of application No. 08/778,093, application No. 11/770,312, which is a continuation of application No. 11/806,527, filed on May 31, 2007, now abandoned, which is a continuation-in-part of application No. 11/092,862, which is a division of application No. 09/842,819, which is a continuation-in-part of application No. 09/579,039, which is a continuation-in-part of application No. 09/473,173, which is a continuation of application No. 09/179,570, which is a continuation-in-part of application No. 08/958,281, which is a continuation-in-part of application No. 08/778,093, said application No. 11/806,527 is a continuation-in-part of application No. 10/747,534, which is a continuation of application No. 10/014,118, filed on Oct. 26, 2001, now Pat. No. 7,101,375, which is a continuation of application No. 09/799,215, which is a continuation-in-part of application No. 09/473,173, which is a continuation-in-part of application No. 09/179,570, which is a continuation of application No. 08/958,281, which is a continuation-in-part of application No. 08/778,093, said application No. 11/806,527 is a continuation-in-part of application No. 10/037,236, which is a continuation-in-part of application No. 09/799,215, which is a continuation-in-part of application No. 09/473,173, which is a continuation of application No. 09/179,570, which is a continuation-in-part of application No. 08/958,281, which is a continuation-in-part of application No. 08/778,093, said application No. 11/806,527 is a continuation-in-part of application No. 10/770,372, which is a division of application No. 09/981,859, which is a continuation-in-part of application No. 09/799,470, which is a continuation-in-part of application No. 09/474,037, which is a division of application No. 09/175,645, which is a continuation-in-part of application No. 08/958,281, which is a continuation-in-part of application No. 08/778,093, said application No. 09/799,470 is a continuation-in-part of application No. 09/473,173, which is a continuation of application No. 09/179,570, which is a continuation-in-part of application No. 08/958,281, which is a continuation-in-part of application No. 08/778,093, said application No. 09/799,470 is a continuation-in-part of application No. 09/200,266, which is a continuation of application No. 09/139,333, which is a continuation-in-part of application No. 08/958,281, which is a continuation-in-part of application No. 08/778,093.

(60) Provisional application No. 60/219,985, filed on Jul. 21, 2000, provisional application No. 60/306,263, filed on Jul. 18, 2001, provisional application No. 60/323,467, filed on Sep. 18, 2001, provisional application No. 60/220,022, filed on Jul. 21, 2000, provisional application No. 60/306,101, filed on Jul. 17, 2001.

(56) References Cited

U.S. PATENT DOCUMENTS

| | | |
|---|---|---|
| 2,677,369 A | 5/1954 | Knowles |
| 3,486,505 A | 12/1969 | Morrison |
| 3,604,487 A | 9/1971 | Gilbert |
| 3,648,691 A | 3/1972 | Lumb et al. |
| 4,011,602 A | 3/1977 | Rybicki et al. |
| 4,257,409 A | 3/1981 | Bacal et al. |
| 4,509,517 A | 4/1985 | Zibelin |
| 4,554,914 A | 11/1985 | Kapp et al. |
| 4,573,454 A | 3/1986 | Hoffman |
| 4,592,341 A | 6/1986 | Omagari et al. |

(56) References Cited

U.S. PATENT DOCUMENTS

| | | |
|---|---|---|
| 4,604,995 A | 8/1986 | Stephens et al. |
| 4,686,970 A | 8/1987 | Dove et al. |
| 4,827,918 A | 5/1989 | Olerud |
| 4,997,432 A * | 3/1991 | Keller .................. 623/17.11 |
| 5,011,484 A | 4/1991 | Breard |
| 5,047,055 A | 9/1991 | Bao et al. |
| 5,092,866 A | 3/1992 | Breard et al. |
| 5,201,734 A | 4/1993 | Cozad et al. |
| 5,306,275 A | 4/1994 | Bryan |
| 5,360,430 A | 11/1994 | Lin |
| 5,366,455 A | 11/1994 | Dove |
| 5,370,697 A * | 12/1994 | Baumgartner ............. 623/17.15 |
| 5,415,661 A | 5/1995 | Holmes |
| 5,437,672 A | 8/1995 | Alleyne |
| 5,454,812 A | 10/1995 | Lin |
| 5,484,440 A | 1/1996 | Allard |
| 5,489,307 A | 2/1996 | Kuslich et al. |
| 5,496,318 A * | 3/1996 | Howland et al. ............. 606/249 |
| 5,522,899 A * | 6/1996 | Michelson .................... 606/279 |
| 5,536,268 A | 7/1996 | Griss |
| 5,545,170 A | 8/1996 | Hart |
| 5,562,735 A | 10/1996 | Margulies |
| 5,571,109 A * | 11/1996 | Bertagnoli ................. 606/86 A |
| 5,599,279 A | 2/1997 | Slotman et al. |
| 5,609,634 A | 3/1997 | Voydeville |
| 5,609,636 A | 3/1997 | Kohrs et al. |
| 5,628,756 A | 5/1997 | Barker, Jr. et al. |
| 5,645,599 A | 7/1997 | Samani |
| 5,653,761 A * | 8/1997 | Pisharodi ................. 606/86 A |
| 5,658,335 A | 8/1997 | Allen |
| 5,662,657 A | 9/1997 | Carn |
| 5,667,513 A | 9/1997 | Torrie et al. |
| 5,674,295 A | 10/1997 | Ray et al. |
| 5,676,702 A | 10/1997 | Ratron |
| 5,683,464 A | 11/1997 | Wagner et al. |
| 5,685,826 A | 11/1997 | Bonutti |
| 5,690,649 A | 11/1997 | Li |
| 5,702,452 A | 12/1997 | Argenson et al. |
| 5,720,751 A * | 2/1998 | Jackson ..................... 606/86 R |
| 5,772,661 A | 6/1998 | Michelson |
| 5,797,909 A | 8/1998 | Michelson |
| 5,800,549 A | 9/1998 | Bao et al. |
| 5,810,815 A | 9/1998 | Morales |
| 5,836,948 A * | 11/1998 | Zucherman et al. ........... 606/249 |
| 5,860,977 A | 1/1999 | Zucherman et al. |
| 5,888,224 A | 3/1999 | Beckers et al. |
| 5,893,890 A | 4/1999 | Pisharodi |
| 5,968,098 A * | 10/1999 | Winslow .................... 623/17.11 |
| 5,976,186 A | 11/1999 | Bao et al. |
| 6,004,326 A * | 12/1999 | Castro et al. ..................... 606/99 |
| 6,022,376 A | 2/2000 | Assell et al. |
| 6,042,582 A | 3/2000 | Ray |
| 6,048,342 A | 4/2000 | Zucherman et al. |
| 6,059,829 A | 5/2000 | Schlapfer et al. |
| 6,063,088 A * | 5/2000 | Winslow ..................... 606/86 A |
| 6,068,630 A | 5/2000 | Zucherman et al. |
| 6,083,225 A | 7/2000 | Winslow et al. |
| 6,086,595 A | 7/2000 | Yonemura et al. |
| 6,113,602 A | 9/2000 | Sand |
| 6,117,174 A * | 9/2000 | Nolan ......................... 623/17.11 |
| 6,132,464 A | 10/2000 | Martin |
| 6,139,549 A | 10/2000 | Keller |
| 6,159,212 A | 12/2000 | Schoedinger, III et al. |
| 6,159,215 A * | 12/2000 | Urbahns et al. ............ 606/86 R |
| 6,171,339 B1 | 1/2001 | Houfburg et al. |
| 6,174,311 B1 | 1/2001 | Branch et al. |
| 6,190,414 B1 * | 2/2001 | Young et al. ............... 623/17.15 |
| 6,224,607 B1 | 5/2001 | Michelson |
| 6,224,631 B1 | 5/2001 | Kohrs |
| 6,235,034 B1 * | 5/2001 | Bray ............................. 606/71 |
| 6,241,729 B1 | 6/2001 | Estes et al. |
| 6,245,072 B1 * | 6/2001 | Zdeblick et al. ............ 606/914 |
| 6,261,296 B1 * | 7/2001 | Aebi et al. .................... 606/90 |
| 6,261,586 B1 | 7/2001 | McKay |
| 6,293,949 B1 | 9/2001 | Justis et al. |
| 6,352,537 B1 | 3/2002 | Strnad |
| 6,364,883 B1 | 4/2002 | Santilli |
| 6,402,750 B1 | 6/2002 | Atkinson et al. |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,554,833 B2 | 4/2003 | Levy |
| 6,565,570 B2 | 5/2003 | Sterett et al. |
| 6,582,433 B2 | 6/2003 | Yun |
| 6,602,260 B2 | 8/2003 | Harari et al. |
| 6,610,065 B1 | 8/2003 | Branch et al. |
| 6,623,486 B1 * | 9/2003 | Weaver et al. ................. 606/281 |
| 6,626,944 B1 | 9/2003 | Taylor |
| 6,645,207 B2 | 11/2003 | Dixon et al. |
| 6,652,533 B2 * | 11/2003 | O'Neil ......................... 606/100 |
| 6,676,665 B2 | 1/2004 | Foley et al. |
| 6,695,842 B2 | 2/2004 | Zucherman et al. |
| 6,709,435 B2 | 3/2004 | Lin |
| 6,723,126 B1 | 4/2004 | Berry |
| 6,733,534 B2 | 5/2004 | Sherman |
| 6,752,832 B2 | 6/2004 | Neumann |
| 6,755,841 B2 * | 6/2004 | Fraser et al. .................... 606/99 |
| 6,761,720 B1 | 7/2004 | Senegas |
| 6,770,096 B2 | 8/2004 | Bolger et al. |
| 6,835,205 B2 | 12/2004 | Atkinson et al. |
| 6,857,343 B1 | 2/2005 | Easterbrooks et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,252,673 B2 | 8/2007 | Lim |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,524,324 B2 | 4/2009 | Winslow et al. |
| 7,582,106 B2 | 9/2009 | Teitelbaum et al. |
| 7,803,162 B2 * | 9/2010 | Marnay et al. ................. 606/99 |
| 7,806,901 B2 * | 10/2010 | Stad et al. ...................... 606/99 |
| 7,867,237 B2 * | 1/2011 | Stad et al. ...................... 606/90 |
| 8,105,381 B2 * | 1/2012 | Marnay et al. ............. 623/17.15 |
| 8,226,691 B2 * | 7/2012 | McDonnell ................... 606/279 |
| 8,303,659 B2 * | 11/2012 | Errico et al. .............. 623/17.14 |
| 8,337,500 B2 * | 12/2012 | Bertagnoli et al. ............. 606/80 |
| 8,349,017 B2 * | 1/2013 | Marnay et al. ............. 623/17.16 |
| 8,425,603 B2 * | 4/2013 | Reichen et al. ............. 623/17.11 |
| 8,500,749 B2 * | 8/2013 | Lee et al. ........................ 606/99 |
| 8,506,634 B2 * | 8/2013 | Marnay et al. ............. 623/17.14 |
| 8,535,326 B2 * | 9/2013 | Beyersdorff et al. ........... 606/99 |
| 8,579,978 B2 * | 11/2013 | Marnay et al. ............. 623/17.15 |
| 2001/0016743 A1 | 8/2001 | Zucherman et al. |
| 2002/0143331 A1 | 10/2002 | Zucherman et al. |
| 2002/0161368 A1 | 10/2002 | Foley et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0083747 A1 * | 5/2003 | Winterbottom et al. ... 623/17.11 |
| 2003/0149438 A1 * | 8/2003 | Nichols et al. .................. 606/99 |
| 2003/0153915 A1 | 8/2003 | Nekozuka et al. |
| 2003/0225408 A1 * | 12/2003 | Nichols et al. .................. 606/61 |
| 2003/0229358 A1 * | 12/2003 | Errico et al. ................... 606/99 |
| 2004/0059318 A1 | 3/2004 | Zhang et al. |
| 2004/0087947 A1 | 5/2004 | Lim et al. |
| 2004/0097931 A1 | 5/2004 | Mitchell |
| 2004/0106927 A1 | 6/2004 | Ruffner et al. |
| 2004/0133280 A1 | 7/2004 | Trieu |
| 2004/0199255 A1 | 10/2004 | Mathieu et al. |
| 2004/0225295 A1 * | 11/2004 | Zubok et al. ................... 606/90 |
| 2004/0249388 A1 | 12/2004 | Michelson |
| 2005/0010293 A1 | 1/2005 | Zucherman et al. |
| 2005/0038445 A1 * | 2/2005 | Errico et al. ................... 606/99 |
| 2005/0049708 A1 | 3/2005 | Atkinson et al. |
| 2005/0090824 A1 | 4/2005 | Shluzas et al. |

(56) References Cited

U.S. PATENT DOCUMENTS

| | | |
|---|---|---|
| 2005/0113842 A1 | 5/2005 | Bertagnoli et al. |
| 2005/0119665 A1 | 6/2005 | Keller |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0216002 A1 | 9/2005 | Simonson |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241613 A1 | 10/2006 | Brueneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1 | 2/2007 | Aschmann et al. |
| 2007/0043362 A1 | 2/2007 | Malandain et al. |
| 2007/0100340 A1 | 5/2007 | Lange et al. |
| 2007/0112354 A1 | 5/2007 | Iwasaki et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2010/0121379 A1 | 5/2010 | Edmond |

FOREIGN PATENT DOCUMENTS

| | | |
|---|---|---|
| EP | 0322334 B1 | 2/1992 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

(56) References Cited

OTHER PUBLICATIONS

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

(56) References Cited

OTHER PUBLICATIONS

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

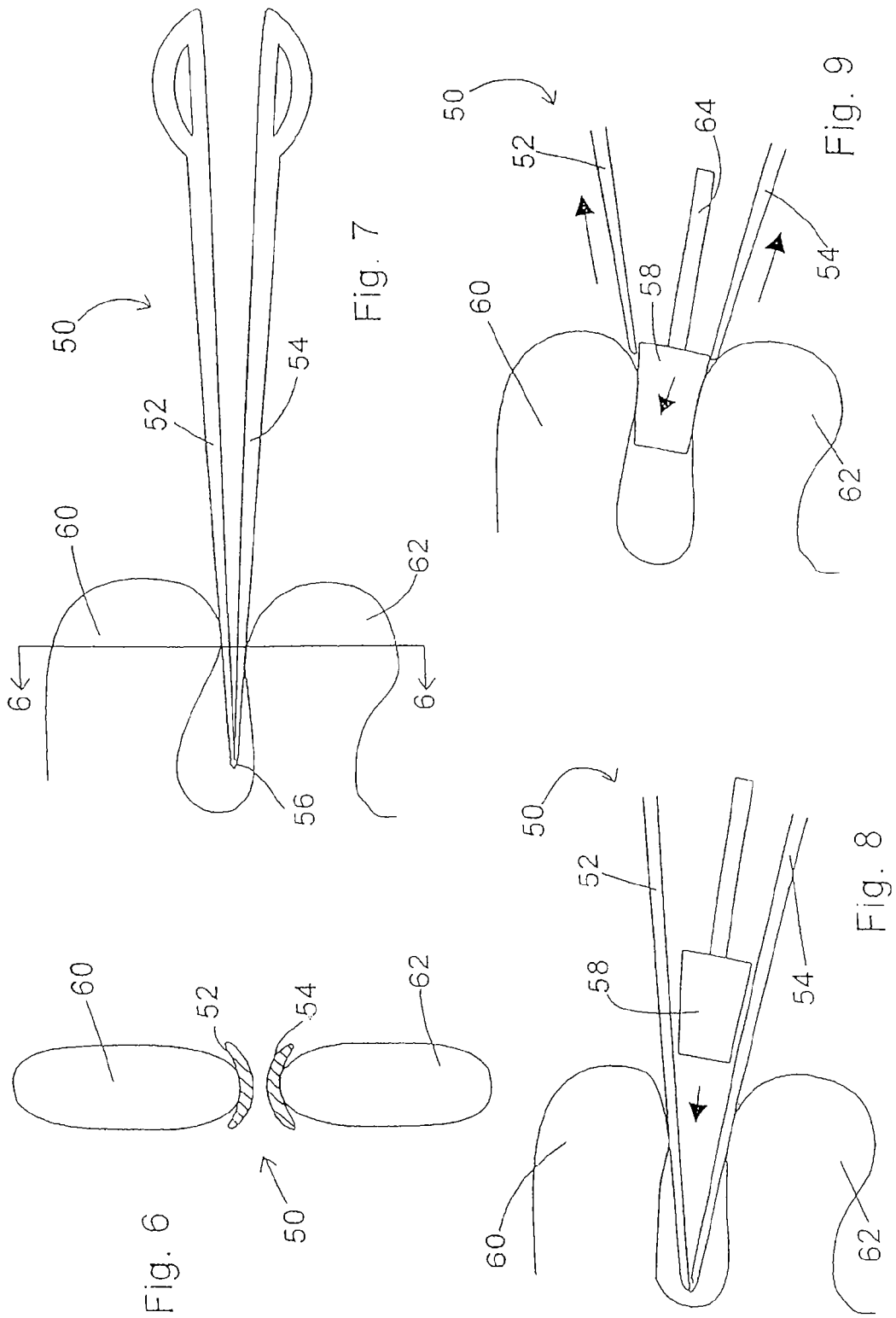

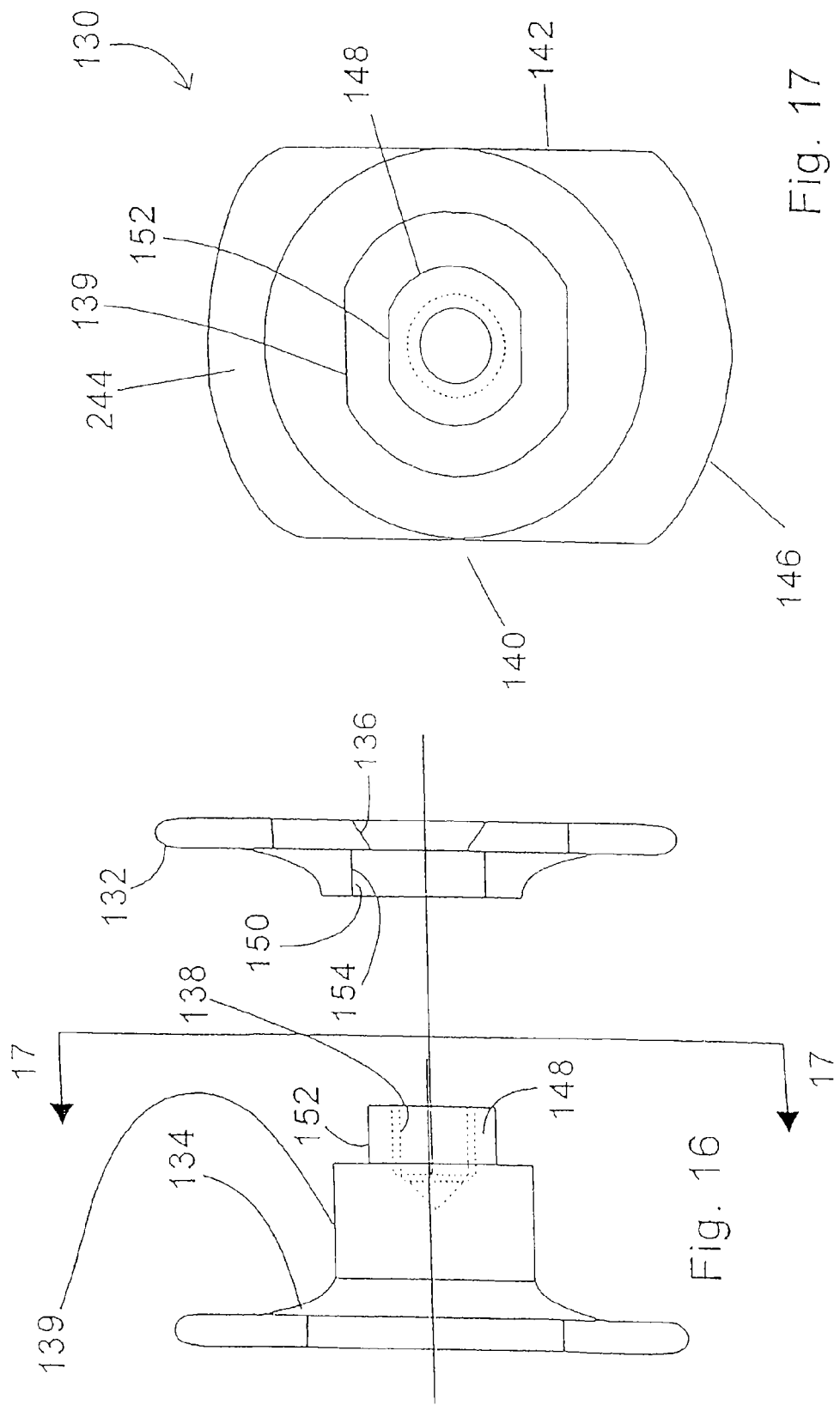

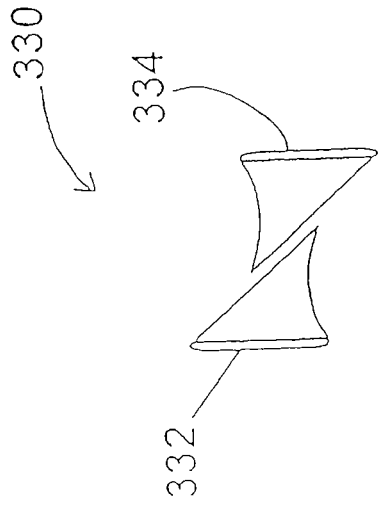
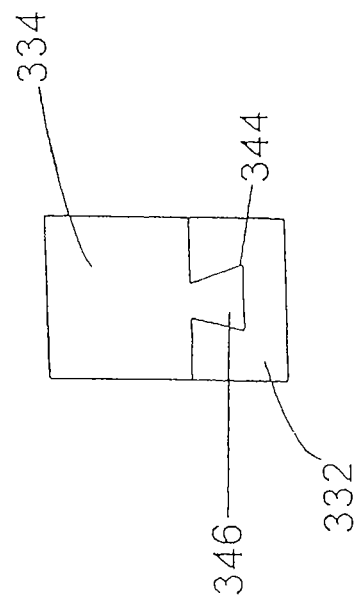
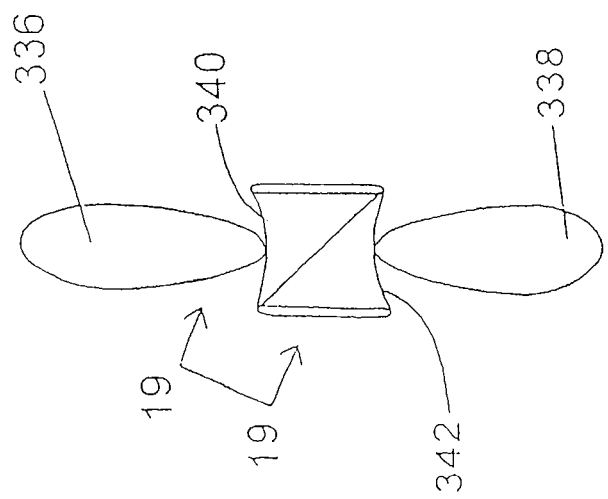

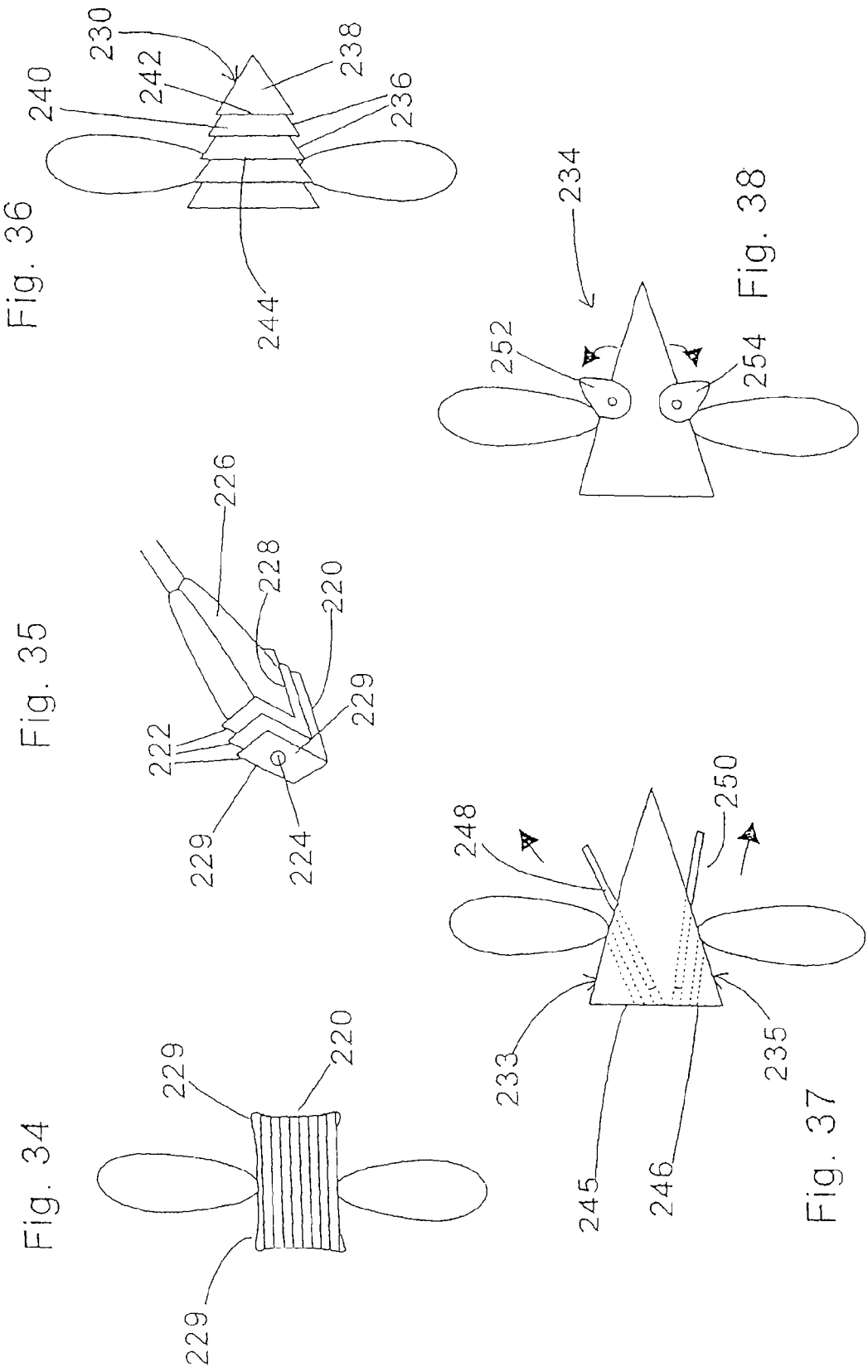

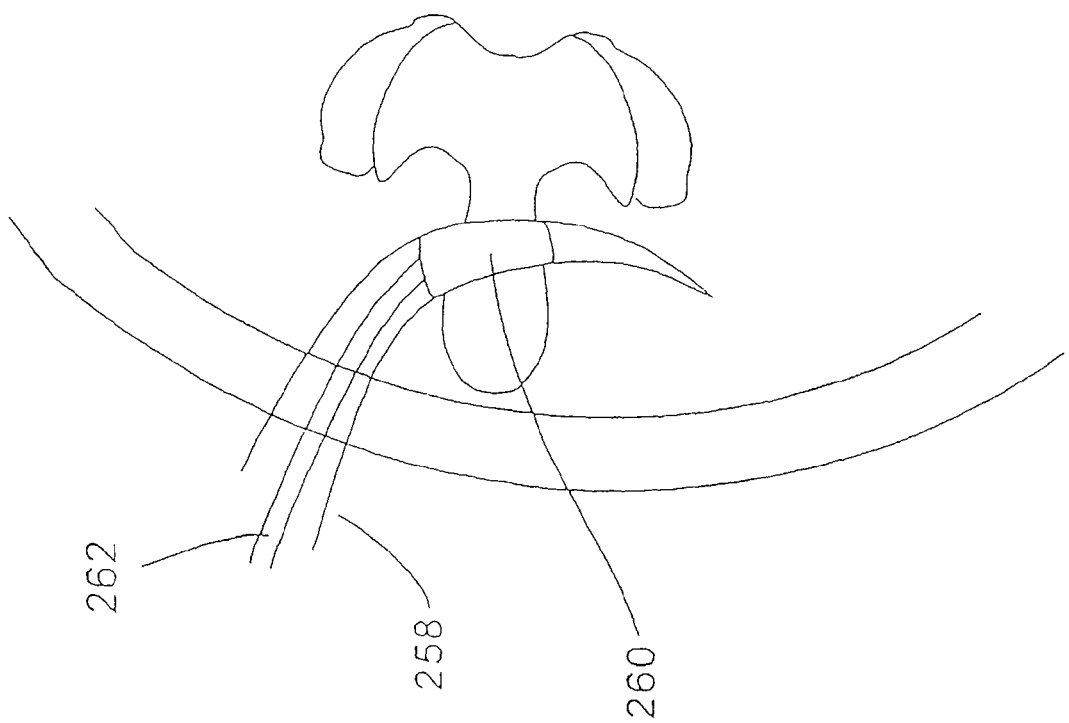

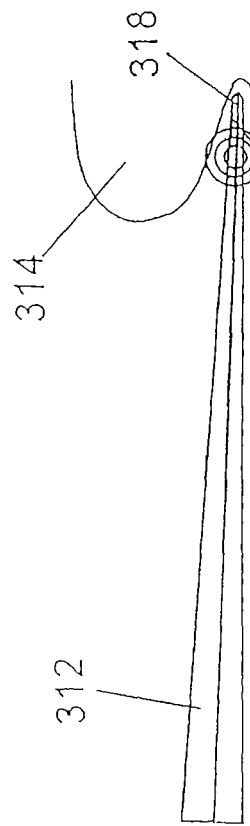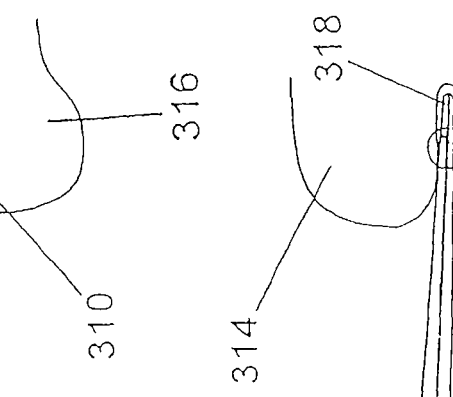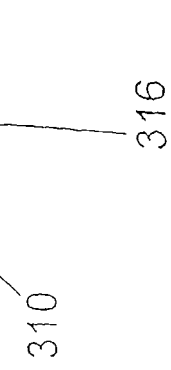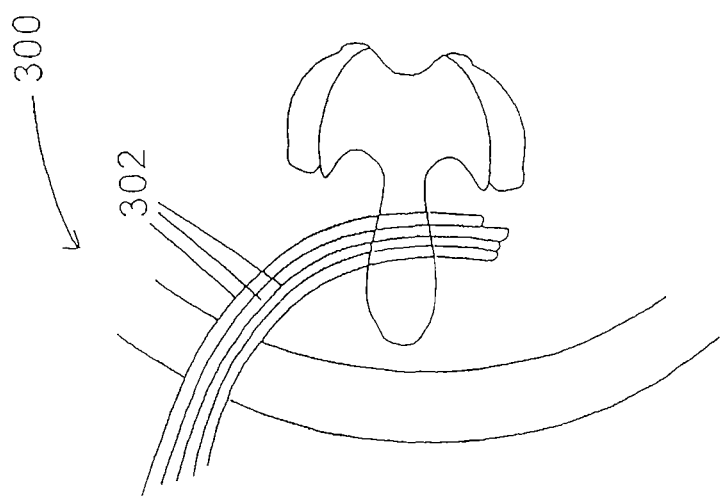

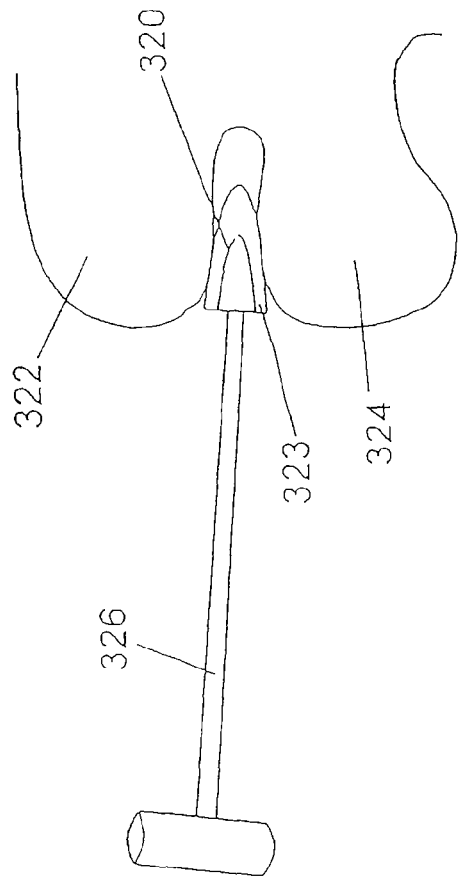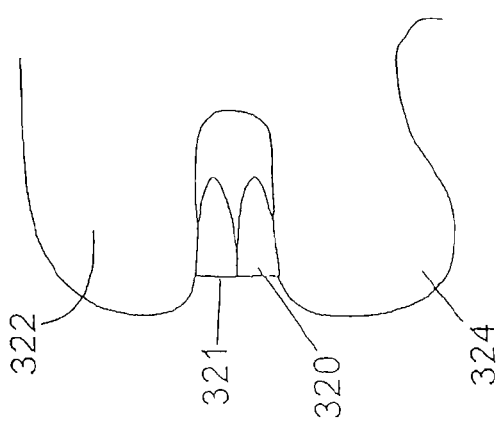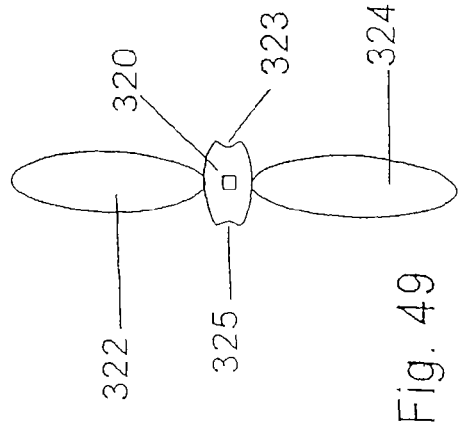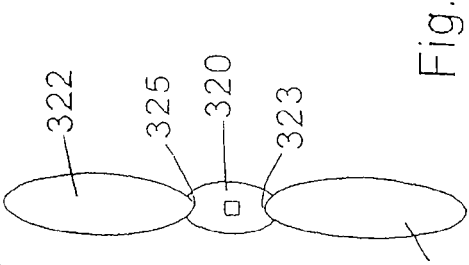
Fig. 48
Fig. 49
Fig. 51
Fig. 50

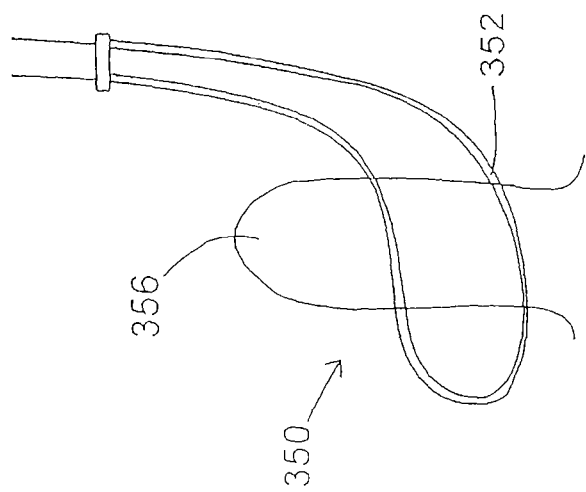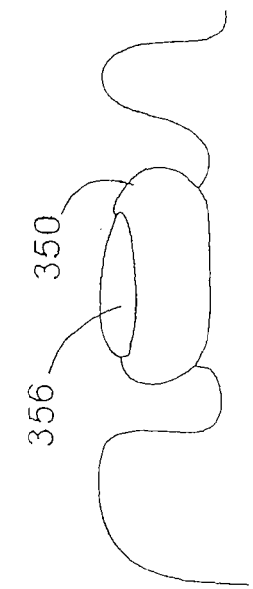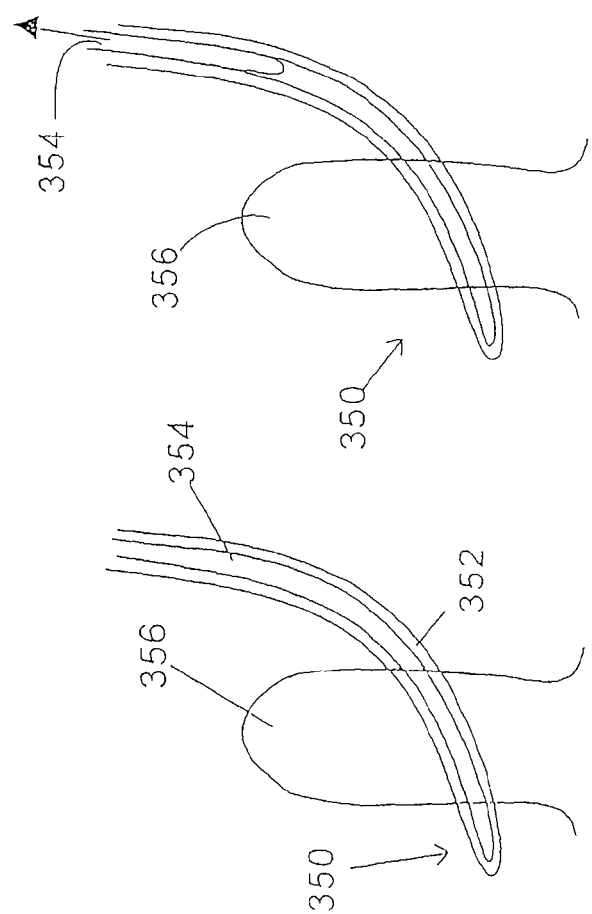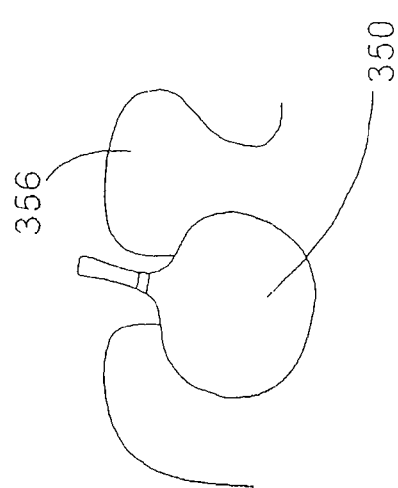
Fig. 52  Fig. 53  Fig. 54  Fig. 55a  Fig. 55b

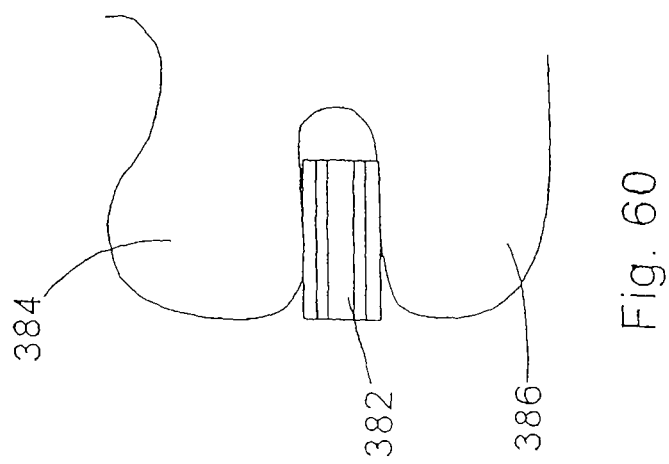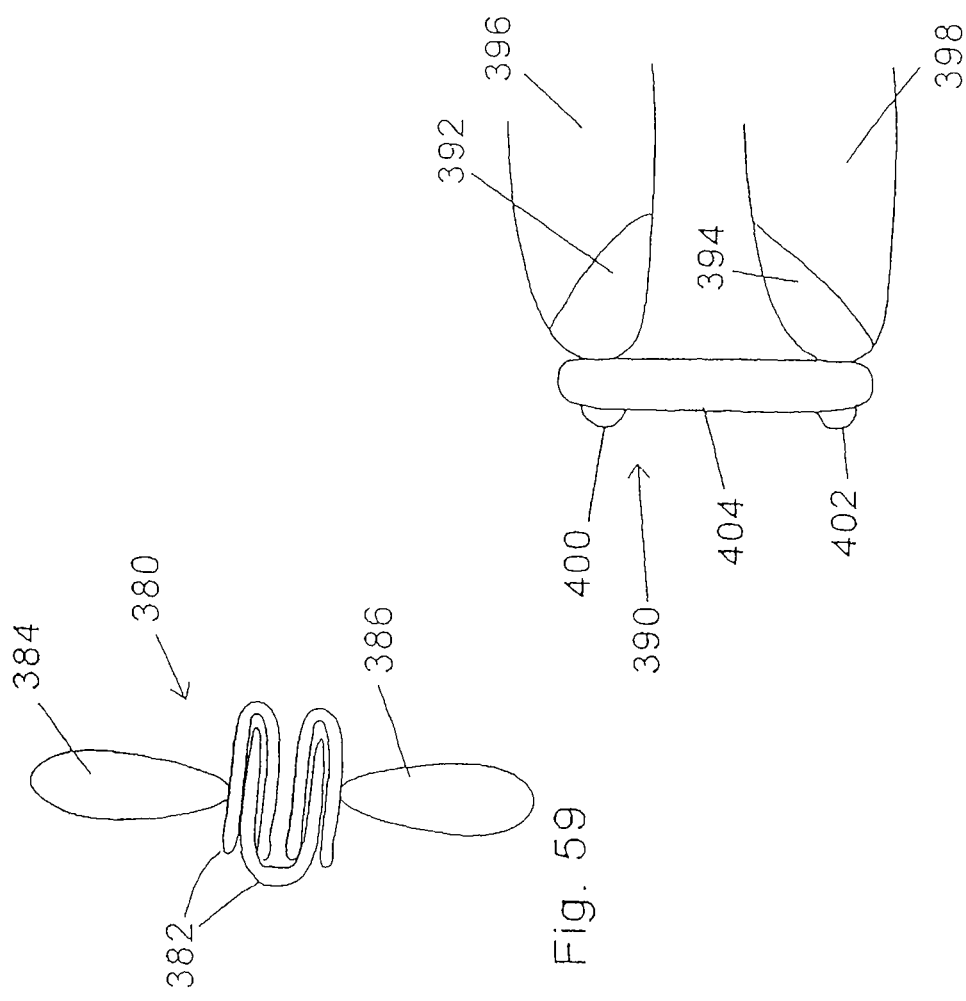

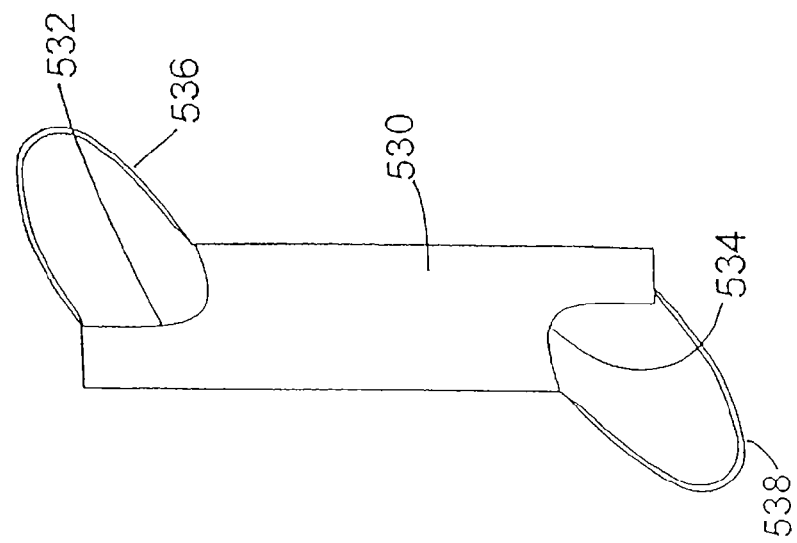
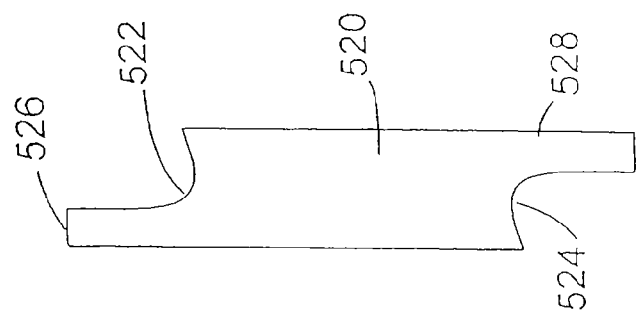
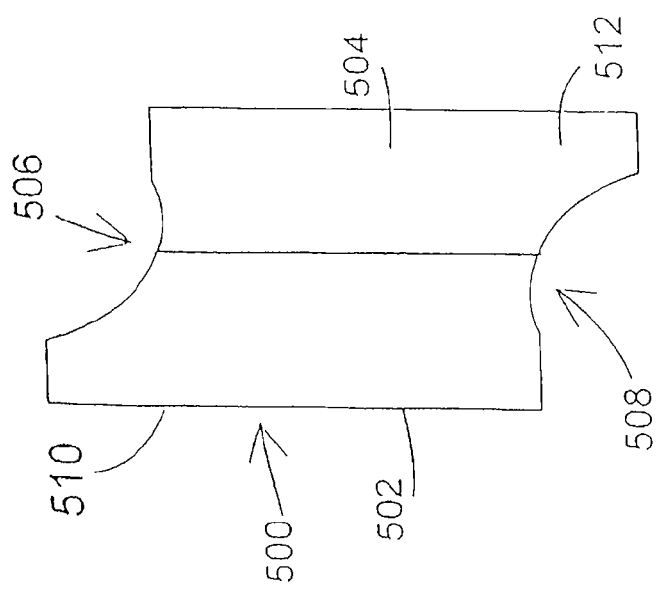

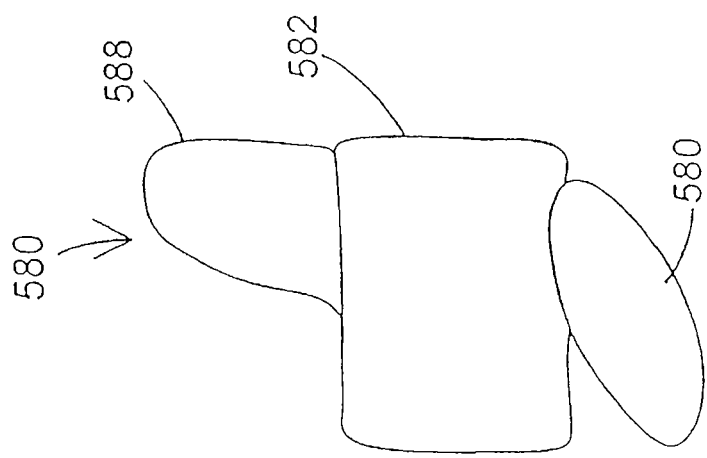
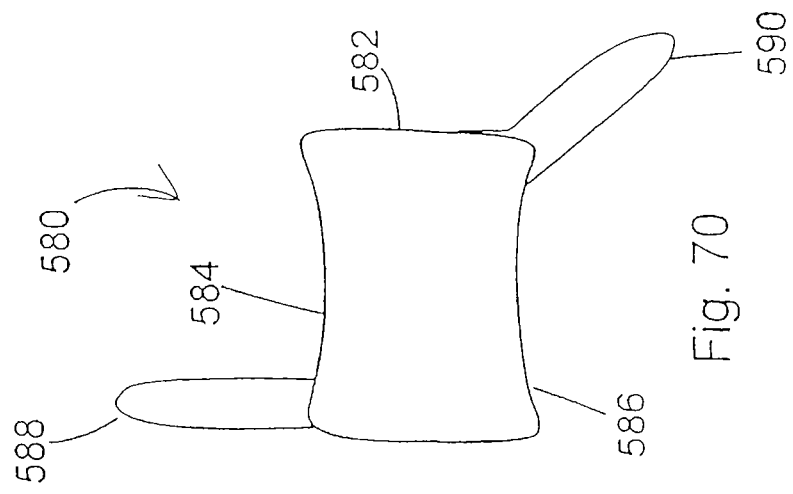
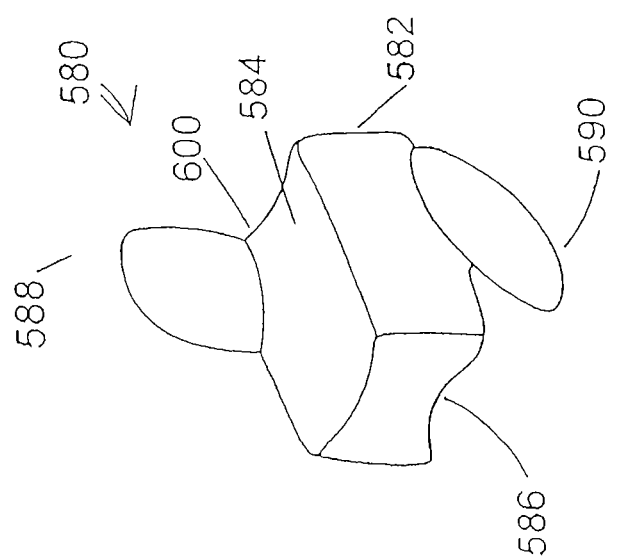

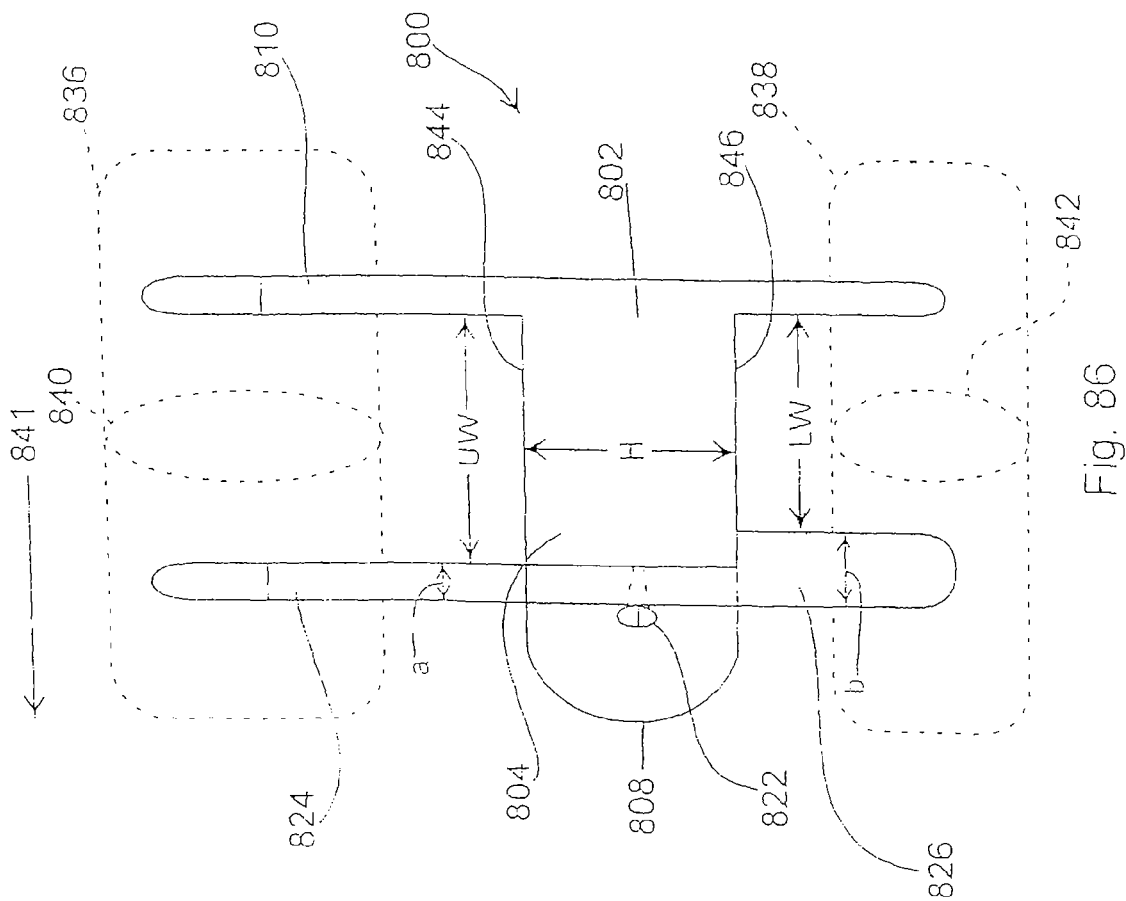

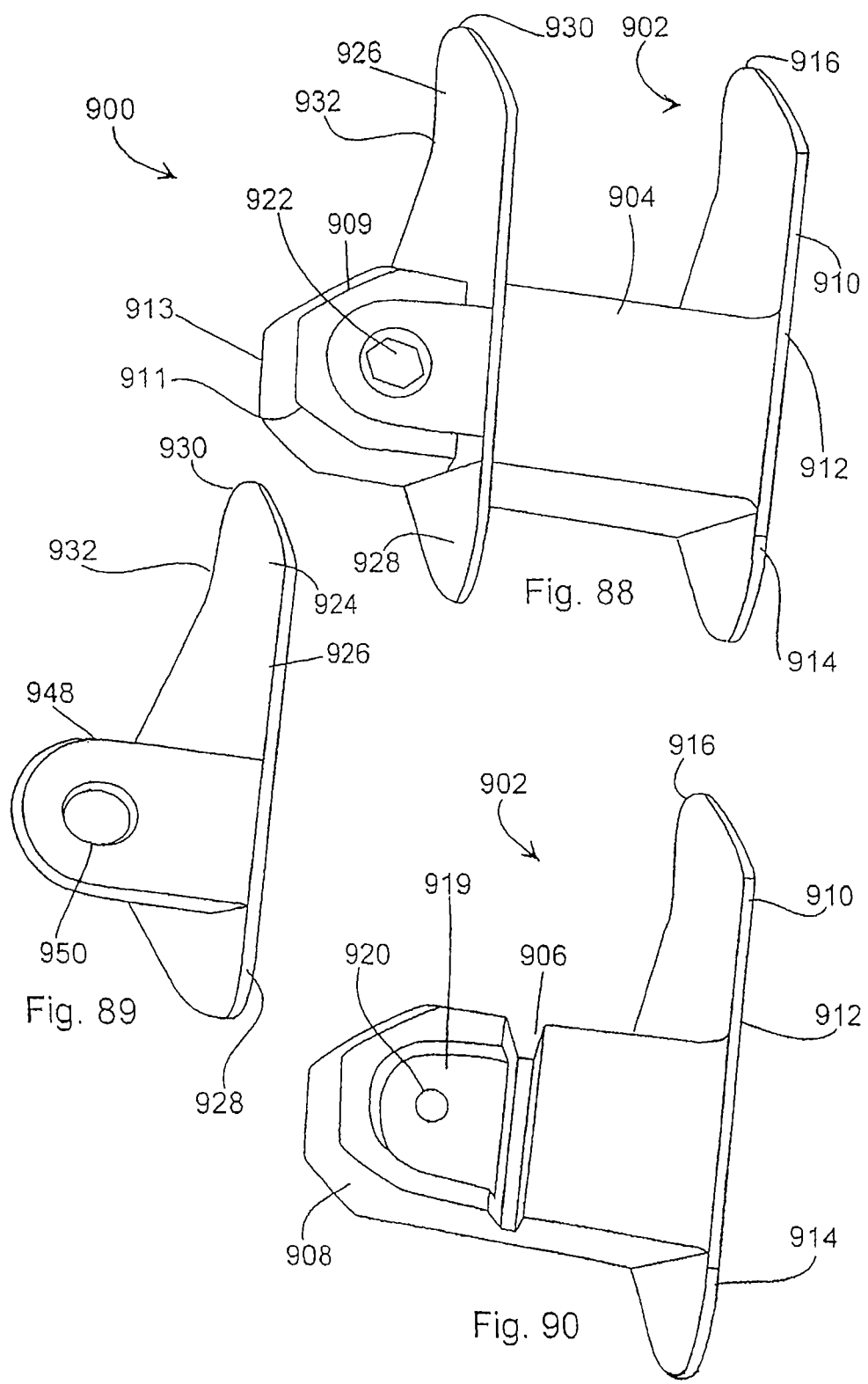

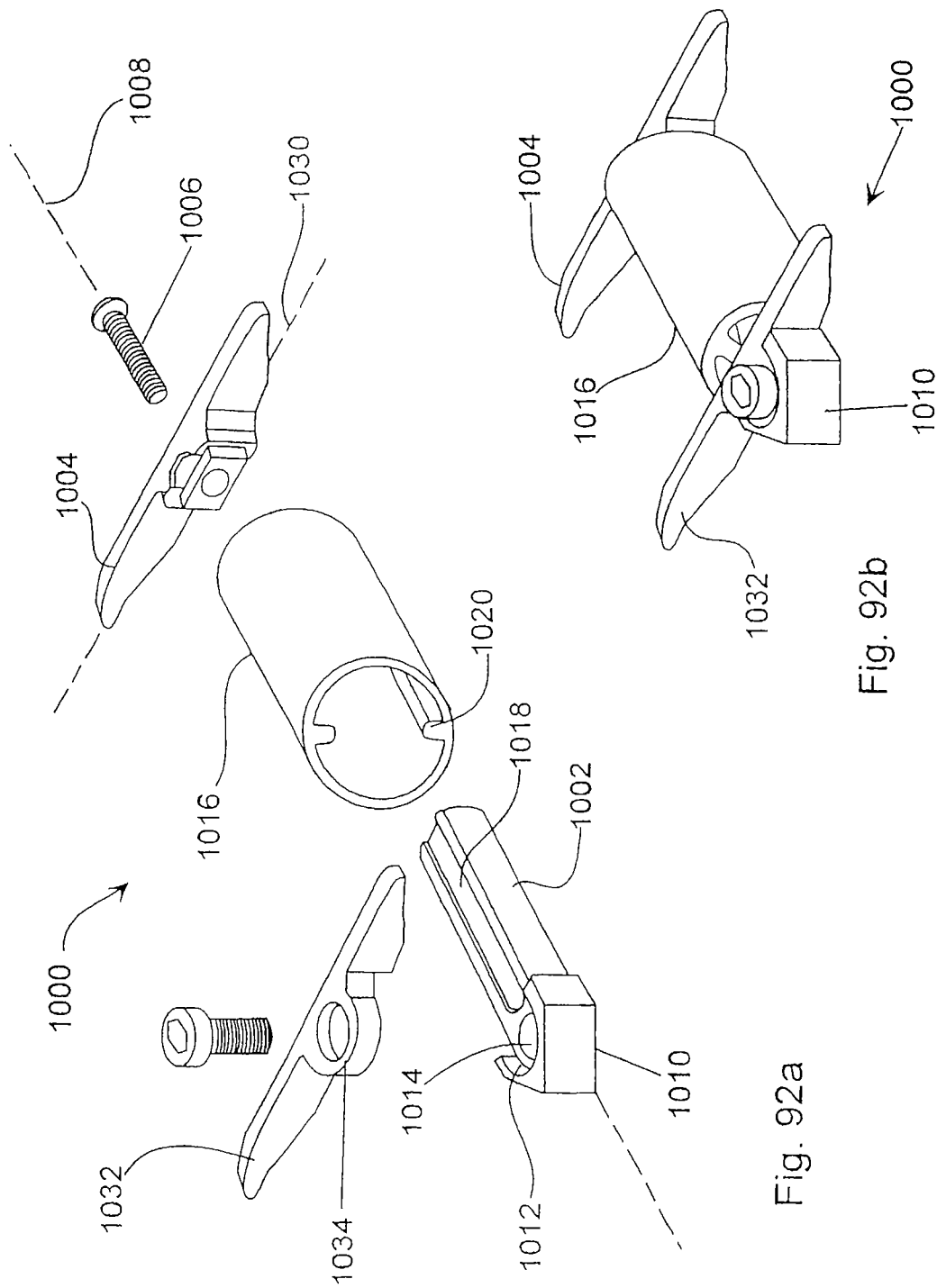

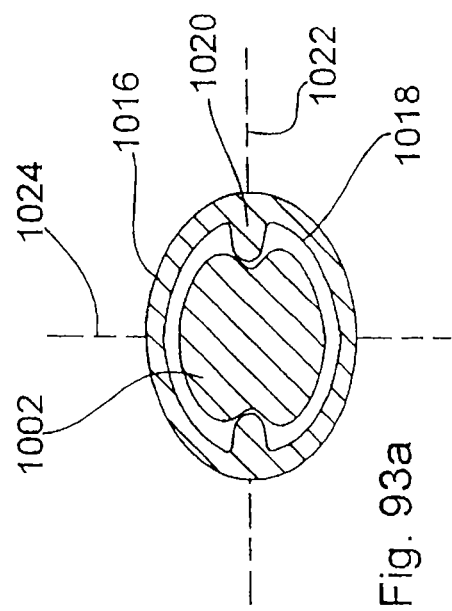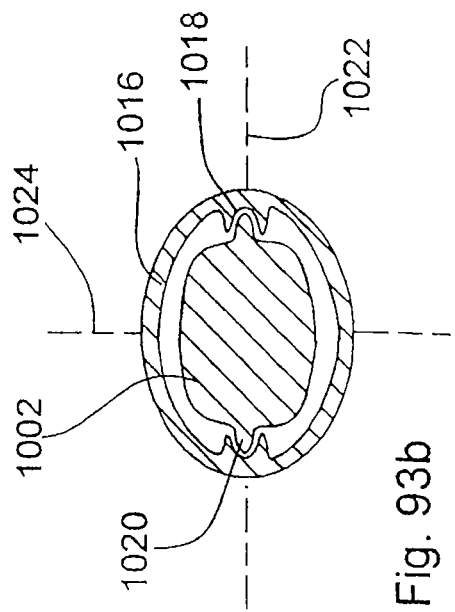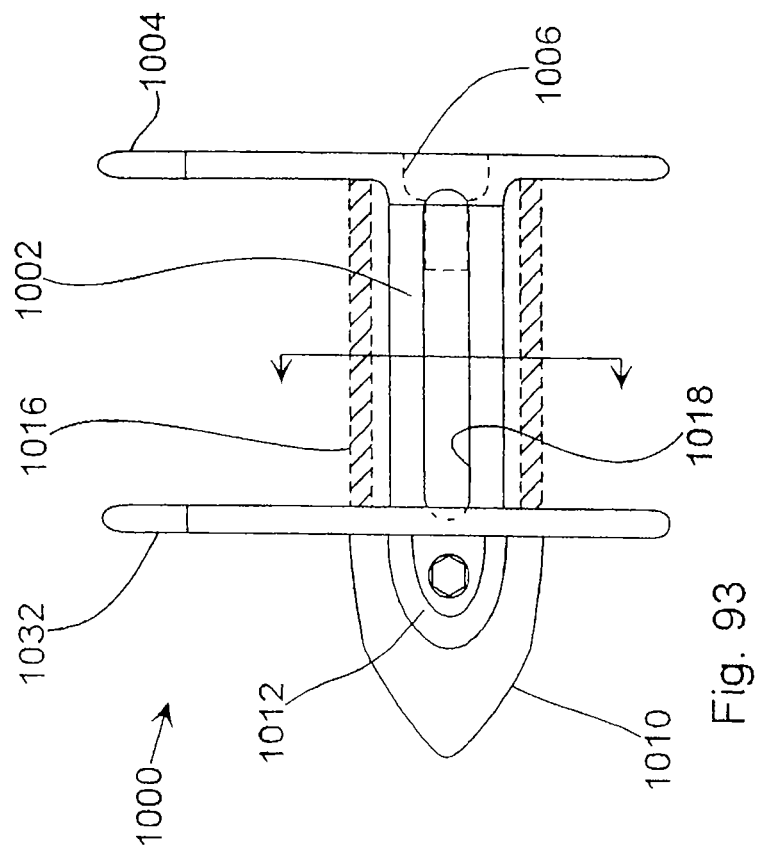

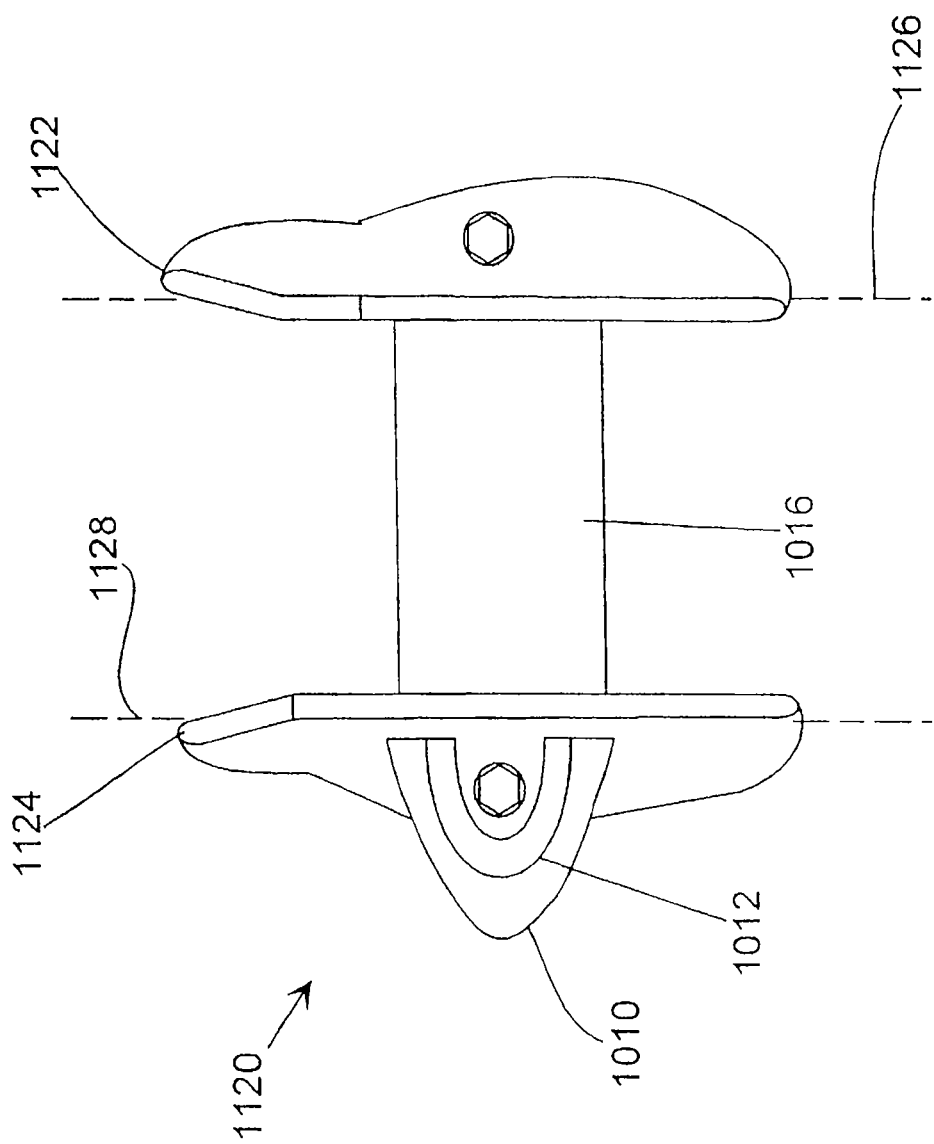

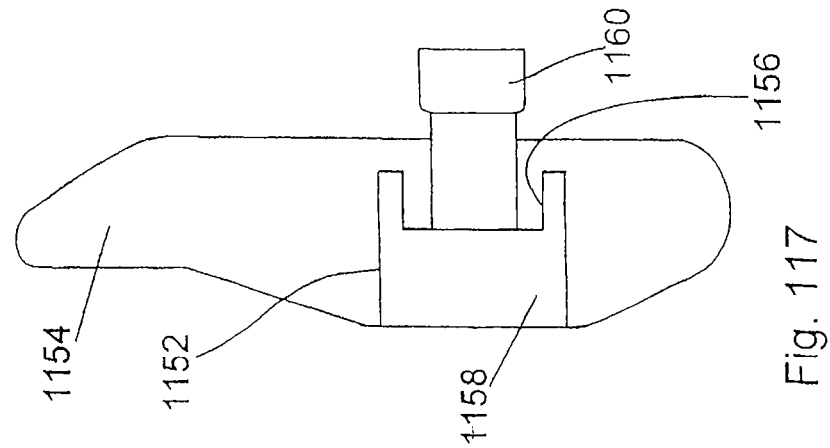
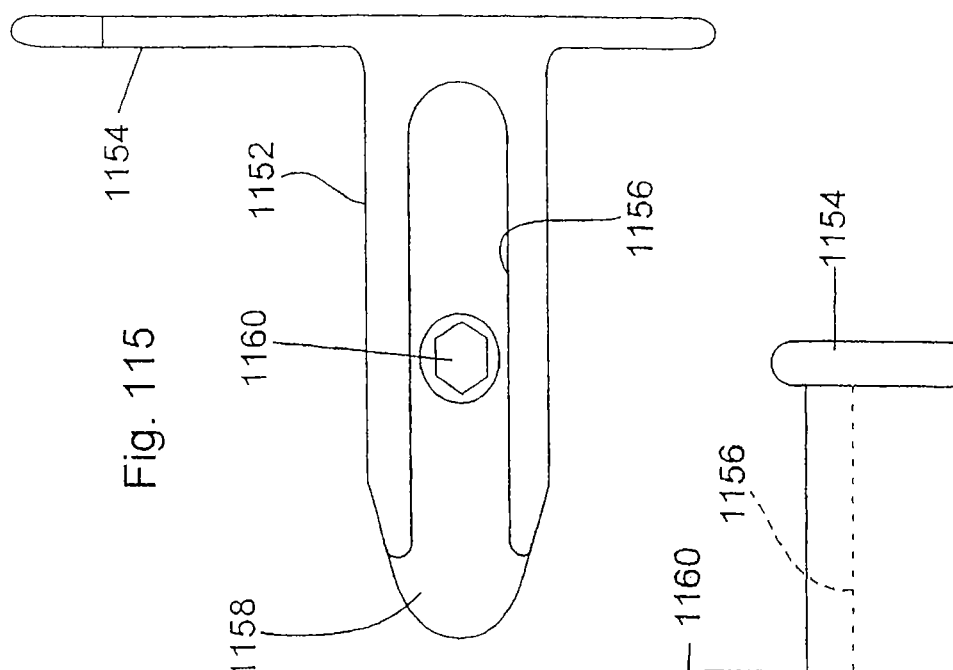
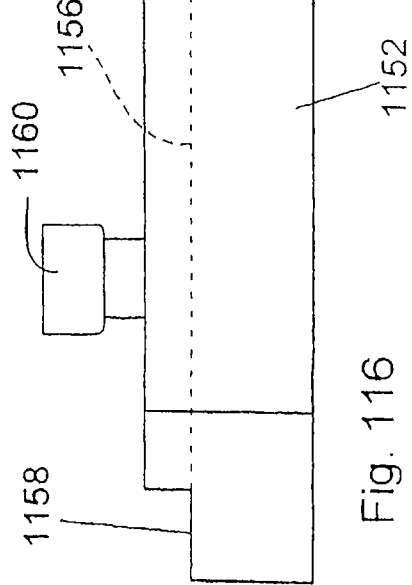

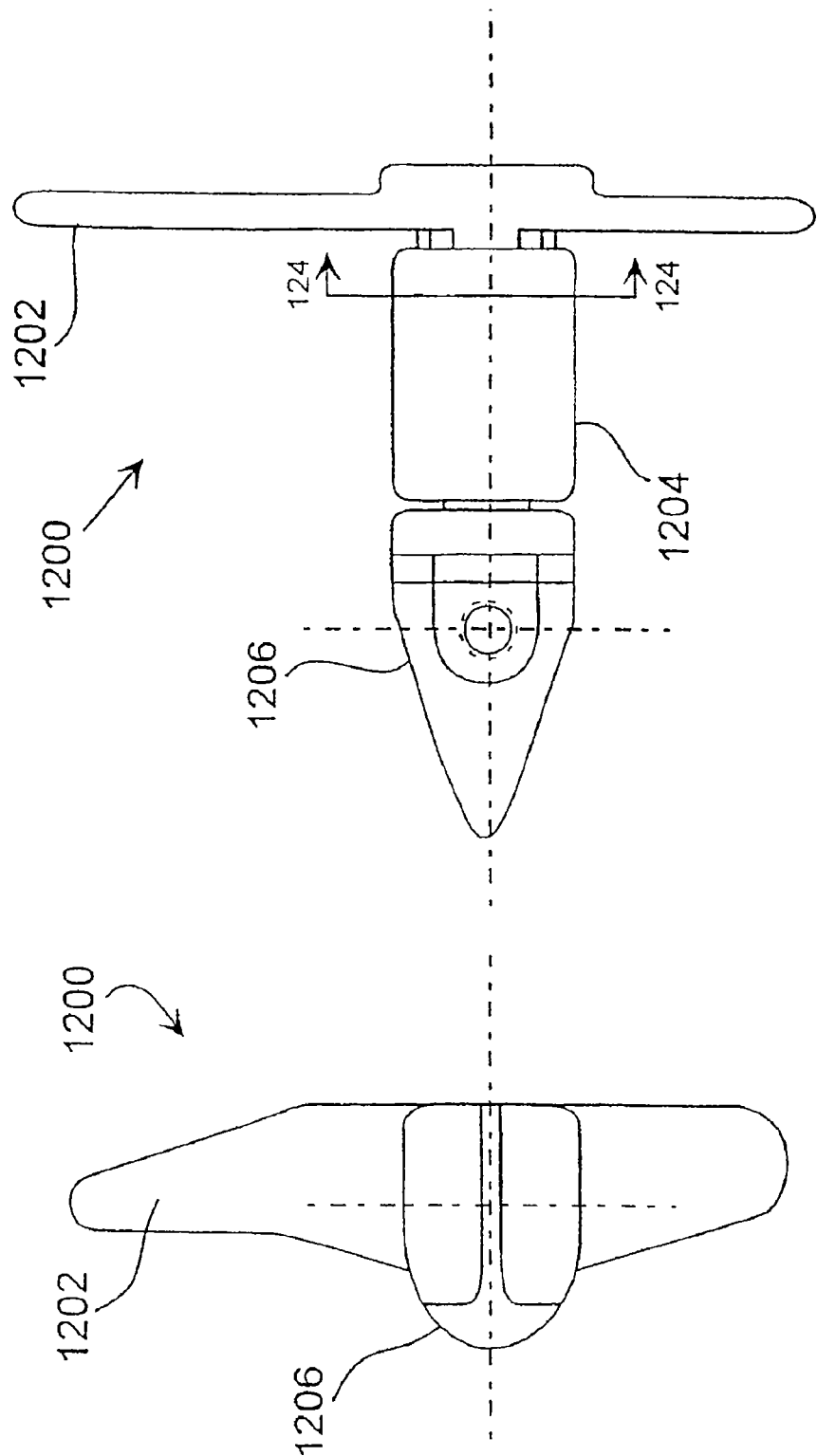

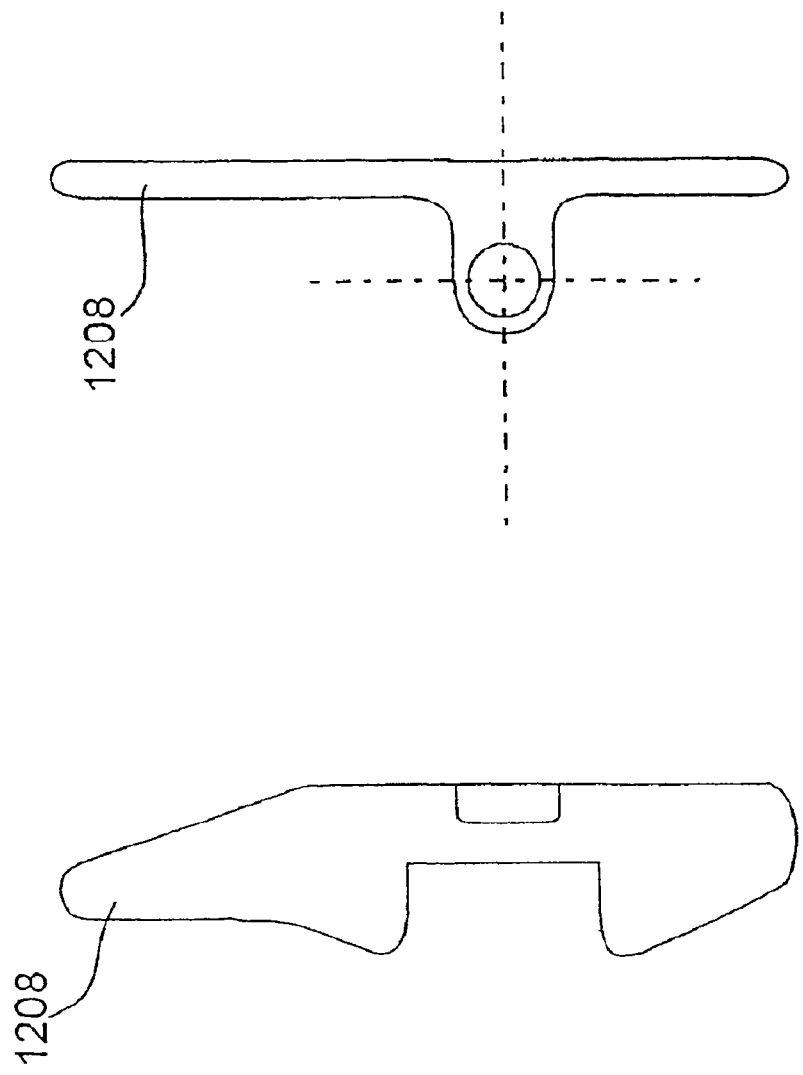

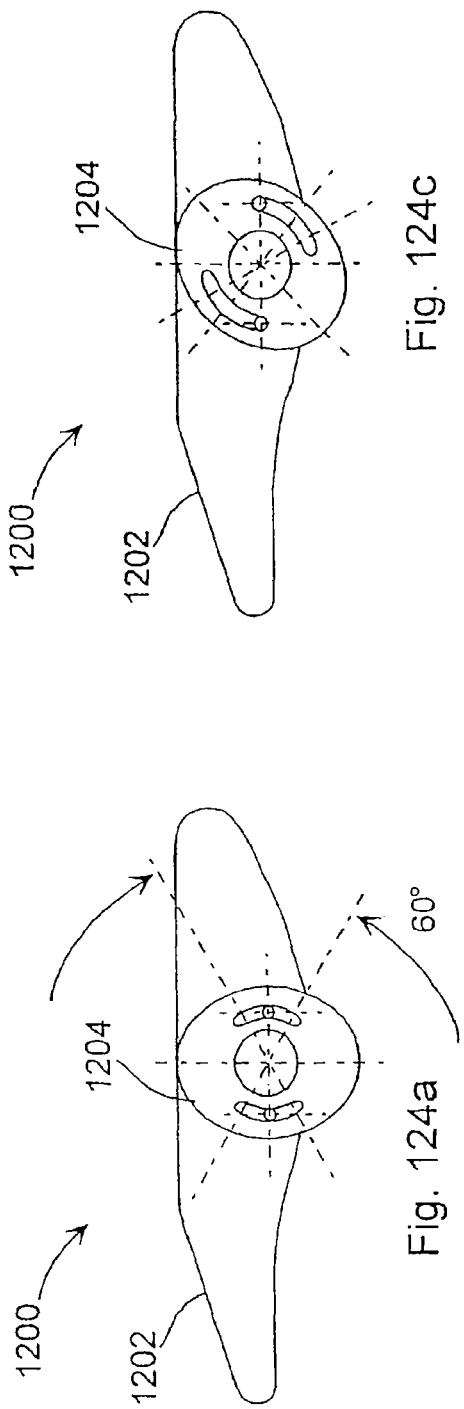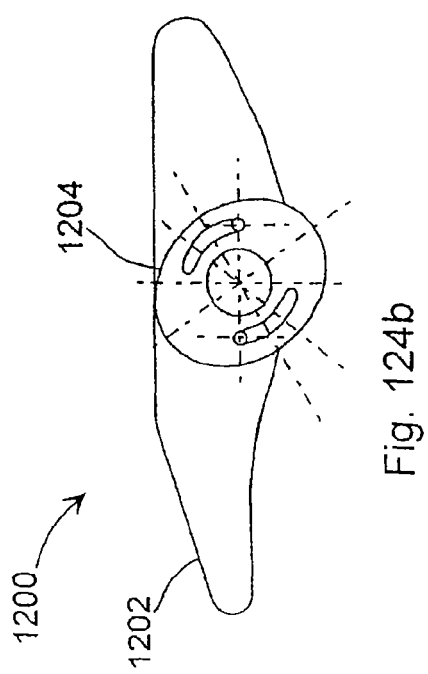

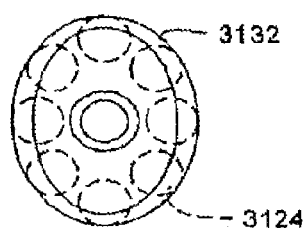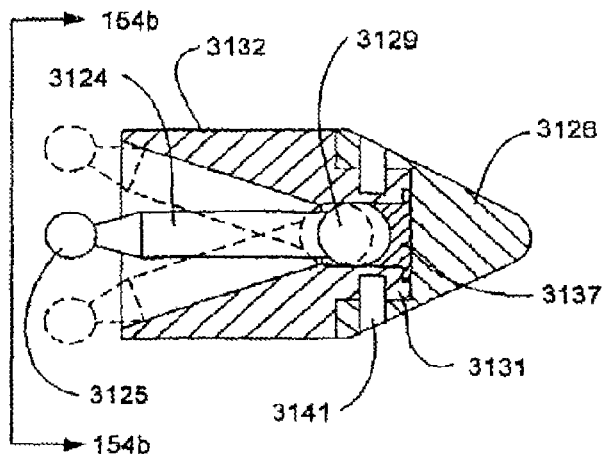
FIG. - 154b    FIG. - 154a
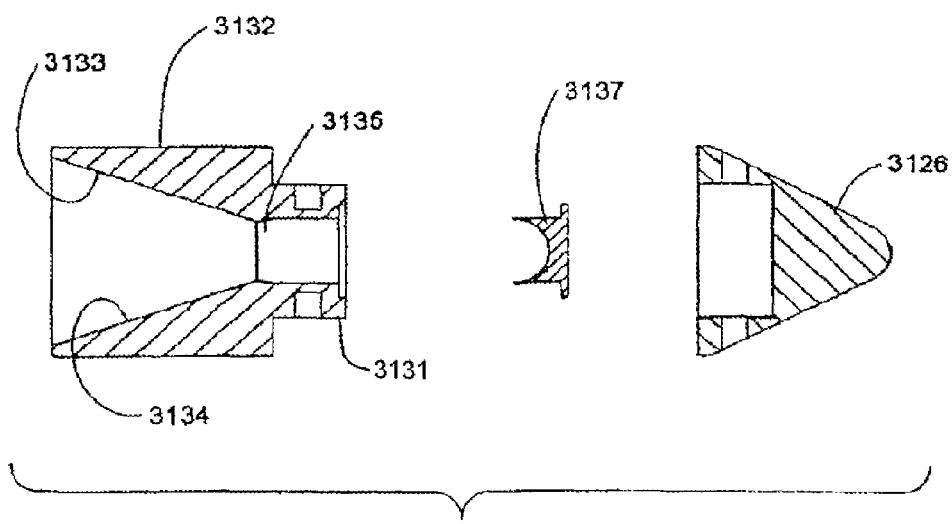
FIG. - 154c

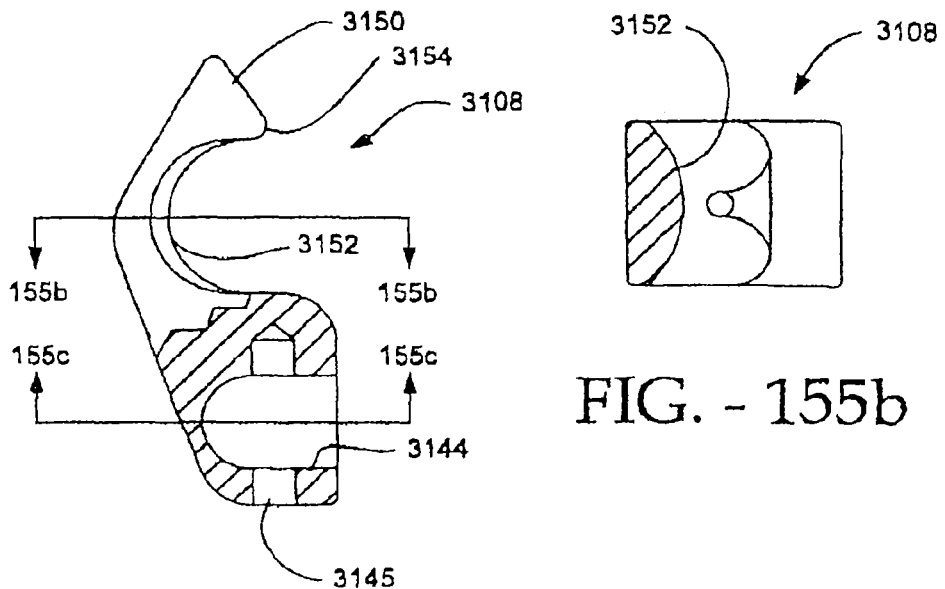
FIG. - 155a
FIG. - 155b
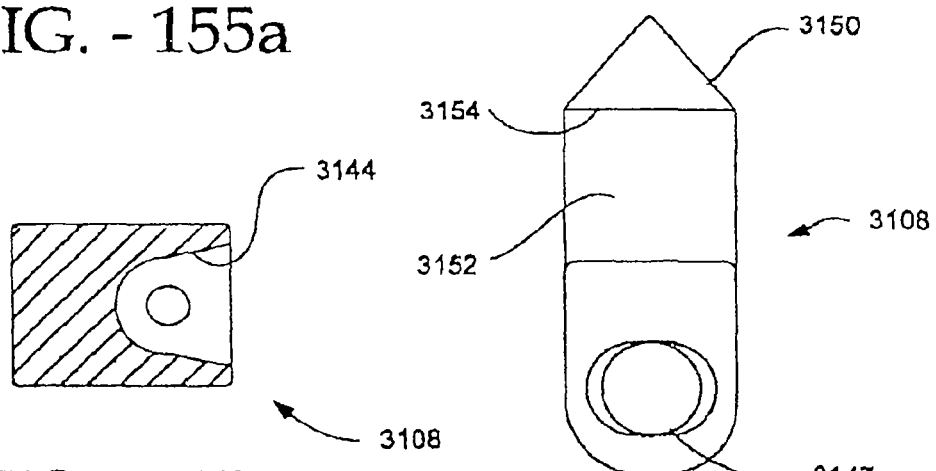
FIG. - 155c
FIG. - 155d
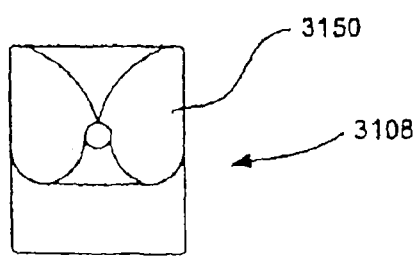
FIG. - 155e

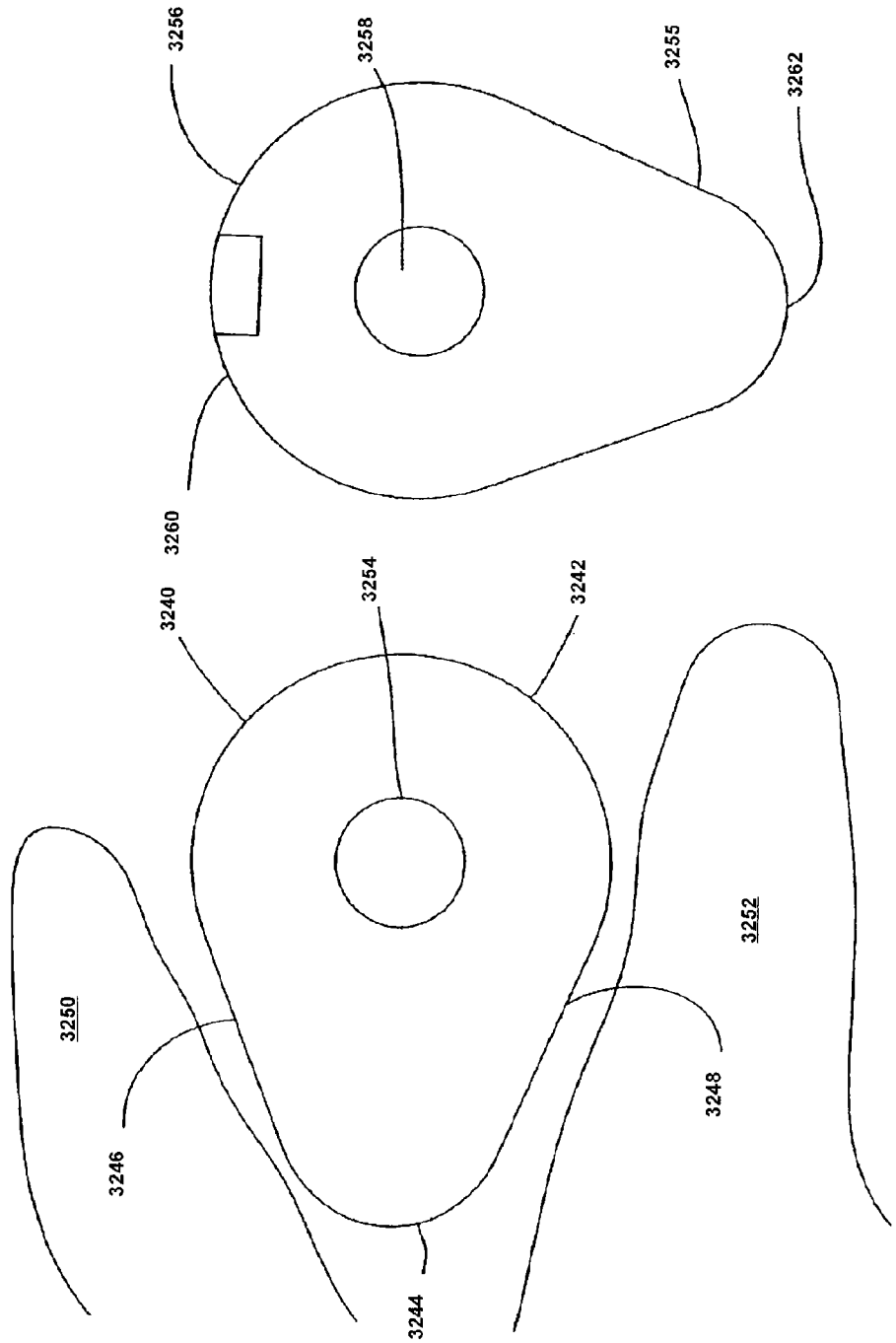

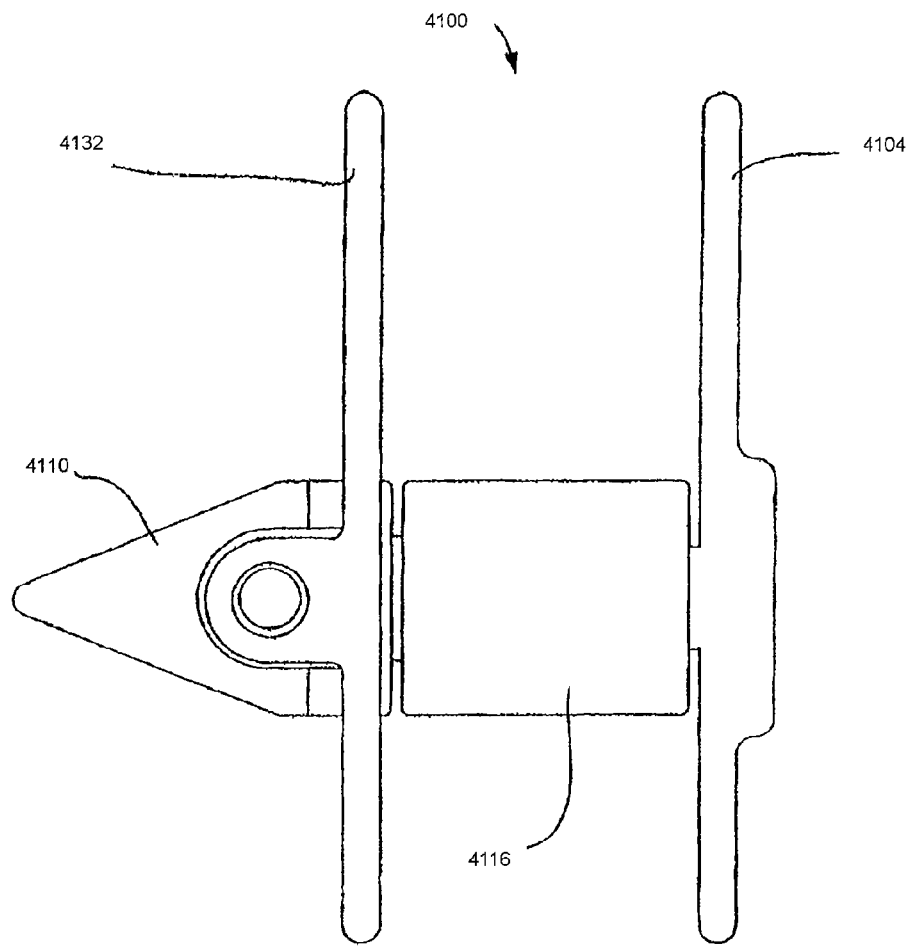
FIG. − 171a

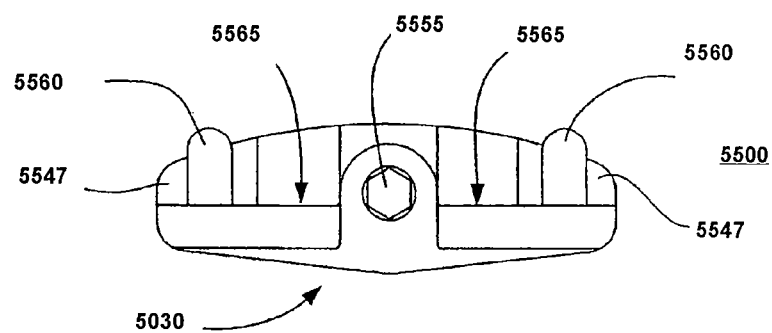
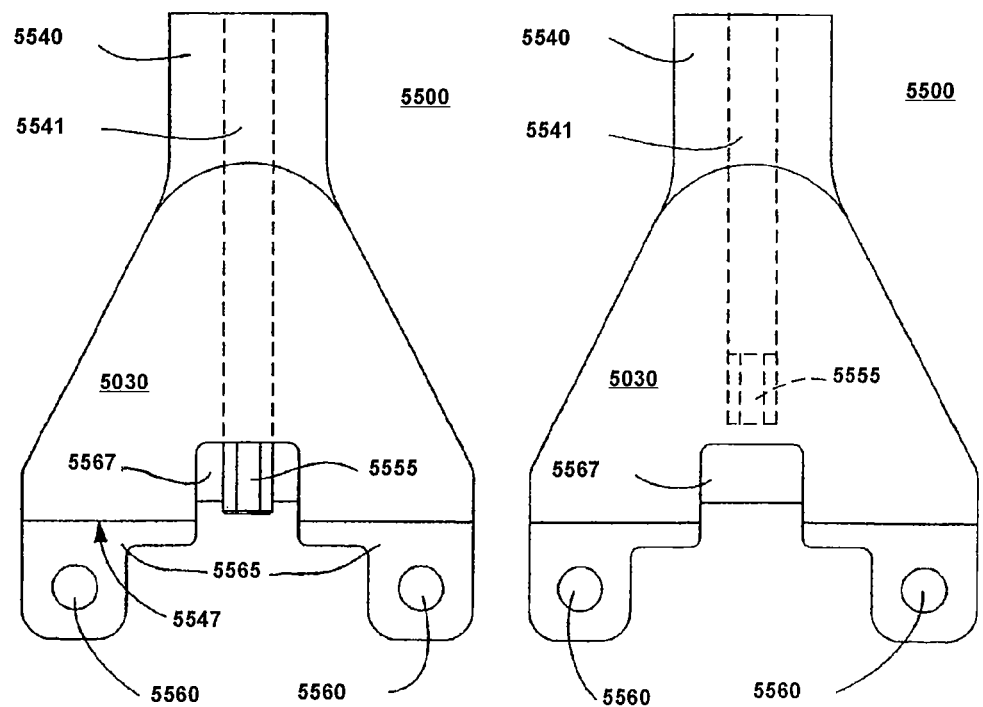
FIG. - 186a
FIG. - 186b  FIG. - 186c

SPINE DISTRACTION IMPLANT AND METHOD

CROSS-REFERENCE TO RELATED APPLICATIONS

This application is a continuation of each of U.S. patent application Ser. Nos. 11/806,529 and 11/806,527, each entitled "Spine Distraction Implant and Method," and filed May 31, 2007 now abandoned; each of which is incorporated herein by reference in its entirety.

Each of U.S. patent application Ser. Nos. 11/806,529 and 11/806,527 is a continuation-in-part of U.S. patent application Ser. No. 11/092,862, entitled "Supplemental Spine Fixation Device and Method," filed Mar. 29, 2005, now U.S. Pat. No. 7,621,939, which is a divisional application of U.S. patent application Ser. No. 09/842,819, entitled "Supplemental Spine Fixation Device," filed Apr. 26, 2001, now U.S. Pat. No. 7,201,751, which claims priority to U.S. Provisional Application Ser. No. 60/219,985, entitled "Supplemental Spine Fixation Device and Method," filed Jul. 21, 2000 and which is a continuation-in-part of U.S. patent application Ser. No. 09/579,039, entitled "Supplemental Spine Fixation Device and Method," filed May 26, 2000, now U.S. Pat. No. 6,451,019, which is a continuation-in-part of U.S. patent application Ser. No. 09/473,173, entitled "Spine Distraction Implant," filed Dec. 28, 1999, now U.S. Pat. No. 6,235,030, which is a continuation of U.S. patent application Ser. No. 09/179,570, entitled "Spine Distraction Implant," filed Oct. 27, 1998, now U.S. Pat. No. 6,048,342, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety.

Each of U.S. patent application Ser. No. 11/806,529 and Ser. No. 11/806,527 is a continuation-in-part of U.S. patent application Ser. No. 10/747,534, entitled "Interspinous Process Distraction System and Method With Positionable Wing and Method," filed Dec. 29, 2003 now abandoned, which is a continuation of U.S. patent application Ser. No. 10/014,118, entitled "Interspinous Process Distraction System and Method With Positionable Wing and Method," filed Oct. 26, 2001, now U.S. Pat. No. 6,695,842, which claims priority to U.S. Provisional Application Ser. No. 60/306,263, entitled "Interspinous Process Distraction System and Method With Positionable Wing and Method," filed Jul. 18, 2001 and which is a continuation-in-part of U.S. patent application Ser. No. 09/799,215, entitled "Spine Distraction Implant," filed Mar. 5, 2001, now U.S. Pat. No. 7,101,375, which is a continuation-in-part of U.S. patent application Ser. No. 09/473,173, entitled "Spine Distraction Implant," filed Dec. 28, 1999, now U.S. Pat. No. 6,235,030, which is a continuation of U.S. patent application Ser. No. 09/179,570, entitled "Spine Distraction Implant," filed Oct. 27, 1998, now U.S. Pat. No. 6,048,342, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety.

Each of U.S. patent application Ser. No. 11/806,529 and Ser. No. 11/806,527 is a continuation-in-part of U.S. patent application Ser. No. 10/037,236, entitled "Interspinous Process Implant and Method With Deformable Spacer," filed Nov. 9, 2001 now abandoned, which claims priority to U.S. Provisional Application Ser. No. 60/323,467, entitled "Interspinous Process Implant and Method With Deformable Spacer," filed Sep. 18, 2001 and which is a continuation-in-part of U.S. patent application Ser. No. 09/799,215, entitled "Spine Distraction Implant," filed Mar. 5, 2001, now U.S. Pat. No. 7,101,375, which is a continuation-in-part of U.S. patent application Ser. No. 09/473,173, entitled "Spine Distraction Implant," filed Dec. 28, 1999, now U.S. Pat. No. 6,235,030, which is a continuation of U.S. patent application Ser. No. 09/179,570, entitled "Spine Distraction Implant," filed Oct. 27, 1998, now U.S. Pat. No. 6,048,342, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety.

Each of U.S. patent application Ser. Nos. 11/806,529 and 11/806,527 is a continuation-in-part of U.S. patent application Ser. No. 10/770,372, entitled "Mating Insertion Instruments for Spinal Implants and Methods of Use," filed Feb. 2, 2004 now U.S. Pat. No. 7,473,268, which is a divisional application of U.S. patent application Ser. No. 09/981,859, entitled "Mating Insertion Instruments for Spinal Implants and Methods of Use," filed Oct. 18, 2001, now U.S. Pat. No. 6,712,819, which claims priority to U.S. Provisional Application Ser. No. 60/306,101, entitled "Mating Insertion Instruments for Spinal Implants and Methods of Use," filed Jul. 17, 2001 and which is a continuation-in-part of U.S. patent application Ser. No. 09/799,470, entitled "Spinal Implants, Insertion Instruments, and Methods of Use," filed Mar. 5, 2001, now U.S. Pat. No. 6,902,566, which claims priority to U.S. Provisional Application Ser. No. 60/220,022, entitled "Spinal Implants, Insertion Instruments, and Methods of Use," filed Jul. 21, 2000 and which is a continuation-in-part of U.S. patent application Ser. No. 09/474,037, entitled "Spine Distraction Implant," filed Dec. 28, 1999, now U.S. Pat. No. 6,190,387, which is a divisional application of U.S. patent application Ser. No. 09/175,645, entitled "Spine Distraction Implant," filed Oct. 20, 1998, now U.S. Pat. No. 6,068,630, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety. U.S. patent application Ser. No. 09/799,470, is also a continuation-in-part of U.S. patent application Ser. No. 09/473,173 entitled "Spine Distraction Implant," filed Dec. 28, 1999, now U.S. Pat. No. 6,235,030, which is a continuation of U.S. patent application Ser. No. 09/179,570, entitled "Spine Distraction Implant," filed Oct. 27, 1998, now U.S. Pat. No. 6,048,342, which is a continuation-in-part of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety. U.S. patent application Ser. No. 09/799,470, is also a continuation-in-part of U.S. patent application Ser. No. 09/200,266 entitled "Spine Distraction Implant and Method," filed Nov. 25, 1998, now U.S. Pat. No. 6,183,471, which is a continuation of U.S. patent application Ser. No. 09/139,333, entitled "Spine Distraction Implant and Method," filed Aug. 25, 1998, now U.S. Pat. No. 5,876,404, which is a continuation of U.S. patent application Ser. No. 08/958,281, entitled "Spine Distraction Implant and Method," filed Oct. 27, 1997, now U.S. Pat. No. 5,860,977, which is a continuation-in-part of U.S. patent application Ser. No. 08/778,093, entitled "Spine Distraction Implant and Method," filed Jan. 2, 1997, now U.S. Pat. No. 5,836,948; each of which is incorporated herein by reference in its entirety.

BACKGROUND

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating such condition which are minimally invasive, can be tolerated by the elderly and can be performed preferably on an outpatient basis.

SUMMARY

The present invention is directed to providing a minimally invasive implant and method for alleviating discomfort associated with the spinal column.

The present invention provides for apparatus and method for relieving pain by relieving the pressure and restrictions on the aforementioned blood vessels and nerves. Such alleviation of pressure is accomplished in the present invention through the use of an implant and method which distract the spinous process of adjacent vertebra in order to alleviate the problems caused by spinal stenosis and facet arthropathy and the like. While the implant and method particularly address the needs of the elderly, the invention can be used with individuals of all ages and sizes where distraction of the spinous process would be beneficial.

In one aspect of the invention, an implant is provided for relieving pain comprising a device positioned between a first spinous process and a second spinous process. The device includes a spinal column extension stop and a spinal column flexion non-inhibitor.

In another aspect of the invention, the implant is positioned between the first spinous process and the second spinous process and includes a distraction wedge that can distract the first and second spinous processes as the implant is positioned between the spinous processes.

In yet another aspect of the present invention, the implant includes a device which is adapted to increasing the volume of the spinal canal and/or the neural foramen as the device is positioned between adjacent spinous processes.

In yet a further aspect of the present invention, a method is presented for relieving pain due to the development of, by way of example only, spinal stenosis and facet arthropathy. The method is comprised of the steps of accessing adjacent first and second spinal processes of the spinal column and distracting the processes a sufficient amount in order to increase the volume of the spinal canal in order to relieve pain. The method further includes implanting a device in order to maintain the amount of distraction required to relieve such pain.

In yet a further aspect of the invention, the method includes implanting a device in order to achieve the desired distraction and to maintain that distraction.

In yet a further aspect of the invention, the implant includes a first portion and a second portion. The portions are urged together in order to achieve the desired distraction.

In still a further aspect of the invention, the implant includes a distracting unit and a retaining unit. The distracting unit includes a body which can be urged between adjacent spinous processes. The body includes a slot. After the distracting unit is positioned, the retaining unit can fit into the slot of the retaining unit and be secured thereto.

In yet a further aspect of the invention, the implant includes a first unit with a central body. A sleeve is provided over the central body and is at least partially spaced from the central body in order to allow for deflection toward the central body.

In a further aspect of the invention, the implant includes a first unit having a central body with a guide and a first wing, with the first wing located at first end of the body. The guide extends from a second end of the body located distally from the first wing. The implant further includes a sleeve provided over said central body. The sleeve is at least partially spaced from the central body in order to allow for deflection of the sleeve toward the central body. The implant further includes a second wing and a device for securing the second wing to the first unit, wherein the sleeve is located between the first and second wings.

In yet another aspect of the invention, an implant system includes a cylindrical sleeve which is inwardly deflectable. The system further includes an insertion tool which includes an insertion guide, a central body, a stop and a handle. The guide and the stop extend from opposite sides of the central body and the handle extend from the stop. A sleeve fits over the guide and against the stop preparatory to being positioned between the two adjacent vertebrae with the insertion tool.

In yet a further aspect of the invention, the implant includes central body and first and second wings and a means for selectively positioning one of the first and second wings relative to the other in order to accommodate spinous processes of different sizes.

Other implants and methods within the spirit and scope of the invention can be used to increase the volume of the spinal canal thereby alleviating restrictions on vessels and nerves associated therewith, and pain.

BRIEF DESCRIPTION OF THE DRAWINGS

FIG. 1 depicts the implant in a more extended configuration than does FIG. 2.

FIGS. 6, 7, 8, 9 and 10 depict apparatus and method for another embodiment of the present invention for creating distraction between adjacent spinous processes.

FIGS. 16, 16a, and 17 depict yet another embodiment of the present invention.

FIGS. 18, 19 and 20 depict yet a further apparatus and method of the present embodiment.

FIGS. 34 and 35 depict yet another apparatus and method of the present invention.

FIGS. 36, 37 and 38 depict three different embodiments of the present invention.

FIGS. 39 and 40 depict yet another apparatus and method of an embodiment of the present invention.

FIG. 45 is yet another depiction of an apparatus and method of the invention.

FIGS. 46 and 47 depict still a further apparatus and method of an embodiment of the invention.

FIGS. 48, 49, 50 and 51 depict yet a further apparatus and method of the invention.

FIGS. 52, 53, 54, 55a and 55b depict another apparatus and method of the invention.

FIGS. 59 and 60 depict still a further embodiment of the invention.

FIG. 61 depict another embodiment of the invention.

FIGS. 64 and 65 depict still a further embodiment of the present invention.

FIG. 66 depicts another embodiment of the invention.

FIGS. 69, 70, 71 and 71a depict a further embodiment of the present invention.

FIGS. 79, 80, 80a, 81, 82, 83, 83a, 84, 85, 86 and 87 depict still a further embodiment of the present invention.

FIGS. 88, 89, 90 and 91 depict yet another embodiment of the present invention.

FIGS. 92, 92a, 92b, 93, 93a, 93b, 93c, 93d, 94, 94a, 94b, 95, 95a, an depict still a further embodiment of the present invention wherein a sleeve is provided which is capable of deflecting response to relative motion between the spinous processes.

FIGS. 108, 109, and 110 depict still another embodiment of the present invention.

FIGS. 111, 112, 113, 114, 115, 116, and 117 depict yet another embodiment of the present invention.

FIGS. 119a and 119b depict side and plan views of still a further embodiment of the present invention.

FIGS. 120a and 120b depict side and plan views of the second wing which can be used in conjunction with the embodiment of the invention of FIGS. 119a and 119b.

FIGS. 124a, 124b and 124c depict a view of the embodiment of the invention of FIGS. 119a and 119b taken through line 124-124 in FIG. 119b shown in with the sleeve in various positions relative to a first wing.

FIG. 128 is still a further embodiment of the invention as depicted in FIG. 93a.

FIGS. 131a and 131b are alternative components of the embodiment of FIG. 131.

FIG. 138a is an alternative component of the embodiment of FIG. 137.

FIG. 138b is an upside down perspective view of a component of the embodiment of FIG. 138.

FIG. 141a is an upside down perspective view of a component of the embodiment of FIG. 141.

FIG. 154a is a sectioned view of the spacer and lead-in nose tissue expander of the invention.

FIG. 154b is an end view of a spacer of FIG. 154a.

FIG. 154c is an exploded view of several of the components of FIG. 154a.

FIG. 155a is a plan, partially sectioned view of an embodiment of a hook of the invention.

FIG. 155b is a sectioned view taken through line 155b-155b of FIG. 155a.

FIG. 155c is a sectioned view taken through line 155c-155c of FIG. 155a.

FIG. 155d is a bottom view of the embodiment of the hook of the invention of 155a.

FIG. 155e is an end view of FIG. 155d.

FIG. 163a is yet a further embodiment of the spacer of the invention which is substantially egg-shaped and positional between adjacent spinous processes.

FIG. 163b is an end view of the base of a lead-in nose usable with the spacer of FIG. 163a.

FIG. 171a is an assembly view of an embodiment of the invention

FIG. 171d is a side view illustrating the second wing of the embodiment of the invention in FIG. 171a.

FIG. 171e is a plane view of the second wing of an embodiment of the invention of FIG. 171a.

FIG. 171f is an end view of the spacer of the embodiment of the invention of FIG. 171a.

FIG. 171g is a cut-away view illustrating the spacer of the embodiment of the invention of FIG. 171a.

FIG. 175b is an end view of the embodiment of the spacer illustrated in FIG. 175a.

FIG. 176a is a perspective view of yet another embodiment of the spacer of the invention.

FIG. 176b is a perspective view of the first outer shell of the spacer illustrated in FIG. 176a.

FIG. 176c is an end view of the embodiment of the spacer shown in FIG. 176a filled with a deformable or compressible material.

FIG. 177 is a perspective view of yet another embodiment of the spacer of the invention.

FIGS. 178a-178b are perspective views of still other embodiments of the spacer of the invention.

FIG. 179a is a perspective view of another embodiment of the present invention.

FIG. 179b is a cut-away view of the embodiment of the invention illustrated in FIG. 9a.

FIG. 180 depicts an exterior view of a main body insertion instrument of one embodiment of this invention for inserting an implant body into the spine of a patient.

FIG. 181 depicts a schematic, sectional, longitudinal view of a main body insertion instrument as depicted in FIG. 180.

FIGS. 182a-182c depict schematic views of an insertion tip of the main body insertion instrument of one embodiment of this invention as shown in FIGS. 180 and 181.

FIG. 182a depicts a side view of the insertion tip of a main body insertion instrument of one embodiment of this invention with a locking pin and spacer engagement pin spacer in the extended position.

FIG. 182b depicts the insertion tip as shown in FIG. 182a with a locking pin and spacer engagement pin spacer in a retracted position.

Figure 182A:
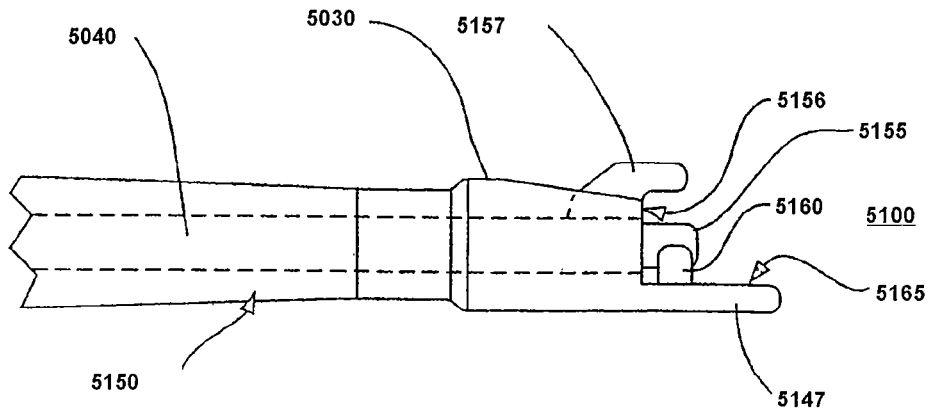
Figure 182B:
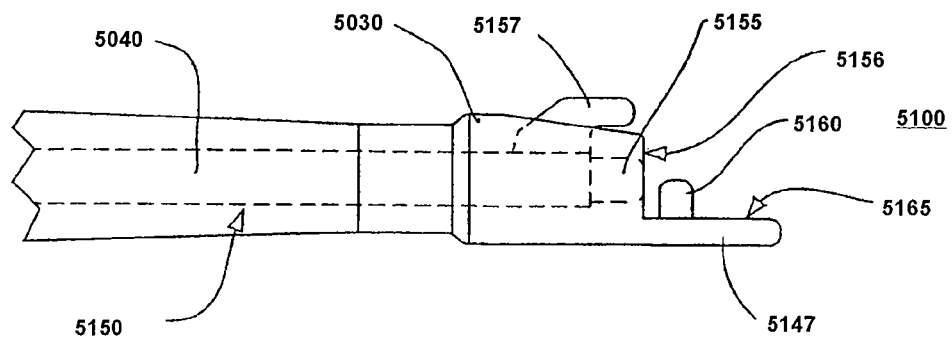
Figure 182C:
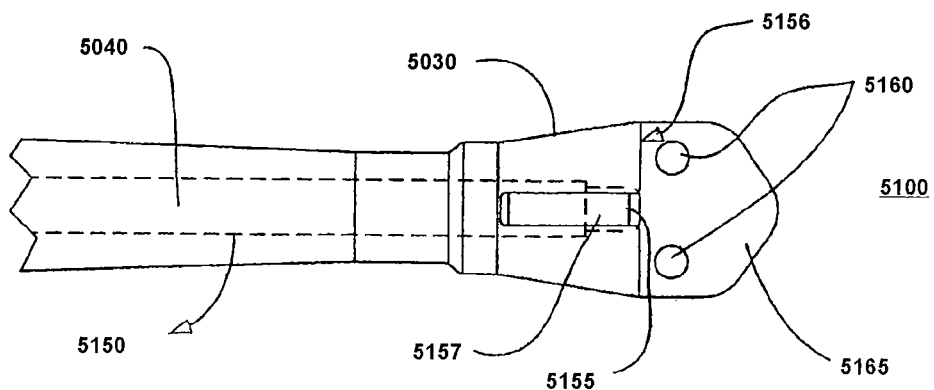

FIG. 182c depicts a top view of the insertion tip of the main body insertion instrument of one embodiment of this invention with the locking pin and engagement pin spacer in a retracted position.

Figure 183A:
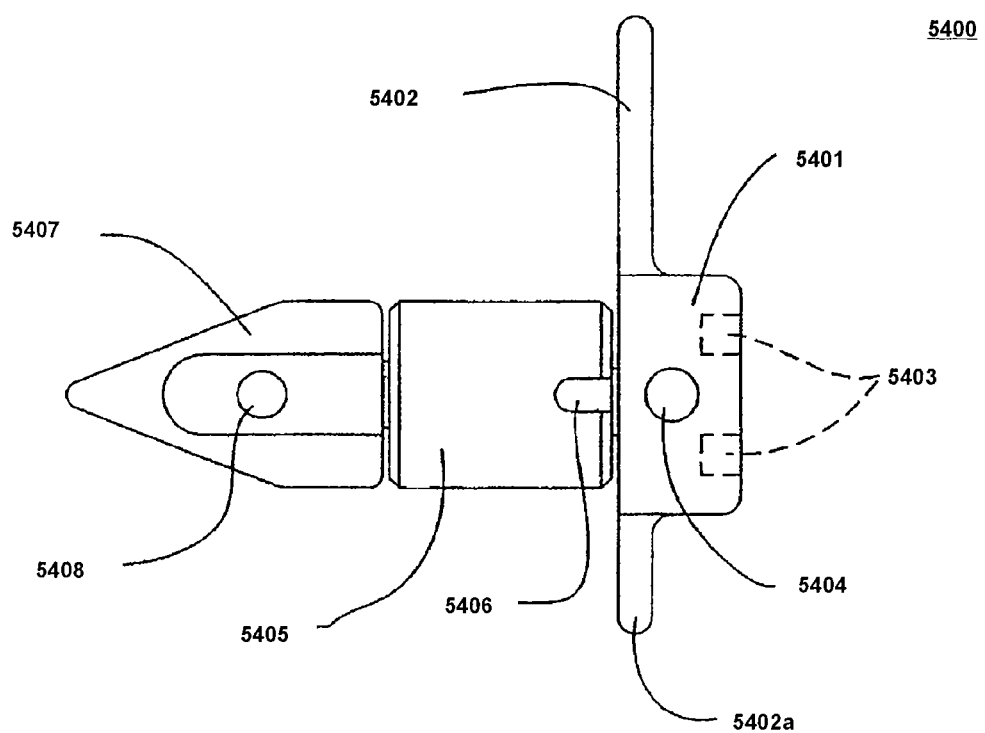

FIG. 183a depicts an embodiment of a main body assembly of a spinal implant of the invention used with a main body insertion instrument of this invention.

Figure 183B:
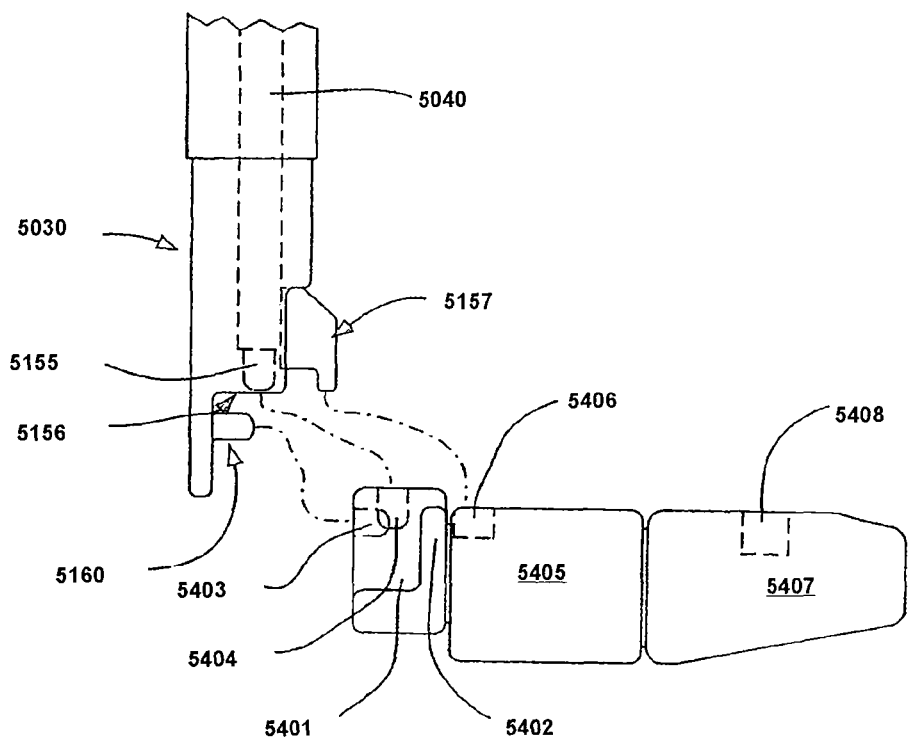

FIG. 183b depicts an embodiment of a main body insertion instrument of this invention and an embodiment of a main body assembly of the invention as shown in FIG. 183a, showing the points of engagement between the assembly and the instrument.

Figure 183C:
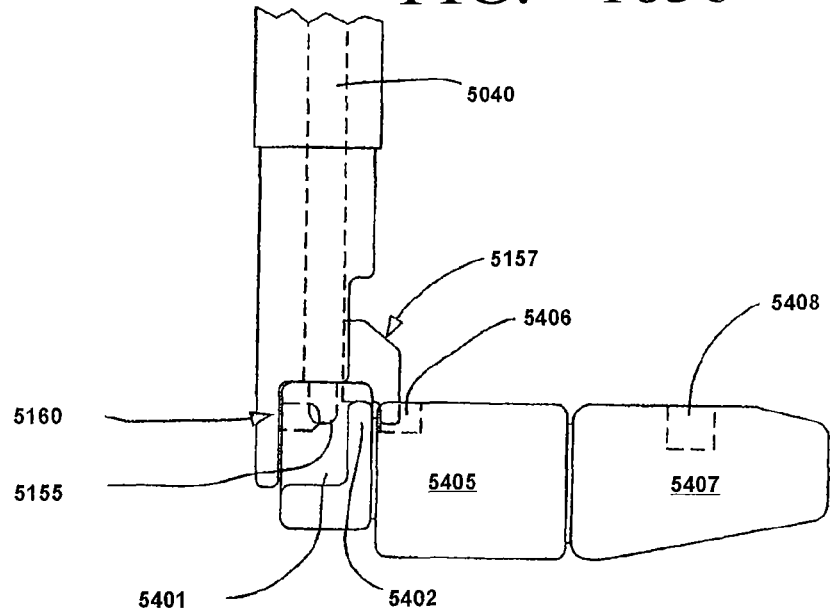

FIG. 183c depicts an embodiment of a main body assembly of the invention and an embodiment of a main body insertion instrument of the invention, both depicted in FIG. 183b, engaged with one another.

Figure 184:
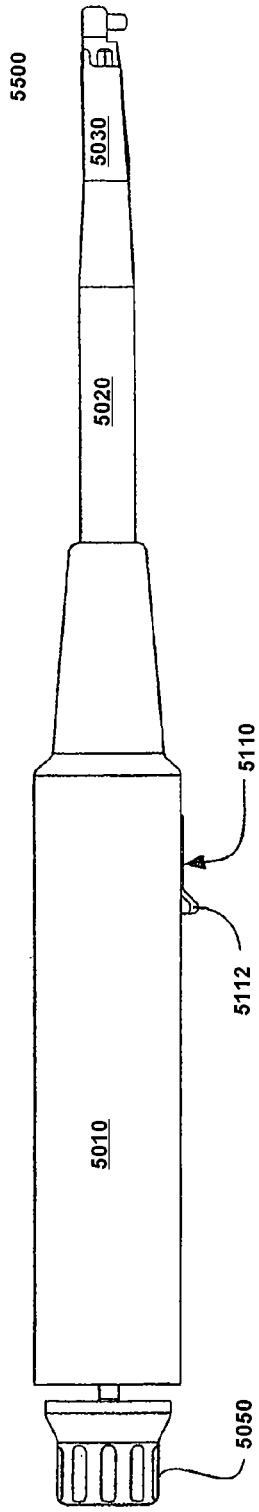

FIG. 184 depicts an exterior view of an embodiment of a wing insertion instrument of the invention.

Figure 185:
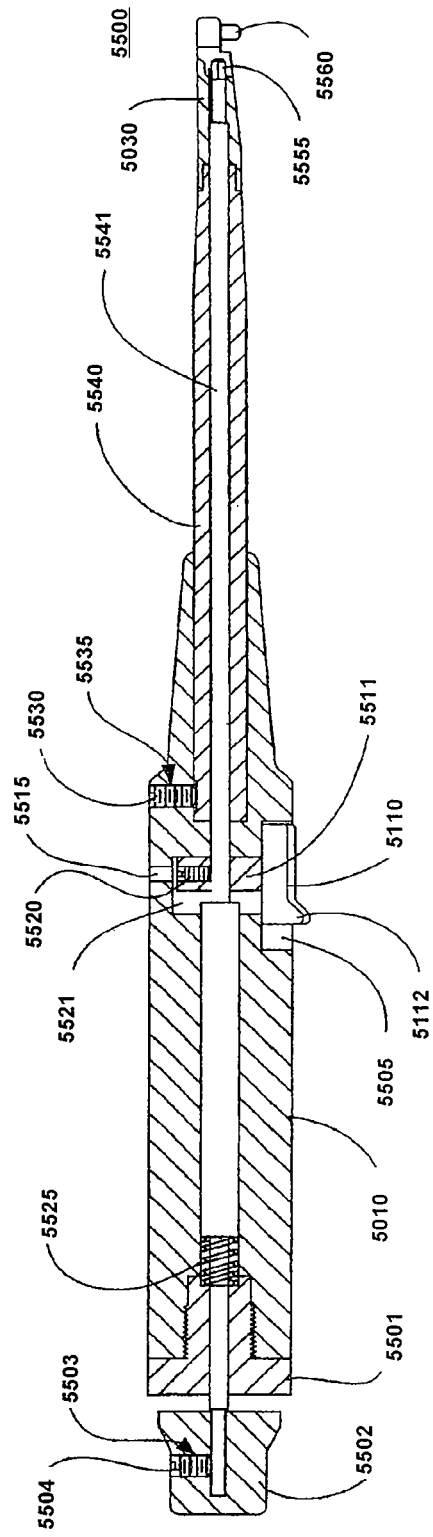

FIG. 185 depicts a schematic, sectioned, longitudinal view of the embodiment of a wing insertion instrument of the invention as shown in FIG. 184

FIG. 186a depicts an end view of an embodiment of an insertion tip of a wing insertion instrument of the invention are depicted in FIGS. 184 and 185.

FIG. 186b depicts a top view of an embodiment of an insertion tip of a wing insertion instrument of the invention as depicted in FIG. 186a with a driver in a distal position.

FIG. 186c depicts a top view of the embodiment of the insertion tip of a wing insertion instrument of the invention as depicted in FIGS. 186a and 186b with the driver in a proximal position.

Figure 187A:
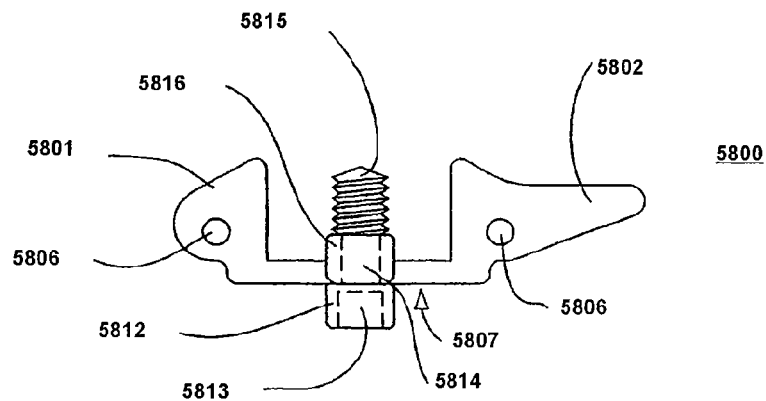

FIG. 187a depicts a side view of an embodiment of a universal wing of the invention which is implantable with a wing insertion instrument of the invention.

Figure 187B:
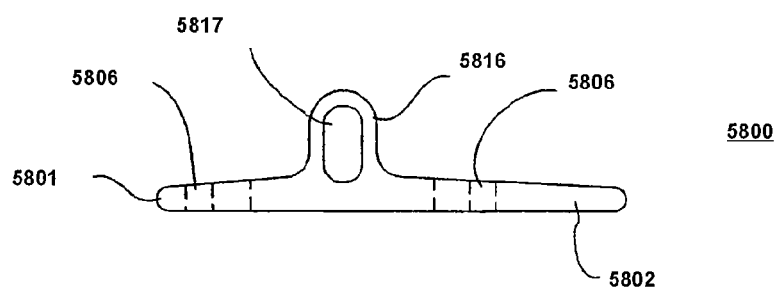

FIG. 187b depicts an end view of an embodiment of a universal wing of the invention are depicted in FIG. 187a without an attachment bolt.

Figure 187C:
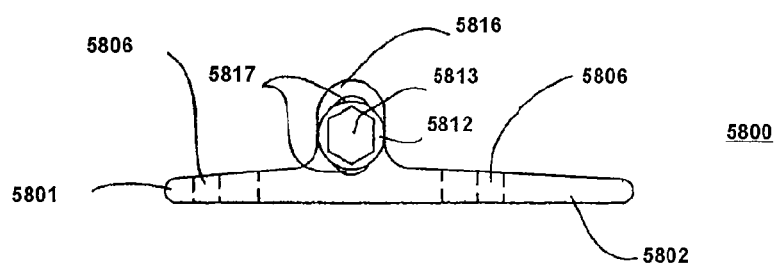

FIG. 187c depicts the embodiment of an embodiment of the universal wing of the invention as shown in FIG. 187b with an attachment bolt.

Figure 188A:
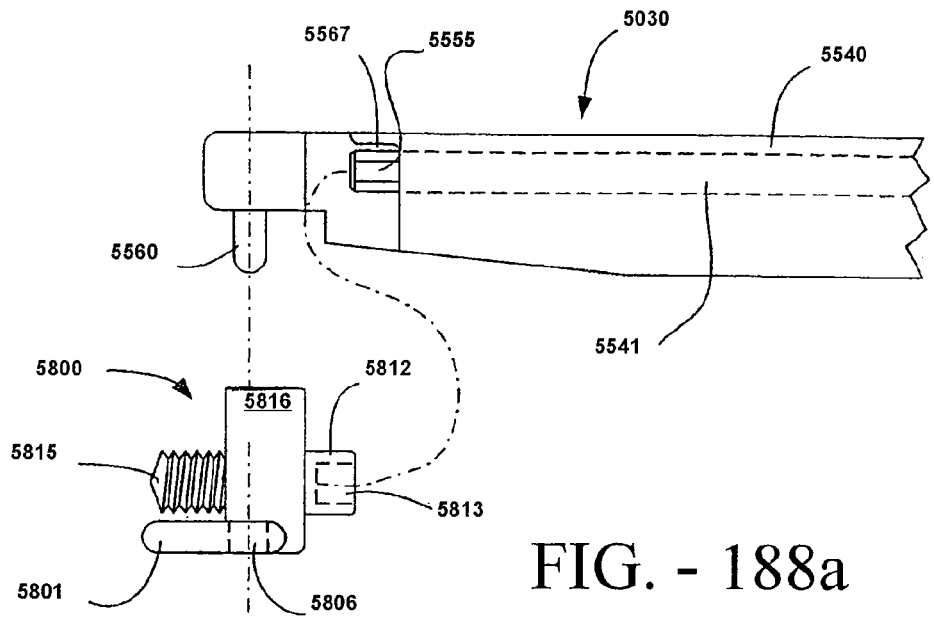
Figure 188B:
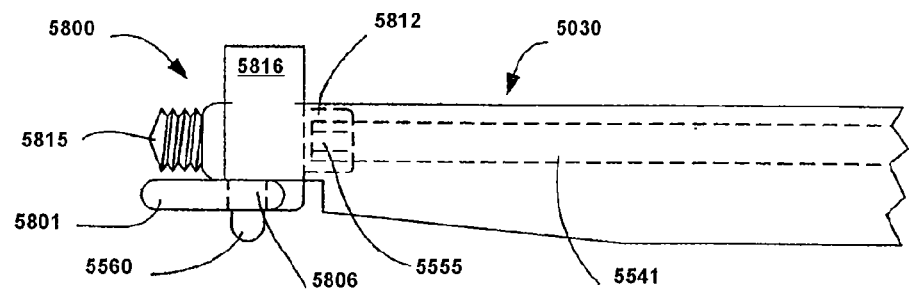
Figure 188C:
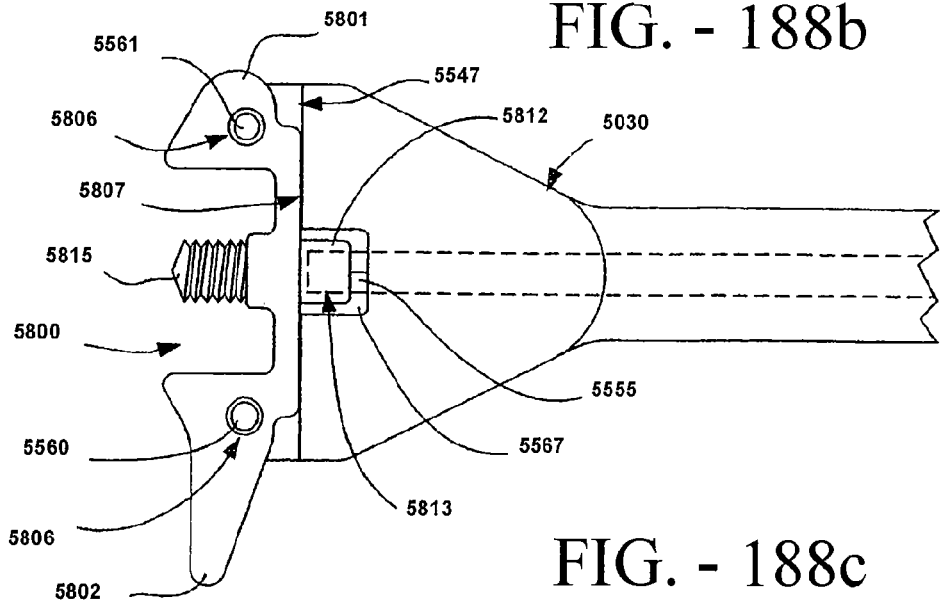
Figures 189A, 189B, 189C, 189D:
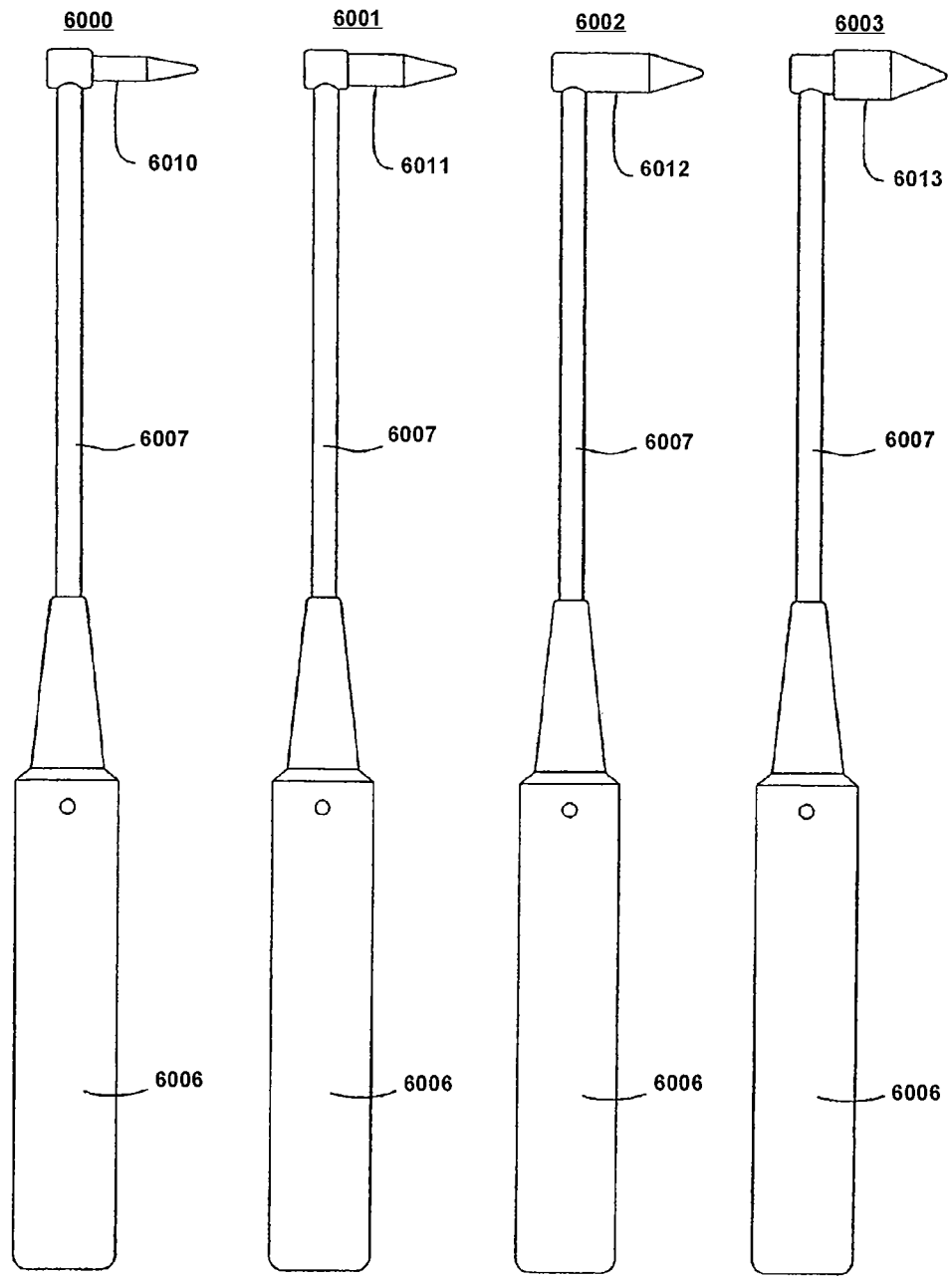

FIGS. 188a-188c depict an embodiment of an insertion tip of a wing insertion instrument of the invention as shown in FIGS. 185 and 186, and an embodiment of a universal wing of the invention. More particularly, FIGS. 188a-188c depict the following.

FIG. 188a is a side view showing the relationships of an embodiment a universal wing of the invention and an embodiment of a wing insertion instrument of the invention, showing the points of engagement.

FIG. 188b is a side view of the embodiment of the universal wing and the wing insertion instrument of the invention depicted in FIG. 188a after engagement.

FIG. 188c is a top view of the embodiment of a universal wing and a wing insertion instrument of the invention as depicted in FIG. 188b.

FIGS. 189a-189d depict trial implantation and distraction instruments of the invention.

Figure 190A:
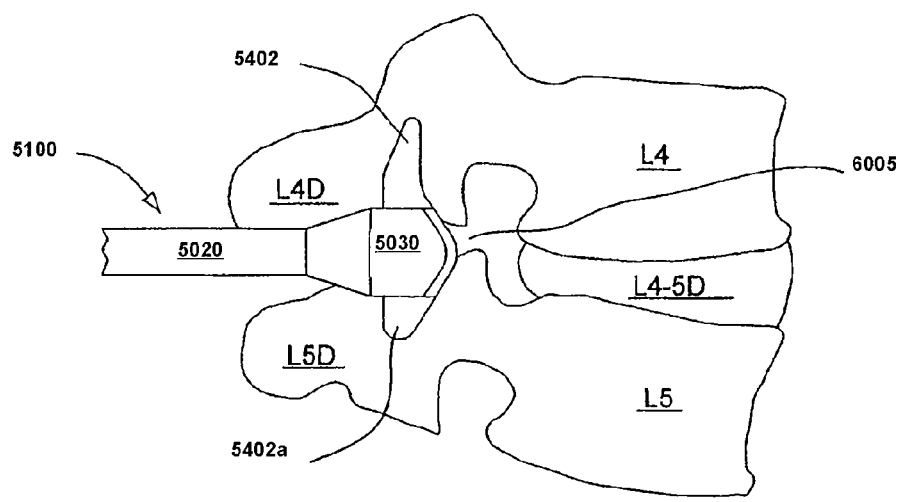
Figure 190B:
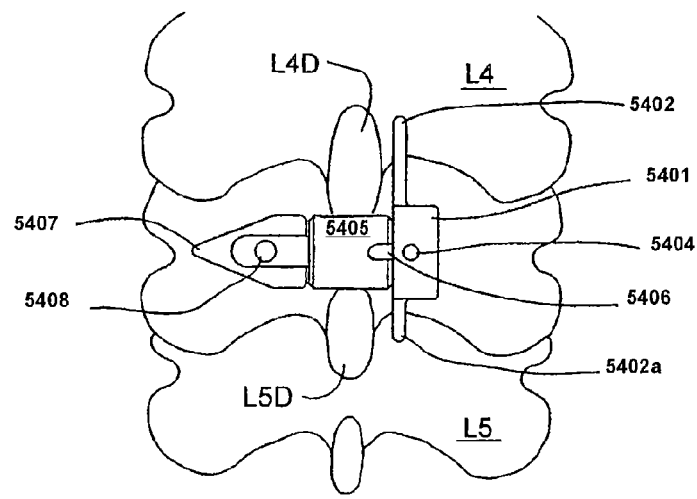

FIGS. 190a and 190b depict the insertion of a main body assembly of the invention into the spine of a patient. More particularly, FIGS. 190a and 190b depict the following.

FIG. 190a depicts a lateral view of a spine, and an embodiment of a main body insertion instrument of the invention engaged with an embodiment of a main body assembly of the invention positioned between spinous processes of adjacent vertebrae of a patient.

FIG. 190b depicts a dorsal view of a spine of a patient depicting an embodiment of a main body assembly of the invention inserted between spinal processes of adjacent vertebrae.

Figure 191:
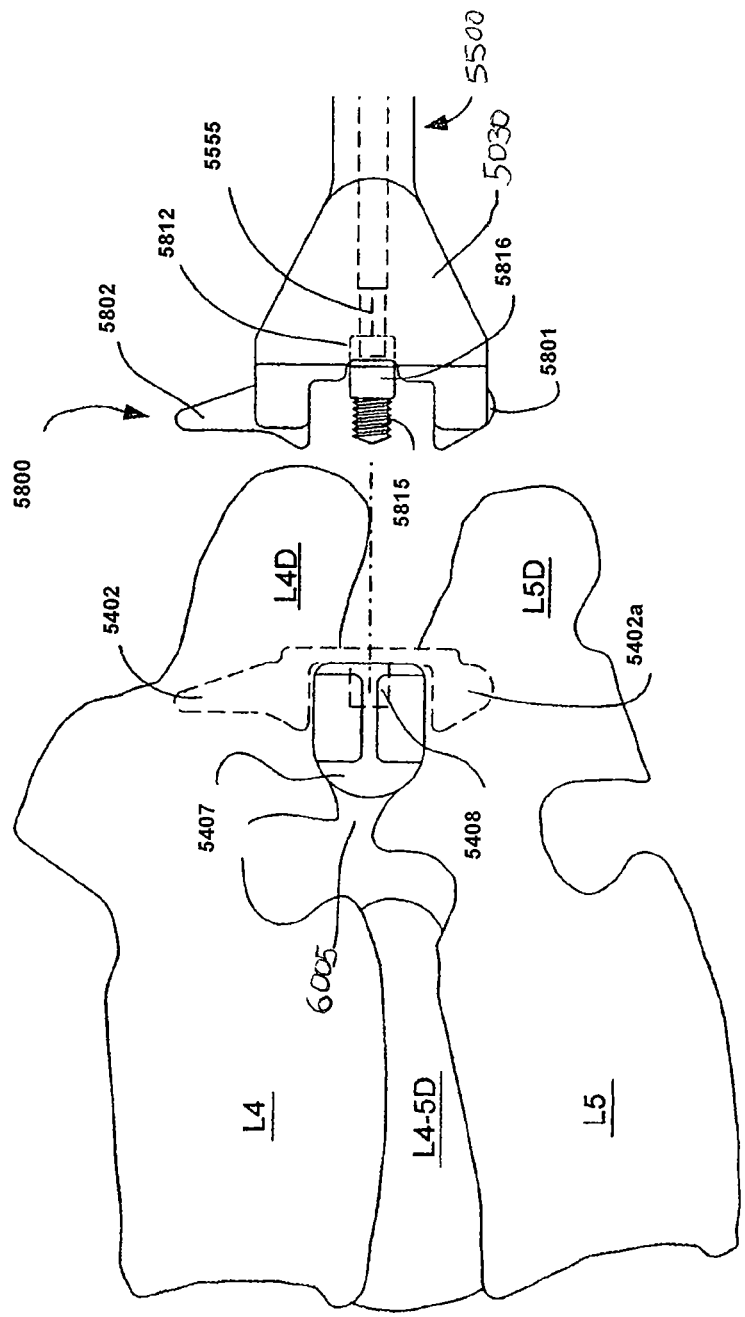

FIG. 191 depicts a lateral view of a spine with an embodiment of a main body assembly of the invention inserted between spinous processes of adjacent vertebrae and a wing implant insertion instrument of the invention engaged with an embodiment of a universal wing of the invention, showing the points of attachment between the embodiment of the main body assembly and the universal wing of the invention.

Figure 192:
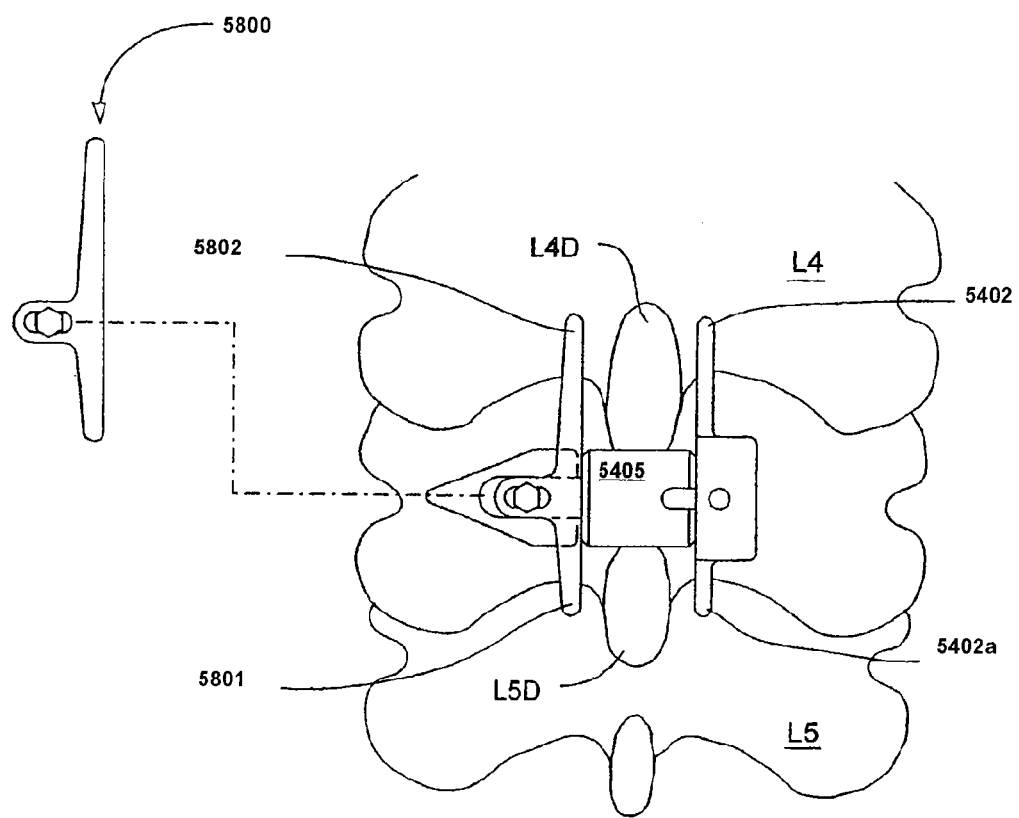

FIG. 192 depicts a dorsal view of a spine with an embodiment of a main body assembly of the invention inserted between spinous processes of adjacent vertebrae, and showing the insertion of an embodiment of a universal wing of the invention and its attachment to the embodiment of main body assembly of the invention.

Figure 193:
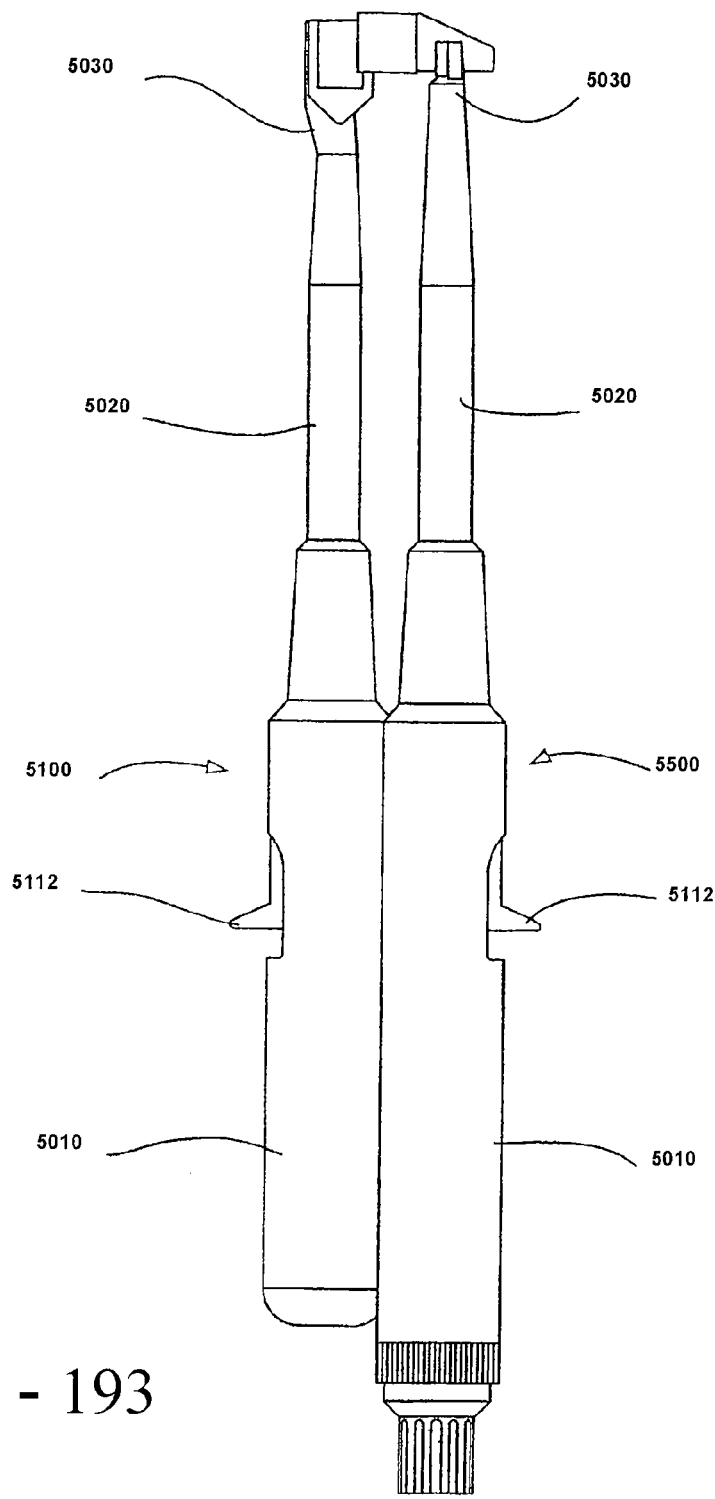

FIG. 193 depicts an alternative embodiment of instruments of the present invention with the handle of the main body insertion instrument nested into an alternate embodiment of the wing insertion instrument of the invention.

Figure 194:
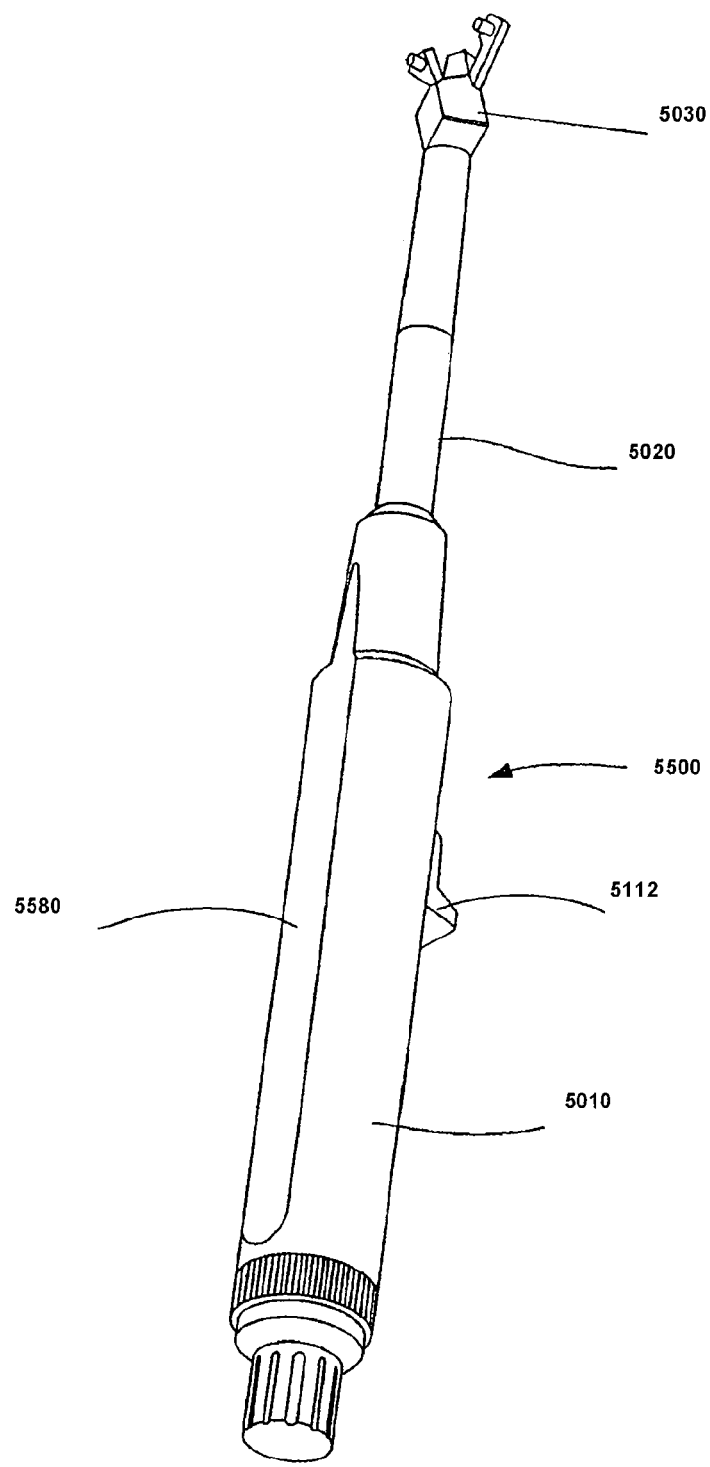

FIG. 194 depicts the wing insertion instrument of FIG. 193.

Figure 195:
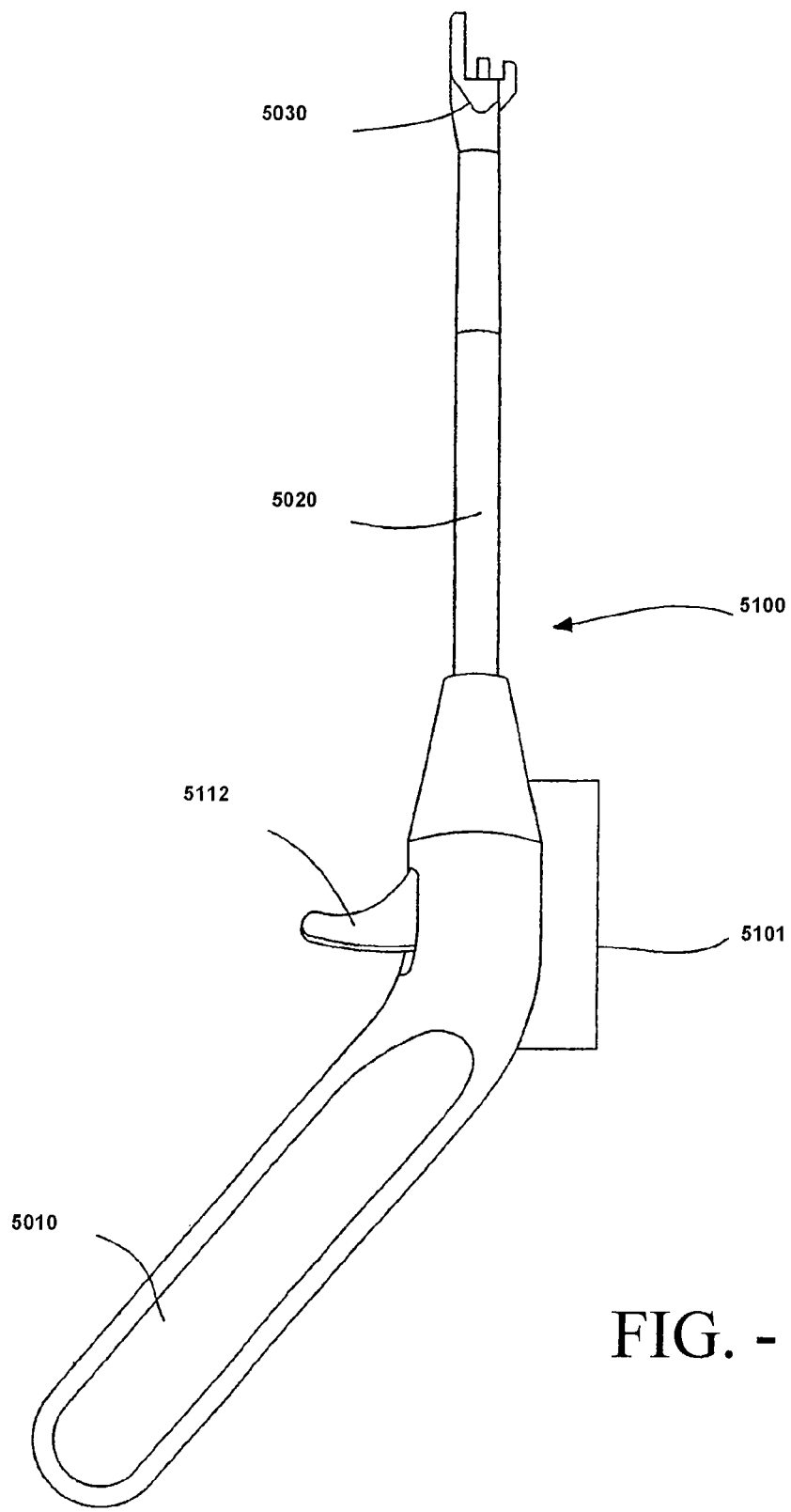

FIG. 195 depicts an alternative embodiment of the main body insertion instrument.

Figure 196:
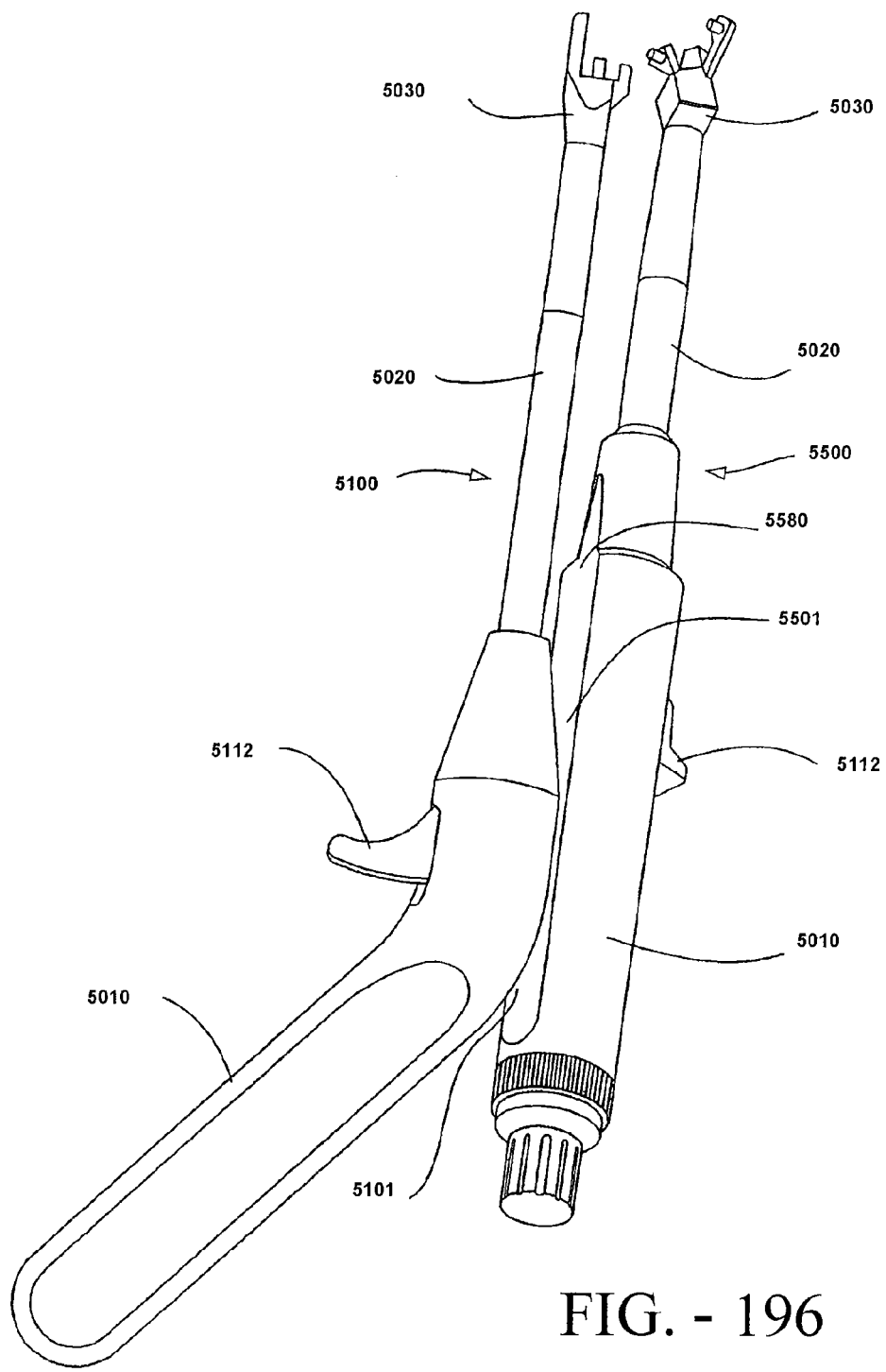

FIG. 196 depicts the alternative embodiment of the main body insertion instrument of FIG. 195 nested into the wing insertion instrument of FIG. 194.

DETAILED DESCRIPTION

Embodiment of FIGS. 1-5a, 5b

A first embodiment of the invention is shown in FIGS. 1-5a, 5b. Implant 20 includes first and second forked ends 22 and 24, each defining a saddle 26, 28 respectively. The forked ends 22, 24 are mated using an interbody piece 30. As can be seen in FIGS. 3a, 3b, the first forked end 22 includes a threaded shaft 32 which projects rearwardly from the saddle 26. The threaded shaft 32 fits into the threaded bore 34 (FIG. 4a) of the interbody piece 30.

The second forked end 24 (FIGS. 5a, 5b) includes a smooth cylindrical shaft 36 which can fit into the smooth bore 38 of the interbody piece 30.

Figure 1:
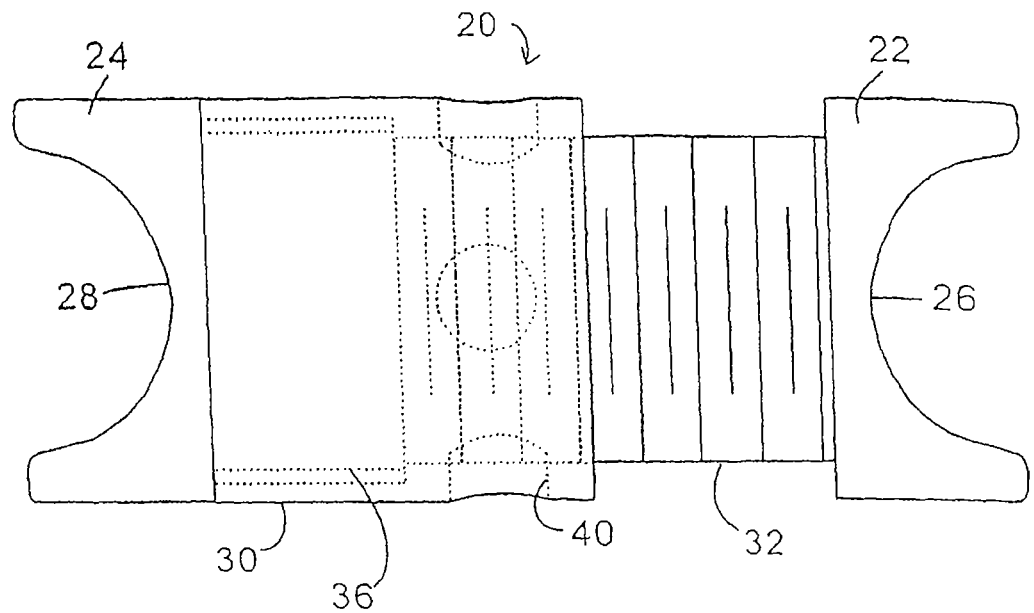
FIGS. 1 and 2 depict an embodiment of an implant of the invention which is adjustable in order to select the amount of distraction required.
Figure 2:
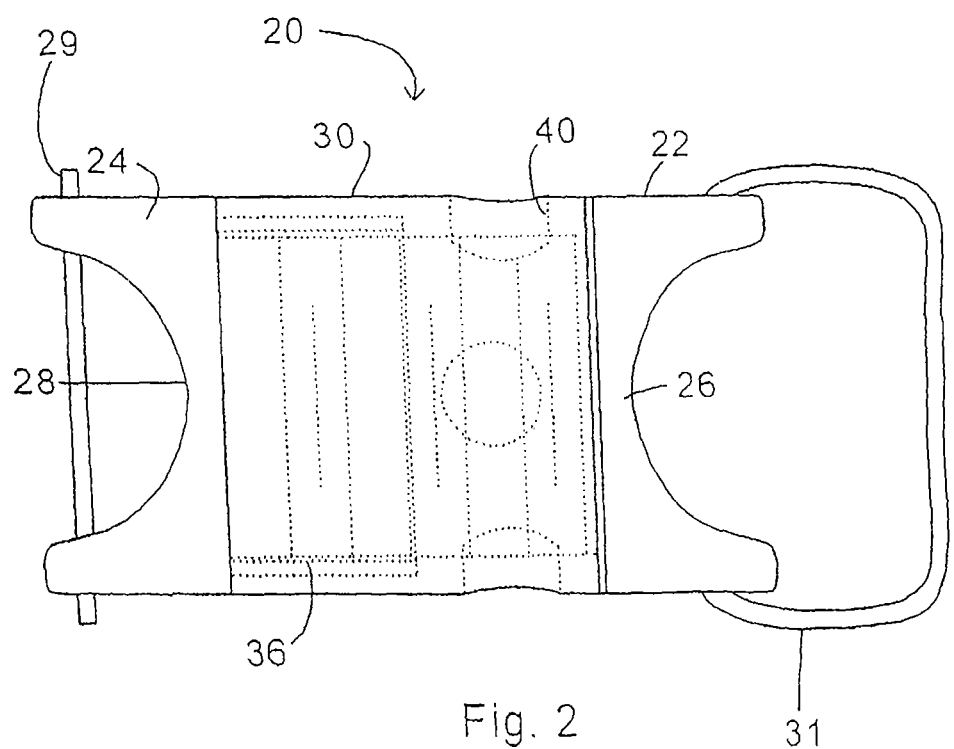
Figure 3A:
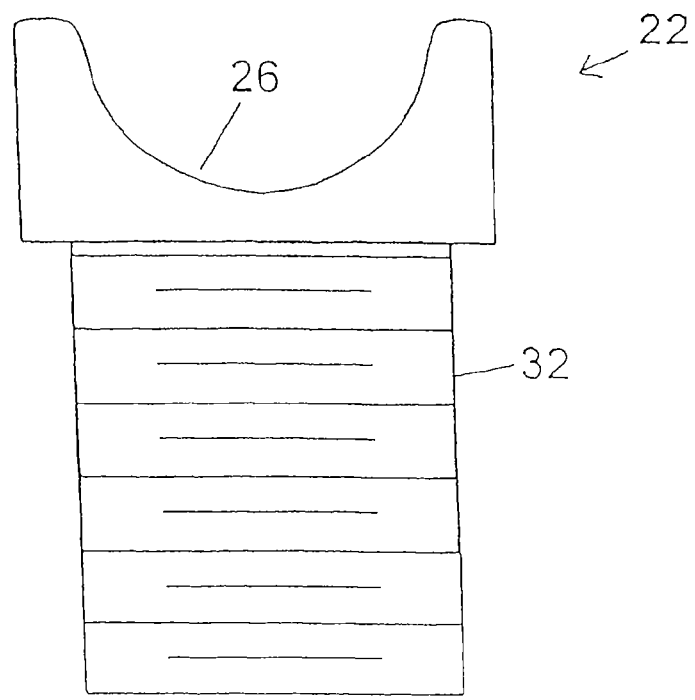
FIGS. 3a and 3b depict side and end views of a first forked and of the embodiment of FIG. 1.
Figure 3B:
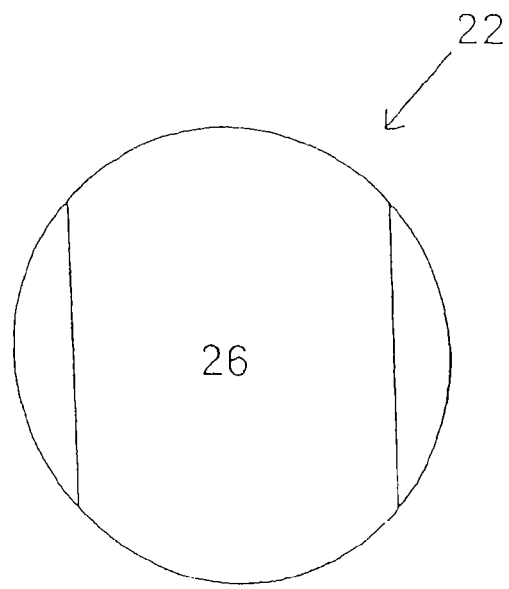
Figure 4A:
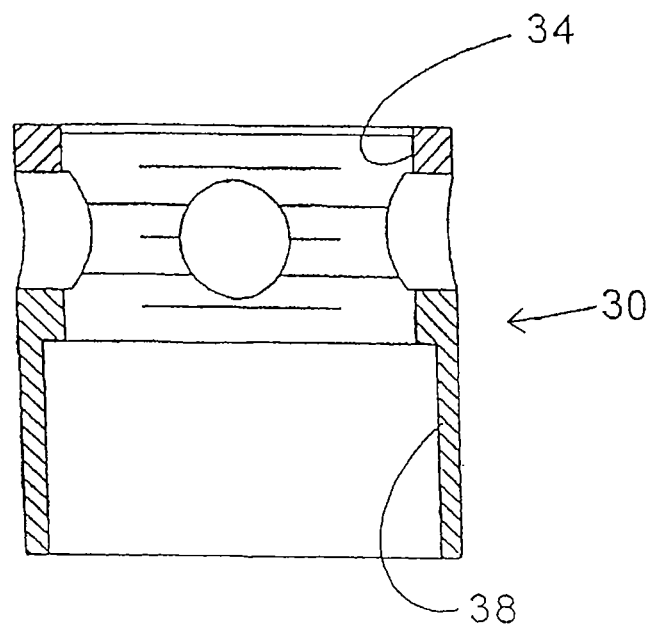
FIGS. 4a and 4b depict side sectioned and end views of an interbody piece of the implant of FIG. 1.
Figure 4B:
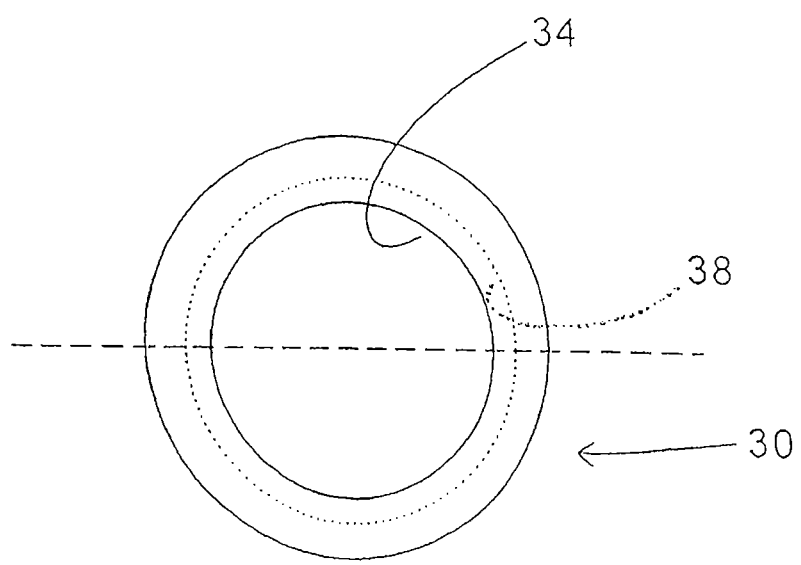
Figure 5A:
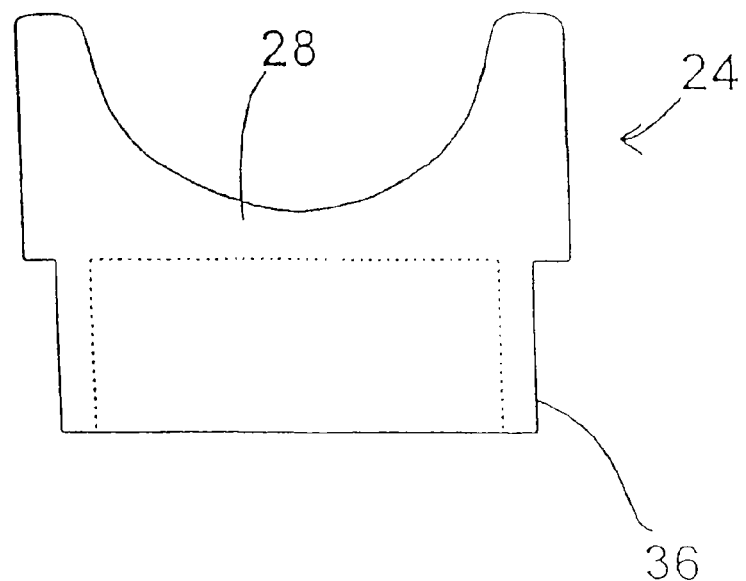
FIGS. 5a and 5b depict side and end views of a second forked end of the embodiment of FIG. 1.
Figure 5B:
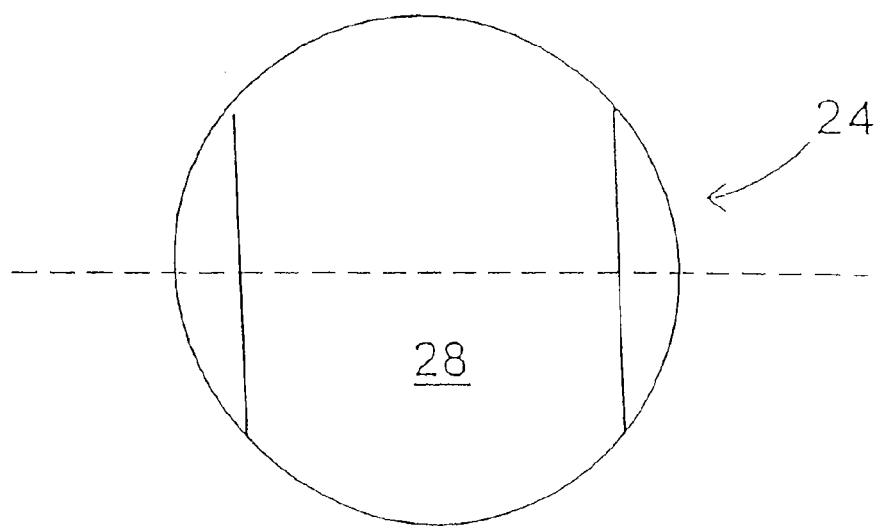

FIG. 1 shows the implant 20 in a fully extended position, while FIG. 2 shows the implant in an unextended position. In the unextended position, it can be seen that the threaded shaft 32 of the first forked end 22 fits inside the hollow cylindrical shaft 36 of the second forked end 24.

For purposes of implantation between adjacent first and second spinous processes of the spinal column, the implant 20 is configured as shown in FIG. 2. The first and second spinous processes are exposed using appropriate surgical techniques and thereafter, the implant 20 is positioned so that saddle 26 engages the first spinous process, and saddle 28 engages the second spinous process. At this point, the interbody piece 30 can be rotated by placing an appropriate tool or pin into the cross holes 40 and upon rotation, the saddle 26 is moved relative to the saddle 28. Such rotation spreads apart or distracts the spinous processes with the resultant and beneficial effect of enlarging the volume of the spinal canal in order to alleviate any restrictions on blood vessels and nerves.

It is noted that this implant as well as the several other implants described herein act as an extension stop. That means that as the back is bent backwardly and thereby placed in extension the spacing between adjacent spinous processes cannot be reduced to a distance less than the distance between the lowest point of saddle 26 and the lowest point of saddle 28. This implant, however, does not inhibit or in any way limit the flexion of the spinal column, wherein the spinal column is bent forward.

Preferably, such a device provides for distraction in the range of about 5 mm to about 15 mm. However, devices which can distract up to and above 22 mm may be used depending on the characteristics of the individual patient.

With all the ligaments (such as the supraspinous ligament) and tissues associated with the spinous processes left intact, the implant 20 can be implanted essentially floating in position in order to gain the benefits of the aforementioned extension stop and flexion non-inhibitor. If desired, one of the saddles 26 can be laterally pinned with pin 29 to one of the spinous processes and the other saddle can be loosely associated with the other spinous processes by using a tether 31 which either pierces or surrounds the other spinous process and then is attached to the saddle in order to position the saddle relative to the spinous process. Alternatively, both saddles can be loosely tethered to the adjacent spinous process in order to allow the saddles to move relative to the spinous processes.

The shape of the saddles, being concave, gives the advantage of distributing the forces between the saddle and the respective spinous process. This ensures that the bone is not resorbed due to the placement of the implant 20 and that the structural integrity of the bone is maintained.

The implant 20 in this embodiment can be made of a number of materials, including but not limited to, stainless steel, titanium, ceramics, plastics, elastics, composite materials or any combination of the above. In addition, the modulus of elasticity of the implant can be matched to that of bone, so that the implant 20 is not too rigid. The flexibility of the implant can further be enhanced by providing additional apertures or perforations throughout the implant in addition to the holes 40 which also have the above stated purpose of allowing the interbody piece 30 to be rotated in order to expand the distance between the saddle 26, 28.

In the present embodiment, it is understood that the spinous processes can be accessed and distracted initially using appropriate instrumentation, and that the implant 20 can be inserted and adjusted in order to maintain and achieve the desired distraction. Alternatively, the spinous process can be accessed and the implant 20 appropriately positioned. Once positioned, the length of the implant can be adjusted in order to distract the spinous processes or extend the distraction of already distracted spinous processes. Thus, the implant can be used to create a distraction or to maintain a distraction which has already been created.

The placement of implants such as implant 20 relative to the spinous process will be discussed herein with other embodiments. However, it is to be noted that ideally, the implant 20 would be placed close to the instantaneous axis of rotation of the spinal column so that the forces placed on the implant 20 and the forces that the implant 20 places on the spinal column are minimized.

Further, it is noted that during the actual process of installing or implanting the implant 20, that the method uses the approach of extending the length of the implant 20 a first amount and then allowing the spine to creep or adjust to this distraction. Thereafter, implant 20 would be lengthened another amount, followed by a period where the spine is allowed to creep or adjust to this new level of distraction. This process could be repeated until the desired amount of distraction has been accomplished. This same method can be used with insertion tools prior to the installation of an implant. The tools can be used to obtain the desired distraction using a series of spinal distraction and spine creep periods before an implant is installed.

Embodiment of FIGS. 6, 7, 8, 9 and 10

Figure 10:
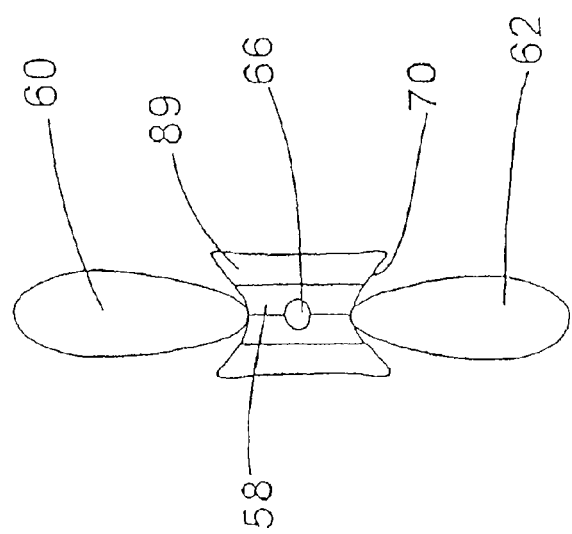

The embodiment of the invention shown in the above FIGS. 6, 7, 8, 9 and 10 includes distraction or spreader tool 50 which has first and second arms 52, 54. Arms 52, 54 are pivotal about pivot point 56 and releaseable from pivot point 56 in order to effect the implantation of implant 58. As can be seen in FIG. 6, in cross-section, the arms 52, 54 are somewhat concave in order to cradle and securely hold the first spinous process 60 relative to arm 52 and the second spinous process 62 relative to arm 54. The distraction tool 50 can be inserted through a small incision in the back of the patient in order to address the space between the first spinous process 60 and the second spinous process 62. Once the tool 50 is appropriately positioned, the arms 52, 54 can be spread apart in order to distract the spinous processes. After this has occurred, an implant 58 as shown in FIGS. 8 and 9, or of a design shown in other of the embodiments of this invention, can be urged between the arms 52, 54 and into position between the spinous processes. After this occurs, the arms 52, 54 can be withdrawn from the spinous processes leaving the implant 58 in place. The implant 58 is urged into place using a tool 64 which can be secured to the implant 58 through a threaded bore 66 in the back of the implant. As can be seen in FIG. 10, the implant 58 includes saddles 68 and 70 which cradle the upper and lower spinous processes 60, 62 in much the same manner as the above first embodiment and also in much the same manner as the individual arms of the tool 50. The saddles as described above tend to distribute the load between the implant and the spinous processes and also assure that the spinous process is stably seated at the lowest point of the respective saddles.

Figure 11:
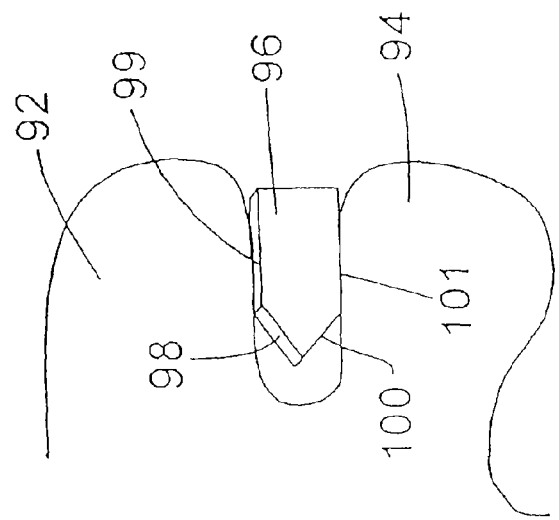
FIGS. 11, 12 and 13 depict yet a further embodiment of the invention for creating distraction between adjacent spinous processes.
Figure 12:
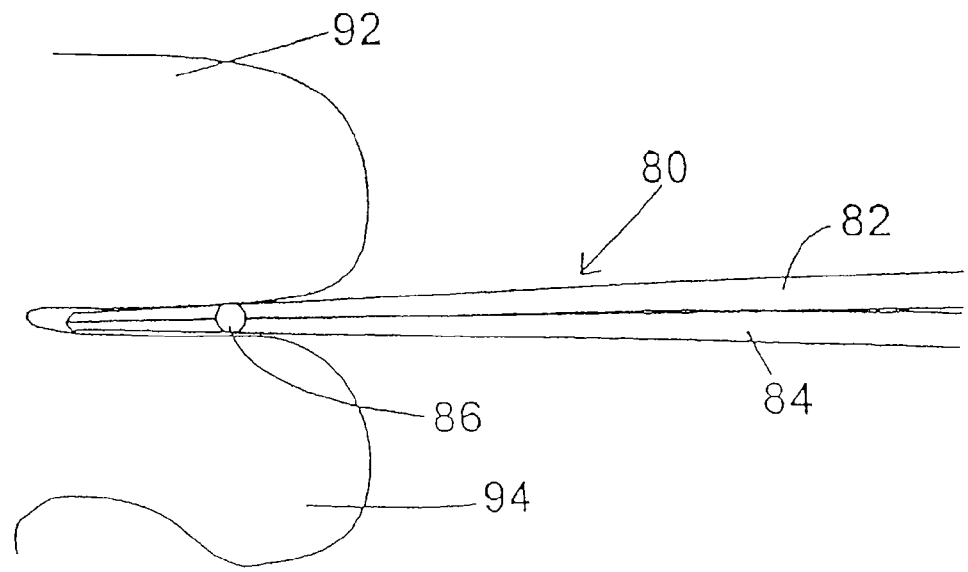
Figure 13:
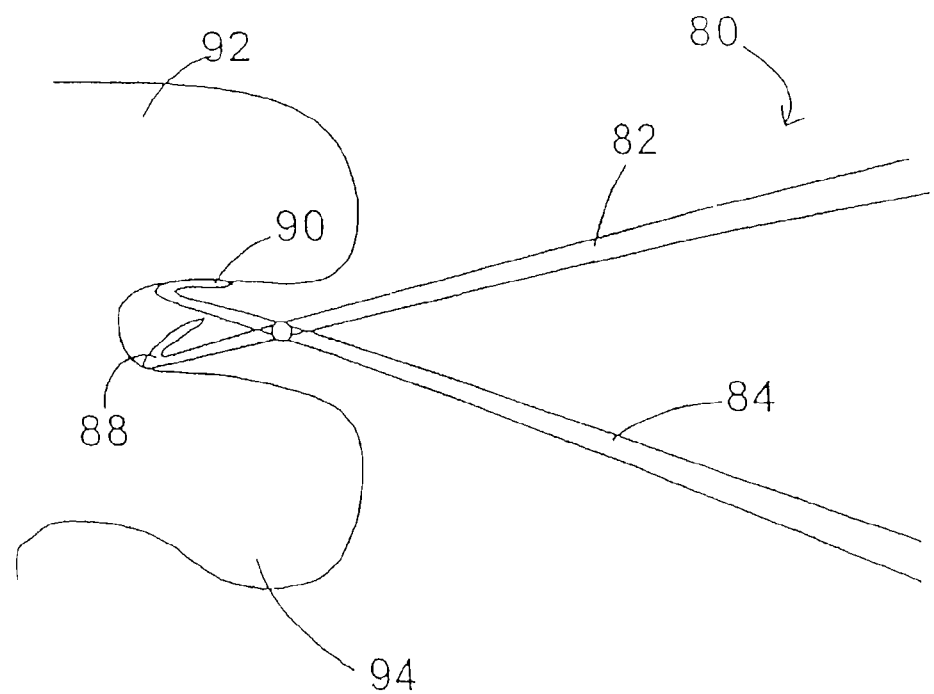

Embodiment of FIGS. 11, 12 and 13

Another embodiment of the apparatus and method of the invention is shown in FIGS. 11, 12 and 13. In this embodiment, the spreader or distraction tool 80 includes first and second arms 82, 84 which are permanently pivoted at pivot point 86. The arms include L-shaped ends 88, 90. Through a small incision, the L-shaped ends 88, 90 can be inserted between the first and second spinous processes 92, 94. Once positioned, the arms 82, 84 can be spread apart in order to distract the spinous processes. The implant 96 can then be urged between the spinous processes in order to maintain the distraction. It is noted that implant 96 includes wedged surfaces or ramps 98, 100. As the implant 96 is being urged between the spinous processes, the ramps further cause the spinous processes to be distracted. Once the implant 96 is fully implanted, the full distraction is maintained by the planar surfaces 99, 101 located rearwardly of the ramps. It is to be understood that the cross-section of the implant 96 can be similar to that shown for implant 58 or similar to other implants in order to gain the advantages of load distribution and stability.

Figure 14:
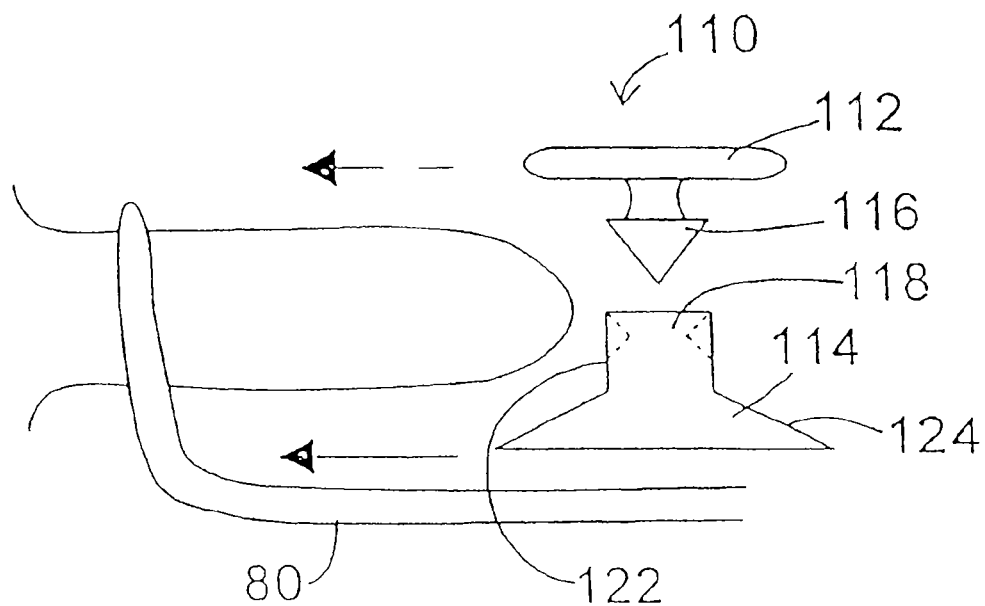
FIGS. 14 and 15 depict a further apparatus and method of an embodiment of the invention for creating distraction.
Figure 15:
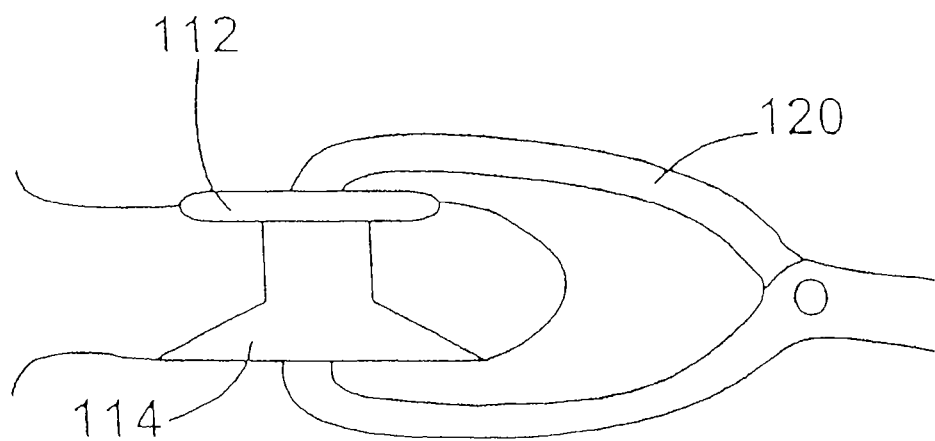

Embodiments of FIGS. 14, 15. 16, 16a, and 17

In FIGS. 14 and 15, yet another embodiment of the invention is depicted. In this embodiment, the implant 110 includes first and second conically shaped members 112, 114. Member 112 includes a male snap connector 116 and member 114 includes a female snap connector 118. With male snap connector 116 urged into female snap connector 118, the first member 112 is locked to the second member 114. In this embodiment, a distraction or spreader tool 80 could be used. Once the spinous process has been spread apart, an implantation tool 120 can be used to position and snap together the implant 110. The first member 112 of implant 110 is mounted on one arm and second member 114 is mounted on the other arm of tool 120. The member 112, 114 are placed on opposite sides of the space between adjacent spinous processes. The members 112, 114 are urged together so that the implant 110 is locked in place between the spinous processes as shown in FIG. 15. It is to be noted that the implant 110 can also be made more self-distracting by causing the cylindrical surface 122 to be more conical, much as surface 124 is conical, in order to hold implant 110 in place relative to the spinous processes and also to create additional distraction.

An alternative embodiment of the implant can be seen in FIGS. 16 and 17. This implant 130 includes first and second members 132, 134. In this particular embodiment, the implants are held together using a screw (not shown) which is inserted through countersunk bore 136 and engages a threaded bore 138 of the second member 134. Surfaces 139 are flattened (FIG. 17) in order to carry and spread the load applied thereto by the spinous processes.

The embodiment of implant 130 is not circular in overall outside appearance, as is the embodiment 110 of FIGS. 14 and 15. In particular, with respect to the embodiment of implant 130 of FIGS. 16 and 17, this embodiment is truncated so that the lateral side 140, 142 are flattened with the upper and lower sides 144, 146 being elongated in order to capture and create a saddle for the upper and lower spinous processes. The upper and lower sides, 144, 146 are rounded to provide a more anatomical implant which is compatible with the spinous processes.

If it is desired, and in order to assure that the first member 132 and the second member 134 are aligned, key 148 and keyway 150 are designed to mate in a particular manner. Key 148 includes at least one flattened surface, such as flattened surface 152, which mates to an appropriately flattened surface 154 of the keyway 150. In this manner, the first member is appropriately mated to the second member in order to form appropriate upper and lower saddles holding the implant 130 relative to the upper and lower spinous processes.

Figure 16A:
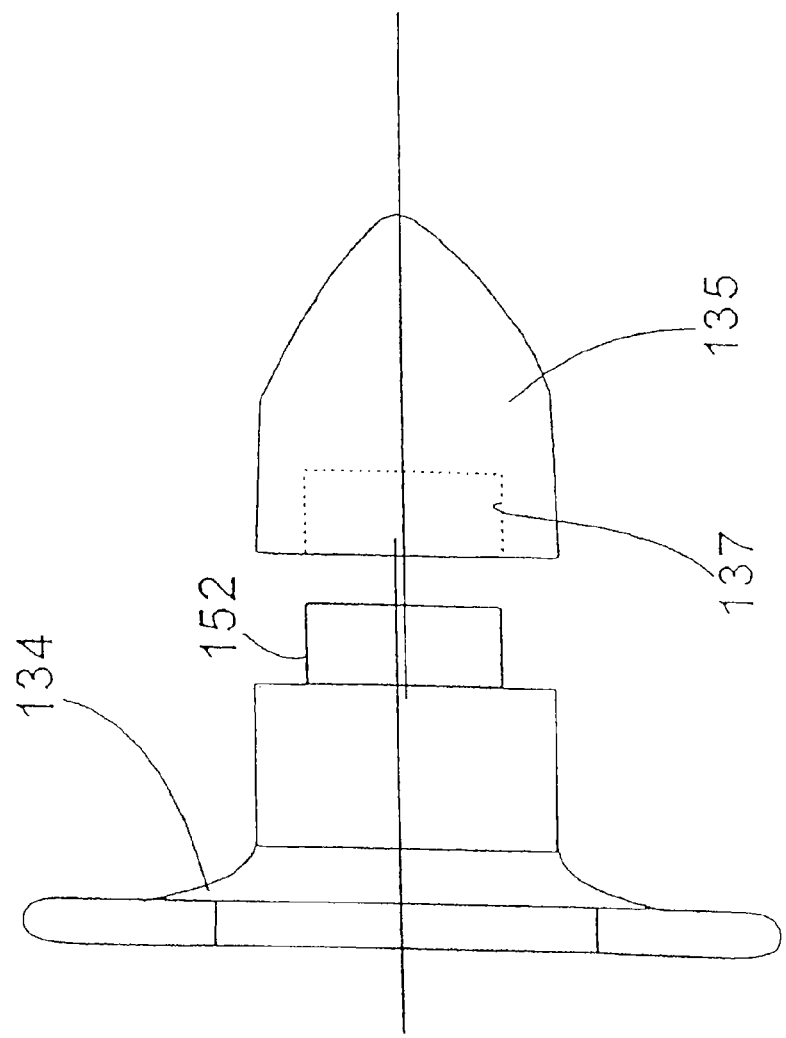

FIG. 16a depicts second member 134 in combination with a rounded nose lead-in plug 135. Lead-in plug 135 includes a bore 137 which can fit snugly over key 148. In this configuration, the lead-in plug 135 can be used to assist in the placement of the second member 134 between spinous processes. Once the second member 134 is appropriately positioned, the lead-in plug 135 can be removed. It is to be understood that the lead-in plug 135 can have other shapes such as pyramids and cones to assist in urging apart the spinous processes and soft tissues in order to position the second member 134.

Embodiment of FIGS. 18, 19 and 20

The implant 330 as shown in FIG. 18 is comprised of first and second mating wedges 332 and 334. In order to implant these wedges 332, 334, the spinous processes are accessed from both sides and then a tool is used to push the wedges towards each other. As the wedges are urged towards each other, the wedges move relative to each other so that the combined dimension of the implant 330 located between the upper and lower spinous processes 336, 338 (FIG. 20), increases, thereby distracting the spinous processes. It is noted that the wedges 332, 334 include saddle 340, 342, which receiving the spinous processes 336, 338. These saddles have the advantages as described hereinabove.

The first or second wedges 332, 334 have a mating arrangement which includes a channel 344 and a projection of 346 which can be urged into the channel in order to lock the wedges 332, 334 together. The channel 334 is undercut in order to keep the projection from separating therefrom. Further, as in other devices described herein, a detent can be located in one of the channel and the projection, with a complimentary recess in the other of the channel and the projection. Once these two snap together, the wedges are prevented from sliding relative to the other in the channel 344.

While the above embodiment was described with respect to wedges, the wedges could also have been designed substantially as cones with all the same features and advantages.

Figure 22:
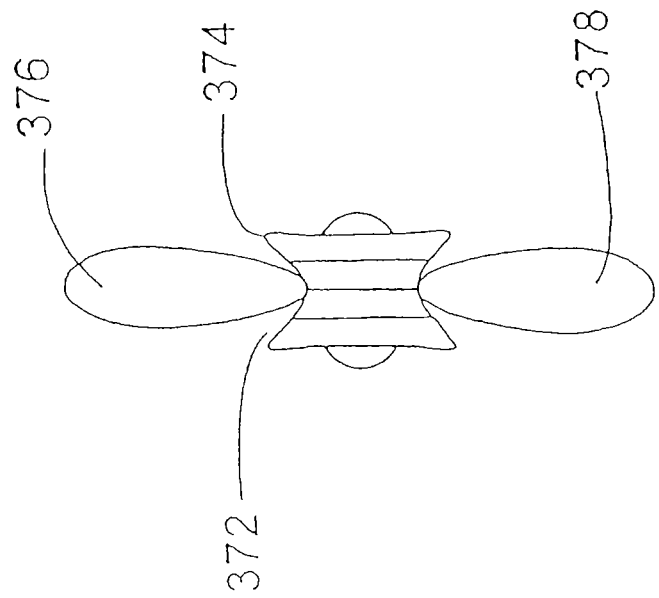
FIGS. 21 and 22 depict still a further embodiment of the present invention.
Figure 21:
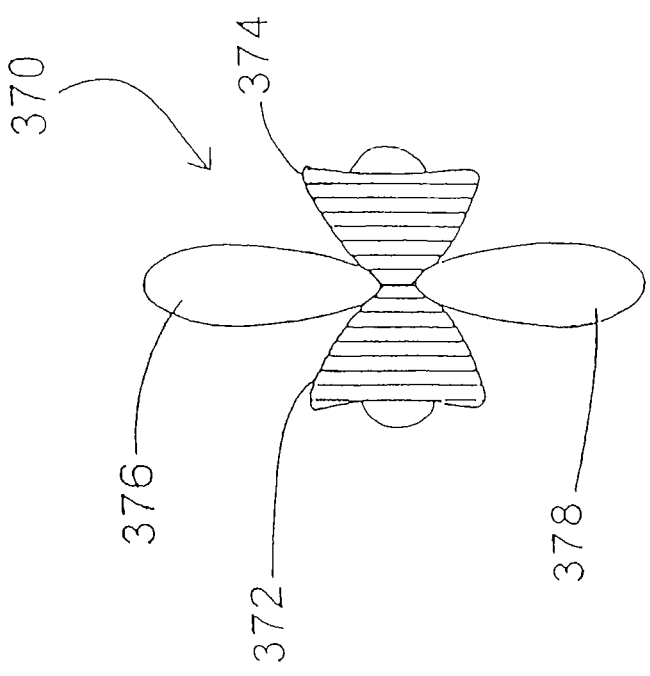

Embodiments of FIGS. 21 and 22

The implant 370 is comprised of first and second distraction cone 372, 374. These cones are made of a flexible material. The cones are positioned on either side of the spinous processes 376, 378 as shown in FIG. 21. Using appropriate tool as shown hereinabove, the distraction cones 372, 374 are urged together. As they are urged together, the cones distract the spinous processes as shown in FIG. 22. Once this has occurred, an appropriate screw or other type of fastening mechanism 380 can be used to maintain the position of the distraction cones 372, 374. The advantage of this arrangement is that the implant 370 is self-distracting and also that the implant, being flexible, molds about the spinous processes as shown in FIG. 22.

Figure 24:
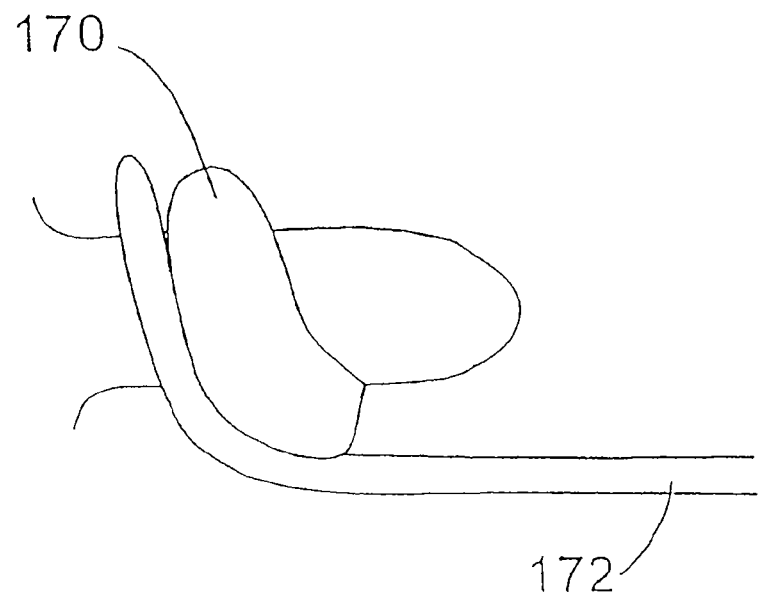
FIGS. 23, 24 and 25 depict another embodiment of the present invention.
Figure 23:
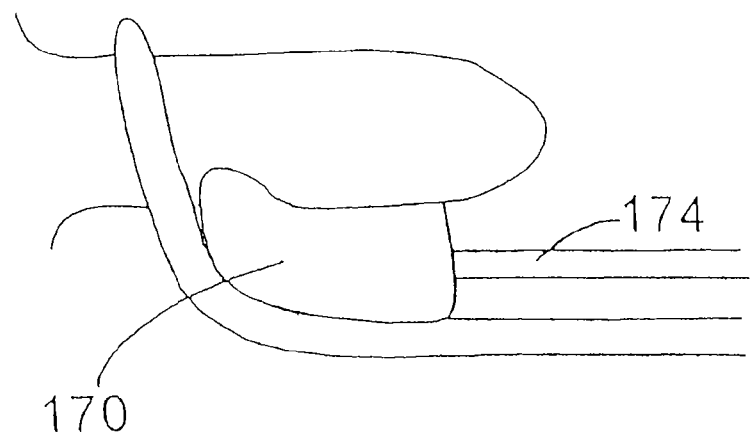
Figure 25:
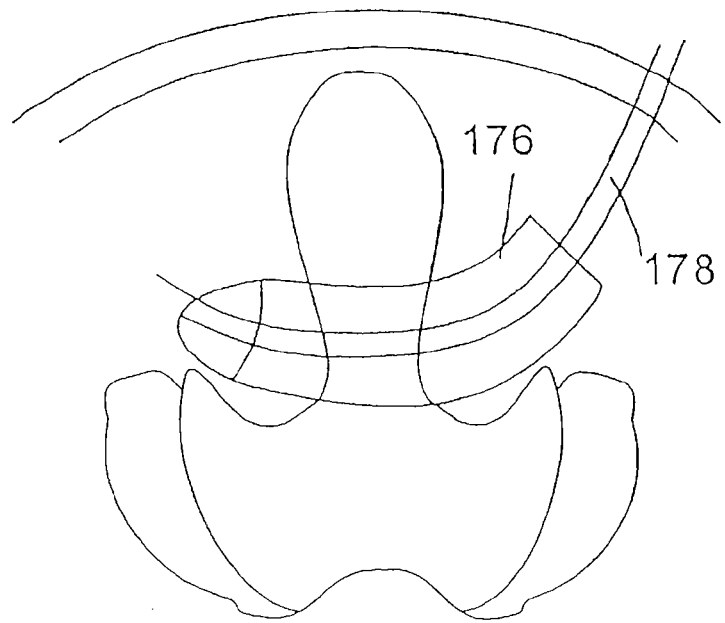

Embodiments of FIGS. 23, 24 and 25

In FIGS. 23 and 24, another embodiment of the implant 170 is depicted. This implant is guided in place using an L-shaped guide 172 which can have a concave cross-section such as the cross-section 52 of retraction tool 50 in FIG. 6 in order to cradle and guide the implant 170 in position. Preferably a small incision would be made into the back of the patient and the L-shaped guide tool 172 inserted between the adjacent spinous processes. The implant 170 would be mounted on the end of insertion tool 174 and urged into position between the spinous processes. The act of urging the implant into position could cause the spinous processes to be further distracted if that is required. Prior to the insertion of the L-shaped guide tool 172, a distraction tool such as shown in FIG. 13 could be used to initially distract the spinous processes.

Implant 170 can be made of a deformable material so that it can be urged into place and so that it can somewhat conform to the shape of the upper and lower spinous processes. This deformable material would be preferably an elastic material. The advantage of such a material would be that the load forces between the implant and the spinous processes would be distributed over a much broader surface area. Further, the implant would mold itself to an irregular spinous process shape in order to locate the implant relative to spinous processes.

With respect to FIG. 25, this implant 176 can be inserted over a guide wire, guide tool or stylet 178. Initially, the guide wire 178 is positioned through a small incision to the back of the patient to a position between the adjacent spinous processes. After this has occurred, the implant is threaded over the guide wire 178 and urged into position between the spinous processes. This urging can further distract the spinous processes if further distraction is required. Once the implant is in place, the guide tool 178 is removed and the incision closed. The insertion tools of FIGS. 23 and 24 can also be used if desired.

Figure 26:
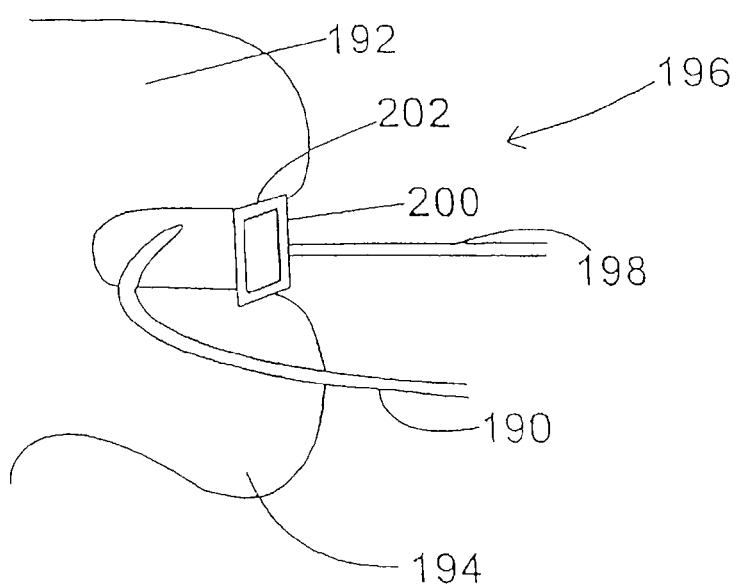
FIGS. 26, 27 and 28 depict another embodiment of the invention.
Figure 28:
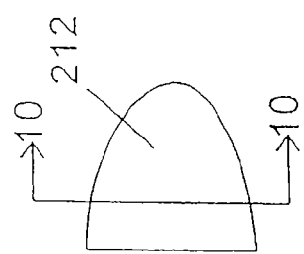
Figure 27:
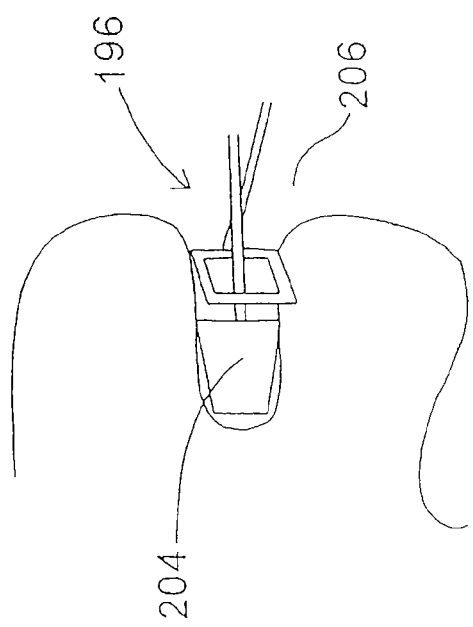

Embodiment of FIGS. 26, 27 and 28

The embodiment shown in FIGS. 26, 27 and 28 uses an implant similar to that depicted in FIGS. 8 and 9 with different insertion tools. As can be seen in FIG. 26, an L-shaped distraction tool 190 is similar to L-shaped distraction tool 80 (FIG. 12), is used to distract the first and second spinous processes 192, 194. After this has occurred, an insertion tool 196 is placed between the spinous processes 192, 194. Insertion tool 196 includes a handle 198 to which is mounted a square-shaped ring 200.

The distraction tool 190 can be inserted through a small incision in the back in order to spread apart the spinous processes. Through the same incision which has been slightly enlarged laterally, an upper end 202 of ring 200 can be initially inserted followed by the remainder of the ring 200. Once the ring is inserted, the ring can be rotated slightly by moving handle 198 downwardly in order to further wedge the spinous processes apart. Once this has been accomplished, an implant such as implant 204 can be inserted through the ring and properly positioned using implant handle 206. Thereafter, the implant handle 206 and the insertion tool 196 can be removed.

Embodiments of FIGS. 29, 30, 31, 32 and 33

Figure 29:
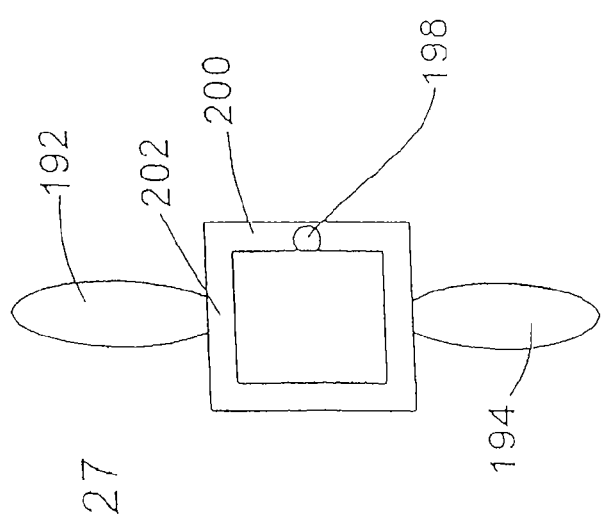
FIGS. 29 and 30 depict side elevational views of differently shaped implants of embodiments of the present invention.
Figure 30:
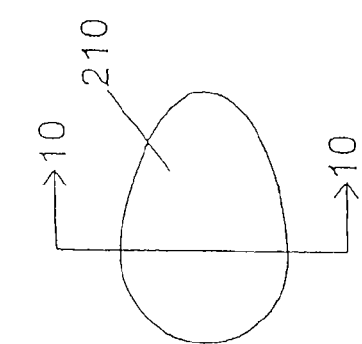

As can be seen in FIGS. 29 and 30, the implants 210, 212, can have different shapes when viewed from the side. These implants are similar to the above-referenced implants 58 (FIG. 8) and 204 (FIG. 28). These implants have cross-sections similar to that shown in FIG. 10 which includes saddles in order to receive and hold the adjacent spinous processes.

Figure 33:
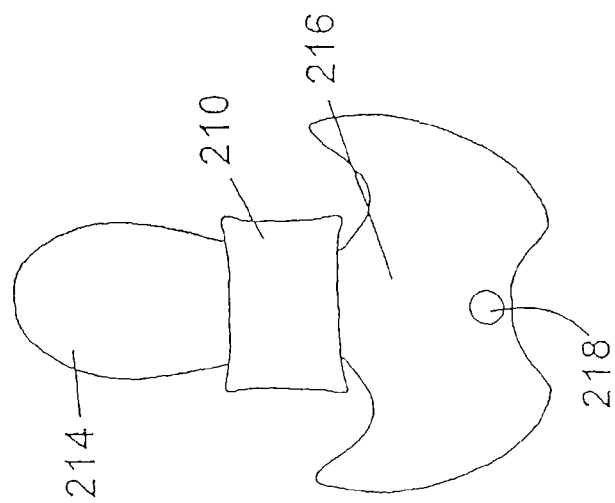
FIGS. 31, 32 and 33 depict various implant positions of an apparatus of the present invention.
Figure 32:
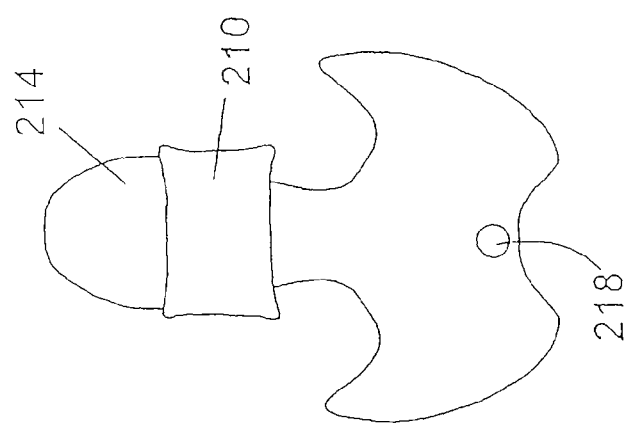
Figure 31:
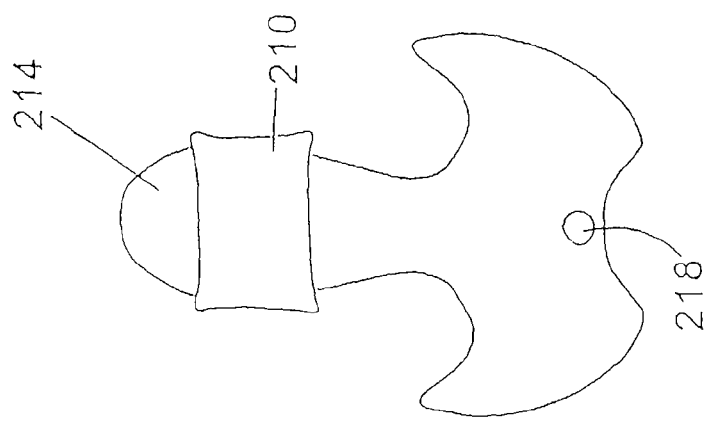

As can be seen in FIGS. 31, 32 and 33, these implants can be placed in different positions with respect to the spinous process 214. Preferably as shown in FIG. 33, the implant 210 is placed closest to the lamina 216. Being so positioned, the implant 210 is close to the instantaneous axis of rotation 218 of the spinal column, and the implant would experience least forces caused by movement of the spine. Thus, theoretically, this is the optimal location for the implant.

As can be seen in FIGS. 31 and 32, the implant can be placed midway along the spinous process (FIG. 32) and towards the posterior aspect of the spinous process (FIG. 31). As positioned shown in FIG. 31, the greatest force would be placed on the implant 210 due to a combination of compression and extension of the spinal column.

Embodiment of FIGS. 34 and 35

Another embodiment of the invention is shown in FIGS. 34 and 35. In these figures, implant 220 is comprised of a plurality of individual leaves 222 which are substantially V-shaped. The leaves include interlocking indentations or detents 224. That is, each leaf includes an indentation with a corresponding protrusion such that a protrusion of one leaf mates with an indentation of an adjacent leaf. Also associated with this embodiment is an insertion tool 226 which has a blunt end 228 which conforms to the shape of an individual leaf 222. For insertion of this implant into the space between the spinous processes as shown in FIG. 29, the insertion tool 226 first insert a single leaf 220. After that has occurred, the insertion tool then inserts a second leaf with the protrusion 224 of the second leaf snapping into corresponding indentation made by the protrusion 224 of the first leaf. This process would reoccur with third and subsequent leaves until the appropriate spacing between the spinous processes was built up. As can be seen in FIG. 29, the lateral edges 229 of the individual leaves 222 are slightly curved upwardly in order to form a saddle for receiving the upper and lower spinous processes.

Embodiments of FIGS. 36, 37 and 38

The embodiments of FIGS. 36, 37 and 38 which include implants 230, 232, and 234 respectively, are designed in such a manner so the implant locks itself into position once it is properly positioned between the spinous processes. Implant 220 is essentially a series of truncated cones and includes a plurality of ever expanding steps 236. These steps are formed by the conical bodies starting with the nose body 238 followed there behind by conical body 240. Essentially, the implant 234 looks like a fir tree placed on its side.

The implant 230 is inserted laterally throughout the opening between upper and lower spinous processes. The first body 238 causes the initial distraction. Each successive conical body distracts the spinous processes a further incremental amount. When the desired distraction has been reached, the spinous processes are locked into position by steps 236. At this point, if desired, the initial nose body 238 of the implant and other bodies 240 can be broken, snapped or sawed off if desired in order to minimize the size of the implant 230. In order for a portion of the implant 230 to be broken or snapped off, the intersection between bodies such as body 238 and 240, which is intersection line 242, would be somewhat weaken with the appropriate removal of material. It is noted that only the intersection lines of the initial conical bodies need to be so weakened. Thus, intersection line 244 between the bodies which remain between the spinous processes would not need to be weaker, as there would be no intention that the implant would be broken off at this point.

FIG. 37 shows implant 232 positioned between upper and lower spinous processes. This implant is wedge-shaped or triangular shaped in cross-sectioned and includes bore pluralities 245 and 246. Through these bores can be placed locking pins 248 and 250. The triangular or wedged-shaped implant can be urged laterally between and thus distract the upper and lower spinous processes. Once the appropriate distraction is reached, pins 248, 250 can be inserted through the appropriate bores of the bore pluralities 245 and 246 in order to lock the spinous processes in a V-shaped valley formed by pins 248, 250 on the one hand and the ramped surface 233, 235 on the other hand.

Turning to FIG. 38, the implant 234 has a triangular-shaped or wedge-shaped body similar to that shown in FIG. 32. In this embodiment, tab 252, 254 are pivotally mounted to the triangular shaped body 234. Once the implant 234 is appropriately positioned in order to distract the spinous processes to the desired amount, the tabs 252, 254 rotate into position in order to hold the implant 234 in the appropriate position.

Figure 40:
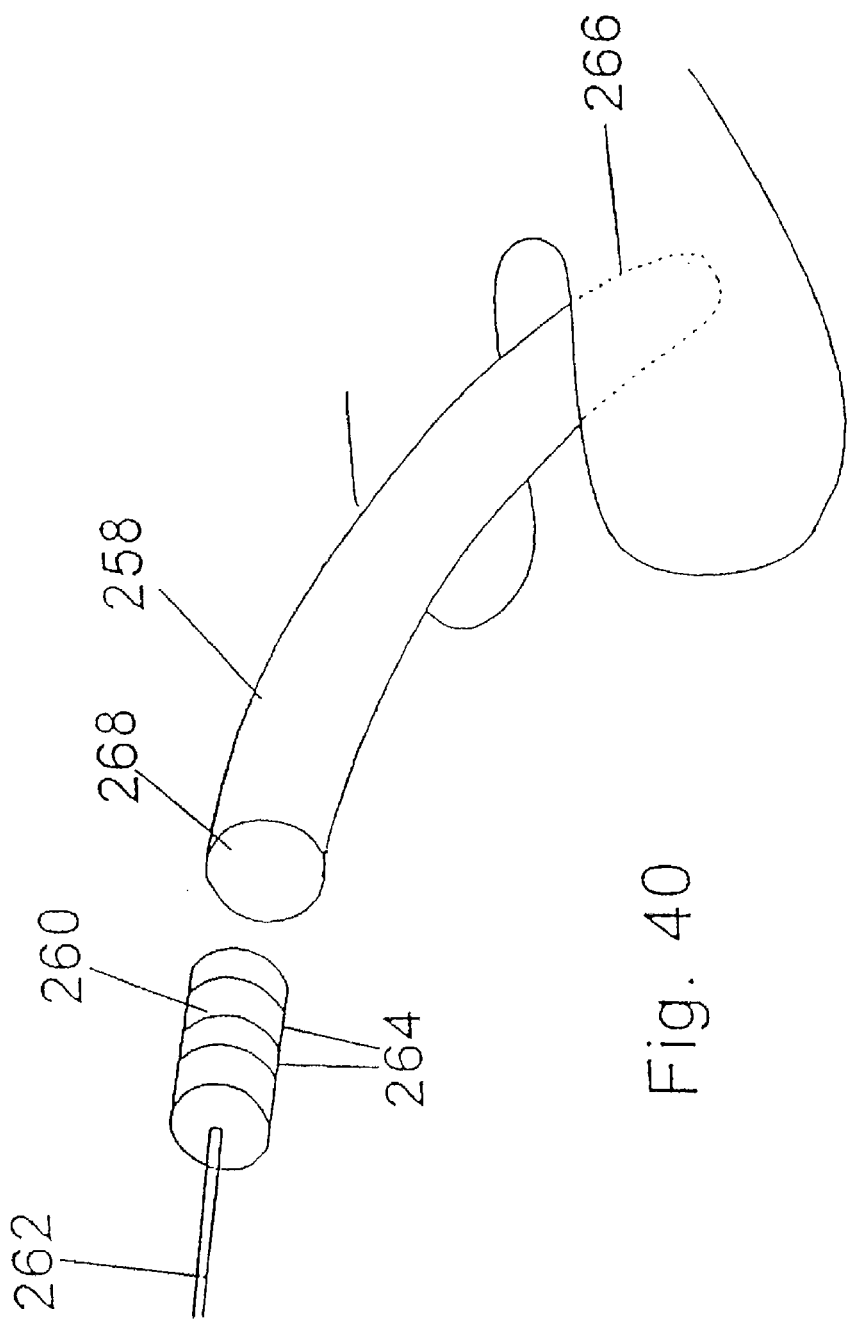

Embodiment of FIGS. 39 and 40

In the embodiment of FIGS. 39 and 40, cannula 258 is inserted through a small incision to a position between upper and lower spinous processes. Once the cannula is properly inserted, an implant 260 is pushed through the cannula 258 using an insertion tool 262. The implant 260 includes a plurality of ribs or indentation 264 that assist in positioning the implant 260 relative to the upper and lower spinal processes. Once the implant 260 is in position, the cannula 258 is withdrawn so that the implant 260 comes in contact with and wedges between the spinous processes. The cannula 258 is somewhat conical in shape with the nose end 266 being somewhat smaller than the distal end 268 in order to effect the insertion of the cannula into the space between the spinous processes.

Further, a plurality of cannula can be used instead of one, with each cannula being slightly bigger than one before. In the method of the invention, the first smaller cannula would be inserted followed by successively larger cannula being placed over the previous smaller cannula. The smaller cannula would then be withdrawn from the center of the larger cannula. Once the largest cannula is in place, and the opening of the skin accordingly expanded, the implant, which is accommodated by only the larger cannula, is inserted through the larger cannula and into position.

Figure 43:
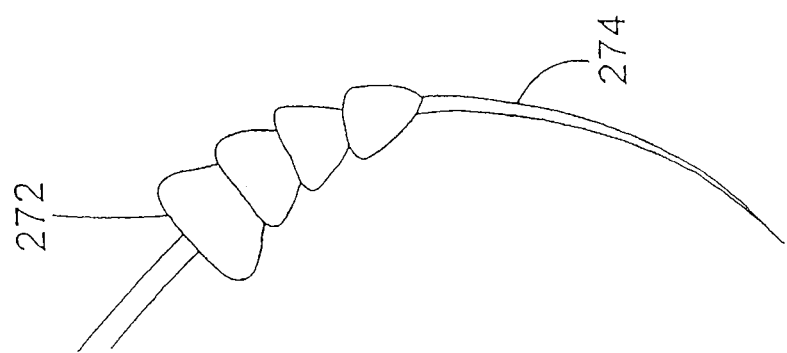
FIGS. 41, 42 and 43 depict yet further embodiments of an apparatus and method of the present invention.
Figure 42:
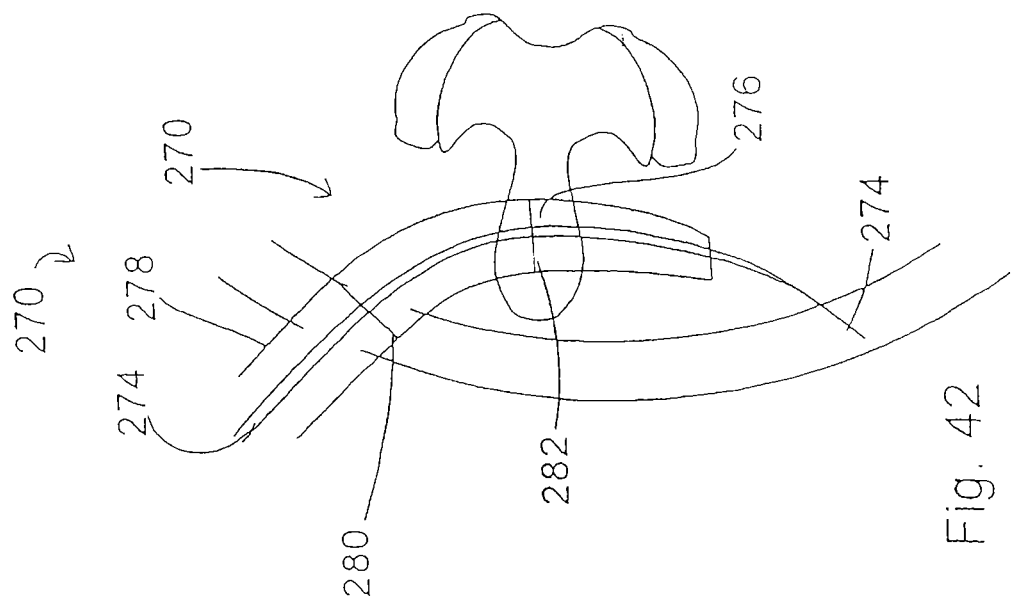
Figure 41:
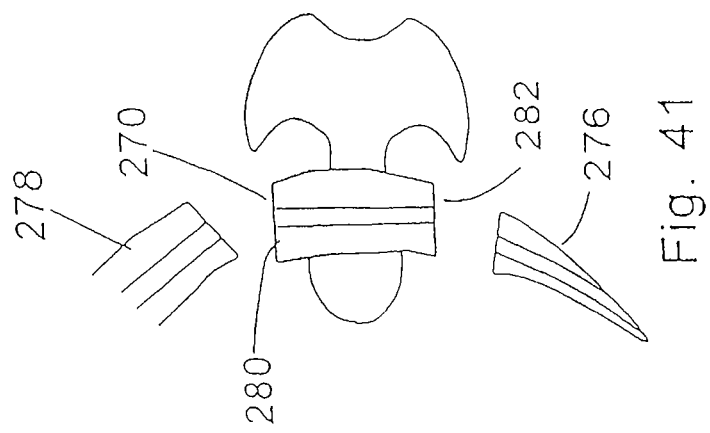

Embodiments of FIGS. 41, 42 and 43

The precurved implant 270 in FIGS. 41 and 42, and precurved implant 272 in FIG. 43 have common introduction techniques which includes a guide wire, guide tool, or stylet 274. For both embodiments, the guide wire 274 is appropriately positioned through the skin of the patient and into the space between the spinous processes. After this is accomplished, the implant is directed over the guide wire and into position between the spinous processes. The precurved nature of the implant assist in (1) positioning the implant through a first small incision in the patient's skin on one side of the space between two spinous processes and (2) guiding the implant toward a second small incision in the patient's skin on the other side of the space between the two spinous processes. With respect to the implant 270, the implant includes a conical introduction nose 276 and a distal portion 278. As the nose 276 is inserted between the spinous processes, this causes distraction of the spinous processes. Break lines 280, 282 are established at opposite sides of the implant 270. Once the implant is properly positioned over the guide wire between the spinous processes, the nose portion 276 and the distal portion 278 can be broken off along the break lines, through the above two incisions, in order to leave the implant 270 in position.

Although only two break lines 280, 282 are depicted, multiple break lines can be provided on implant 270 so that the implant can continue to be fed over the guide wire 278 until the appropriate width of the implant 270 creates the desired amount of distraction. As described hereinabove, the break lines can be created by perforating or otherwise weakening the implant 270 so that the appropriate portions can be snapped or sawed off.

With respect to the precurved implant 272, this implant is similar in design to the implant 230 shown in FIG. 36. This implant 272 in FIG. 47, however, is precurved and inserted over a guide wire 274 to a position between the spinous processes. As with implant 230 in FIG. 43, once the appropriate level of this distraction has been reached and if desired, sections of the implant 272 can be broken, snapped or sawed off as described hereinabove in order to leave a portion of the implant wedged between the upper and lower spinous processes.

Figure 44:
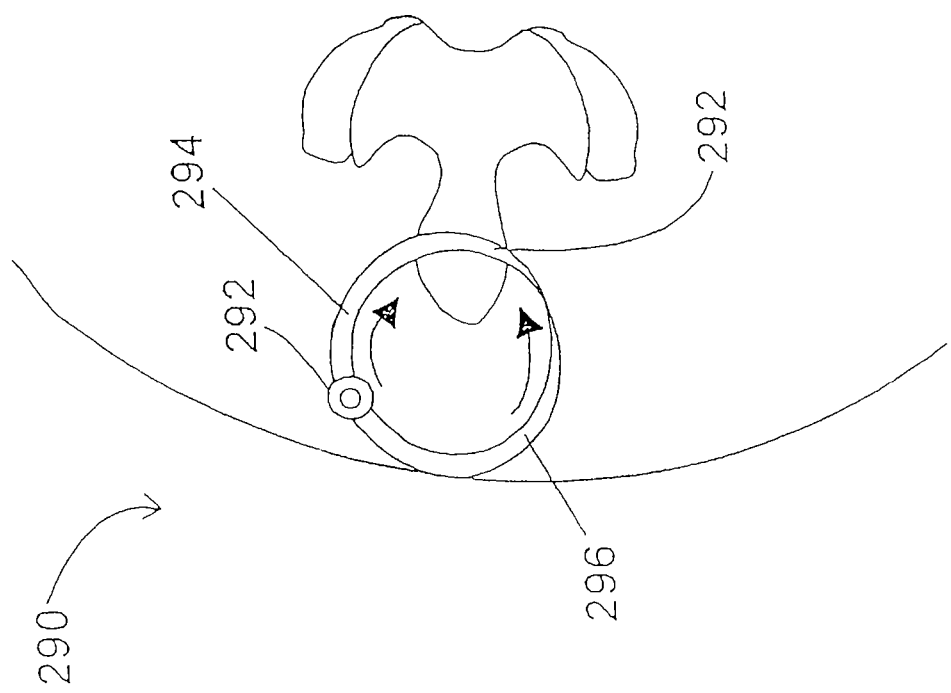
FIG. 44 is still a further embodiment of an implant of the invention.

Embodiment of FIG. 44

A further embodiment of the invention is shown in FIG. 44. This embodiment includes a combination insertion tool and implant 290. The insertion tool and implant 290 is in the shape of a ring which is hinged at point 292. The ring is formed by a first elongated and conically shaped member 294 and a second elongated and conically shaped member 296. Members 294 and 296 terminate in points and through the use of hinge 292 are aligned and meet. Through similar incisions on both sides of the spinous processes, first member and second member are inserted through the skins of the patient and are mated together between the spinous processes. After this has occurred, the implant 290 is rotated, for example clockwise, so that increasingly widening portions of the first member 292 are used to distract the first and second spinous processes. When the appropriate level of distraction has occurred, the remainder of the ring before and after the section which is located between the spinous processes can be broken off as taught hereinabove in order to maintain the desired distraction. Alternatively, with a small enough ring, the entire ring can be left in place with the spinous processes distracted.

Embodiment of FIG. 45

In FIG. 45, the implant 300 is comprised of a plurality of rods or stylets 302 which are inserted between the upper and lower spinous processes. The rods are designed much as described hereinabove so that they may be broken, snapped or cut off. Once these are inserted and the appropriate distraction has been reached, the stylets are broken off and a segment of each stylet remains in order to maintain distraction of the spinous process.

Embodiment of FIGS. 46 and 47

Implant 310 of FIGS. 46 and 47 is comprised of a shape memory material which coils upon being released. The material is straightened out in a delivery tool 312. The delivery tool is in position between upper and lower spinous processes 314, 316. The material is then pushed through the delivery tool. As it is released from the delivery end 318 of the delivery tool, the material coils, distracting the spinous processes to the desired amount. Once this distraction has been achieved, the material is cut and the delivery tool removed.

Embodiments of FIGS. 48, 49, 50 and 51

As can be seen in FIG. 48, the implant 320 is delivered between upper and lower spinous processes 322 and 324, by delivery tool 326. Once the implant 320 is in place between the spinous processes, the delivery tool is given a 90° twist so that the implant goes from the orientation as shown in FIG. 49, with longest dimension substantially perpendicular to the spinous processes, to the orientation shown in FIG. 50 where the longest dimension is in line with and parallel to the spinous processes. This rotation causes the desired distraction between the spinous processes. Implant 320 includes opposed recesses 321 and 323 located at the ends thereof.

Rotation of the implant 320 causes the spinous processes to become lodged in these recesses.

Alternatively, the insertion tool 326 can be used to insert multiple implants 320, 321 into the space between the spinous processes 322, 324 (FIG. 51). Multiple implants 320, 321 can be inserted until the appropriate amount of distraction is built up. It is to be understood in this situation that one implant would lock to another implant by use of, for example, a channel arrangement wherein a projection from one of the implants would be received into and locked into a channel of the other implant. Such a channel arrangement is depicted with respect to the other embodiment.

Embodiment of FIGS. 52, 53, 54, 55a and 55b

The embodiment of FIGS. 52 through 55b is comprised of a fluid-filled dynamic distraction implant 350. This implant includes a membrane 352 which is placed over pre-bent insertion rod 354 and then inserted through an incision on one side of the spinous process 356. The bent insertion rod, with the implant 350 thereover, is guided between appropriate spinous processes. After this occurs, the insertion rod 354 is removed leaving the flexible implant in place. The implant 350 is then connected to a source of fluid (gas, liquid, gel and the like) and the fluid is forced into the implant causing it to expand as shown in FIG. 54, distracting the spinal processes to the desired amount. Once the desired amount of distraction has occurred, the implant 350 is closed off as is shown in FIG. 55a. The implant 350 being flexible, can mold to the spinous processes which may be of irregular shape, thus assuring positioning. Further, implant 350 acts as a shock absorber, damping forces and stresses between the implant and the spinous processes.

A variety of materials can be used to make the implant and the fluid which is forced into the implant. By way of example only, viscoelastic substances such as methylcellulose, or hyaluronic acid can be used to fill the implant. Further, materials which are initially a fluid, but later solidify, can be inserted in order to cause the necessary distraction. As the materials solidify, they mold into a custom shape about the spinous processes and accordingly are held in position at least with respect to one of two adjacent spinous processes. Thus, it can be appreciated that using this embodiment and appropriate insertion tools the implant can be formed about one spinous process in such a manner that the implant stays positioned with respect to that spinous process (FIG. 55b). With such an embodiment, a single implant can be used as an extension stop for spinous process located on either side, without restricting flexion of the spinal column.

It is to be understood that many of the other implants disclosed herein can be modified so that they receive a fluid in order to establish and maintain a desired distraction much in the manner as implant 350 receives a fluid.

Figure 58:
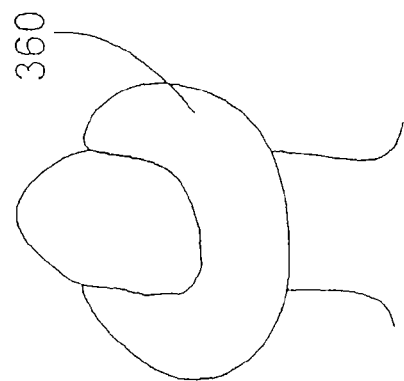
FIGS. 56, 57 and 58 depict yet a further apparatus and method of the invention.
Figure 57:
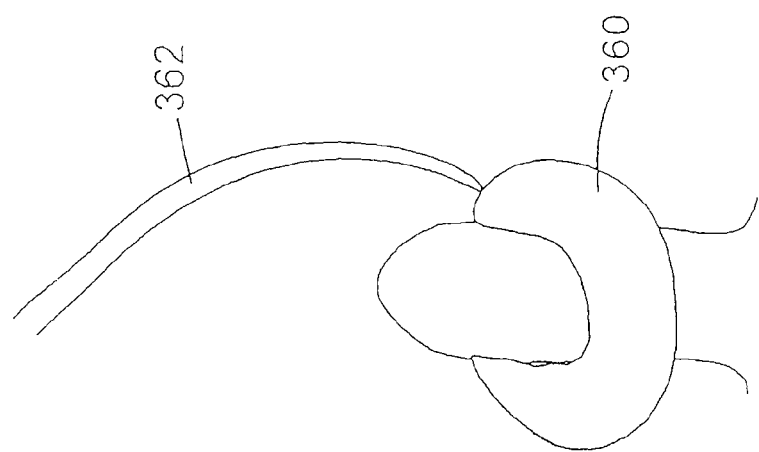
Figure 56:
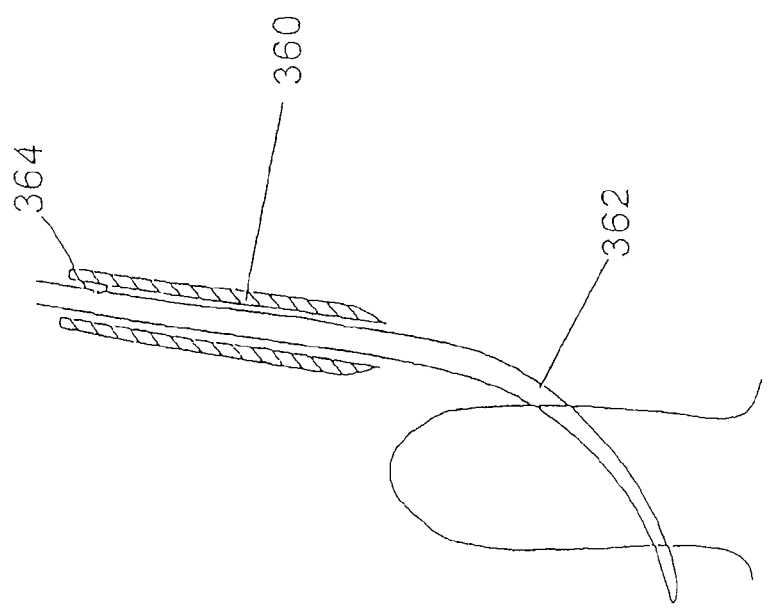

Embodiment of FIGS. 56, 57 and 58

The implant 360 as shown in FIG. 56 is comprised of a shape memory material such as a plastic or a metal. A curved introductory tool 362 is positioned between the appropriate spinous processes as described hereinabove. Once this has occurred, bore 364 of the implant is received over the tool. This act can cause the implant to straighten out. The implant is then urged into position and thereby distracts the spinous processes. When this has occurred, the insertion tool 362 is removed, allowing the implant to assume its pre-straightened configuration and is thereby secured about one of the spinous processes. Such an arrangement allows for an implant that is an extension stop and does not inhibit flexion of the spinous column. Alternatively, the implant can be temperature sensitive. That is to say that the implant would be more straightened initially, but become more curved when it was warmed by the temperature of the patient's body.

Embodiments of FIGS. 59 and 60

In this embodiment, the implant 380 is comprised of a plurality of interlocking leaves 382. Initially, a first leaf is positioned between opposed spinous processes 384, 386. Then subsequently, leafs 382 are interposed between the spinous processes until the desired distraction has been built up. The leaves are somewhat spring-like in order to absorb the shock and can somewhat conform to the spinous processes.

Embodiment of FIG. 61

The implant 390 of FIG. 61 includes the placement of shields 392, 394 over adjacent spinous processes 396, 398. The shields are used to prevent damage to the spinous processes. These shields include apertures which receives a self-tapping screw 400, 402. In practice, the shields are affixed to the spinous processes and the spinous processes are distracted in the appropriate amount. Once this has occurred, a rod 404 is used to hold the distracted position by being screwed into each of the spinous processes through the aperture in the shields using the screws as depicted in FIG. 61.

Figure 62:
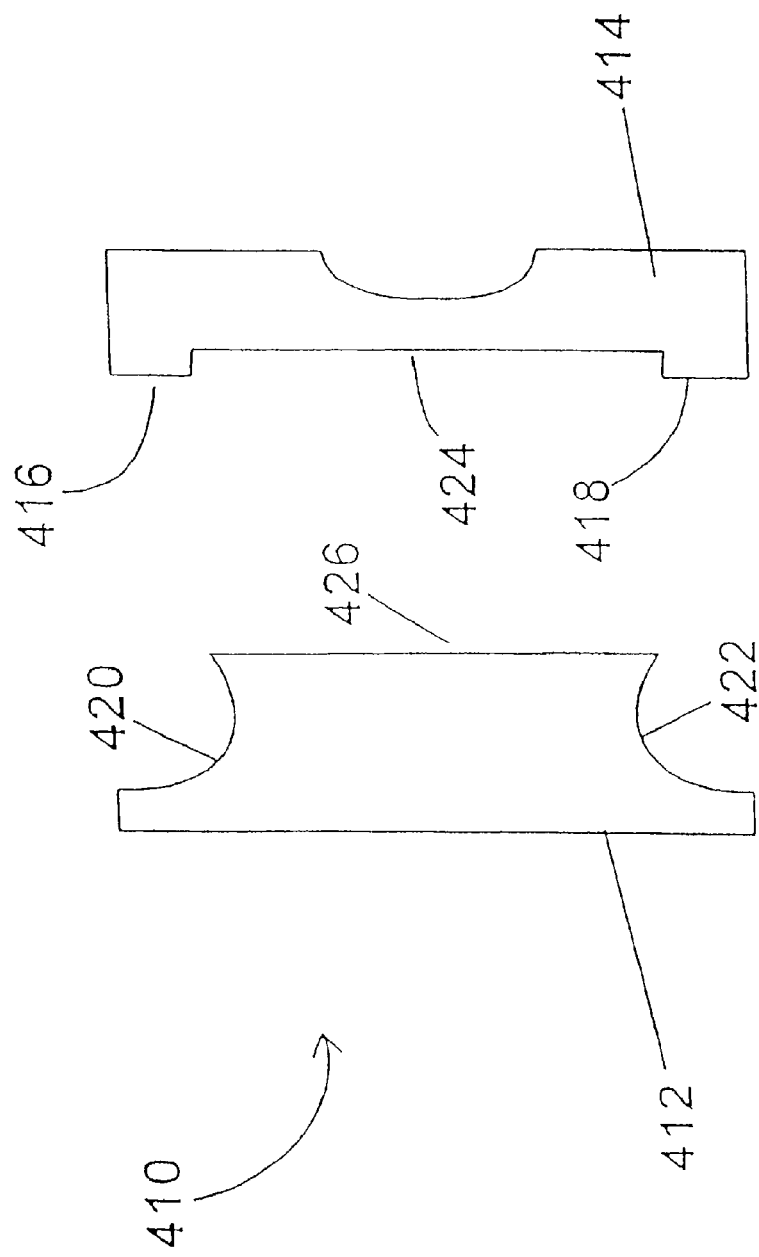
FIGS. 62 and 63 depict yet another embodiment of the present invention.
Figure 63:
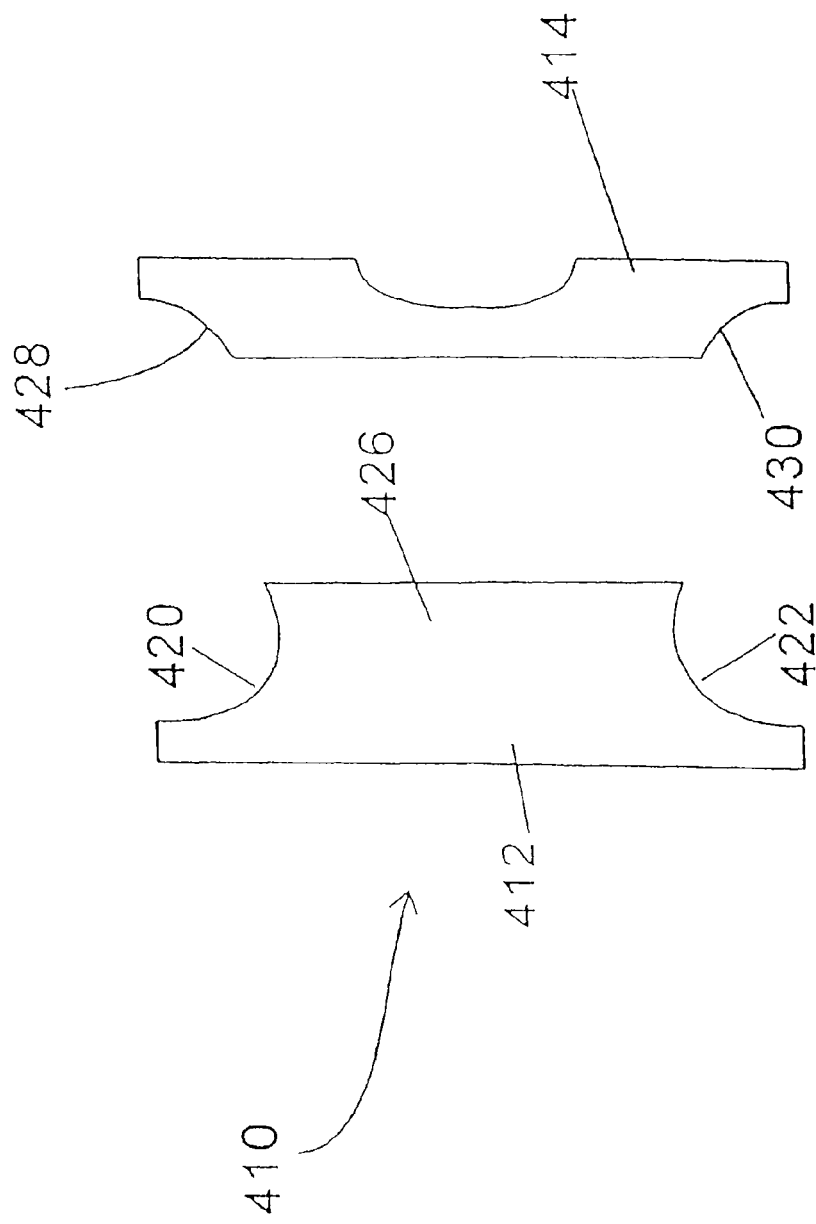

Embodiment of FIGS. 62 and 63

Implant 410 of FIGS. 62, 63 is comprised of first and second members 412, 414 which can be mated together using an appropriate screw and threaded bore arrangement to form the implant 410. Main member 412 and mating member 414 form implant 410. Accordingly, the implant 410 would have a plurality of members 414 for use with a standardized first member 412. FIGS. 62 and 64 show different types of mating members 414. In FIG. 62, the mating member 414 includes projections 416 and 418 which act like shims. These projections are used to project into the space of saddles 420, 422 of the first member 412. These projections 416, 418 can be of varying lengths in order to accommodate different sizes of spinous processes. A groove 424 is placed between the projections 416, 418 and mates with an extension 426 of the first member 412.

As shown in FIG. 63, the projections of the embodiment shown in FIG. 62 are removed and recesses 428, 430 are substituted therefor. These recesses expand the area of the saddles 420, 422 in order to accommodate larger spinous processes.

Embodiment of FIGS. 64, 65 and 66

The embodiments of FIGS. 64, 65 and 66 are similar in design and concept to the embodiment of FIGS. 62 and 63. In FIG. 64, the implant 500 includes the first and second members 502, 504. These members can be secured together with appropriate screws or other fastening means as taught in other embodiments. Implant 500 includes first and second saddles 506, 508 which are formed between the ends of first and second members 502, 504. These saddles 506, 508 are used to receive and cradle the adjacent spinous processes. As can be seen in FIG. 64, each saddle 506, 508 is defined by a single projection or leg 510, 512, which extends from the appropriate first and second members 502, 504. Unlike the embodiment found in FIGS. 62 and 63, each of the saddles is defined by only a single leg as the ligaments and other tissues associated with the spinous processes can be used to ensure that the implant is held in an appropriate position. With the configuration of FIG. 64, it is easier to position the implant relative to the spinous processes as each saddle is defined by only a single leg and thus the first and second members can be more easily worked into position between the various tissues.

In the embodiment of FIG. 65, the implant 520 is comprised of a single piece having saddles 522 and 524. The saddles are defined by a single leg 526, 528 respectively. In order for this implant 520 to be positioned between the spinous processes, an incision is made between lateral sides of adjacent spinous processes. The single leg 526 is directed through the incision to a position adjacent to an opposite lateral side of the spinous process with the spinous process cradled in the saddle 522. The spinous processes are then urged apart until saddle 524 can be pivoted into position into engagement with the other spinous process in order to maintain the distraction between the two adjacent spinous processes.

The embodiment of FIG. 66 is similar to that of FIG. 65 with an implant 530 and first and second saddles 532 and 534. Associated with each saddle is a tether 536, 538 respectively. The tethers are made of flexible materials known in the trade and industry and are positioned through bores in the implant 530. Once appropriately positioned, the tethers can be tied off. It is to be understood that the tethers are not meant to be used to immobilize one spinous process relative to the other, but are used to guide motion of the spinous processes relative to each other so that the implant 530 can be used as an extension stop and a flexion non-inhibitor. In other words, the saddles 532, 534 are used to stop spinal column backward bending and extension. However, the tethers do not inhibit forward bending and spinal column flexion.

Figure 68:
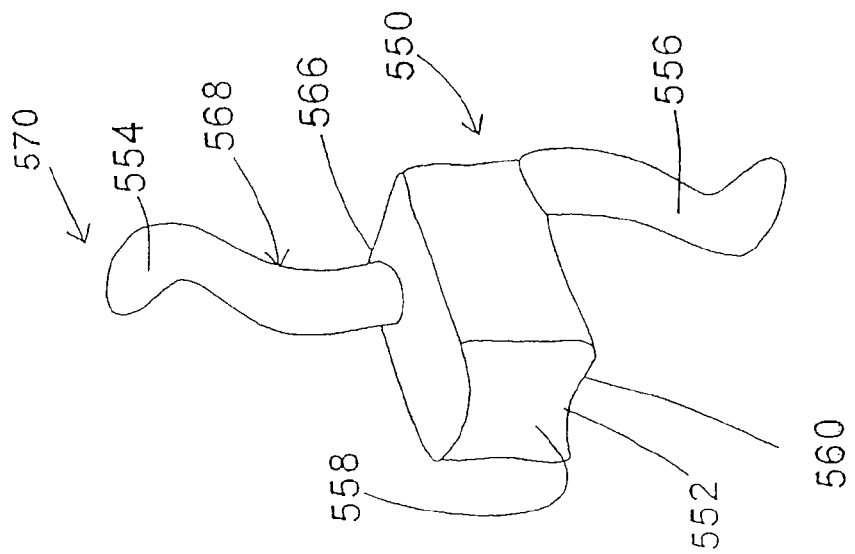
FIGS. 67 and 68 depict yet another embodiment of the present invention.
Figure 67:
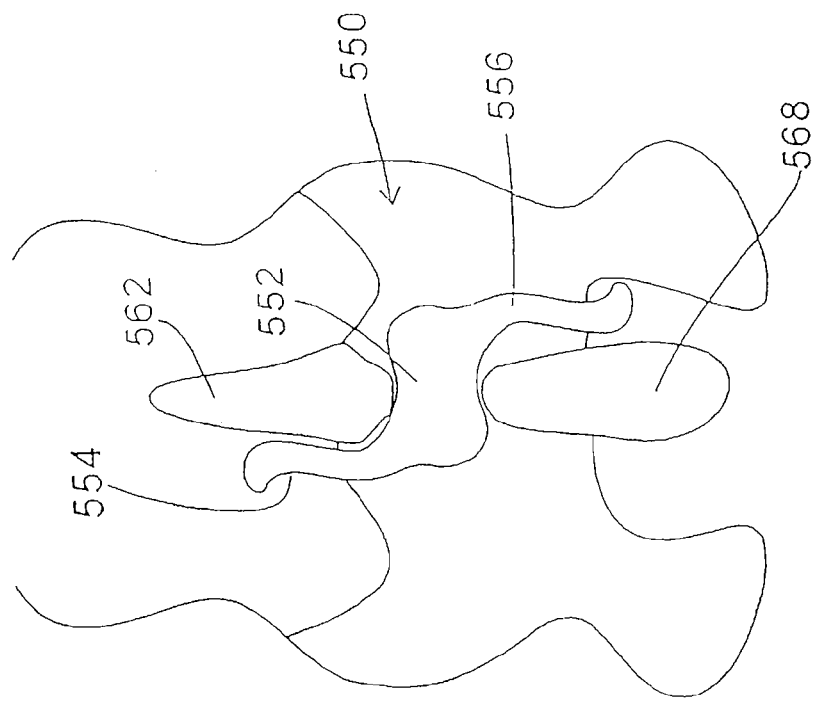

Embodiments of FIGS. 67, 68

The implant 550 is Z-shaped and includes a central body 552 and first and second arms 554, 556, extending in opposite directions therefrom. The central body 552 of the implant 550 includes first and second saddles 558 and 560. The first and second saddles 558 and 560 would receive upper and lower spinous processes 562, 568. The arms 554, 556 are accordingly located adjacent the distal end 566 (FIG. 68) of the central body 552. The first and second arms 554, 556, act to inhibit forward movement, migration or slippage of the implant 550 toward the spinal canal and keep the implant in place relative to the first and second spinal processes. This prevents the implant from pressing down on the ligamentum flavum and the dura. In a preferred embodiment, the central body would have a height of about 10 mm with each of the arms 554, 556 have a height of also about 10 mm. Depending on the patient, the height of the body could vary from about less than 10 mm to about greater than 24 mm. As can be seen in FIGS. 67 and 68, the first and second arms 554, 556 are additionally contoured in order to accept the upper and lower spinous processes 556, 558. In particular, the arms 554, 556 as can be seen with respect to arm 554 have a slightly outwardly bowed portion 568 (FIG. 68) with a distal end 570 which is slightly inwardly bowed. This configuration allows the arm to fit about the spinous process with the distal end 570 somewhat urged against the spinous process in order to guide the motion of the spinous process relative to the implant. These arms 554, 556 could if desired to be made more flexible than the central body 552 by making arms 554, 556 thin and/or with perforations, and/or other material different than that of the central body 550. As with the last embodiment, this embodiment can be urged into position between adjacent spinous processes by directing an arm into a lateral incision so that the central body 552 can be finally positioned between spinous processes.

Embodiment of FIGS. 69, 70, 71 and 71a

FIGS. 69, 70 and 71 are perspective front, end, and side views of implant 580 of the invention. This implant includes a central body 582 which has first and second saddles 584, 586 for receiving adjacent spinous processes. Additionally, the implant 580 includes first and second arms 588 and 590. The arms, as with the past embodiment, prevent forward migration or slippage of the implant toward the spinal canal. First arm 588 projects outwardly from the first saddle 584 and second arm 590 projects outwardly from the second saddle 586. In a preferred embodiment, the first arm 588 is located adjacent to the distal end 600 of the central body 582 and proceeds only partly along the length of the central body 582. The first arm 588 is substantially perpendicular to the central body as shown in FIG. 70. Further, the first arm 588, as well as the second arm 590, is anatomically rounded.

The second arm 590, projecting from second saddle 586, is located somewhat rearward of the distal end 600, and extends partially along the length of the central body 582. The second arm 590 projects at a compound angle from the central body 582. As can be seen in FIGS. 70 and 71, the second arm 590 is shown to be at about an angle of 45° from the saddle 586 (FIG. 70). Additionally, the second arm 590 is at an angle of about 45° relative to the length of the central body 580 as shown in FIG. 71. It is to be understood that other compound angles are within the spirit and scope of the invention as claimed.

In a preferred embodiment, the first and second arms 588, 590 have a length which is about the same as the width of the central body 582. Preferably, the length of each arm is about 10 mm and the width of the central body is about 10 mm. However, the bodies with the widths of 24 mm and greater are within the spirit and scope of the invention, along with first and second arms ranging from about 10 mm to greater than about 24 mm. Further, it is contemplated that the embodiment could include a central body having a width of about or greater than 24 mm with arms being at about 10 mm.

It is to be understood that the embodiment of FIGS. 69, 70 and 71 as well as the embodiment of FIGS. 67 and 68 are designed to preferably be positioned between the L4-L5 and the L5-S1 vertebral pairs. The embodiment of FIGS. 69, 70, 71 is particularly designed for the L5-S1 position with the arms being designed to conform to the sloping surfaces found therebetween. The first and second arms are thus contoured so that they lie flat against the lamina of the vertebra which has a slight angle.

The embodiment of FIGS. 69, 70, and 71 as with the embodiment of FIGS. 67 and 68 is Z-shaped in configuration so that it may be inserted from one lateral side to a position between adjacent spinous processes. A first arm, followed by the central body, is guided through the space between the spinous processes. Such an arrangement only requires that a incision on one side of the spinous process be made in order to successfully implant the device between the two spinous processes.

Figure 71A:
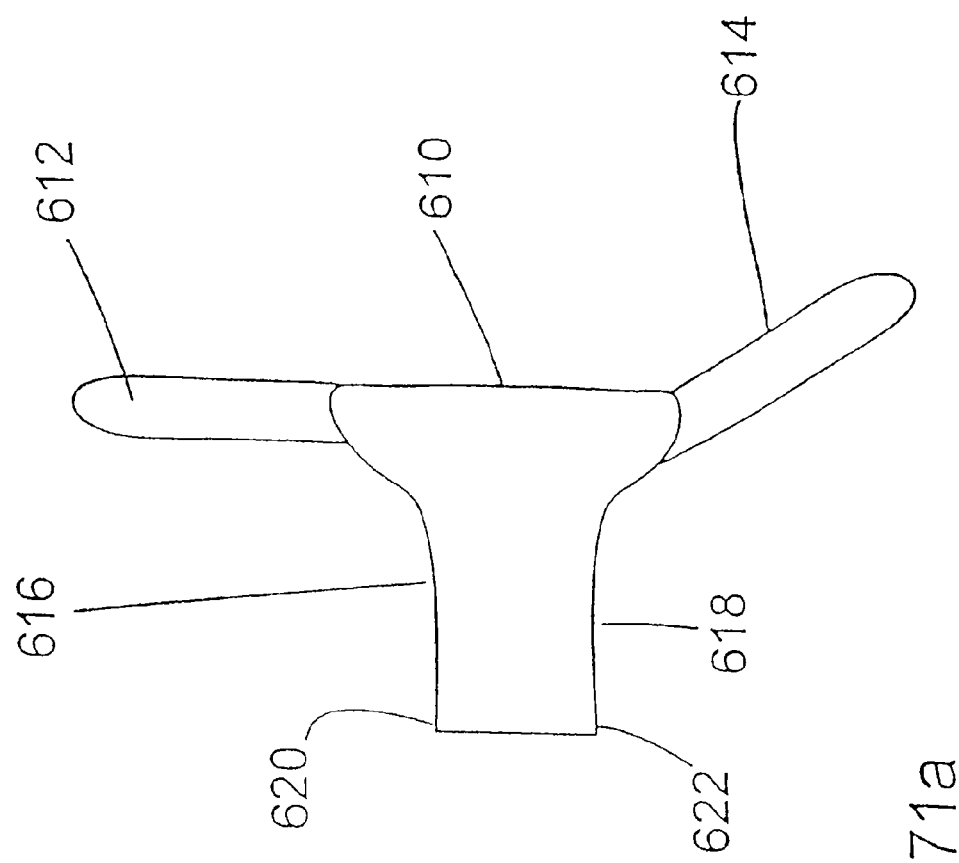

The implant 610 of FIG. 71a is similar to that immediately above with the first arm 612 located on the same side of the implant as the second arm 614. The first and second saddle 616, 618 are slightly modified in that distal portion 620, 622 are somewhat flattened from the normal saddle shape in order to allow the implant to be positioned between the spinous processes from one side. Once in position, the ligaments and tissues associated with the spinous processes would hold the implant into position. Tethers also could be used if desired.

Figure 72:
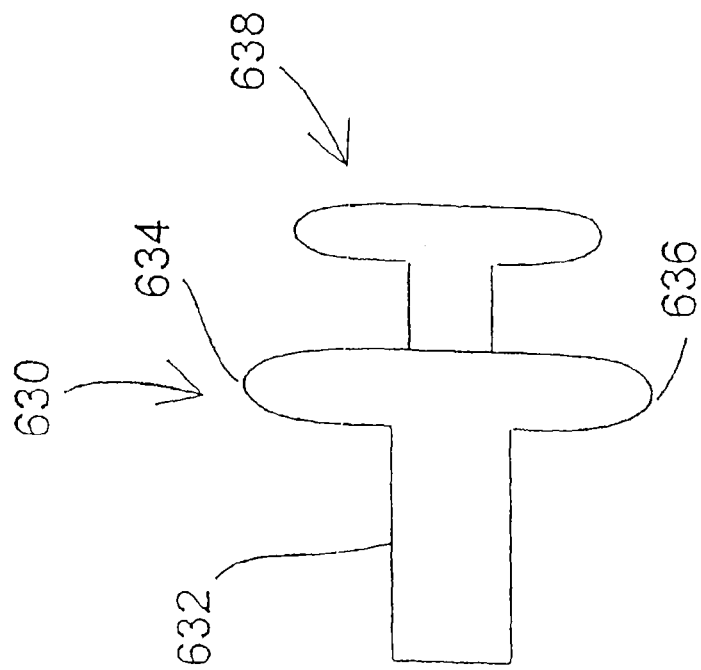
FIGS. 72 and 73 depict still another embodiment of the invention.
Figure 73:
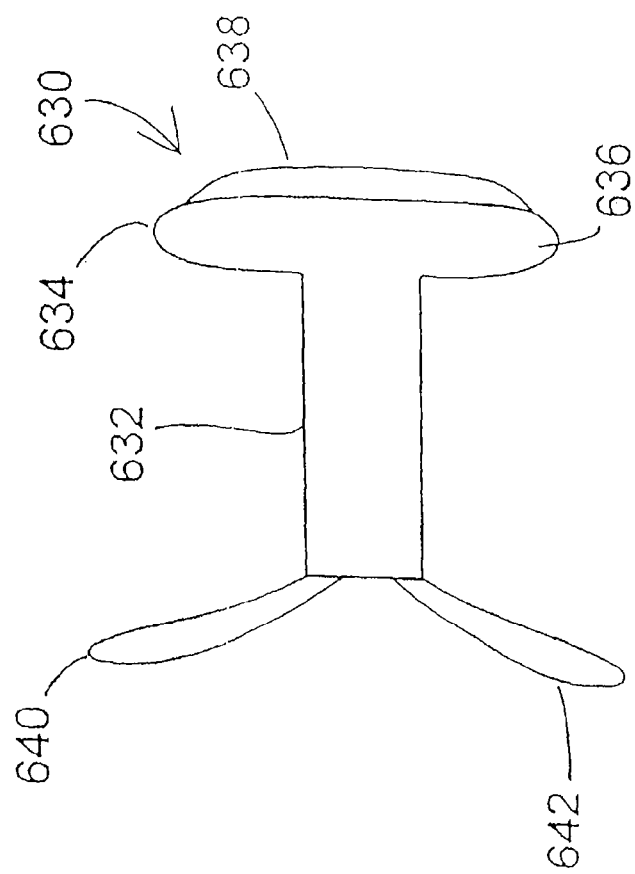

Embodiment of FIGS. 72, 73

Implant 630 is also designed so that it can be inserted from one side of adjacent spinous processes. This insert 630 includes a central body 632 with the first and second arms 634, 636 extending on either side thereof. As can be seen in FIG. 72, a plunger 638 is positioned to extend from an end of the central body 632. As shown in FIG. 72, the plunger 638 is fully extended and as shown in FIG. 73, the plunger 638 is received within the central body 632 of the implant 630. With the plunger received into the implant 632, the third and fourth arms or hooks 640, 642 can extend outwardly from the central body 632. The third and fourth arms or hooks 640, 642 can be comprised of a variety of materials, such as for example, shape memory metal materials or materials which have a springy quality.

For purposes of positioning the implant 630 between adjacent spinous processes, the plunger 638 is pulled outwardly as shown in FIG. 72. The central body 632 is then positioned between adjacent spinous processes and the plunger 638 is allowed to move to the position of FIG. 73 so that the third and fourth arms 640, 642 can project outwardly from the central body 632 in order to hold the implant 630 in position between the spinous processes.

Plunger 638 can be spring biased to the position as shown in FIG. 73 or can include detents or other mechanisms which lock it into that position. Further, the third and fourth arms themselves, as deployed, can keep the plunger in the position as shown in FIG. 73.

Embodiments of FIGS. 74, 75, 76, 77, and 78

Figure 74:
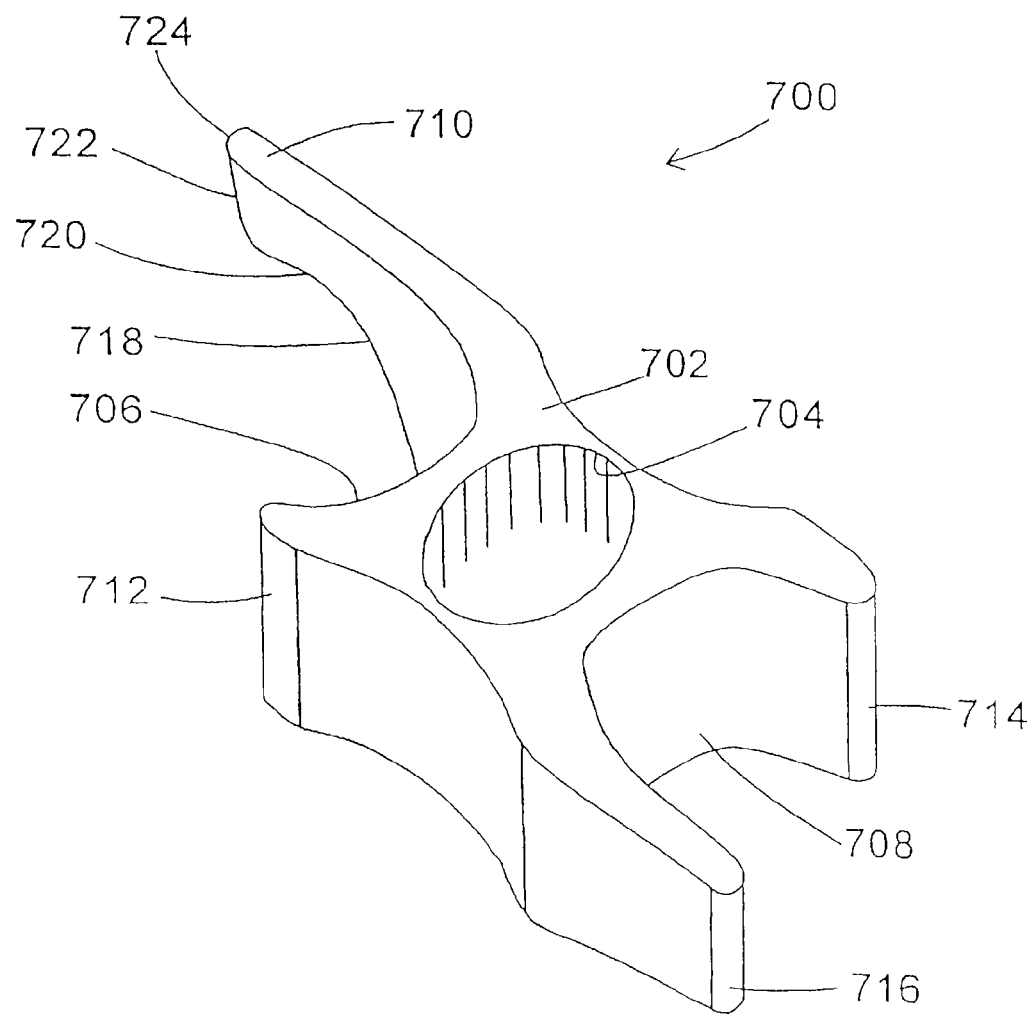
FIGS. 74, 75, 76, 77, and 78 depict still other embodiments of the invention.
Figure 75:
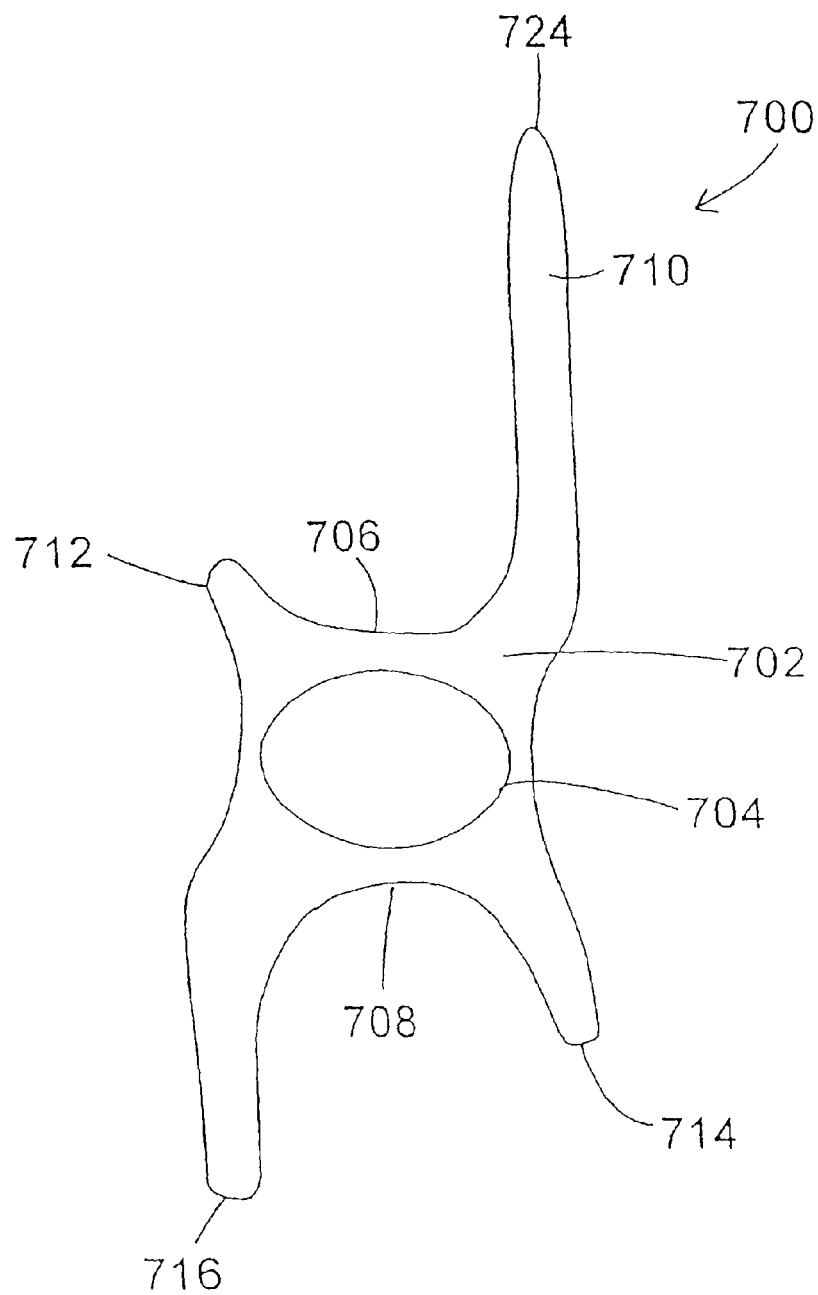
Figure 76:
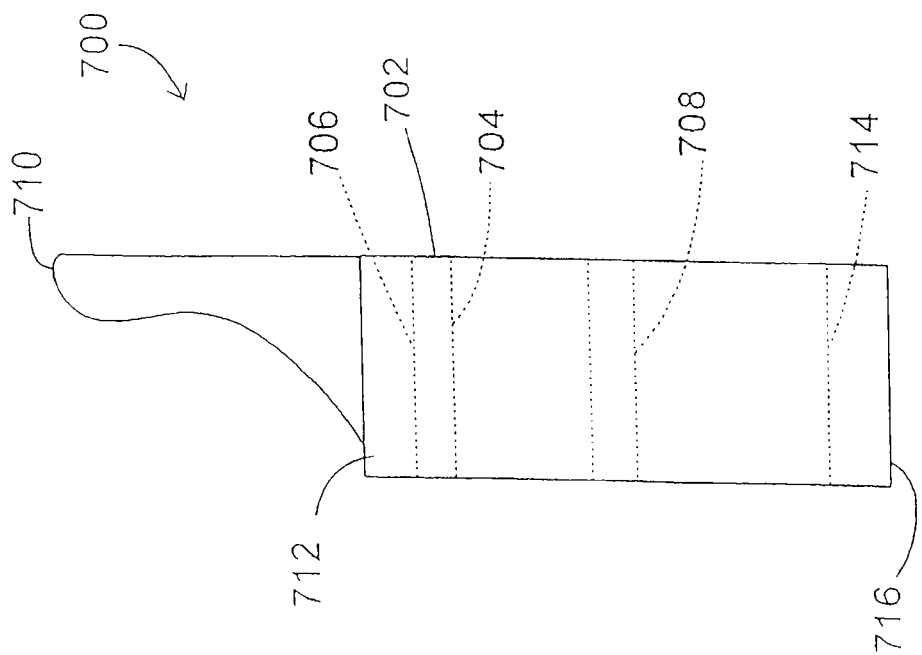

Other embodiments of the invention are shown in FIGS. 74 through 78. FIGS. 74, 75 and 76 disclose implant 700. Implant 700 is particularly suited for implantation between the L4-L5 and L5-S1 vertebra. As can be seen in FIG. 74, the implant 700 includes a central body 702 which has a bore 704 provided therein. Bore 704 is used in order to adjust the modulus of elasticity of the implant so that it is preferably approximately two times the anatomical load placed on the vertebra in extension. In other words, the implant 700 is approximately two times stiffer than the normal load placed on the implant. Such an arrangement is made in order to ensure that the implant is somewhat flexible in order to reduce potential resorption of the bone adjacent to the implant. Other modulus values can be used and be within the spirit of the invention.

Implant 700 includes first and second saddle 706, 708 which are used to receive and spread the load from the upper and lower spinous processes. The saddle 706 is defined by first and second arms 710 and 712. The second saddle 708 is defined by third and fourth arms 714 and 716. As can be seen in FIG. 74, the first arm 710, in a preferred embodiment, is approximately two times the length of the body 702 with the second arm being approximately less than a quarter length of the body. Third arm 714 is approximately one times the length of the body 702 with the fourth arm 716 being, in this preferred embodiment, approximately one and a half times the length of the body 702. The arms are designed in such a way that the implant (1) can be easily and conveniently inserted between the adjacent spinous processes, (2) will not migrate forwardly toward the spinal canal, and (3) will hold its position through flexion and extension as well as lateral bending of the spinal column.

Figure 77:
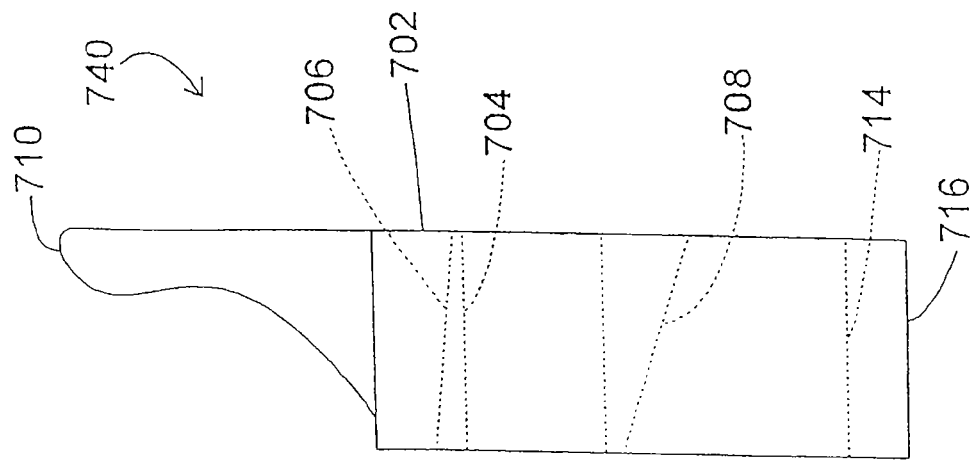
Figure 78:
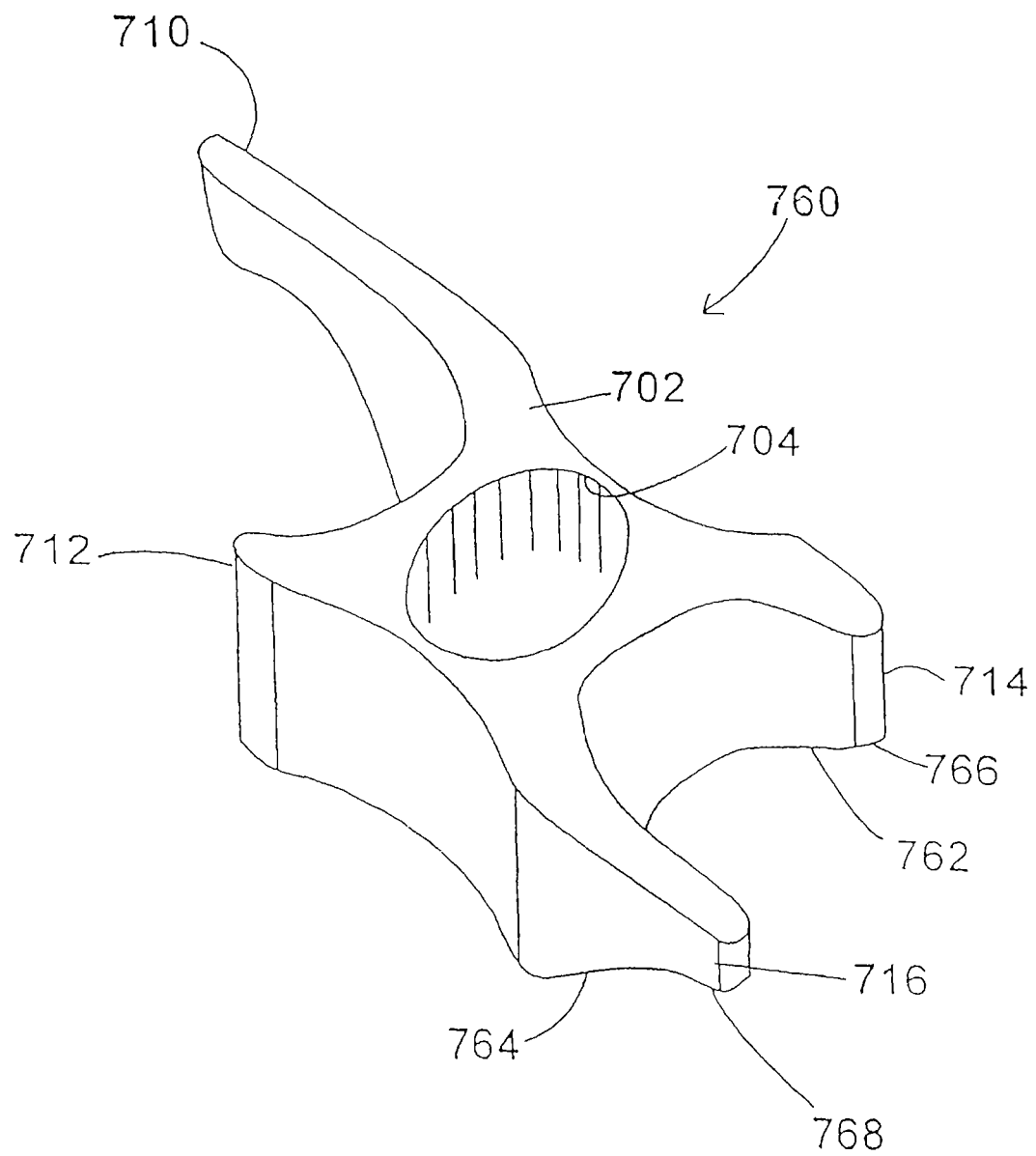
Figure 81:
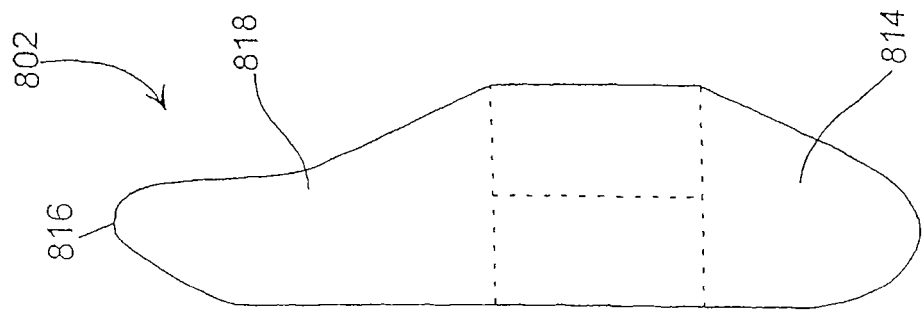

First arm 710 is in addition designed to accommodate the shape of the vertebrae. As can be seen in FIG. 74, the first arm 710 becomes narrower as it extends away from the body 702. The first arm 710 includes a sloping portion 718 followed by a small recess 720 ending in a rounded portion 722 adjacent to the end 724. This design is provided to accommodate the anatomical form of for example the L4 vertebra. It is to be understood that these vertebra have a number of surfaces at roughly 30° angles and that the sloping surfaces of this embodiment and the embodiments shown in FIGS. 77 and 78 are designed to accommodate these surfaces. These embodiments can be further modified in order to accommodate other angles and shapes.

The second arm 712 is small so that it is easy to insert between the spinous processes, yet still define the saddle 706. The fourth arm 716 is larger than the third arm 714, both of which are smaller than the first arm 710. The third and fourth arms are designed so that they define the saddle 706, guide the spinous processes relative to the implant 700 during movement of the spinal column, and yet are of a size which makes the implant easy to position between the spinous processes.

The procedure, by way of example only, for implanting the implant 700 can be to make an incision laterally between two spinous processes and then initially insert first arm 710 between the spinous processes. The implant and/or appropriate tools would be used to distract the spinous processes allowing the third leg 714 and the central body 702 to fit through the space between the spinous processes. The third leg 714 would then come to rest adjacent the lower spinous processes on the opposite side with the spinous processes resting in the first and second saddle 706, 708. The longer fourth leg 716 would then assist in the positioning of the implant 700.

FIG. 77 includes an implant 740 which is similar to implant 700 and thus have similar numbering. The saddle 706, 708 of implant 740 have been cantered or sloped in order to accommodate the bone structure between, by way of example, the L4-L5 and the L5-S1 vertebra. As indicated above, the vertebra in this area have a number of sloping surfaces in the range of about 30°. Accordingly, saddle 706 is sloped at less than 30° and preferably about 20° while saddle 708 is sloped at about 30° and preferably more than 30°.

The implant 760 as shown in FIG. 78 is similar to implant 700 in FIG. 74 and is similarly numbered. Implant 760 includes third and fourth legs 714, 716 which have sloping portions 762, 764 which slope toward ends 766, 768 of third and fourth arm 714, 716 respectively. The sloping portions accommodate the form of the lower vertebra against which they are positioned. In the preferred embodiment, the sloping portions are of about 30°. However, it is to be understood that sloping portions which are substantially greater and substantially less than 30° can be included and be within the spirit and scope of the invention.

Embodiment of FIGS. 79, 80, 80a, 81, 82, 83, 83a, 84, 85, 86 and 87

Figure 80:
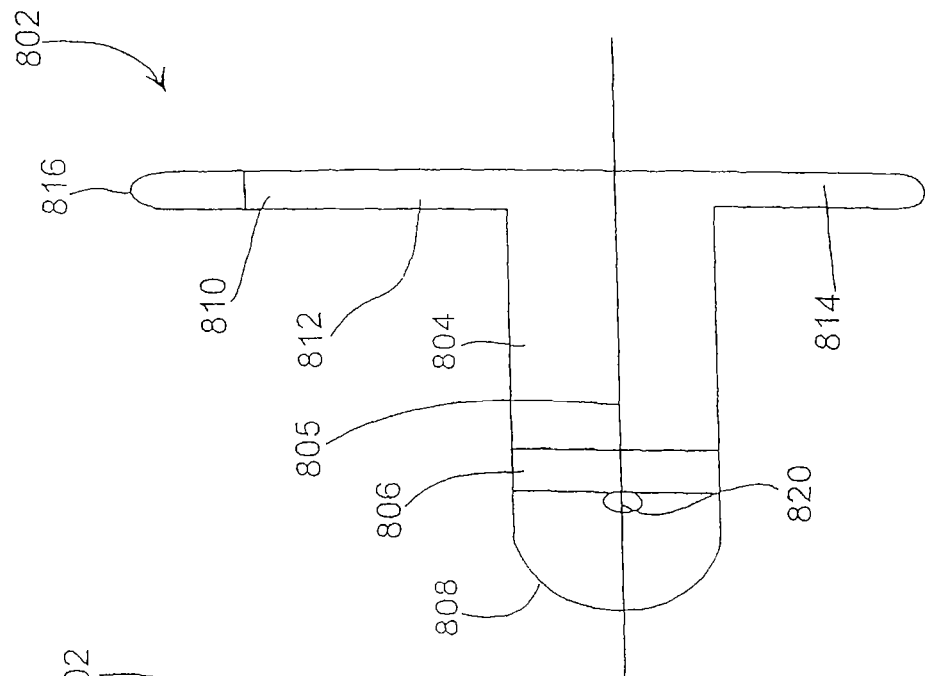
Figure 79:
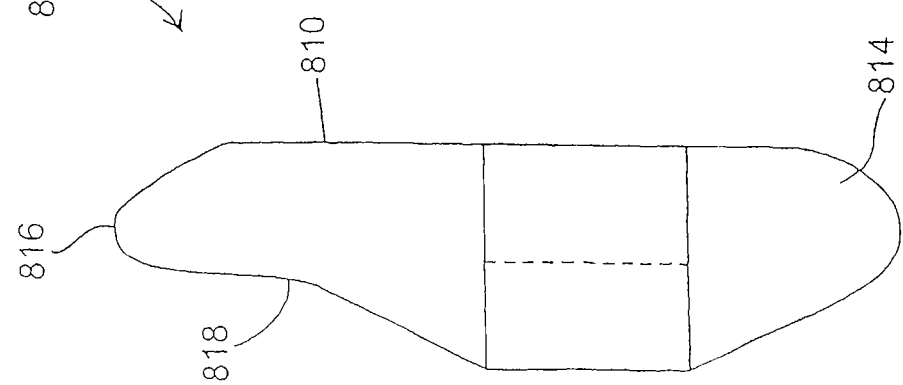
Figure 83A:
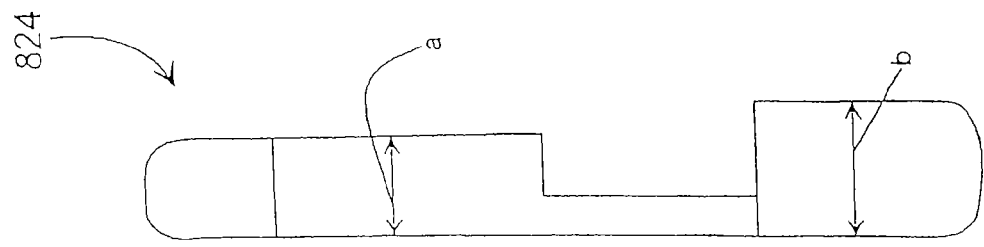
Figure 83:
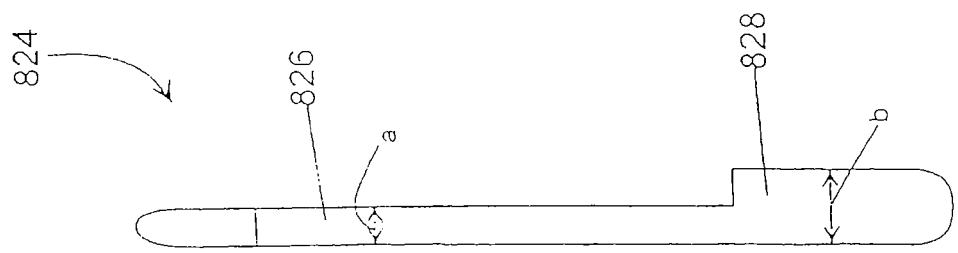
Figure 84:
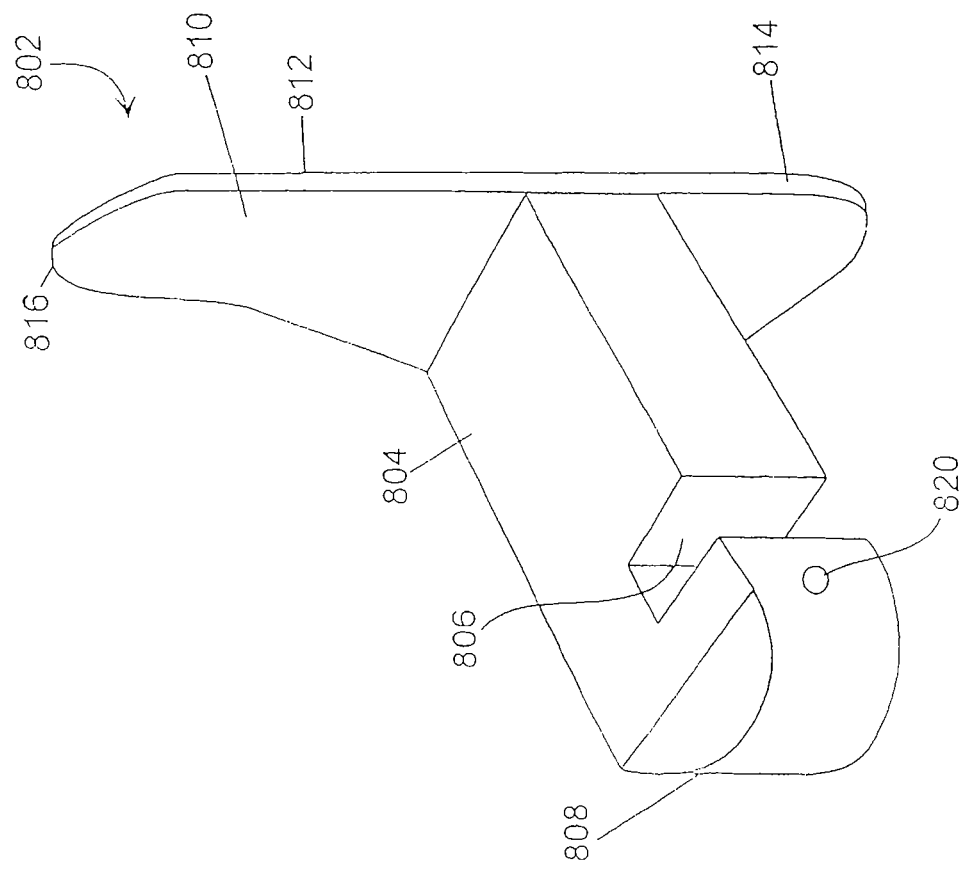

Another embodiment of the invention is shown in FIGS. 79-87 and includes implant 800 (FIG. 86). Implant 800 includes a distracting unit 802 which is shown in left side, plan, and right side views of FIGS. 79, 80 and 81. A perspective view of the distraction unit is shown in FIG. 84. The distracting unit as can be seen in FIG. 80 includes a distracting body 804, with longitudinal axis 805, which body 804 has a groove 806 and a rounded or bulbous end 808 which assist in the placement of the distracting body between adjacent spinous process so that an appropriate amount of distraction can be accomplished. Extending from the distracting body 804 is a first wing 810 which in FIG. 80 is substantially perpendicular to the distracting body 804. Such wings which are not perpendicular to the body are within the spirit and scope of the invention. First wing 810 includes a upper portion 812 and a lower portion 814. The upper portion 810 (FIG. 79) includes a rounded end 816 and a small recess 818. The rounded end 816 and the small recess 818 in the preferred embodiment are designed to accommodate the anatomical form or contour of the L4 (for a L4-L5 placement) or L5 (for a L5-S1 placement) superior lamina of the vertebra. It is to be understood that the same shape or variations of this shape can be used to accommodate other lamina of any vertebra. The lower portion 814 is also rounded in order to accommodate in the preferred embodiment in order to accommodate the vertebrae. The distracting unit further includes a threaded bore 820 which in this embodiment accepts a set screw 822 (FIG. 86) in order to hold a second wing 824 (FIGS. 82, 83) in position as will be discussed hereinbelow.

The threaded bore 820 in this embodiment slopes at approximately 45° angle and intersects the slot 806. With the second wing 824 in position, the set screw 822 when it is positioned in the threaded bore 820 can engage and hold the second wing 824 in position in the slot 806.

Figure 82:
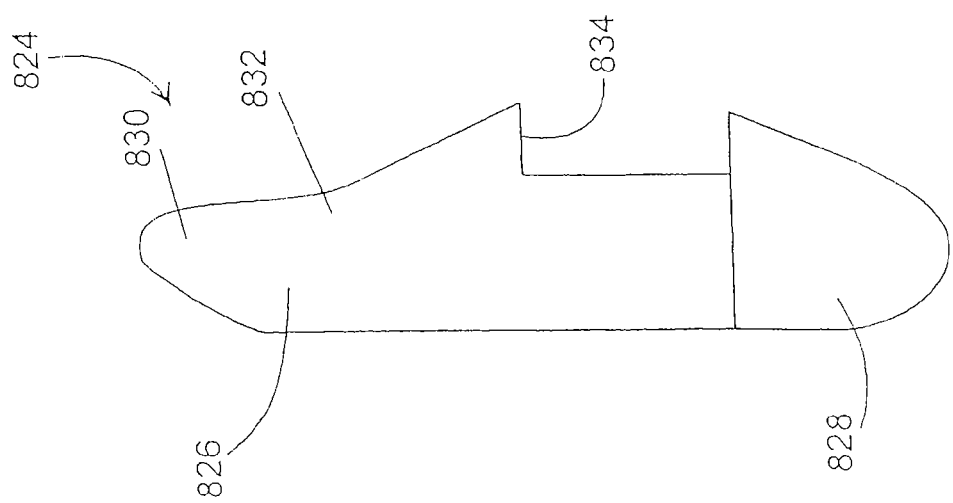
Figure 85:
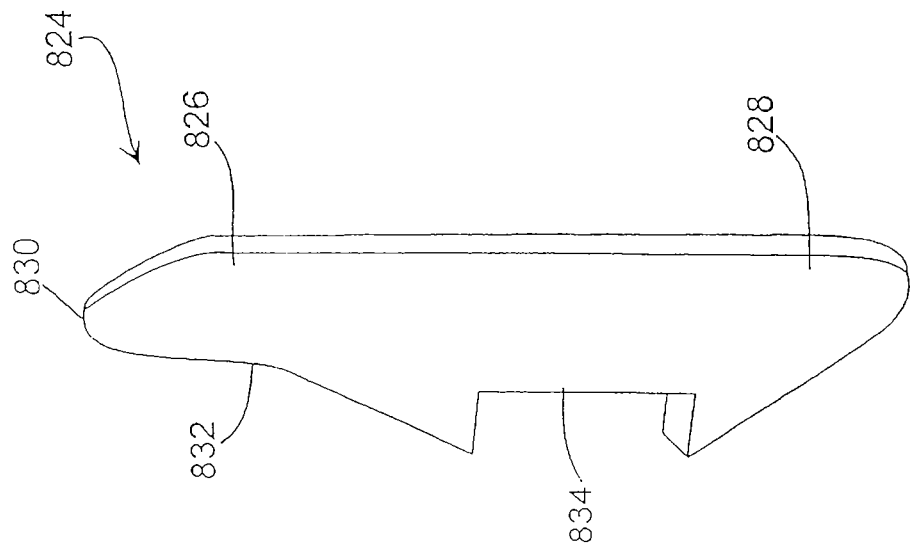

Turning to FIGS. 82, 83 and 85, left side, plan and perspective views of the second wing 824 are depicted. The second wing 824 is similar in design to the first wing. The second wing includes an upper portion 826 and a lower portion 828. The upper portion includes a rounded end 830 and a small recess 832. In addition, the second wing 824 includes a slot 834 which mates with the slot 806 of the distracting unit 802. The second wing 824 is the retaining unit of the present embodiment.

As can be seen in FIGS. 83 and 86, the second wing or retaining unit 824 includes the upper portion 826 having a first width "a" and the lower portion 828 having a second width "b". In the preferred embodiment, the second width "b" is larger than first width "a" due to the anatomical form or contour of the L4-L5 or L5-S1 laminae. As can be seen in FIG. 83a in second wing or retaining unit 824, the widths "a" and "b" would be increased in order to, as described hereinbelow, accommodate spinous processes and other anatomical forms or contours which are of different dimensions. Further, as appropriate, width "a" can be larger than width "b". Thus, as will be described more fully hereinbelow, the implant can include a universally-shaped distracting unit 802 with a plurality of retaining units 824, with each of the retaining units having different widths "a" and "b". During surgery, the appropriately sized retaining unit 824, width with the appropriate dimensions "a" and "b" can be selected to match to the anatomical form of the patient.

FIG. 86 depicts an assembled implant 800 positioned adjacent to upper and lower laminae 836, 838 (which are shown in dotted lines) of the upper and lower vertebrae. The vertebrae 836, 838 are essentially below the implant 800 as shown in FIG. 86. Extending upwardly from the vertebrae 836, 838, and between the first and second wings 810, 824, are the upper and lower spinous processes 840, 842. It is to be understood that in a preferred embodiment, the fit of the implant between the spinous processes can be such that the wings do not touch the spinous processes, as shown in FIG. 86, and be within the spirit and scope of the invention.

Figure 87:
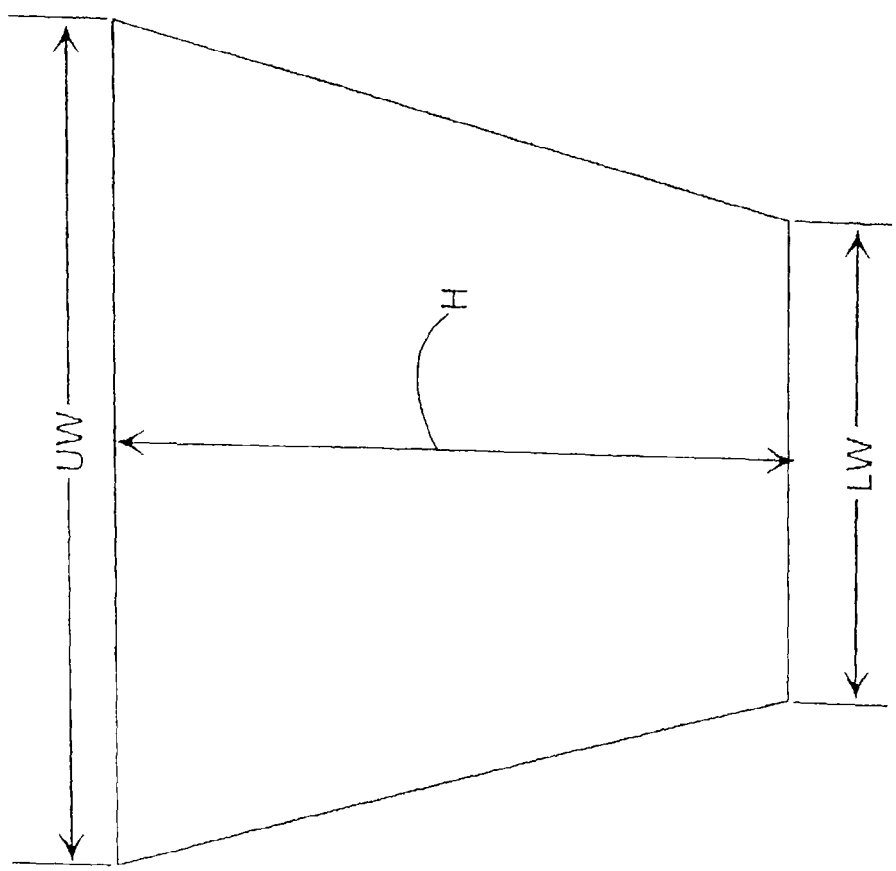
Figure 91:
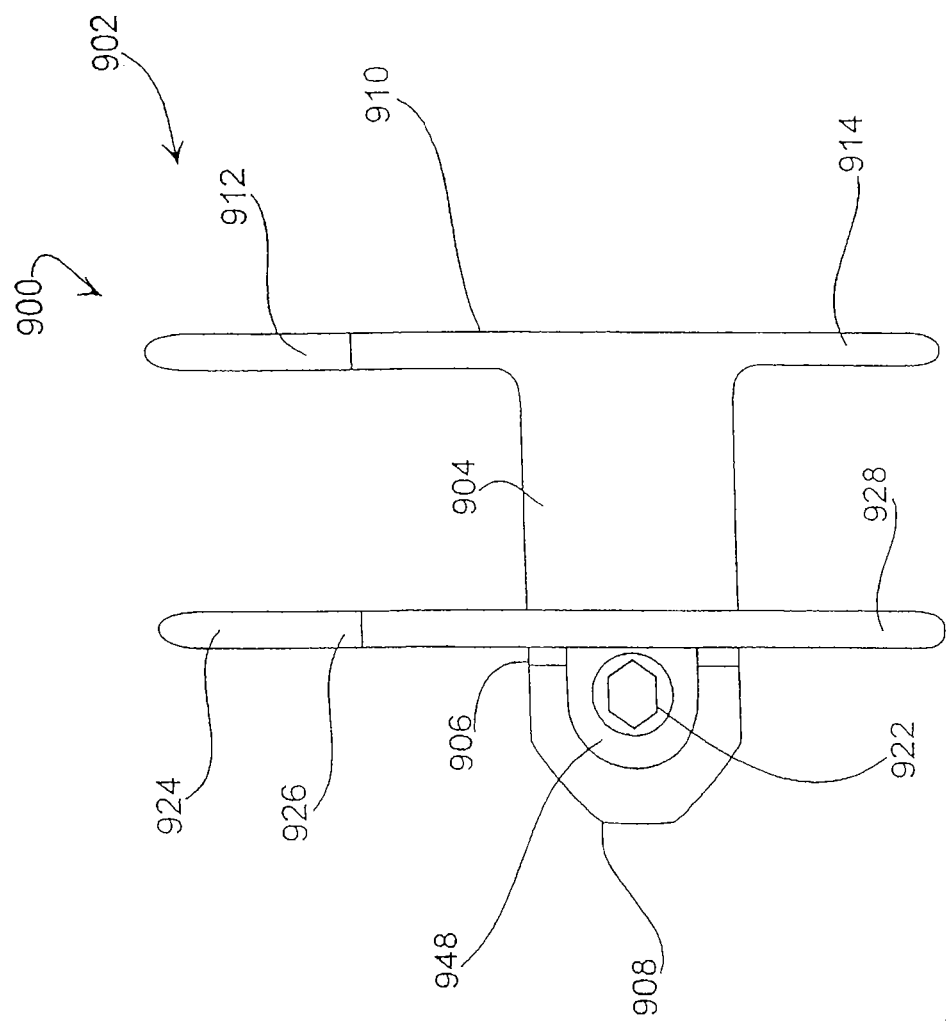

The implant 800 includes, as assembled, an upper saddle 844 and the lower saddle 846. The upper saddle 844 has an upper width identified by the dimension "UW". The lower saddle 846 has a lower width identified by the dimension "LW". In a preferred embodiment, the upper width is greater than the lower width. In other embodiments, the "UW" can be smaller than the "LW" depending on the anatomical requirements. The height between the upper and lower saddles 844, 846 is identified by the letter "h". These dimensions are carried over into FIG. 87 which is a schematic representation of the substantially trapezoidal shape which is formed between the upper and lower saddles. The table below gives sets of dimensions for the upper width, lower width, and height as shown in FIG. 87. This table includes dimensions for some variations of this embodiment.

| Variation | 1 | 2 | 3 |
| --- | --- | --- | --- |
| Upper Width | 8 | 7 | 6 |
| Lower Width | 7 | 6 | 5 |
| Height | 10 | 9 | 8 |

For the above table, all dimensions are given in millimeters.

For purposes of surgical implantation of the implant 800 into a patient, the patient is preferably positioned on his side (arrow 841 points up from an operating table) and placed in a flexed (tucked) position in order to distract the upper and lower vertebrae.

In a preferred procedure, a small incision is made on the midline of the spinous processes. The spinous processes are spread apart or distracted with a spreader. The incision is spread downwardly toward the table, and the distracting unit 802 is preferably inserted upwardly between the spinous processes 840 and 842 in a manner that maintains the distraction of spinous processes. The distracting unit 802 is urged upwardly until the distracting or bulbous end 808 and the slot 806 are visible on the other wide of the spinous process. Once this is visible, the incision is spread upwardly away from the table and the retaining unit or second wing 824 is inserted into the slot 806 and the screw 822 is used to secure the second wing in position. After this had occurred, the incisions can be closed.

An alternative surgical approach requires that small incisions be made on either side of the space located between the spinous processes. The spinous processes are spread apart or distracted using a spreader placed through the upper incision. From the lower incision, the distracting unit 802 is preferably inserted upwardly between the spinous processes 840 and 842 in a manner that urges the spinous processes apart. The distracting unit 802 is urged upwardly until the distracting or bulbous end 808 and the slot 806 are visible through the second small incision in the patient's back. Once this is visible, the retaining unit or second wing 824 is inserted into the slot 806 and the screw 822 is used to secure the second wing in position. After this has occurred, the incisions can be closed.

The advantage of either of the above present surgical procedures is that a surgeon is able to observe the entire operation, where he can look directly down onto the spinous processes as opposed to having to view the procedure from positions which are to the right and to the left of the spinous processes. Generally, the incision is as small as possible and the surgeon is working in a bloody and slippery environment. Thus, an implant that can be positioned directly in front of a surgeon is easier to insert and assemble than an implant which requires the surgeon to shift from side to side. Accordingly, a top-down approach, as an approach along a position to anterior line is preferred so that all aspects of the implantation procedure are fully visible to the surgeon at all times. This aides in the efficient location of (i) the distracting unit between the spinous processes, (ii) the retaining unit in the distracting unit, and (iii) finally the set screw in the distracting unit.

FIG. 80a shows an alternative embodiment of the distracting unit 802a. This distracting unit 802a is similar to distracting unit 802 in FIG. 80 with the exception that the bulbous end 808a is removable from the rest of the distracting body 804a as it is screwed into the threaded bore 809. The bulbous end 808a is removed once the distracting unit 802a is positioned in the patient in accordance with the description associated with FIG. 86. The bulbous end 808a can extend past the threaded bore 820 by about 1 cm in a preferred embodiment.

Embodiment of FIGS. 88, 89, 90 and 91

Another embodiment of the invention is shown in FIGS. 88, 89, 90 and 91. In this embodiment, the implant is identified by the number 900. Other elements of implant 900 which are similar to implant 800 are similarly numbered but in the 900 series. For example, the distracting unit is identified by the number 902 and this is in parallel with the distracting unit 802 of the implant 800. The distracting body is identified by the number 904 in parallel with the distracting body 804 of the implant 800. Focusing on FIG. 90, the distracting unit 902 is depicted in a perspective view. The distracting unit includes slot 906 which is wider at the top than at the bottom. The reason for this is that the wider upper portion of the slot 906, which is wider than the second wing 924 (FIG. 89), is used to, allow the surgeon to easily place the second wing 924 into the slot 906 and allow the wedge-shaped slot 906 to guide the second wing 924 to its final resting position. As can be see in FIG. 91, in the final resting position, the largest portion of the slot 906 is not completely filled by the second wing 924.

The end 908 of implant 900 is different in that it is more pointed, having sides 909 and 911 which are provided at about 45° angles (other angles, such as by way of example only, from about 30° to about 60° are within the spirit of the invention), with a small flat tip 913 so that the body 904 can be more easily urged between the spinous processes.

The distracting unit 902 further includes a tongue-shaped recess 919 which extends from the slot 906. Located in the tongue-shaped recess is a threaded bore 920.

As can be seen in FIG. 89, a second wing 924 includes a tongue 948 which extends substantially perpendicular thereto and between the upper and lower portions 926, 928. The tab 948 includes a bore 950. With the second wing 924 positioned in the slot 906 of the distracting unit 902 and tab 948 positioned in recess 919, a threaded set screw 922 can be positioned through the bore 950 and engage the threaded bore 920 in order to secure the second wing or retaining unit 924 to the distracting unit 902. The embodiment 900 is implanted in the same manner as embodiment 800 previously described. In addition, as the bore 922 is substantially perpendicular to the distracting body 904 (and not provided at an acute angle thereto), the surgeon can even more easily secure the screw in place from a position directly behind the spinous processes.

Embodiment of FIGS. 92, 92a, 92b, 93, 93a, 93b, 93c, 93d, 94, 94a, 94b, 95, 95a, and 96

Figure 92:
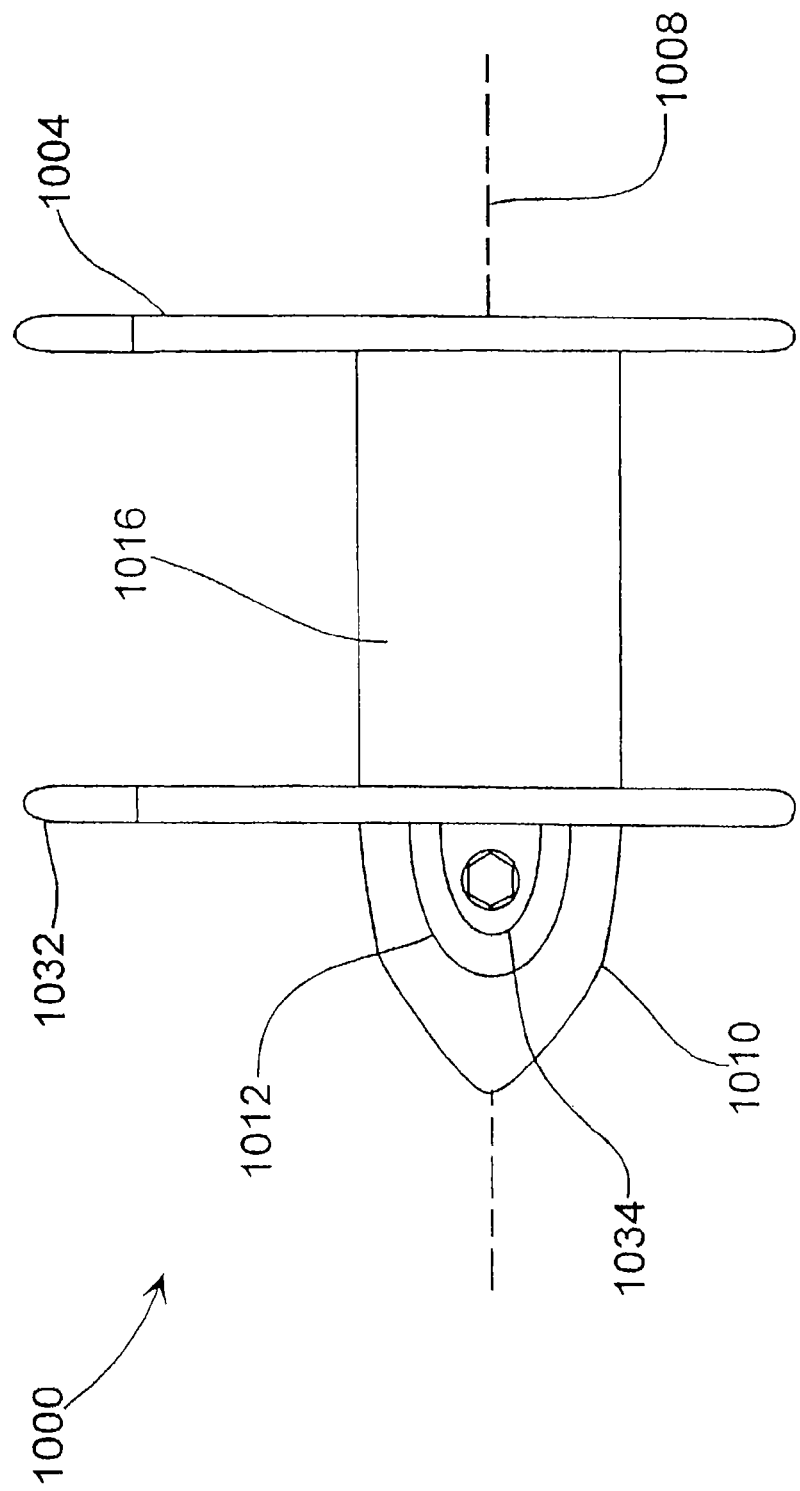

Still a further embodiment of the invention is depicted in FIGS. 92, and 92a. In this embodiment, the implant 1000 as can be seen in FIG. 92a includes a central elongated body 1002 which has positioned at one end thereof a first wing 1004. Wing 1004 is similar to the first wing previously described with respect to the embodiment of FIG. 88. Bolt 1006 secures wing 1004 to body 1002 in this embodiment. Bolt 1006 is received in a bore of the body 1002 which is along the longitudinal axis 1008 of body. It is to be understood that in this embodiment, the first unit is defined by the central body 1002, the first wing 1004, and the guide 1010.

Figure 93C:
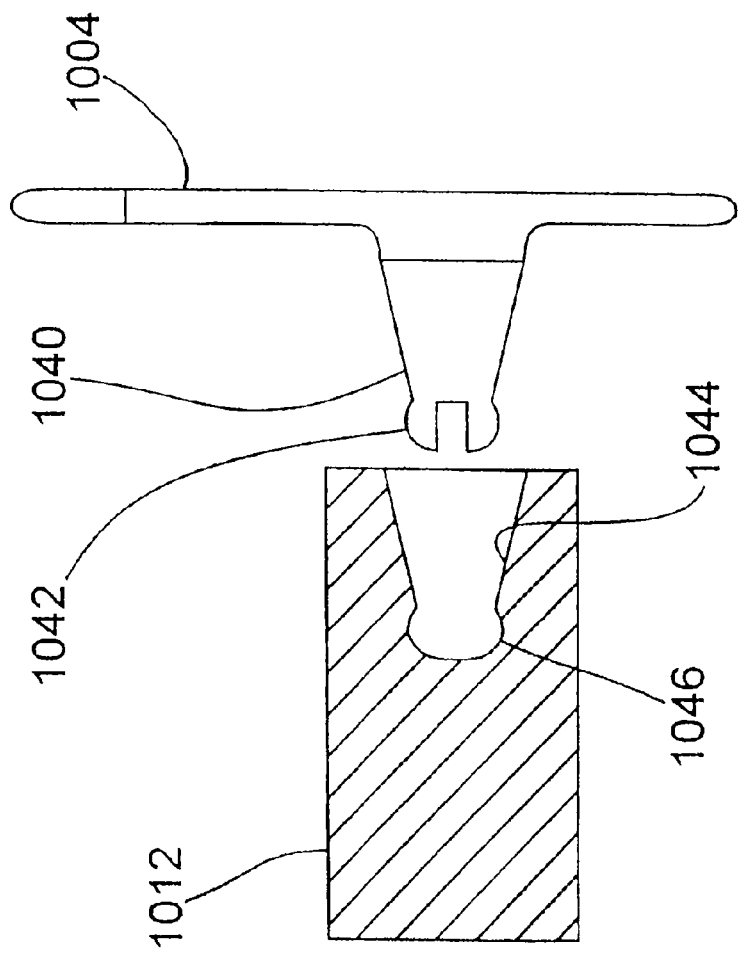

Alternatively, the first wing can be secured to the central body with a press fit and detent arrangement as seen in FIG. 93c. In this arrangement, the first wing has a protrusion 1040 extending preferably about perpendicularly from the first wing, with a flexible catch 1042. The protrusion and flexible catch are press fit into a bore 1044 of the central body with the catch received in a detent 1046.

Figure 93D:
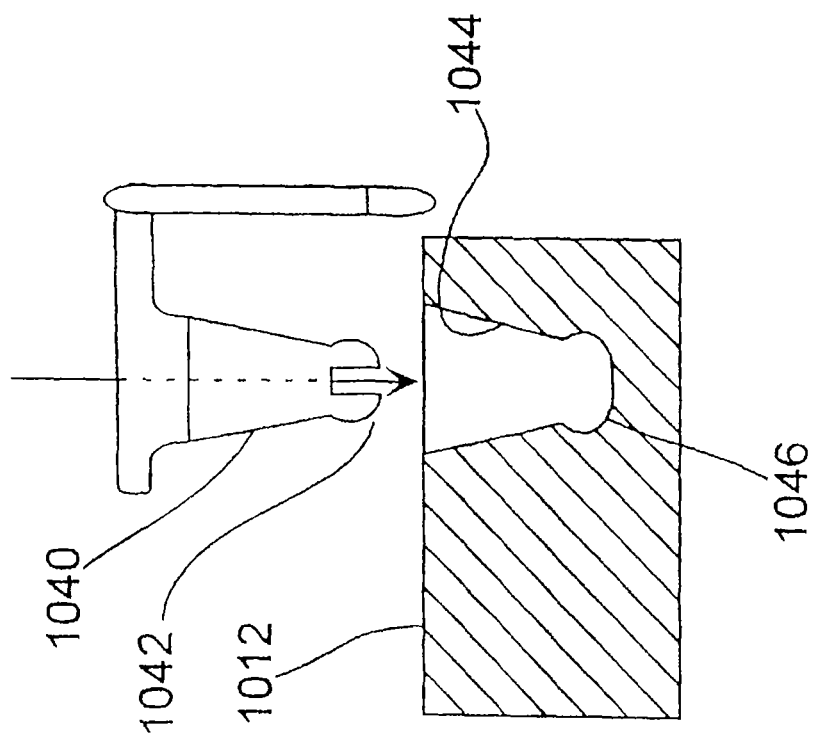

In yet another alternative embodiment, the first wing can be designed as shown in FIG. 93d with the protrusion directed substantially parallel to the first wing from a member that joins the first wing to the protrusion. Thus in this embodiment, the first wing is inserted into the body along the same direction as the second wing is inserted.

Positioned at the other end of the central body 1002 is a guide 1010. In this particular embodiment, guide 1010 is essentially triangularly-shaped so as to be a pointed and arrow-shaped guide. Alternatively, guide 1010 could be in the shape of a cone with lateral truncated sides along the longitudinal axis 1008. Guide 1010 includes a recess 1012 having a threaded bore 1014. Recess 1012 is for receiving a second wing 1032 as will be described hereinbelow.

Additionally, it is also to be understood that the guide 1010 can be bulbous, cone-shaped, pointed, arrow-shaped, and the like, in order to assist in the insertion of the implant 1000 between adjacent spinous processes. It is advantageous that the insertion technique disturb as little of the bone and surrounding tissue or ligaments as possible in order to (1) reduce trauma to the site and facilitate early healing, and (2) not destabilize the normal anatomy. It is to be noted that with the present embodiment, there is no requirement to remove any of the bone of the spinous processes and depending on the anatomy of the patient, there may be no requirement to remove or sever ligaments and tissues immediately associated with the spinous processes.

The implant 1000 further includes a sleeve 1016 which fits around and is at least partially spaced from the central body 1002. As will be explained in greater detail below, while the implant may be comprised of a bio-compatible material such as titanium, the sleeve is comprised preferably of a superelastic material which is by way of example only, a nickel titanium material (NiTi), which has properties which allow it to withstand repeated deflection without fatigue, while returning to its original shape. The sleeve could be made of other materials, such as for example titanium, but these materials do not have the advantages of a super-elastic material.

FIG. 93a is a cross-section through the implant 1000 depicting the central body 1002 and the sleeve 1016. As can be seen from the cross-section of FIG. 93a in a preferred embodiment, both the central body 1002 and the sleeve 1016 are substantially cylindrical and oval or elliptically-shaped. An oval or elliptical shape allows more of the spinous process to be supported by the sleeve, thereby distributing the load between the bone and the sleeve more evenly. This reduces the possibility of fracture to the bone or bone resorption. Additionally, an oval or elliptical shape enhances the flexibility of the sleeve as the major axis of the sleeve, as described below, is parallel to the longitudinal direction of the spinous process. However, other shapes such as round cross-sections can come within the spirit and scope of the invention.

In this particular embodiment, the central body 1002 includes elongated grooves 1018, along axis 1008, which receives elongated spokes 1020 extending from the internal surface of the cylinder 1016.

In a preferred embodiment, both the cross-section of the central body and the sleeve have a major dimension along axis 1022 and a minor dimensional along axis 1024 (FIG. 93*a*). The spokes 1020 are along the major dimension so that along the minor dimension, the sleeve 1016 can have its maximum inflection relative to the central body 1002. It is to be understood that the central body along the minor dimension 1024 can have multiple sizes and can, for example, be reduced in thickness in order to increase the ability of the sleeve 1016 to be deflected in the direction of the central body 1002.

Alternatively as can be seen in FIG. 93*b*, the central body 1002 can include the spokes 1020 and the sleeve 1016 can be designed to include the grooves 1018 in order to appropriately space the sleeve 1016 from the central body 1002.

In other embodiments, the sleeve can have minor and major dimensions as follows:

| Minor Dimension | Major Dimension |
| --- | --- |
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

In one preferred embodiment, said sleeve has a cross-section with a major dimension and a minor dimension and said major dimension is greater than said minor dimension and less than about two times said minor dimension. In said embodiment, said guide has a cross-section which is adjacent to said sleeve with a guide major dimension about equal to said sleeve major dimension and a guide minor dimension about equal to said sleeve minor dimension. Further in said embodiment, said guide extends from said central body with a cross-section which reduces in size in a direction away from said central body.

In another preferred embodiment, said guide is cone-shaped with a base located adjacent to said sleeve. Further, said guide has a base cross-section about the same as the oval cross-section of said sleeve.

Thus, from the above, it is evident that preferably a major dimension of the sleeve correspond with a major dimension of the central body and a minor dimension of the sleeve corresponds with a minor dimension of the central body. Additionally, it is evident that the major dimension of the sleeve 1016 is substantially perpendicular to a major dimension of the first wing 1004 along longitudinal axis 1030 (FIG. 92*a*). This is so that as discussed above, when the implant 1000 is properly positioned between the spinous processes, a major portion of the sleeve comes in contact with both the upper and lower spinous processes in order to distribute the load of the spinous processes on the sleeve 1016 during spinal column extension.

As indicated above, the preferred material for the sleeve 1016 is a super-elastic material and more preferably one comprised of an alloy of nickel and titanium. Such materials are available under the trademark Nitinol. Other super-elastic materials can be used as long as they are bio-compatible and have the same general characteristics of super-elastic materials. In this particular embodiment, a preferred super-elastic material is made up of the following composition of nickel, titanium, carbon, and other materials as follows:

| | |
| --- | --- |
| Nickel | 55.80% by weight |
| Titanium | 44.07% by weight |
| Carbon | <0.5% by weight |
| Oxygen | <0.5% by weight |

Figure 118:
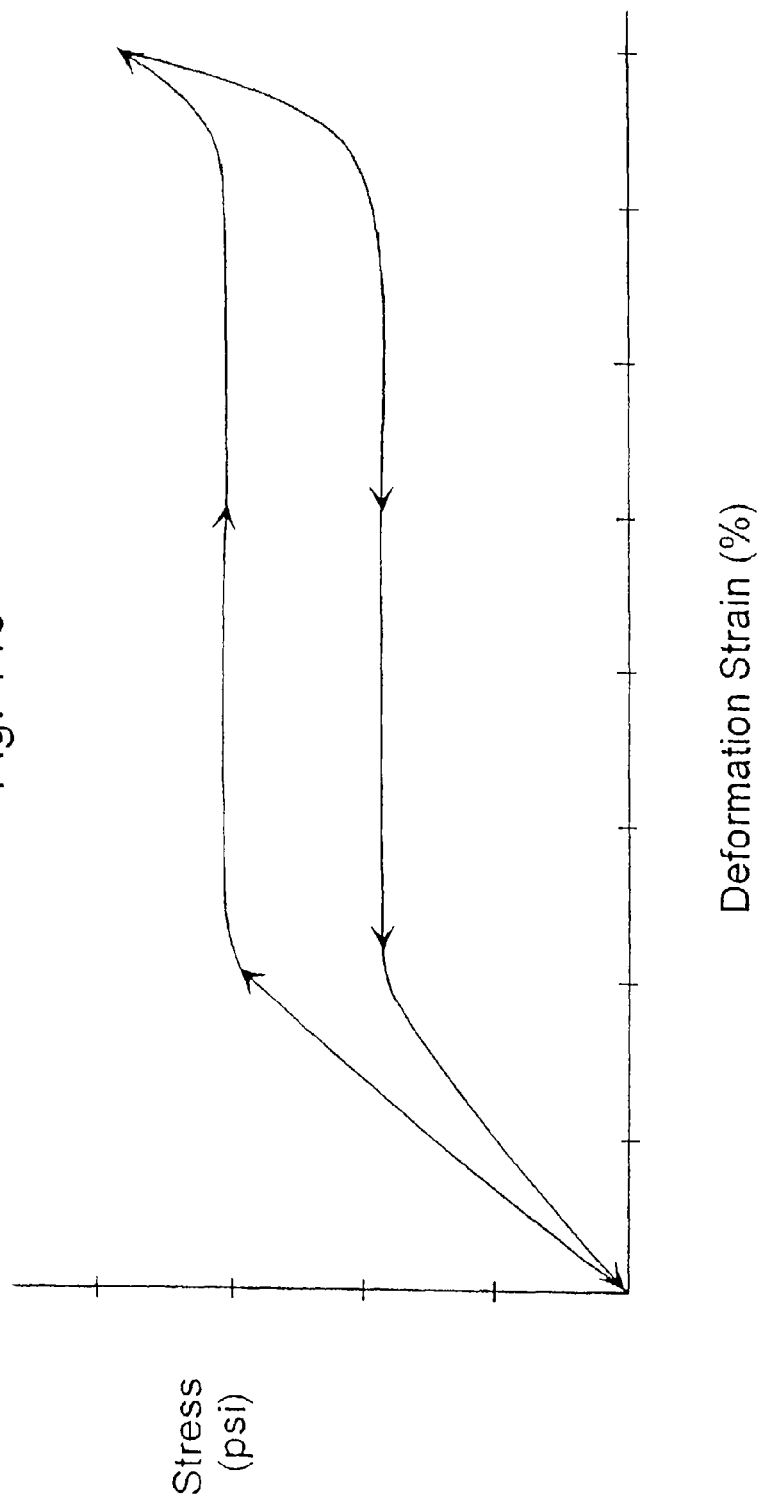
FIG. 118 depicts a graph showing characteristics of a preferred material usable with several of the embodiments of the present invention.

In particular, this composition of materials is able to absorb about 8% recoverable strain. Of course, other materials which can absorb greater and less than 8% can come within the spirit and scope of the invention. This material can be repeatably deflected toward the central body and returned to about its original shape without fatigue. Preferably and additionally, this material can withstand the threshold stress with only a small amount of initial deforming strain and above the threshold stress exhibit substantial and about instantaneous deformation strain which is many times the small amount of initial deforming strain. Such a characteristic is demonstrated in FIG. 118 where it is shown that above a certain threshold stress level, deformation strain is substantially instantaneous up to about 8%. FIG. 118 shows a loading and unloading curve between stress and deformation strain for a typical type of super-elastic material as described above.

Preferably, the above super-elastic material is selected to allow deformation of up to about, by way of example only, 8%, at about 20 lbs. to 50 lbs. force applied between a spinous processes. This would cause a sleeve to deflect toward the central body absorbing a substantial amount of the force of the spinous processes in extension. Ideally, the sleeves are designed to absorb 20 lbs. to 100 lbs. before exhibiting the super-elastic effect (threshold stress level) described above. Further, it is possible, depending on the application of the sleeve and the anatomy of the spinal column and the pairs of spinous processes for a particular individual, that the sleeve can be designed for a preferable range of 20 lbs. to 500 lbs. of force before the threshold stress level is reached. Experimental results indicate that with spinous processes of an older individual, that at about 400 pounds force, the spinous process may fracture. Further, such experimental results also indicate that with at least 100 pounds force, the spinous process may experience some compression. Accordingly, ideally the super-elastic material is designed to deform or flex at less than 100 pounds force.

In a preferred embodiment, the wall thickness of the sleeve is about 1 mm or $^{40}/_{1000}$ of an inch (0.040 in.). Preferably the sleeve is designed to experience a combined 1 mm deflection. The combined 1 mm deflection means that there is ½ mm of deflection at the top of the minor dimension and a ½ mm deflection at the bottom of the minor dimension. Both deflections are toward the central body.

In a particular embodiment where the sleeve is more circular in cross-section, with an outer dimension of 0.622 in. and a wall thickness of 0.034 in., a 20 lb. load causes a 0.005 in. deflection and a 60 lb. load causes a 0.020 in. deflection (approximately ½ mm). A 100 lb. load would cause a deflection of about 0.04 in. or approximately 1 mm.

Thus in summary, the above preferred super-elastic material means that the sleeve can be repeatedly deflected and returned to about its original shape without showing fatigue. The sleeve can withstand a threshold stress with a small amount of deforming strain and at about said threshold stress exhibit about substantially instantaneous deformation strain which is many times the small amount of the forming strain. In other words, such super-elastic qualities mean that the material experiences a plateau stress where the material supports a constant force (stress) over very large strain range as exhibited in FIG. 118.

It is to be understood that for this particular embodiment, bar stock of the super-elastic material is machined into the appropriate form and then heat treated to a final temperature to set the shape of the material by increasing the temperature of the material to 932° Fahrenheit and holding that temperature for five (5) minutes and then quickly quenching the sleeve in water. It is also to be understood that preferably the present nickel titanium super-elastic alloy is selected to have a transition temperature $A_f$ of about 59° Fahrenheit (15° C.). Generally for such devices the transition temperature can be between 15° C. to 65° C. (59° F. to 149° F.), and more preferably 10° C. to 40° C. (50° F. to 104° F.). Preferably, the material is maintained in the body above the transition temperature in order to exhibit optimal elasticity qualities.

Alternatively, and preferably, the sleeve can be fabricated by wire Electrical Discharge Machining (EDM) rather than machined. Additionally, the sleeve can be finished using a shot blast technique in order to increase the surface strength and elasticity of the sleeve.

Figure 94B:
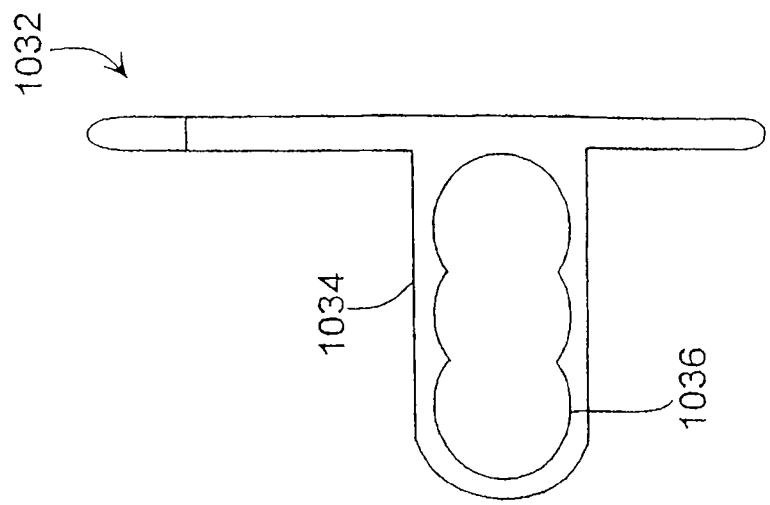
Figure 94A:
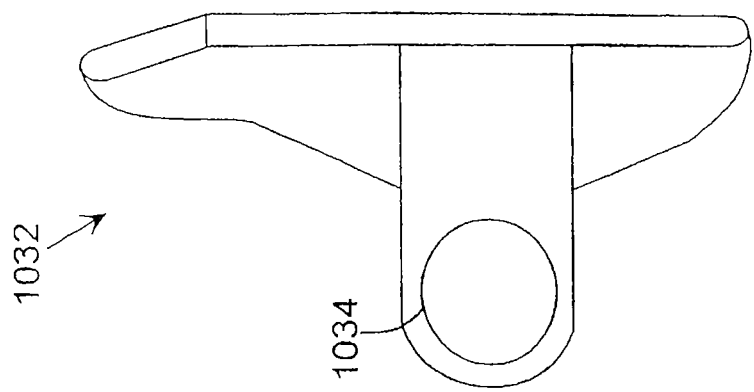
Figure 94:
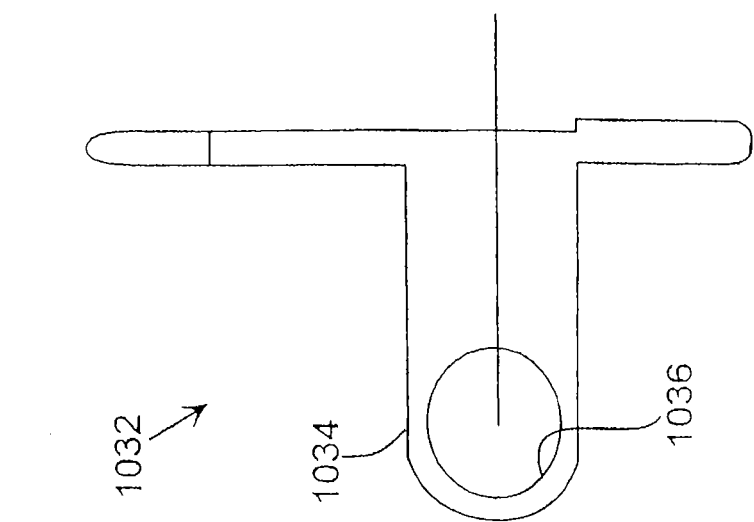
Figure 96:
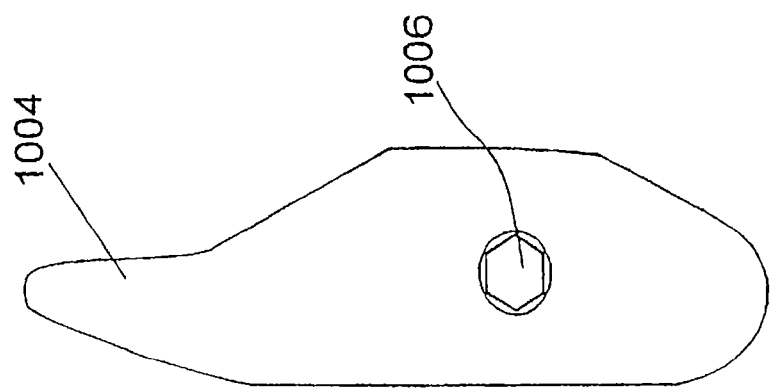
Figure 95A:
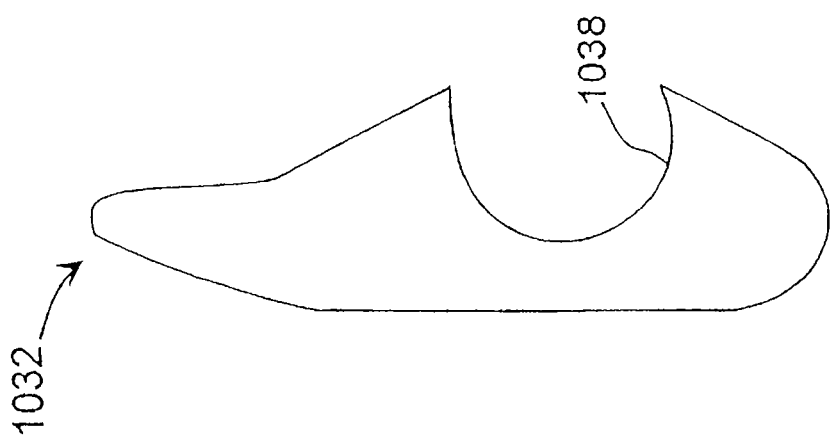
Figure 95:
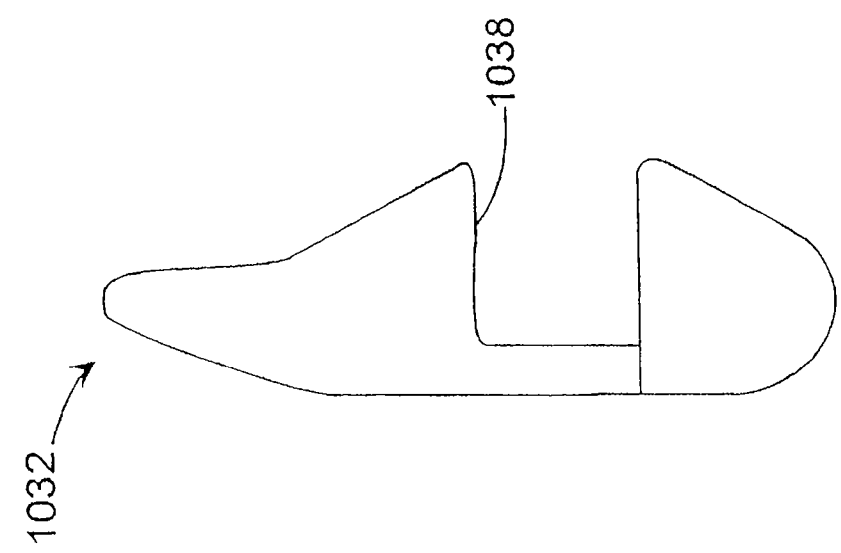

Top and side views of the second wing 1032 are shown in FIGS. 94 and 95. Second wing 1032 as in several past embodiments includes a tab 1034 with a bore 1036 which aligns with the bore 1014 of the guide 1010. In this particular embodiment, the second wing 1032 includes a cut-out 1038 which is sized to fit over the guide 1010, with the tab 1034 resting in the recess 1012 of the guide 1010.

An alternative configuration of the second wing 1032 is depicted in FIG. 94*a*. In this configuration, the second wing 1032 is held at acute angle with respect to the tab 1034. This is different from the situation in the embodiment of FIGS. 94 and 95 where the second wing is substantially perpendicular to the tab. For the embodiment of the second wing in FIG. 94*a*, such embodiment will be utilized as appropriate depending on the shape of the spinous processes.

With respect to the alternative second wing 1032 depicted in FIGS. 94*b* and 95*a*, elongated tab 1034 has a plurality of closely positioned bores 1036. The bores, so positioned, appear to form a scallop shape. Each individual scallop portion of the bore 1036 can selectively hold the bolt in order to effectively position the second wing 1032 in three different positions relative to the first wing 1004. The cut-out 1038 (FIG. 95*a* of this alternative embodiment) is enlarged over that of FIG. 95 as in a position closest to the first wing 1004, the second wing 1032 is immediately adjacent and must conform to the shape of the sleeve 1016.

Figure 97:
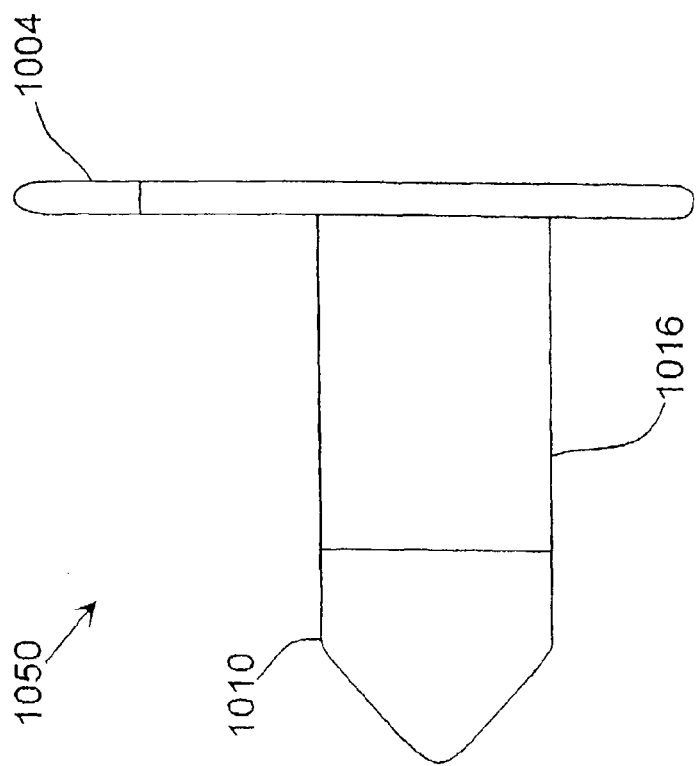
FIG. 97 depicts still another embodiment of the present invention.

Embodiment of FIG. 97

Implant 1050 of FIG. 97 is similar to the implant 1000 in FIG. 92 with the major difference being that a second wing is not required. The implant 1050 includes a central body as does implant 1000. The central body is surrounded by a sleeve 1016 which extends between a first wing 1004 and a guide 1010. The guide 1010 in this embodiment is substantially cone-shaped without any flats and with no bore as there is no need to receive a second wing. The sleeve and the central body as well as the first wing and guide act in a manner similar to those parts of the implant 1000 in FIG. 92. It is to be understood a cross-section of this implant 1050 through sleeve 1016 can preferably be like FIG. 93*a*. This particular embodiment would be utilized in a situation where it was deemed impractical or unnecessary to use a second wing. This embodiment has the significant advantages of the sleeve being comprised of super-elastic alloy materials as well as the guide being utilized to guide the implant between spinous processes while minimizing damage to the ligament and tissue structures found around the spinous processes.

Figure 98:
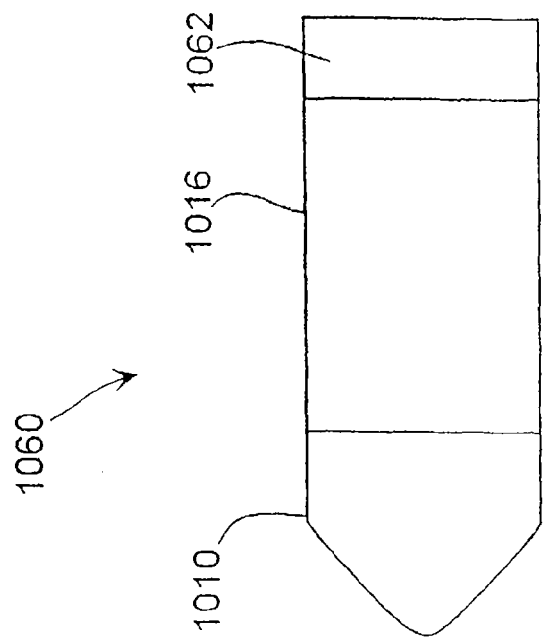
FIG. 98 depicts yet a further embodiment of the present invention.

Embodiment of FIG. 98

Implant 1060 is depicted in FIG. 98. This implant is similar to the implants 1000 of FIG. 92 and the implant 1050 of FIG. 97, except that this implant does not have either first or second wings. Implant 1060 includes a sleeve 1016 which surrounds a central body just as central body 1002 of implant 1000 in FIG. 93. It is to be understood that a cross-section of this implant 1060 through sleeve 1016 can preferably be like FIG. 93*a*. Implant 1060 includes a guide 1010 which in this preferred embodiment is cone-shaped. Guide 1010 is located at one end of the central body. At the other end is a stop 1062. Stop 1062 is used to contain the other end of the sleeve 1016 relative to the central body. This embodiment is held together with a bolt such as bolt 1006 of FIG. 93 that is used for the immediate above two implants. For the implant 1060 of FIG. 98, such a device would be appropriate where the anatomy between the spinous processes was such that it would be undesirable to use either a first or second wing. However, this embodiment affords all the advantageous described hereinabove (FIGS. 92 and 97) with respect to the guide and also with respect to the dynamics of the sleeve.

Figure 99:
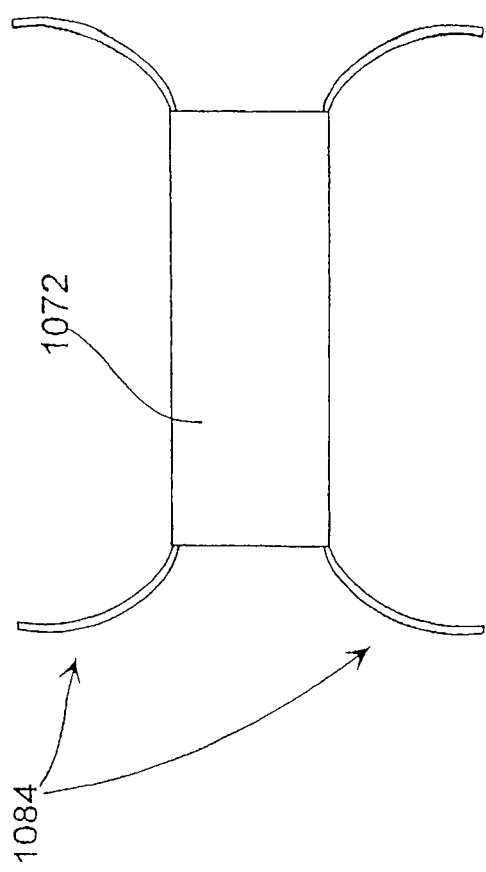
FIGS. 99 and 100 depict still another embodiment of the present invention including an insertion tool.
Figure 100:
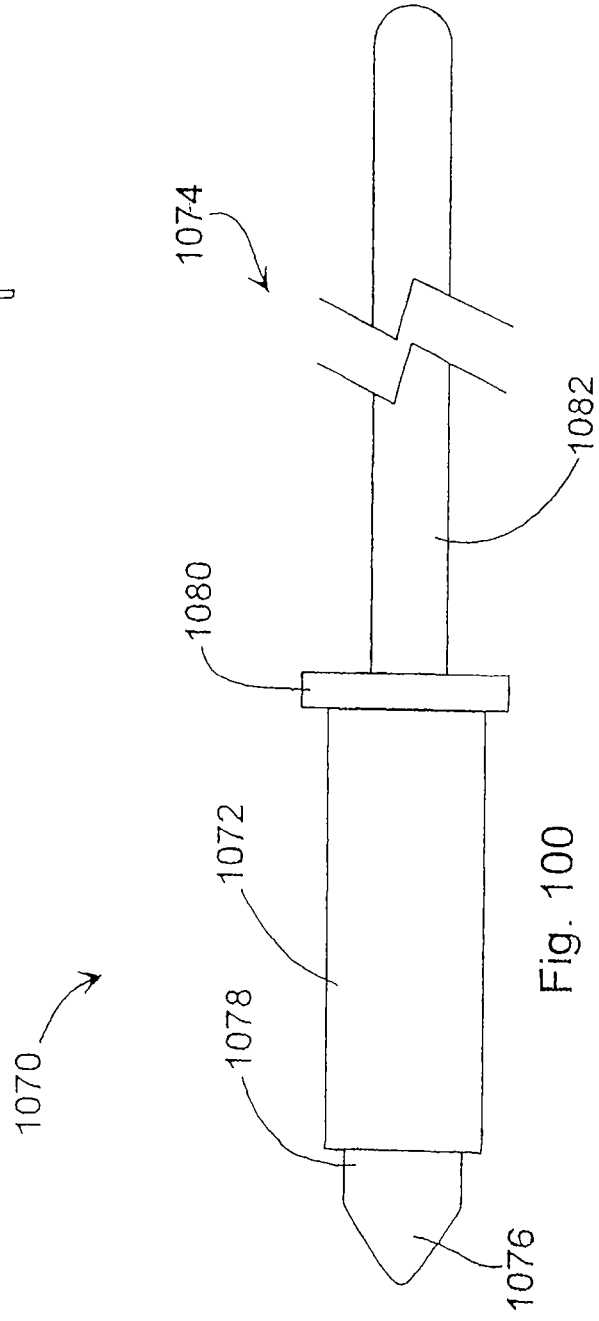

Embodiment of FIGS. 99 and 100

FIGS. 99 and 100 depict an implant system 1070. Implant system 1070 includes a sleeve 1072 which is similar to and has the advantageous of sleeve 1016 of the embodiment in FIG. 92. Sleeve 1072 does not, however, have any spokes. Additionally, implant system 1070 includes an insertion tool 1074. Insertion tool 1074 includes a guide 1076 which in a preferred embodiment is substantially cone-shaped. Guide 1076 guides the insertion of the sleeve 1072 and the insertion tool 1074 between adjacent spinous processes. The insertion tool 1074 further includes a central body 1078, a stop 1080, and a handle 1082. The guide 1076 at its base has dimensions which are slightly less than the internal dimensions of the sleeve 1074 so that the sleeve can fit over the guide 1076 and rest against the stop 1080. The tool 1074 with the guide 1076 is used to separate tissues and ligaments and to urge the sleeve 1072 in the space between the spinous processes. Once positioned, the guide insertion tool 1074 can be removed leaving the sleeve 1072 in place. If desired, after the sleeve is positioned, position maintaining mechanisms such as springy wires 1084 made out of appropriate material such as the super-elastic alloys and other materials including titanium, can be inserted using a cannula through the center of the sleeve 1072. Once inserted, the ends of the retaining wires 1084 (FIG. 99) extend out of both ends of the sleeve 1072, and due to this springy nature, bent at an angle with respect to the longitudinal axis of the sleeve 1072. These wires help maintain the position of the sleeve relative to the spinous processes.

Embodiment of FIGS. 101, 102, 102a, 103, 104, 105, 106, and 107

Figure 101:
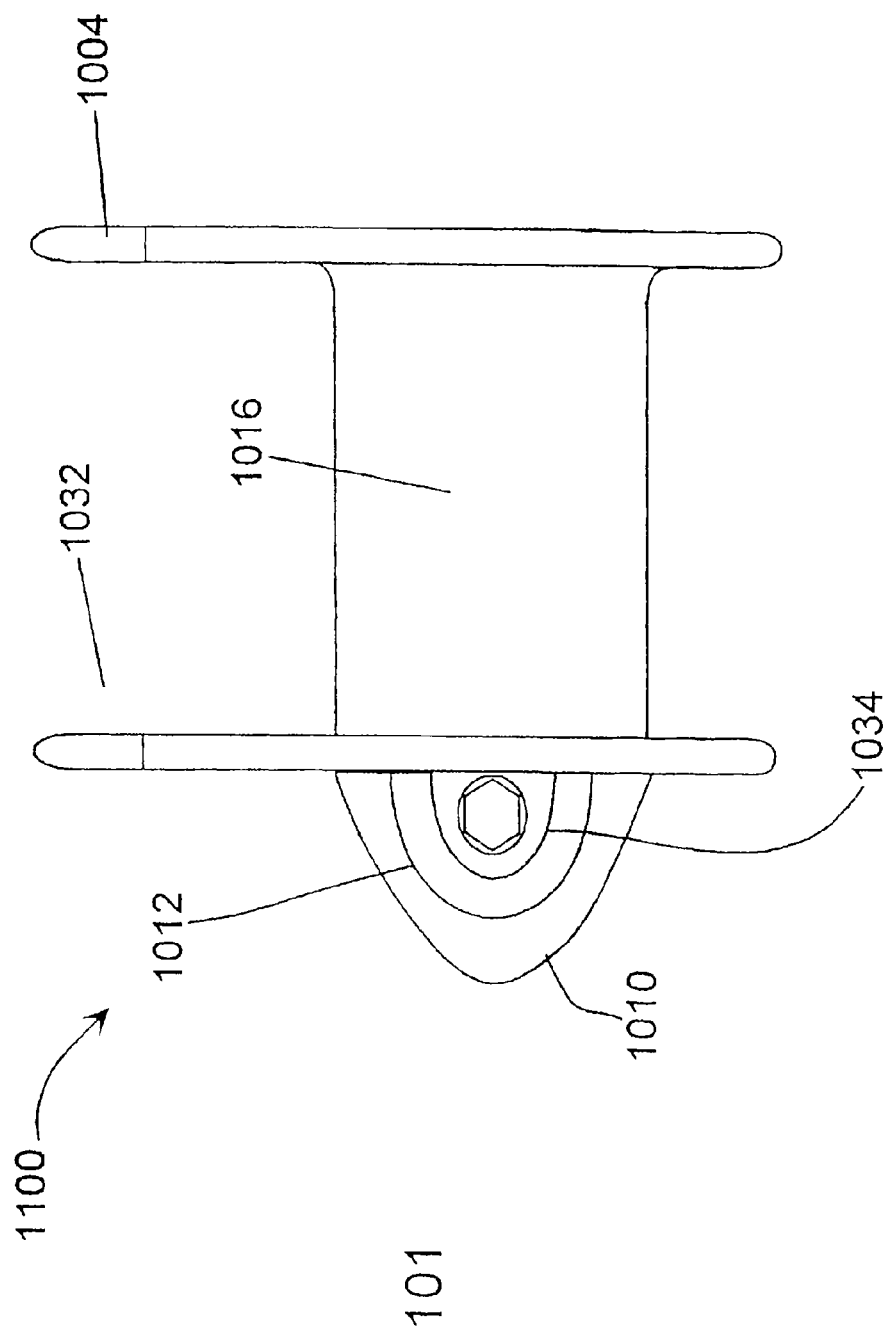
FIGS. 101, 102, 102a, 103, 104, 105, 106, and 107 depict still a further embodiment of the present invention.

Another embodiment of the invention can be seen in FIG. 101 which includes implant 1100. Implant 1100 has many similar features that are exhibited with respect to implant 1000 in FIG. 92. Accordingly, elements with similar features and functions would be similarly numbered. Additionally, features that are different from implant 1100 can be, if desired, imported into and become a part of the implant 1000 of FIG. 92.

As with implant 1000, implant 1100 includes a central body 1002 (FIG. 102) with a first wing 1004 and a bolt 1006 which holds the first wing and the central body together. In this particular embodiment, the central body is made in two portions. The first portion 1102 is in the shape of a truncated cone with an oval or elliptical base and a second portion 1104 includes a cylindrical central portion with a distal end in the shape of a truncated cone 1103 with an oval or elliptical base. In addition, in this particular embodiment, formed with the central body is the guide 1010 which has an oval or elliptical base. Bolt 1006 is used to secure the first wing through the second portion 1104 with the first portion 1102 held in-between. In this particular embodiment, the guide 1010 in addition to including recess 1012 and bore 1014 includes a groove 1106 which receives a portion of the second wing 1032.

Figure 102A:
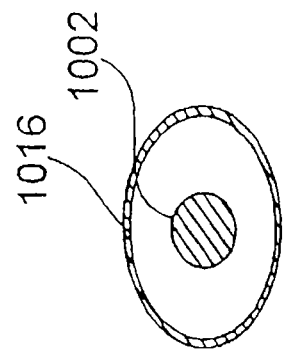
Figure 102:
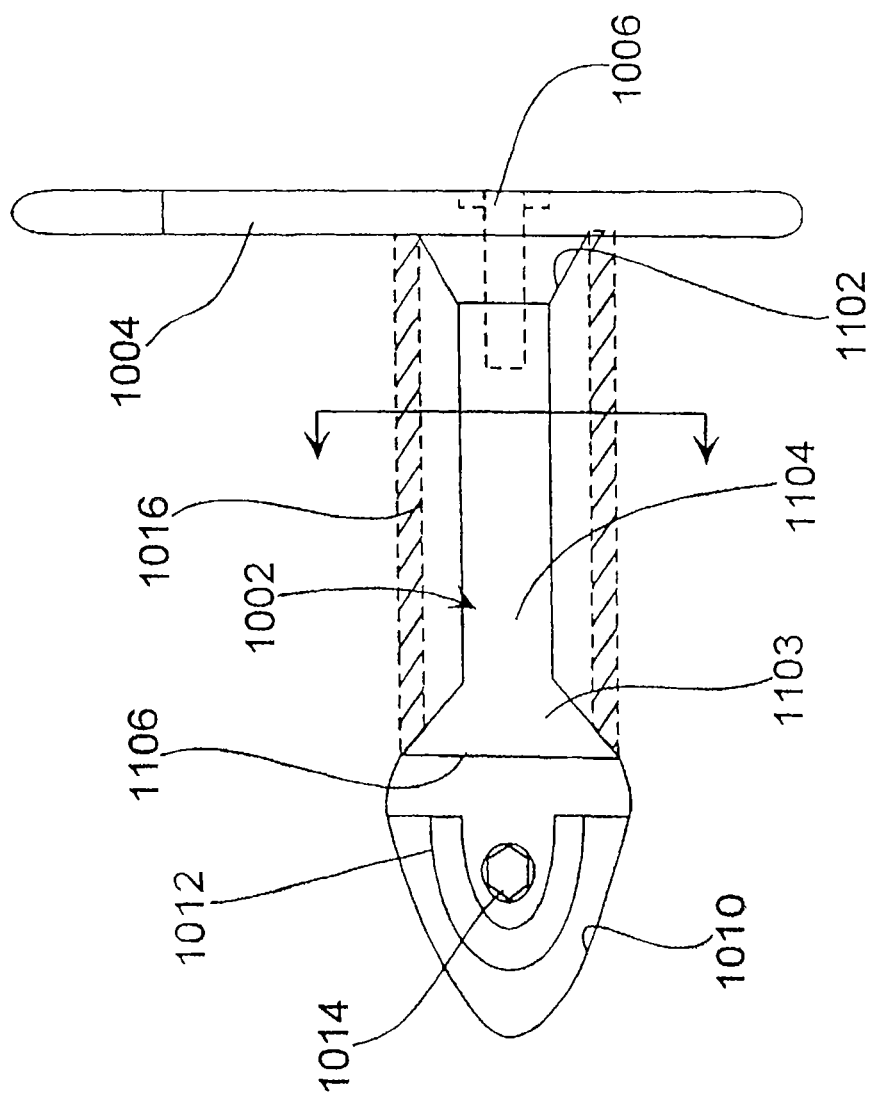

In this particular embodiment, the sleeve 1016 is preferably oval or elliptical in shape as can be seen in FIG. 102a. The central body can be oval, elliptical or circular in cross-section, although other shapes are within the spirit and scope of the invention. The sleeve 1016 held in position due to the fact that the truncated conical portion 1102 and the corresponding truncated conical portion 1103 each have a base that is elliptical or oval in shape. Thus, the sleeve is held in position so that preferably the major dimension of the elliptical sleeve is substantially perpendicular to the major dimension of the first wing. It is to be understood that if the first wing is meant to be put beside the vertebrae so that the first wing is set at an angle other than perpendicular with respect to the vertebrae and that the sleeve may be held in a position so that the major dimension of the sleeve is at an angle other than perpendicular to the major dimension of the first wing and be within the spirit and scope of the invention. This could be accomplished by tightening bolt 1006 with the first wing 1004 and sleeve 1016 so positioned. In such a configuration, the major dimension of the sleeve would be preferably positioned so that it is essentially parallel to the length of the adjacent spinous processes. So configured, the elliptical or oval shape sleeve would bear and distribute the load more evenly over more of its surface.

It is to be understood that the sleeve in this embodiment has all the characteristics and advantages described hereinabove with respect to the above-referenced super-elastic sleeves.

Figure 105:
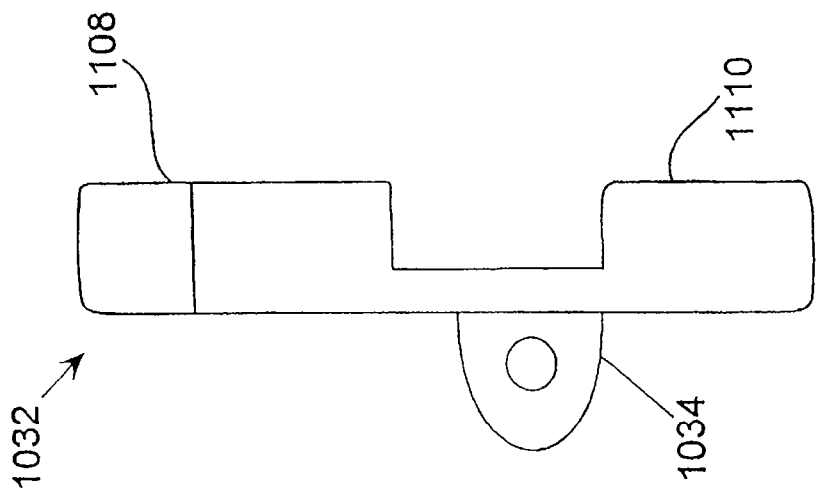
Figure 104:
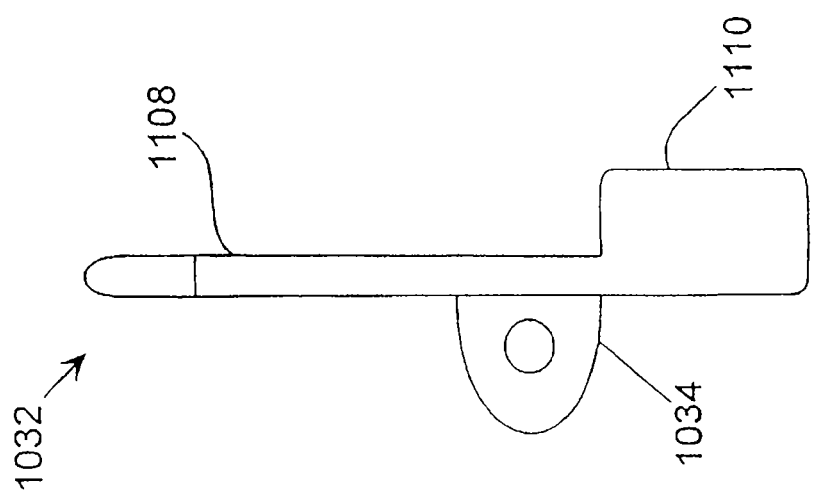
Figure 103:
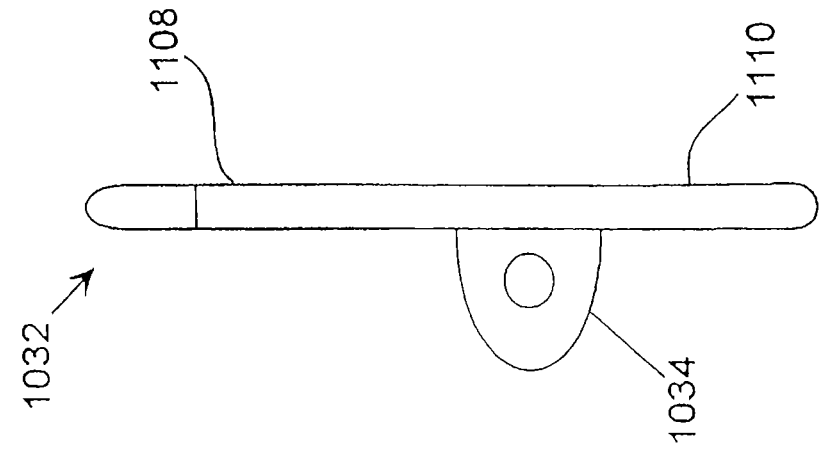

The second wing as discussed above, can come in a variety of shapes in order to provide for variations in the anatomical form of the spinous processes. Such shapes are depicted in FIGS. 103, 104, 105, 106, and 107. In each configuration, the second wing 1032 has a upper portion 1108 and a lower portion 1110. In FIG. 104, the lower portion is thicker than the upper portion in order to accommodate the spinous process, where the lower spinous process is thinner than the upper spinous process. In FIG. 105, both the upper and lower portions are enlarged over the upper and lower portions of FIG. 103 to accommodate both the upper and lower spinous processes being smaller. That is to say that the space between the upper and lower portions of the first and second wings are reduced due to the enlarged upper and lower portions of the second wing.

Figure 107:
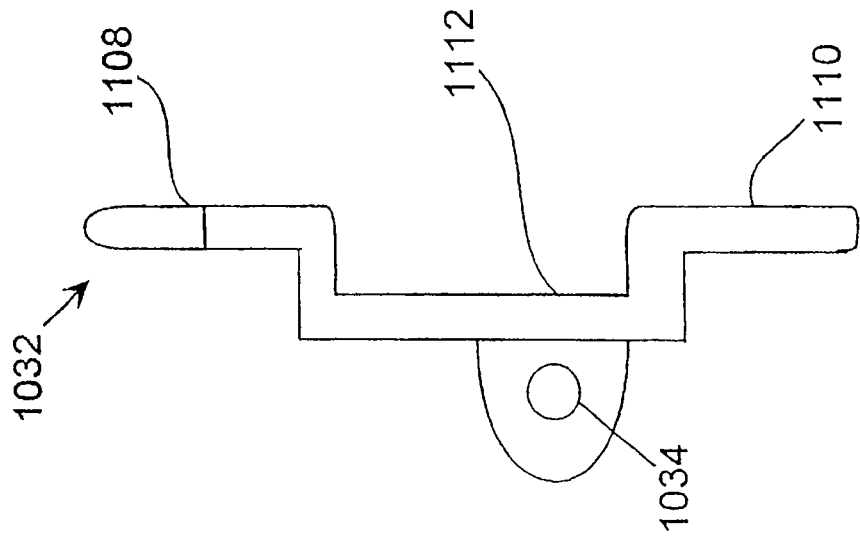
Figure 106:
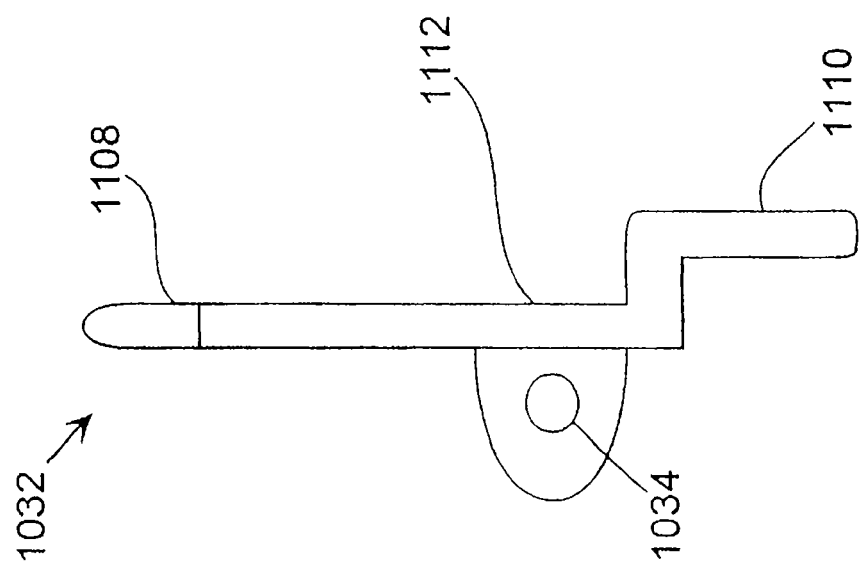

Alternative embodiments of second wings, as shown in FIGS. 104 and 105, are depicted in FIGS. 106 and 107. In these FIGS. 106 and 107, the second wing 1032 accommodates the same anatomical shape and size of the spinous processes as does the second wing in FIGS. 104 and 105 respectively. However, in the embodiments of the second wing 1032 of FIGS. 106 and 107, substantial masses have been removed from the wings. The upper and lower portions 1108 and 1110 are essentially formed or bent in order to extend from the central portion 1112 of the second wing 1032.

It is to be understood that in this embodiment, if desired, the second wing may not have to be used, depending on the anatomy of the spinal column of the body, and this embodiment still has the significant advantages attributable to the guide 1010 and the functionality of the sleeve 1016.

Figure 109:
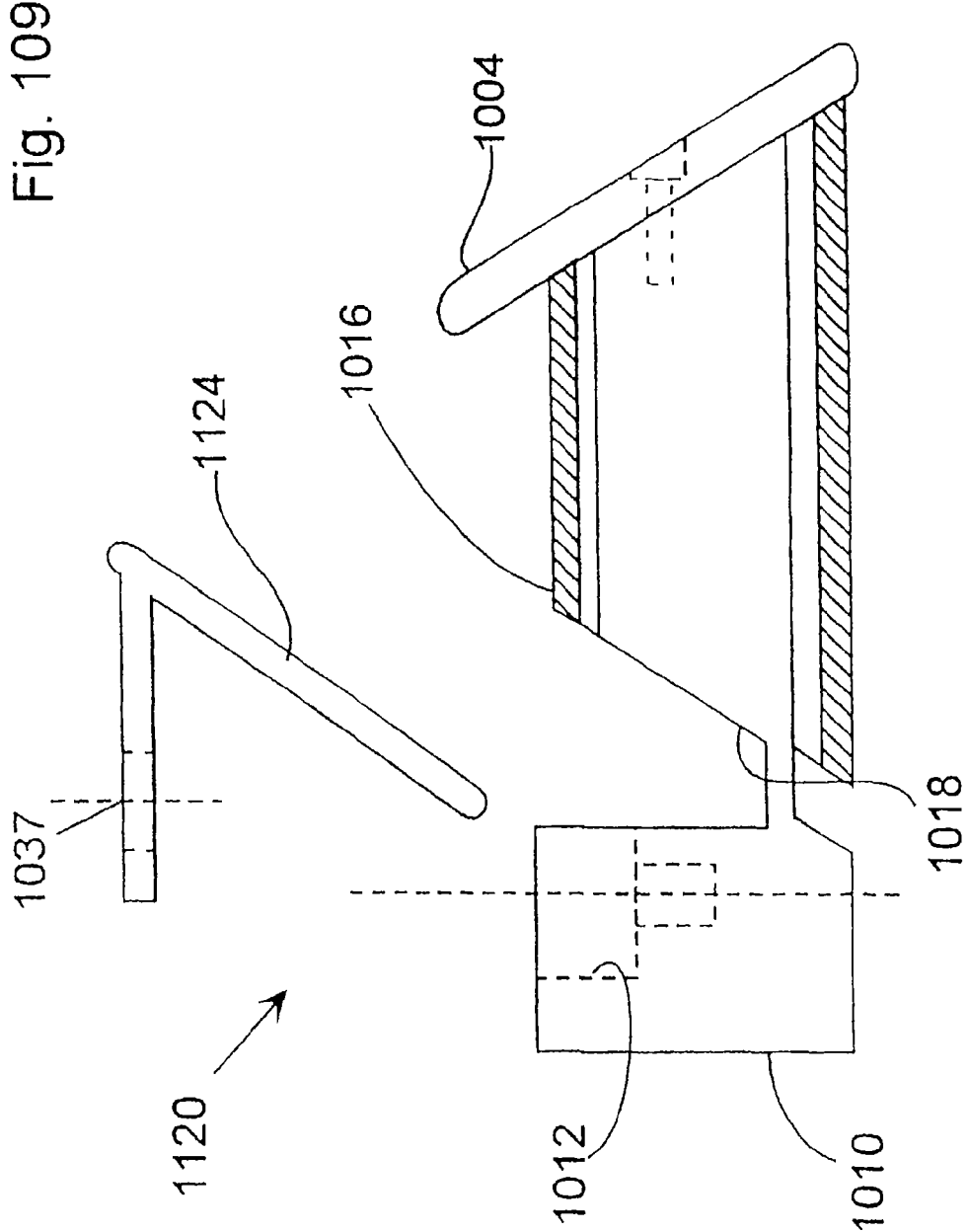
Figure 110:
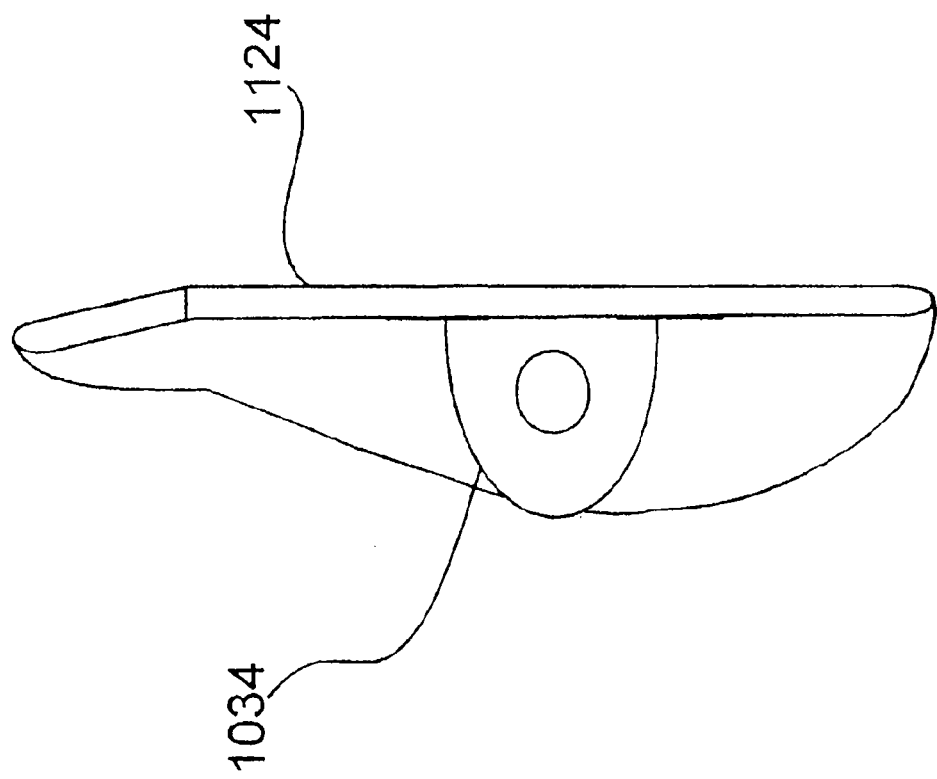

Embodiment of FIGS. 108, 109, and 110

The implant 1120 as shown in FIGS. 108 and 109, is similar to implant 1100 which is in turn similar to implant 1000. Such similar details have already been described above and reference here is made to the unique orientation of the first and second wings 1122 and 1124. These wings have longitudinal axis 1126 and 1128 respectfully. As can be seen in these figures, the first and second wings 1122, 1124 have been rotated so that they both slope inwardly and if they were to continue out of the page of the drawing of FIG. 108, they would meet to form an A-frame structure as is evident from the end view of FIG. 109. In this particular embodiment, as can be seen in FIGS. 109 and 110, the tab 1034 is provided an acute angle to the remainder of the second wing 1124. Further, the groove 1018 formed in the implant is sloped in order to accept the second wing 1124. Accordingly, this present implant 1120 is particularly suited for an application where the spinous process is wider adjacent to the vertebral body and then narrows in size at least some distance distally from the vertebral body. It is to be understood that a cross-section of this implant 1120 through sleeve 1016 can preferably be like FIG. 93a.

Embodiment of FIGS. 111, 112, 113, 114, 115, 116, and 117

Figure 111:
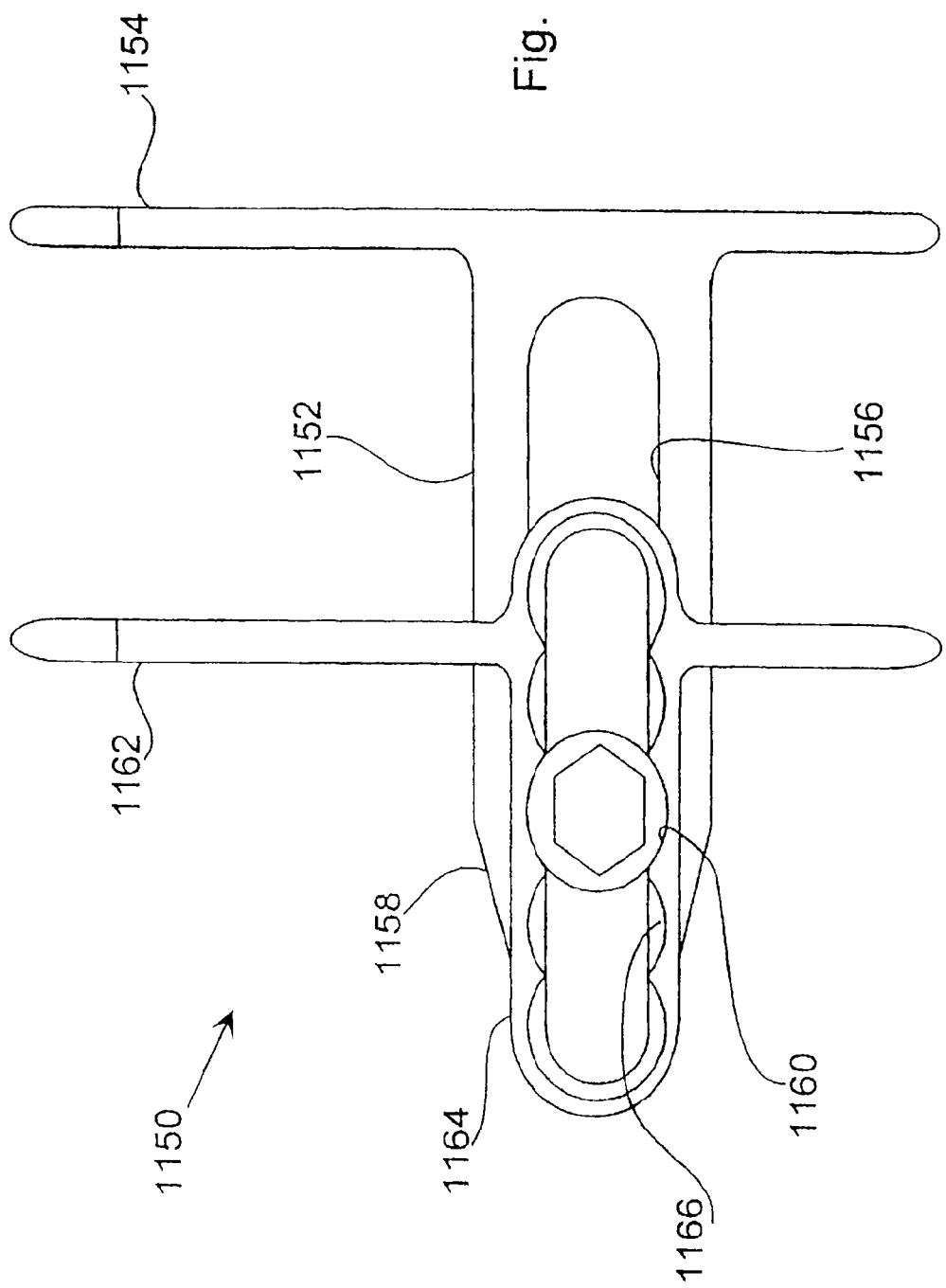

An additional embodiment of the implant 1150 is shown in FIG. 111. Implant 1150 has features similar to those described with respect to FIG. 94b.

Implant 1150 includes a central body 1152 with a first wing 1154, where central body 1152 includes elongated groove 1156 which extends to the guide 1158. A screw 1160 is received in a threaded bore located in the elongated groove 1156.

The second wing 1162 includes a central body 1164 which is substantially perpendicular to the second wing 1162.

Figure 112:
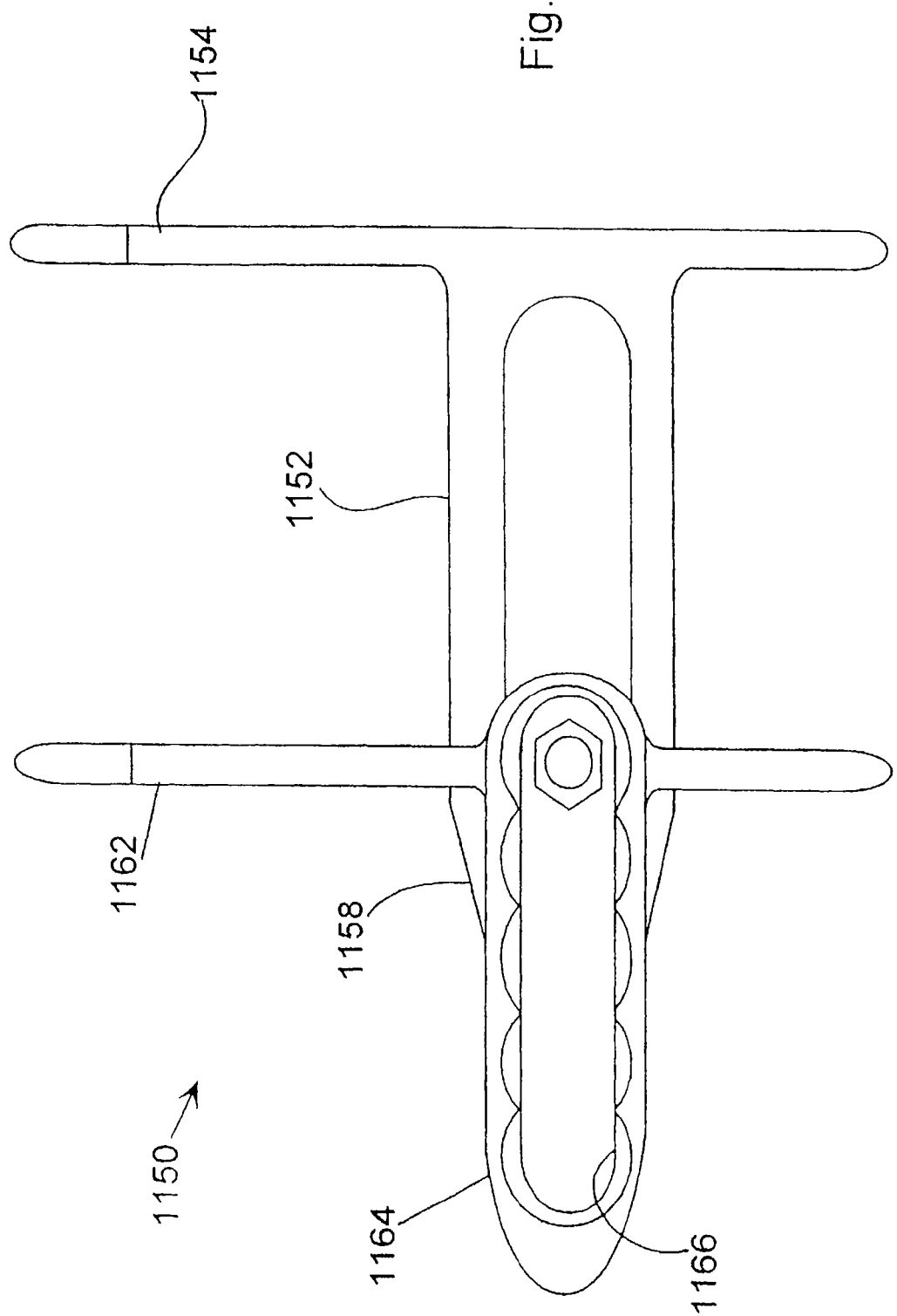
Figure 114:
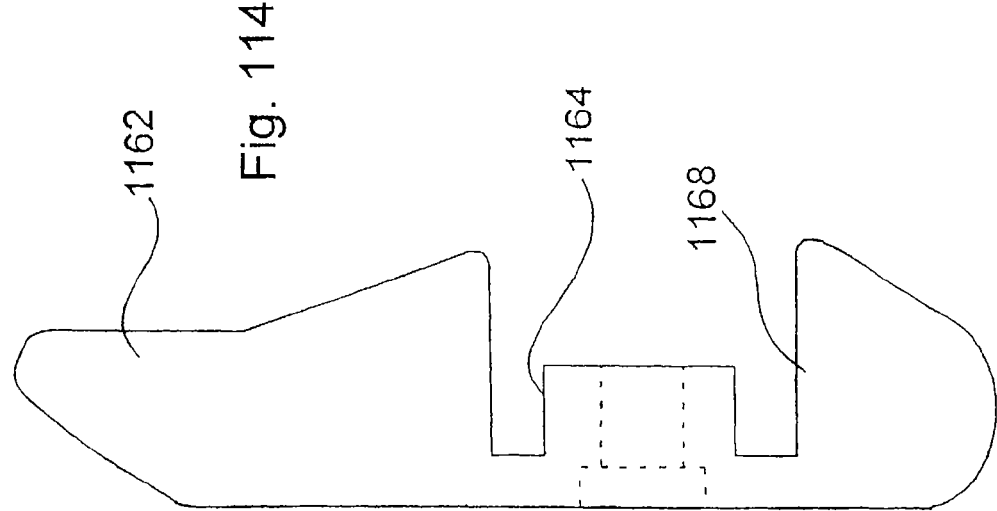
Figure 113:
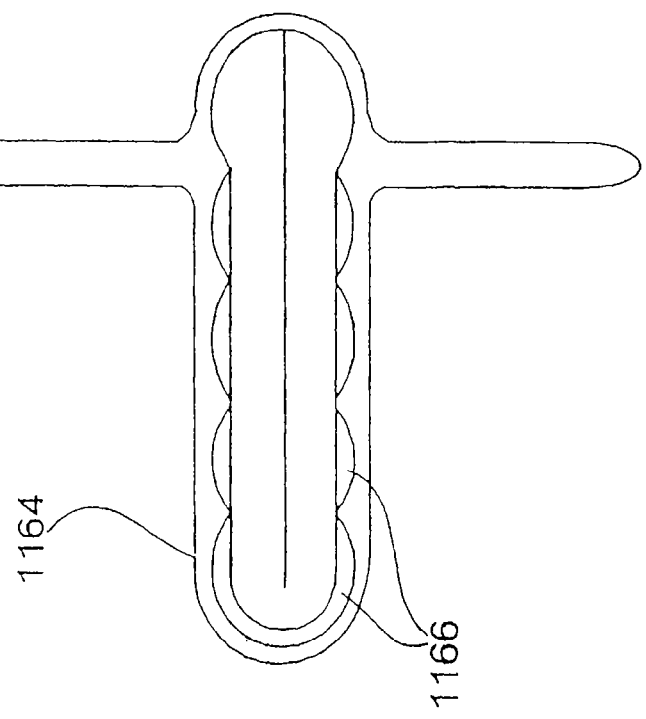

The central body 1164 includes a plurality of bores 1166 provided therein. These bores are formed adjacent to each other in order to define a plurality of scallops, each scallop capable of retaining bolt 1160 therein. As can be seen in FIG. 114, the second wing includes a cut-out 1168 such that with the central body 1164 of the second wing received in the groove 1156 of the central body associated with the first wing, the remainder of the second wing is received over the central body 1152 of the implant 1150. With this implant 1150, the distance between the first and second wings can be adjusted by selectively placing the bolt 1160 through one of the five specified bores defined by the scalloped plurality of bores 1166. Accordingly, FIG. 112 depicts the implant where the first and second wings are widest apart in order to accommodate spinous processes of greater thickness. FIG. 111 shows the middle position between the first and second wings in order to accommodate average size spinous processes.

It is to be understood that preferably during the surgical process, the central body 1152 is urged between spinous processes. After this has occurred, the second wing is guided by the other sides of the spinous processes from a path which causes the plane of the second wing to move substantially parallel to the plane of the first wing until the central body 1164 associated with the second wing 1162 is received in the groove of 1156 of the central body 1152 associated with the first wing 1154. After this has occurred, the bolt 1160 is positioned through aligned bores associated with the second wing 1162 and the central body 1152 in order to secure the second wing to the central body.

While embodiment 1150 does not depict a sleeve such as sleeve 1016, such a sleeve 1016 could be placed over body 1152 and be within the spirit of the invention.

Embodiments of FIGS. 119*a*, 119*b*, 120*a*, 120*b*, 121*a*, 121*b*, 122*a*, 122*b*, 122*c*, 123*a*, 123*b*, 124*a*, 124*b*, and 124*c*

Implant 1200 of the invention is depicted in FIGS. 119*a* and 119*b*. This implant includes the first wing 1202 and sleeve 1204 and a guide 1206. An alternative to this embodiment further includes, as required, second wing 1208 as depicted in FIGS. 120*a* and 120*b*.

Figure 121B:
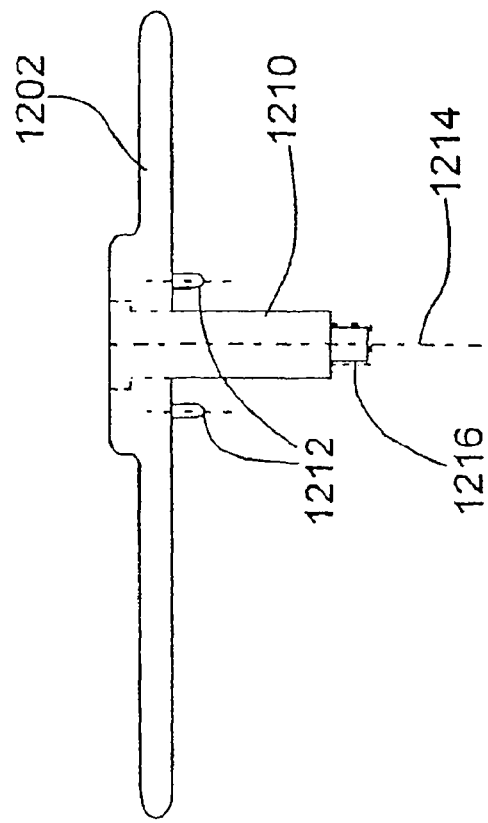
FIGS. 121a and 121b depict side and plan views of the first wing and central body of the embodiment of the invention depicted in FIGS. 119a and 119b.
Figure 121A:
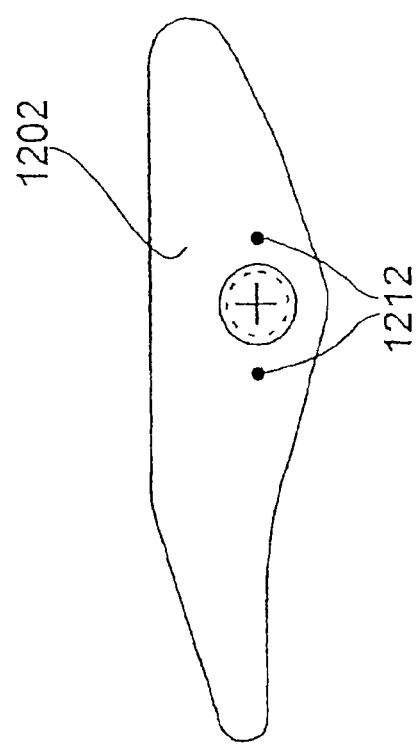

As can be seen in FIGS. 121*a* and 121*b*, the first wing 1202 includes a bore which receives a central body 1210. Preferably, the central body is pressed fit through the bore of the first wing although it is to be understood that other securing mechanisms such as through the use of threads and still other mechanisms can be used to accomplish this task. Additionally, in this particular embodiment first and second pins 1212 extend from the first wing 1202, each along an axis which is substantially parallel to the longitudinal axis 1214 of the central body 1210. In this particular embodiment, the distal end 1216 of the central body 1210 is threaded in order to be coupled to the guide 1206.

Figure 122C:
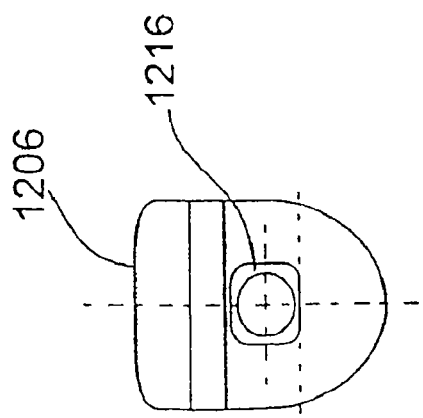
FIGS. 122a, 122b, and 122c depict top, side and end views of a guide which is a portion of the embodiment of the invention of FIGS. 119a and 119b.
Figure 122B:
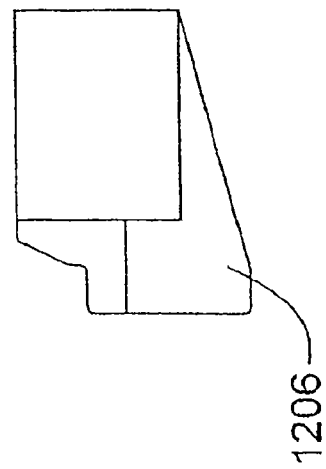
Figure 122A:
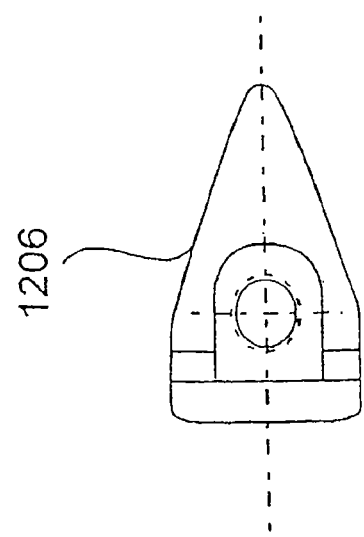

As can be seen in FIGS. 122*a*, 122*b* and 122*c*, the guide 1206 in this particular embodiment is pointed in order to allow the implant to be inserted between, and if necessary distract, adjacent spinous processes. The guide 206 includes a threaded bore 1218 which is designed to accept the threaded end 1216 of the central body 1210 in order to secure the guide to the central body and additionally for purposes of retaining the sleeve between the guide 1206 and the first wing 1202.

Figure 123B:
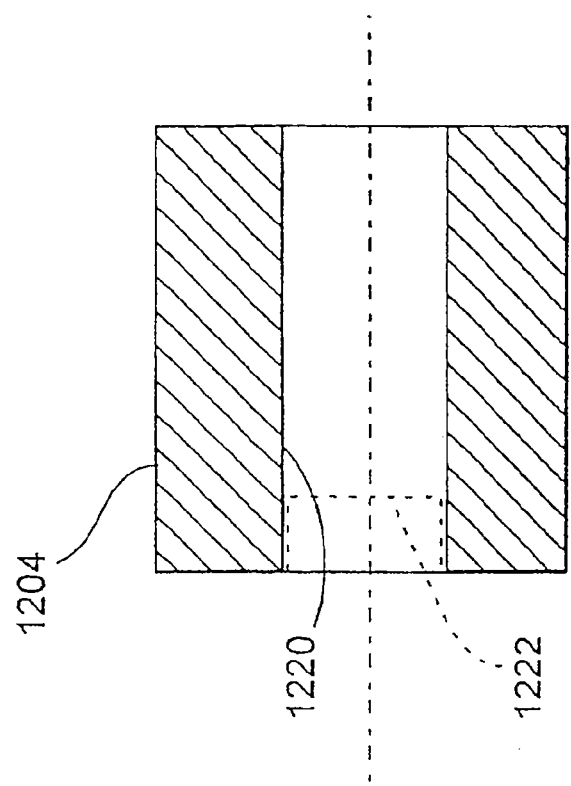
FIGS. 123a and 123b depict an end view and a cross-sectioned view respectfully of the sleeve of the embodiment of the invention of FIGS. 119a and 119b.
Figure 123A:
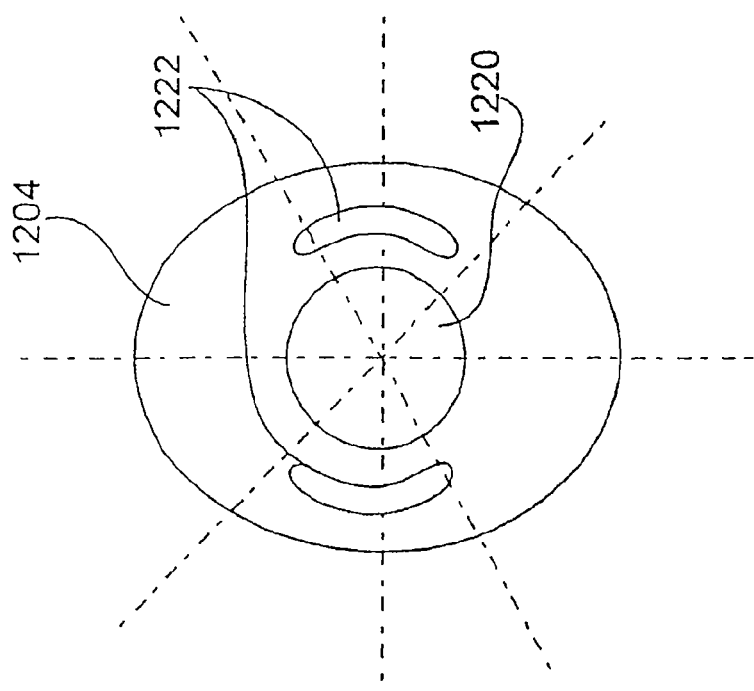

As can be seen in FIG. 123*a* the sleeve 1204 is preferably cylindrical, and oval or elliptical in shape in cross-section. It is to be understood that sleeve 1204 can have other shapes as described throughout the specification and be within the spirit and scope of the invention. In this particular embodiment, sleeve 1204 has at least one major diameter and one minor diameter in cross-section. Sleeve 1204 includes a central bore 1220 which extends the length of sleeve 1204 and curve grooves 1222 which are formed about central bore 1220 and extend only part way into the body of the sleeve. In this particular embodiment, the curved grooves 1222 describe an arc of about 60°. It is to be understood that in other embodiment, this arc can be less than 60° and extend past 120°.

The sleeve 1204 is received over the central body 1210 of the implant 1200 and can rotate thereon about the longitudinal axis 1214 of the central body 1210. When this particular embodiment is assembled, the grooves 1222 have received therein the pins 1212 that extend from the first wing 1202. Accordingly, the pins inserted in the grooves 1222 assist in the positioning of the sleeve relative to the remainder of the implant 1200. With the pins 1212 received in the curved grooves 1222, the pins limit the extent of the rotation of the sleeve about the central body and relative to the first wing.

As can be seen in FIGS. 124*a*, 124*b*, and 124*c*, the sleeve is free to rotate relative to the longitudinal axis of the central body 1210 and thus relative to the first wing 1202 of the embodiment shown in FIGS. 119*a* and 119*b*. The sleeve can rotate relative to a second wing 1208, when the second wing is utilized in conjunction with the embodiment of FIGS. 119*a* and 119*b*. The pins limit the rotation of the sleeve. In an alternative embodiment, the pins are eliminated so that the sleeve can rotate to any position relative to the first wing.

It is to be understood that the sleeve can be comprised of biologically acceptable material such as titanium. Additionally, it can be comprised of super-elastic material such as an alloy of nickel and titanium, much as described hereinabove with respect to other embodiments.

The great advantage of the use of the sleeve 1204 as depicted in the embodiment of FIGS. 119*a* and 119*b* is that the sleeve can be rotated and repositioned with respect to the first wing 1202, and/or the second wing 1208 should the second wing be used in the embodiment, in order to more optimally position the implant 1200 between spinous processes. It is to be understood that the cortical bone or the outer shell of the spinous processes is stronger at an anterior position adjacent to the vertebral bodies of the vertebra than at a posterior position distally located from the vertebral bodies. Accordingly, there is some advantage of having the implant 1200 placed as close to the vertebral bodies as is possible. In order to facilitate this and to accommodate the anatomical form of the bone structures, as the implant is inserted between the vertebral bodies and urged toward the vertebral bodies, the sleeve 1204 can be rotated relative to the wings, such as wing 1202, so that the sleeve is optimally positioned between the spinous processes, and the wing 1202 is optimally positioned relative to the spinous processes. Without this capability, depending on the anatomical form of the bones, it is possible for the wings to become some what less than optimally positioned relative to the spinous processes.

Figure 127:
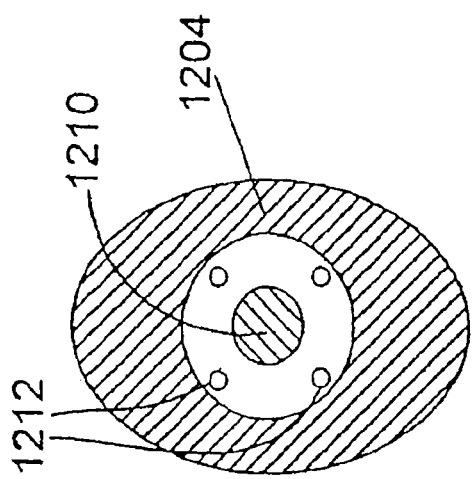
FIG. 127 depicts yet a further embodiment of the invention as depicted in FIGS. 119a and 119b.
Figure 126:
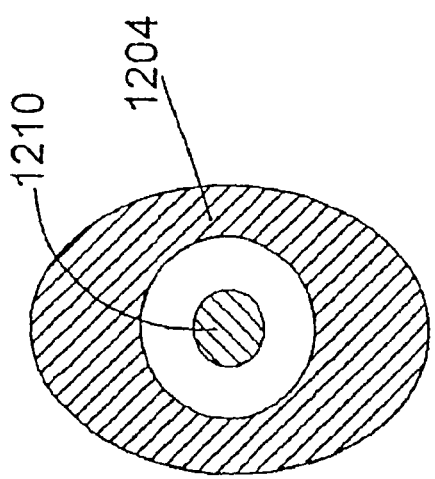
FIG. 126 depicts yet a further alternative embodiment of the invention depicted in FIGS. 119a and 119b.
Figure 125:
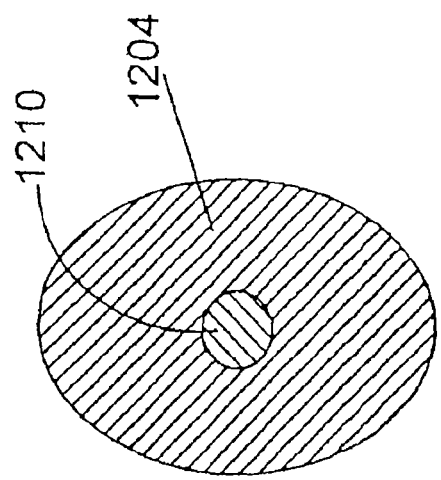
FIG. 125 depicts an alternative embodiment of the invention as depicted in FIGS. 119a and 119b.

Embodiments of FIGS. 125, 126, and 127

FIGS. 125, 126 and 127 depict three alternative embodiments of the invention as can be seen through a line parallel to line 124-124 of FIG. 119*b*.

In FIG. 125, the sleeve 1204 is rotatable about central body 1210. In this embodiment, however, the sleeve 1204 design does not include the grooves 1222 as previously depicted in the embodiment shown in FIG. 123*a*. Thus, without pins, the sleeve is completely free to rotate about the central body 1210.

An alternative embodiment is shown in FIG. 126. In this embodiment, the sleeve 1204 is essentially a thin wall cylinder which is spaced from the central body 1210. Sleeve 1204 is free to move relative to central body 1210. Sleeve 1204 can rotate relative to central body 1210. In addition, sleeve 1204 can take a somewhat cocked or skewed position relative to central body 1210.

A further embodiment, it is shown in FIG. 127. This embodiment is somewhat similar to the embodiment shown in FIG. 126 except that in this case, several pins project from the first wing in order to some what limit and restrict the motion of the sleeve 1204. As shown in FIG. 127, four pins are depicted. It is to be understood however that such an embodiment can include one, two, three, four or more pins and be within the spirit and scope of the invention. It is to be understood that if the embodiment is used with a second wing, that similar pins can extend from the second wing. However, in the embodiment using a second wing, the pins would preferably be somewhat flexible so that they could snap into the inside of the sleeve 1204 as the second wing is inserted relative to the central body and secured in place. In the embodiment shown in FIG. 127, the sleeve 1204 is free to rotate about the longitudinal axis of the central body 1210 and is somewhat restricted in this motion and its ability to become skewed relative to the longitudinal axis of the central body by the pins.

Figure 129:
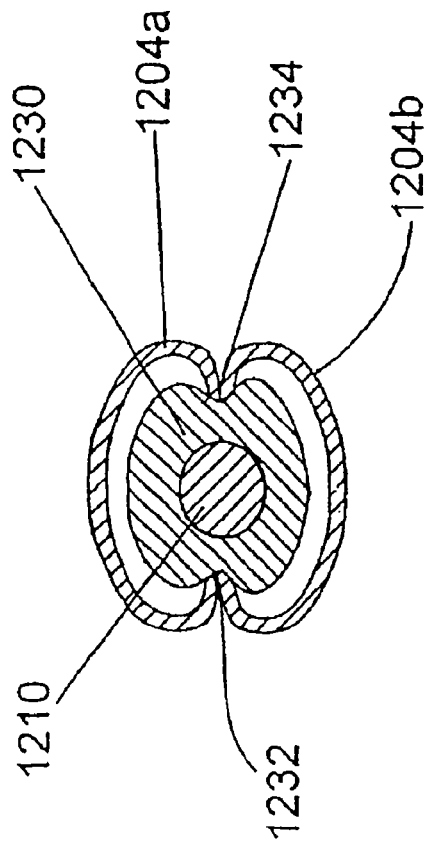
FIG. 129 depicts still a further embodiment of the invention as depicted in FIGS. 119a and 119b.
Figure 128:
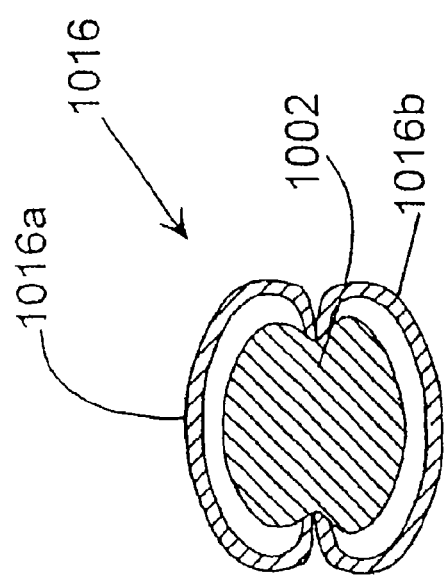

Embodiments of FIGS. 128 and 129

The embodiments of FIG. 128 is an advantageous alternative to that of FIG. 93a. In this embodiment, the central body 1002 is similar to that as shown in FIG. 93a. The sleeve 116 is comprised of two sleeve portions 1016a and 1016b. The sleeve portions are preferably formed from flat stock material which is substantially easier to form than having the sleeve formed or machined from solid bar stock material. A further advantage of the sleeve 1016, if formed of super-elastic material, is that the sleeve can be formed in a manner which optimizes the super-elastic characteristics of such material in order to enhance its ability to repeatedly deflect under load. In this particular embodiment, the sleeve portions 1016a and 1016b are somewhat C-shaped and then after being formed, are snapped into the grooves of the central body 1002.

An alternative embodiment of the invention is shown in FIG. 128. This embodiment is most favorably used with the embodiment of FIGS. 119a and 119b. In this particular embodiment, the sleeve 1204 is designed to rotate about the central body 1210. Sleeve 1204 includes a central member 1230 which includes a bore that receives the central body 1210. The central member 1230 is rotatable about the central body 1210 of the implant 1200. The central member 1230 includes first and second grooves 1232 and 1234. These grooves can receive C-shaped sleeve members 1204a and 1204b. These C-shaped sleeve members are similar in construction and design to the C-shaped sleeve members shown above with respect to FIG. 128. These sleeve members can be snapped into position relative to the central member 1230 of the sleeve 1204. It is to be understood that other mechanisms can be used to secure the C-shaped sleeve member relative to the central member of the sleeve and be within the spirit and scope of the invention. Further, it is to be understood that the sleeve members 1204a and 1204b can be formed from a single flat stock material such that one of the grooves 1232 and 1234 receives continuous piece of flat material which has been appropriately bent and the other grooves receives two ends of the sleeve.

Embodiments of FIGS. 130-136

Figure 130:
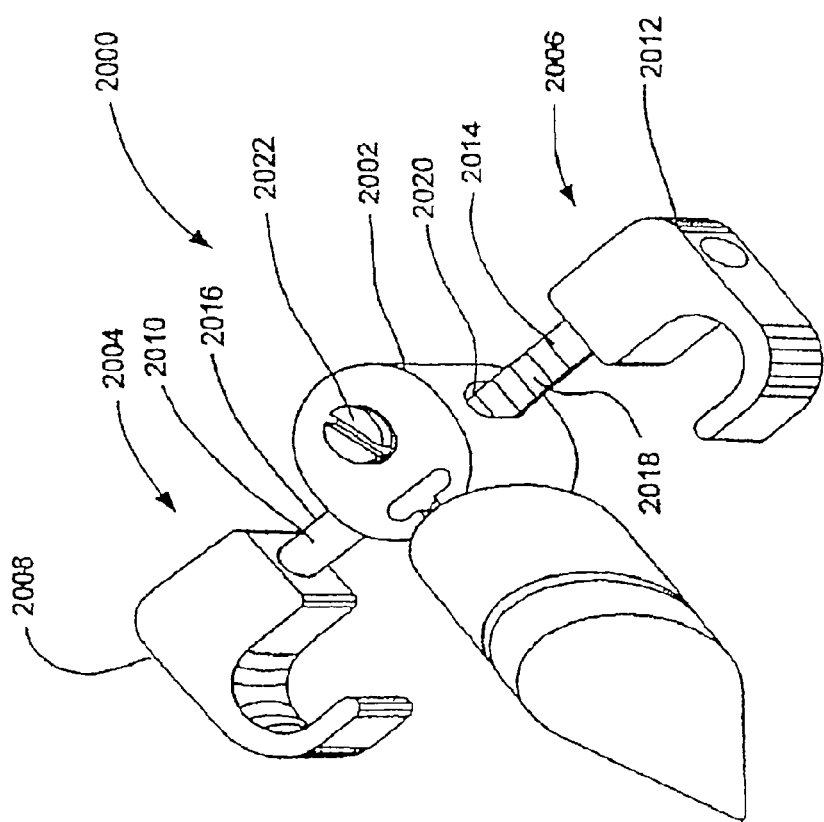
FIG. 130 is a perspective view of a first embodiment of the invention.
Figure 131:
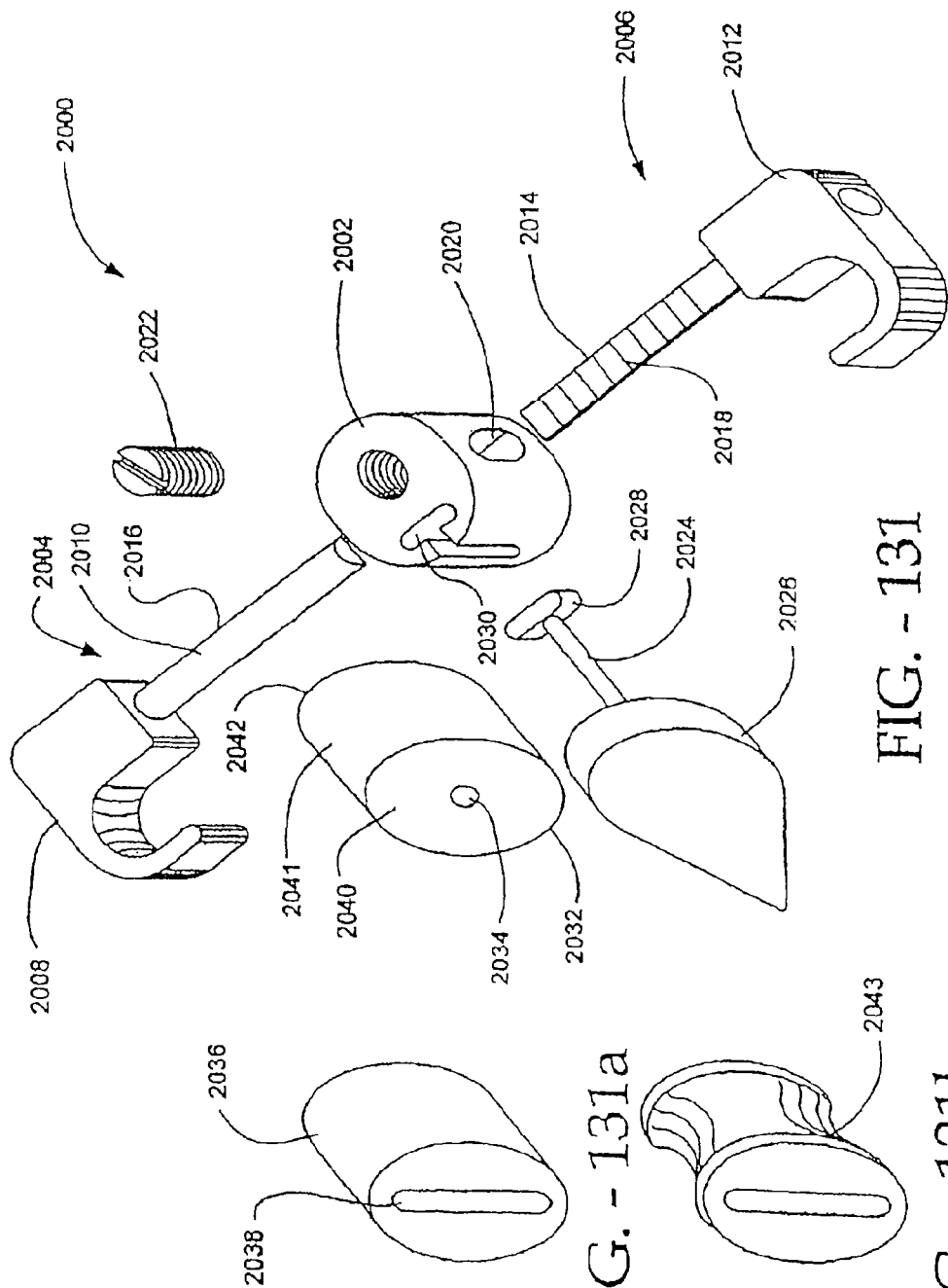
FIG. 131 is an exploded view of the embodiment of the invention of FIG. 130.
Figure 132:
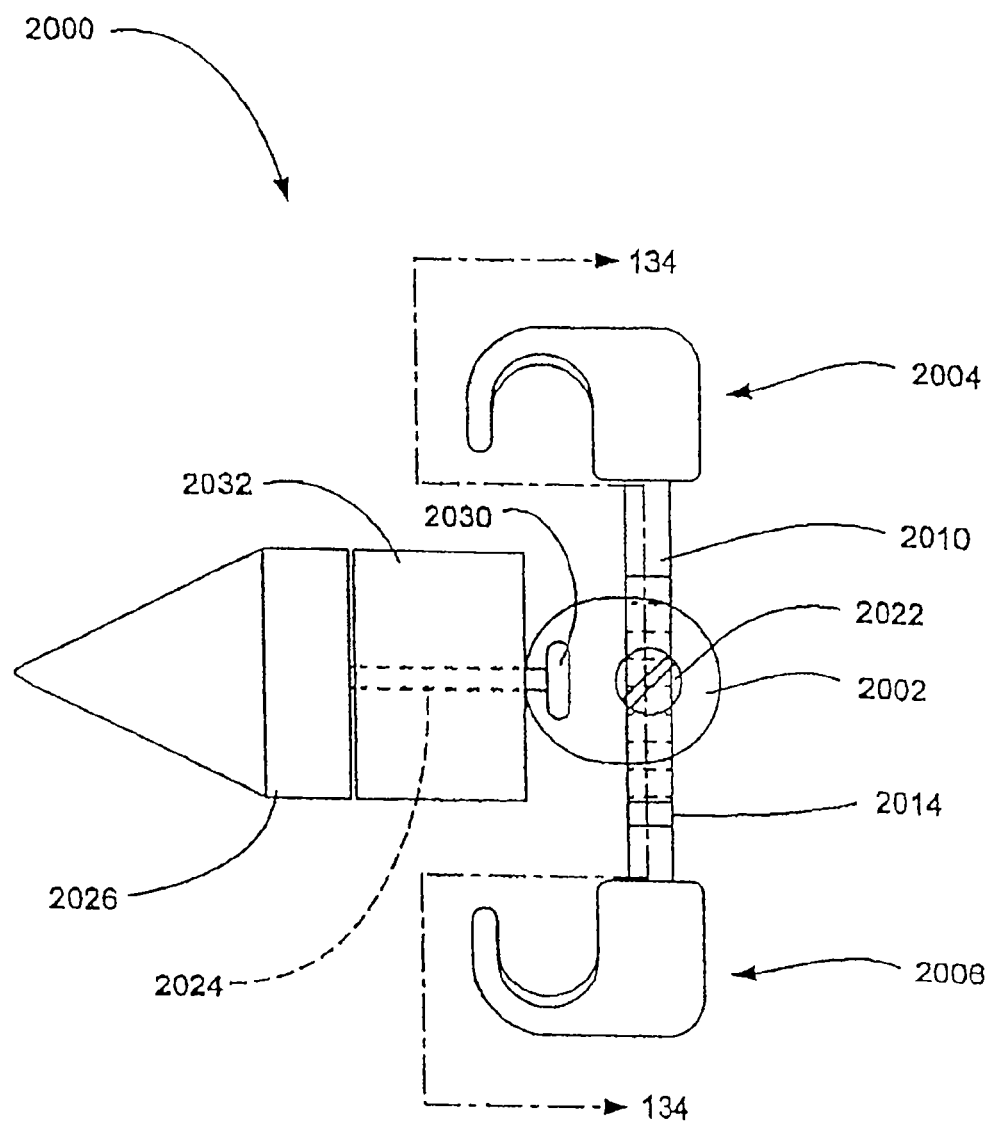
FIG. 132 is a plan view of the embodiment of the invention of FIG. 130.
Figure 133A:
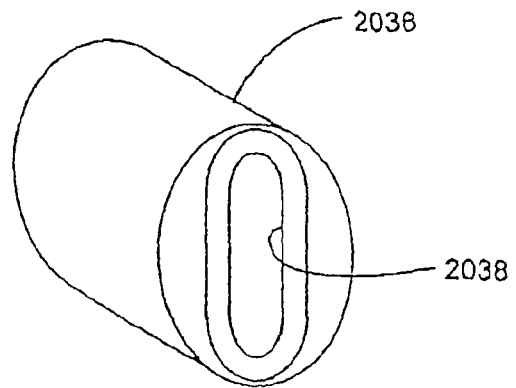
FIGS. 133a, 133b, 133c, and 133d are perspective, first end, second end, and sectional views of a spacer or sleeve of the embodiment of the invention depicted in FIG. 130.
Figures 133B, 133C:
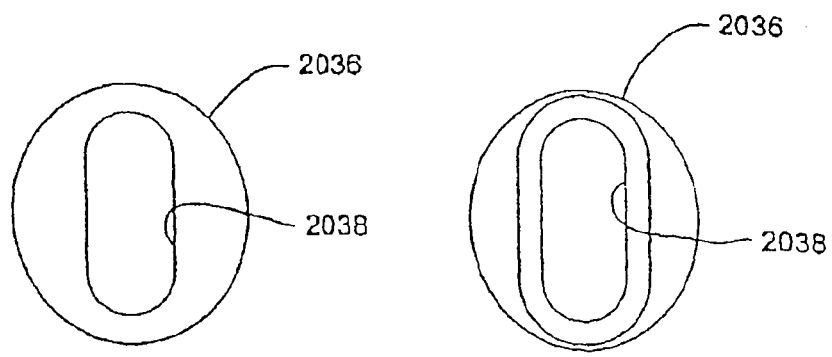
Figure 133D:
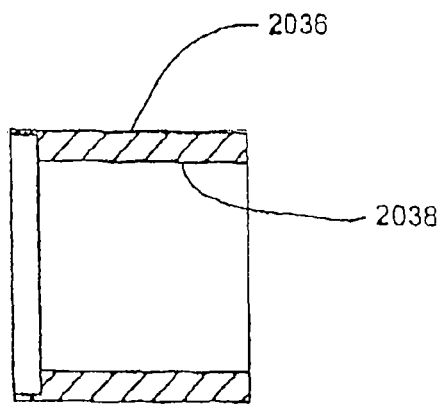
Figure 134:
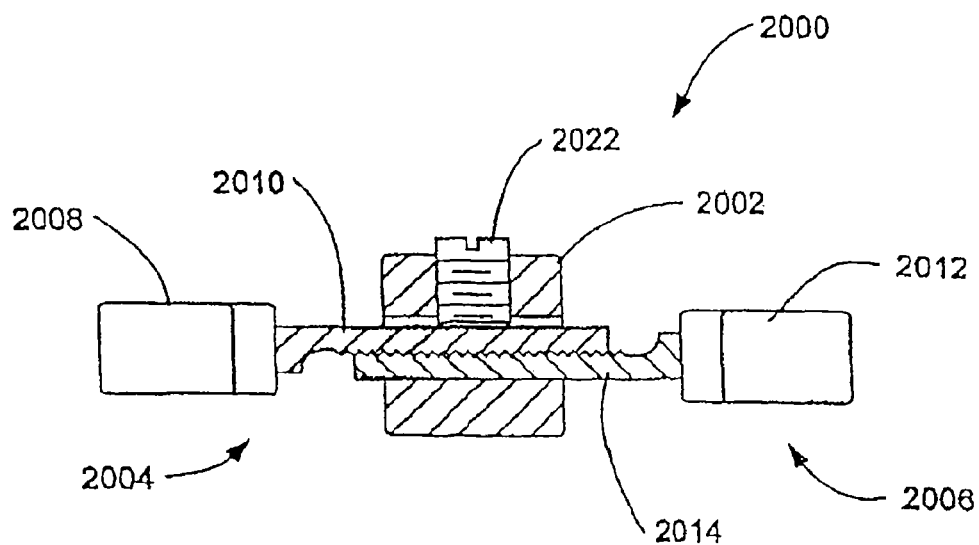
FIG. 134 is a cross sectional view of an embodiment of the invention taken through line 134-134 in FIG. 132.

Embodiment 2000 of the supplemental spine fixation device of the invention is depicted in FIG. 130. This embodiment 2000 includes a hub 2002 to which is adjustably secured a first hook member 2004 and a second hook member 2006. First hook member 2004 includes a hook 2008 which is more fully described hereinbelow, and a shaft 2010 extending therefrom. Similarly, second hook member 2006 includes a hook 2012 and a shaft 2014 extending therefrom. As described more fully hereinbelow, hook 2008 is swivelly or pivotably mounted to shaft 2010. It is to be understood that the description and functionality of first hook member 2004 applies equally well to that of second hook member 2006. The shaft 2010 in this embodiment includes a rack 2016 which can mate selectively with rack 2018 of hook member 2006. These two racks 2016 and 2018 interlock in a multitude of positions in order to adjust the position of first and second hook members 2004 and 2006, relative to each other and relative to the hub 2002. The shafts 2010 and 2014 are positioned through bore 2020 in the hub 2002, selectively interlocked together and are then lockingly positioned using a locking mechanism such as the screw 2022. As is described more fully below, the hooks 2008 and 2012 are designed and shaped to fit around spinous processes. Further, the hooks 2008 and 2012 are swivelly mounted to the shafts 2010 and 2014 in order to accommodate the various sizes, shapes, and positions of spinous processes of the human population.

Movably mounted to the hub 2002 is a shaft 2024 (FIG. 131) and extending from the shaft 2024 is an inter-spinous process guide 2026. The shaft 2024 at a proximal end includes a crossbar or tab 2028 which is slidingly or movingly received in a slot 2030 of the hub 2002. Once the tab 2028 is received in the slot 2030, the slot can be pinched off or slightly deformed at its open end using a punch or other mechanism in order to prevent the tab 2028, and thus the shaft 2024 and the guide 2026 from being removed from the hub 2002. With the tab 2028 located in the slot 2030, the shaft and also the guide 2026 extending from the distal end of the shaft 2024 are free to move relative to the hub and also relative to the first hook member 2004 and the second hook member 2006. This movement, as well as the ability of the hooks 2008 and 2012 to swivel on the shafts 2010 and 2014, allow the embodiment 2000 to conform to the spinous process anatomy.

Movably mounted on the shaft 2024 is a spacer or sleeve 2032. Spacer 2032 includes a central bore 2034 through which the shaft 2024 extends. The spacer 2032 is thus able to rotate about the shaft 2034. The spacer 2032 is cylindrical and in this particular embodiment is oval or elliptical in shape. In addition, the base of the guide 2026 is also somewhat elliptical in shape in order to make a smooth transition between the guide 2026 and the spacer 2032 as the guide and spacer are inserted between the spinous processes in order to distract apart the spinous processes during the insertion process. As the spacer 2032 is rotatable on the shaft 2024, and as the spacer 2032 is elliptically shaped, it can be inserted in one position and then as the entire embodiment 2000 is positioned to the final securing position, the spacer 2032 can rotate about the shaft 2024 to accommodate the shape of the space between the spinous processes as the spacer is moved from a posterior position to an anterior position.

The spacer 2032 can include a second alternative spacer embodiment 2036 (FIG. 131a) in substitution for the spacer 2032. Spacer 2036 includes an elongated slot 2038 into which the shaft 2024 can be received. Elongated slot 2038 not only allows the spacer 2036 to rotate about the shaft 2024, it also allows it to translate relative to shaft 2024. Such translation in this embodiment is substantially perpendicular to the shaft, in any direction to which the spacer 2036 is rotated. Thus, in this embodiment the degrees of freedom which accommodate the anatomical shape of the spinous processes and the space therebetween, including the ligaments and tissues associated therewith, include (1) the ability of the hooks 2004, 2006 to swivel on the shafts, (2) the ability of the hooks 2004, 2006 to move relative to the hub 2002 and be locked to the hub, (3) the ability of the shaft 2024 to move in the slot 2030 of the hub, and (4) finally the ability of the spacer 2036 to both rotate and translate on the shaft 2024.

Before proceeding to more specific details of this embodiment 2000, it is to be understood that the same features of the spacer, the shaft, and the lead-in guide, which are found in other embodiments such as by way of example only, the embodiments of FIGS. 10, 16, 20, 22, 86, 88, 92, and 119b, and other figures, can be incorporated into this embodiment. By way of example only, the implant 2000 can be comprised of stainless steel, titanium or other biologically acceptable materials. The shape of the lead-in plug can be cone shaped, pyramid shaped, and other shapes with a small lead-in cross-section expanding into a larger cross-section which is similar to the cross-section of the spacer 2032, in order to gradually distract apart the spinous processes to a sufficient distance so that the spacer 2032 or the spacer 2036 can conveniently fit between the spinous processes. Further, the spacer, as shown in the other embodiments, can include a spacer made of stainless steel or titanium, or of a super-elastic material or of a silicone. The spacer besides being cylindrical can, from parallel planar end 2040 to parallel planar end 2042, be saddle-shaped along surface 2041 so that the ends are high and the center portions are low in order to more fully accommodate the shape of the spinous processes and also to spread the load across a broader contact surface between the spinous processes and the spacer. For example, the spacer 2032 could have a shape such as the saddle shape defined by the mated together components of the embodiment of FIG. 16. Further, the dimensions of this embodiment as applied to the guide 2006 and the spacer 2032 can be acquired from other embodiments presented herein.

The shape of the guide 2026 and the spacer 2032 is such that for purposes of insertion between spinous processes, the spinous processes to do not need to be altered or cut away in any manner in order to accommodate this implant. Further, the associated ligaments do not need to be cut away and there would be very little or no damage to the other adjacent and surrounding tissues. Similarly, the hook members 2004, 2006, are appropriately shaped and also pivotable so that alteration of the spinous process is not required.

Returning to FIGS. 135a-135f and FIG. 136, the design of the hook members 2004 and 2006 are more fully depicted and described. As indicated above, the description will be made with respect to first hook member 2004. This description applies equally to second hook member 2006. As can be seen in FIG. 135b, the first hook member 2004 includes a shaft 2010 which is received in a bore 2044 of the hook 2008. This bore receives a rounded ball end 2046 seated against a somewhat circular seat 2048. A screw 2050 (FIG. 135f) is received in the bore 2044 in order to retain the rounded ball end 2046. The other end of the bore 2044, end 2052, as can be seen in FIG. 135f is oval or elliptical in shape. This allows the hook 2008 to swivel side to side on the shaft 2010 in order to accommodate the spinous process while somewhat restricting the back and forth rocking of the hook 2008 relative to the shaft 2010. This freedom of motion can be seen in FIG. 136 with respect to the upper spinous processes 2054. The hook can swivel side to side in order to accommodate the shape of the upper spinous processes 2054. The lower hook 2006 additionally can move in order to accommodate the lower spinous processes 2056. As can be seen in FIGS. 135c and 135d, the hook 2008 can swivel about 15°. on either side of a central longitudinal axis of the shaft 2010.

Figure 135A:
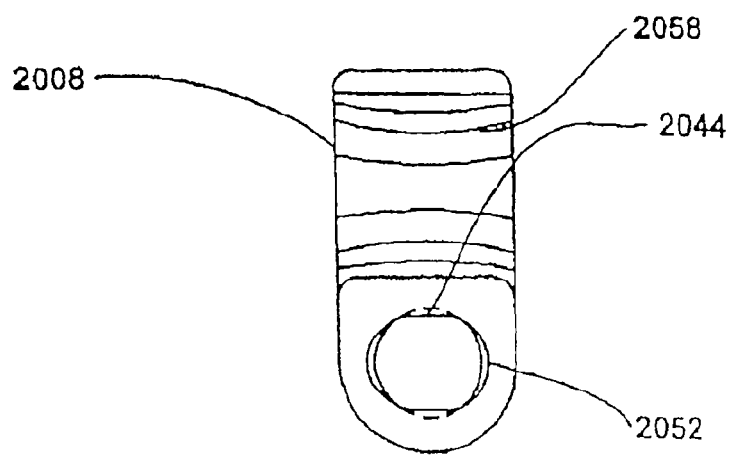
FIGS. 135a-135f are various views of an embodiment of the hook mechanism of the embodiment of the invention of FIG. 130.
Figure 135B:
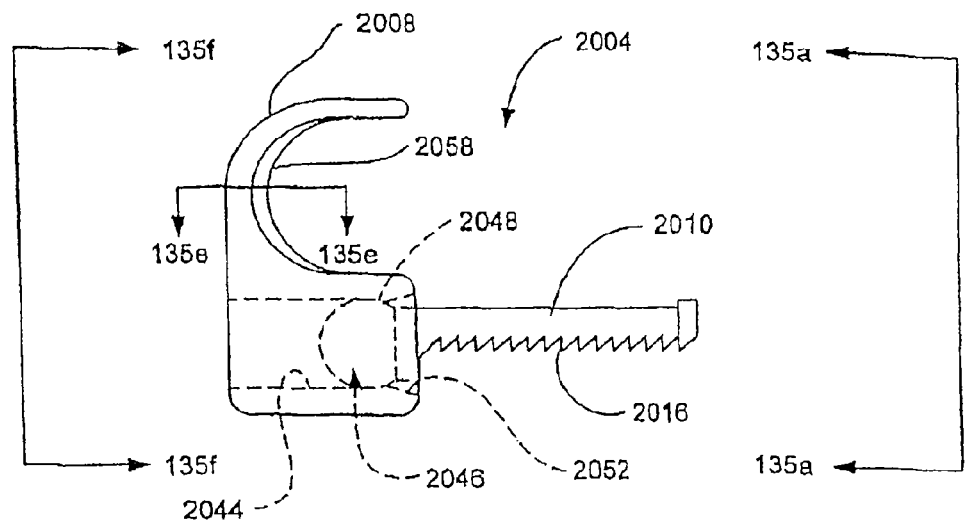
Figure 135C:
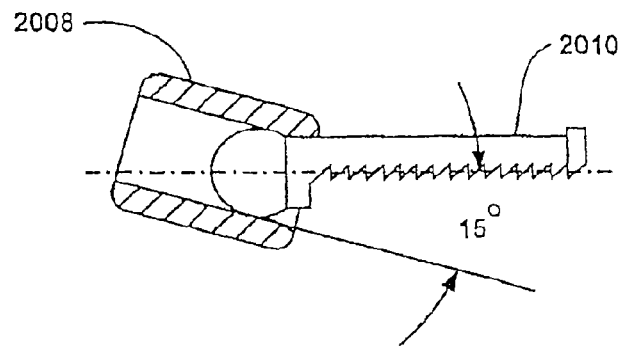
Figure 135D:
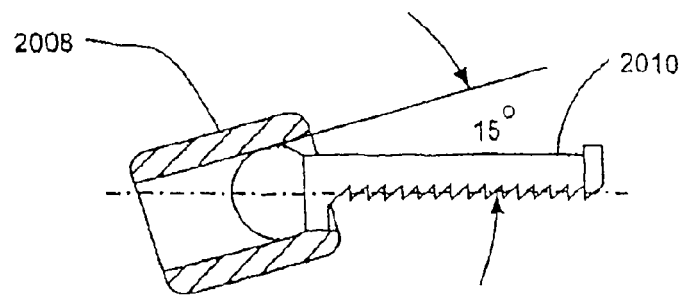
Figure 135E:
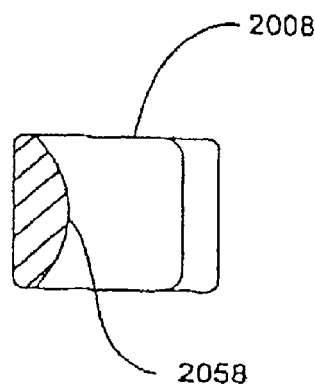
Figure 135F:
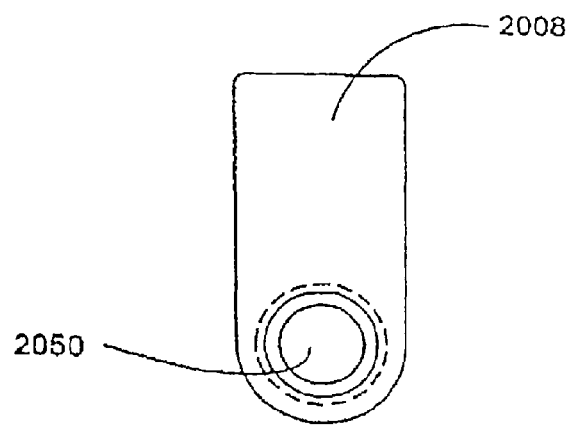

Additionally with respect to the hook 2008, as can be seen in FIGS. 135a, 135b, and 135e, the hook includes a convex inner surface 2058 in order to accommodate the varying surface shape of the spinous processes, and in order to even out the load transferred between the hook and the spinous processes.

Figure 136:
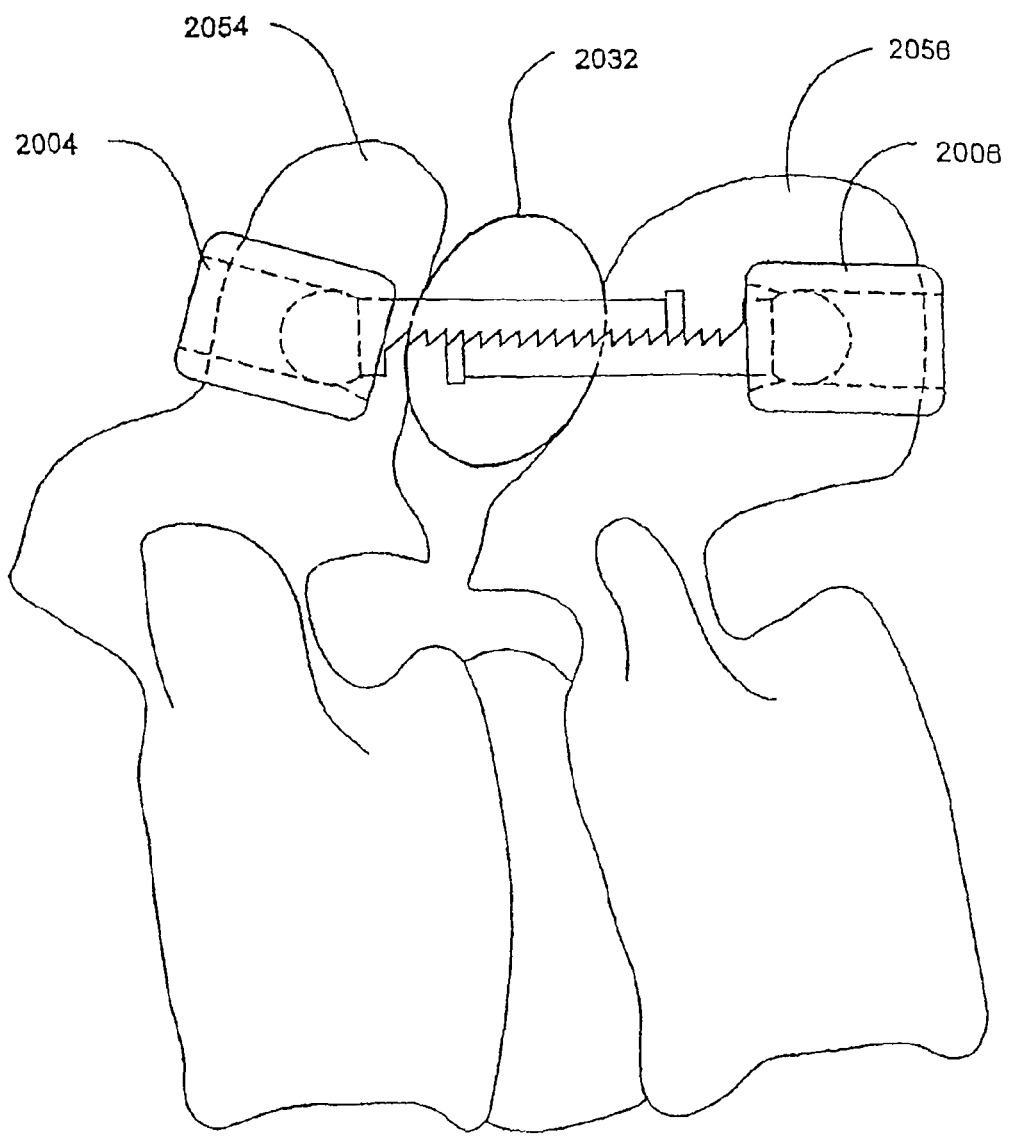
FIG. 136 is a schematical representation of an embodiment of the invention as positioned with respect to adjacent spinous processes.
Figure 137:
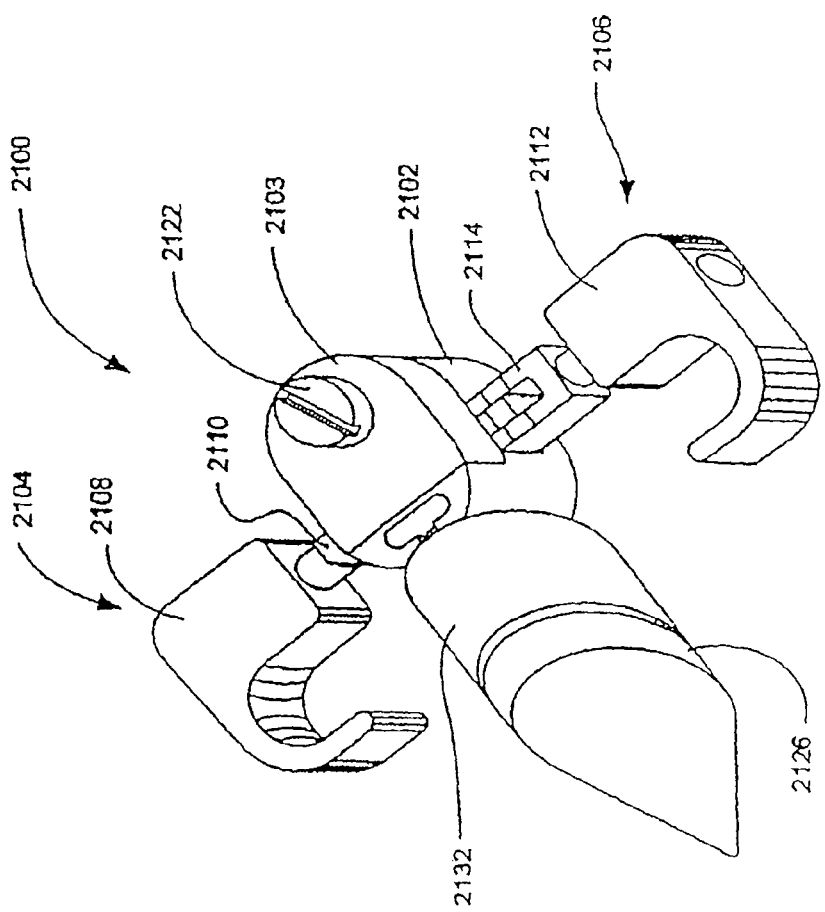
FIG. 137 is a perspective view of another embodiment of the invention.

The embodiment 2000 can be implanted in a number of methods, preferably, once a spine fixation device is implanted between the vertebral bodies. In this particular embodiment, through a small incision the hub, spacer, and guide are inserted with the guide and spacer inserted between the spinous processes. Once this is accomplished, a first hook member and then a second hook member is secured about the respective spinous processes. The shafts of the hook members are then inserted through the bore of the hub 2002 until the spinous processes are brought tight against the spacer. The hooks are appropriately positioned on the spinous processes as depicted in FIG. 136. After this has been accomplished, the securing mechanism 2022 is tightened in order to lock the hooks in place and to secure the spinous processes in a rigid manner relative to each other and relative to the distracting spacer 2032. Alternatively, the spinous ligaments can hold the spinous processes tightly against the spacer and the hooks can be moved and locked into tight contact with the spinous processes.

The above procedure can have variations. By way of example only, the hooks can be inserted first through the incision and then the guide, spacer and hub can be inserted. Once this is accomplished the hooks can be mated to the hub.

In another embodiment and method not depicted, the physician can insert the shaft 2024 on which the spacer 2032 is mounted into the slot 2030 of the hub 2002 and can close off the slot with a securing screw in order to retain shaft 2024. This process is in contrast to the shaft being secured in the slot during the manufacturing process. The securing screw would be similar to securing screw 2022 and would be placed in a bore made at the top of slot 2030. The physician could accordingly insert the tab 2028 of the shaft 2024 in the slot 2030, and then secure the tab in place with the securing screw.

Still an alternative method would be for the device 2000 to be inserted through a larger incision, with device 2000 fully assembled. Once inserted the screw 2022 could be loosened so that the hook members could be positioned around spinous processes at about the same time that the guide and spacer are inserted between the spinous processes. Once this is accomplished, the spinous processes could be drawn down tightly around the spacer, with the hooks tightly around the spinous processes and secured firmly into the hub 2002 with the securing screw 2022.

In all of the above procedures, it is advantageous that the device 2000 can address the adjacent spinous processes from one side of the spinous processes and not require exposure of both sides of the spinous processes and thus the procedure is less traumatic to the surgical site.

Still an alternate insertion method would be to insert the device fully assembled with the hook rotated at 90° to the final position shown in FIG. 130. Once the hooks are positioned adjacent to the spinous processes, the hooks could be rotated to the position shown in FIG. 130. Then simultaneously the guide and spacer could be inserted between the spinous processes, as the hooks are positioned about the spinous processes. The hooks are then drawn together, causing the spinous processes to be held firmly against the spacer. Once this is accomplished the screw 2022 can be securely fastened to the hub 2002.

With respect to the embodiment of FIG. 130, this embodiment as fully described above can be used as a supplemental fixation or augmentation device for the lumbar level fusion of the L4/L5 vertebrae and above vertebrae, and also for the L5/S1 and below vertebrae. Thus, this device 2000 can be used with respect to fusion of any of the vertebrae up and down the spinous processes.

Embodiments of FIGS. 137-140

Figure 138:
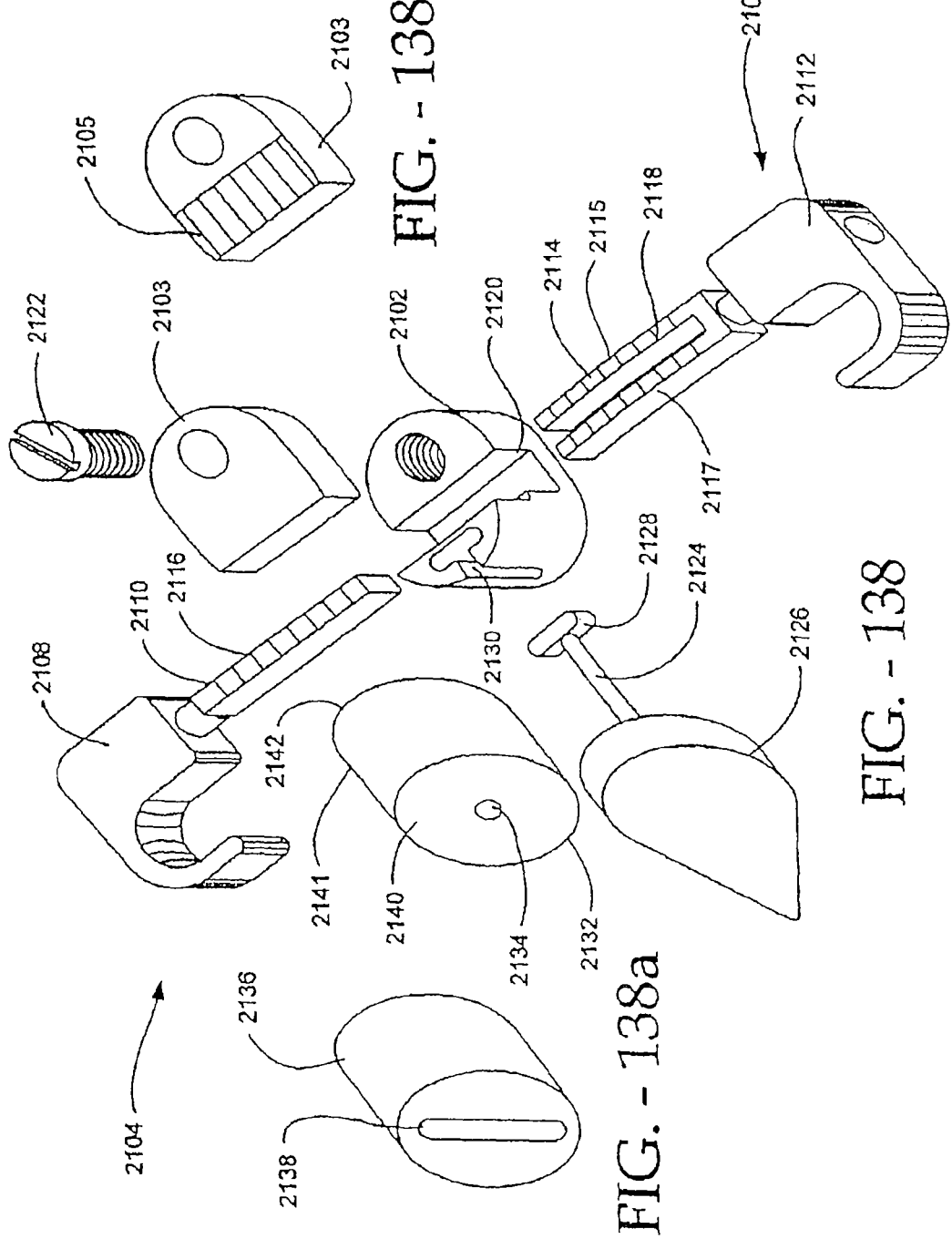
FIG. 138 is an exploded view of the embodiment of the invention of FIG. 137.
Figure 139:
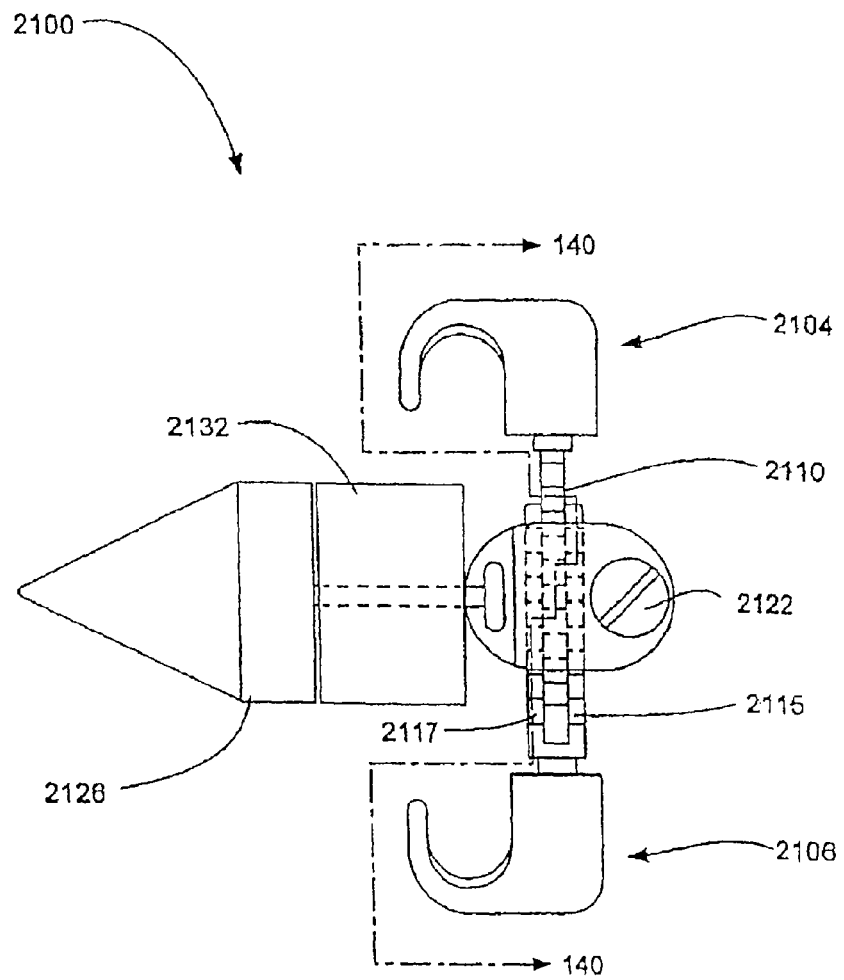
FIG. 139 is a plan view of the embodiment of the invention of FIG. 137.
Figure 140:
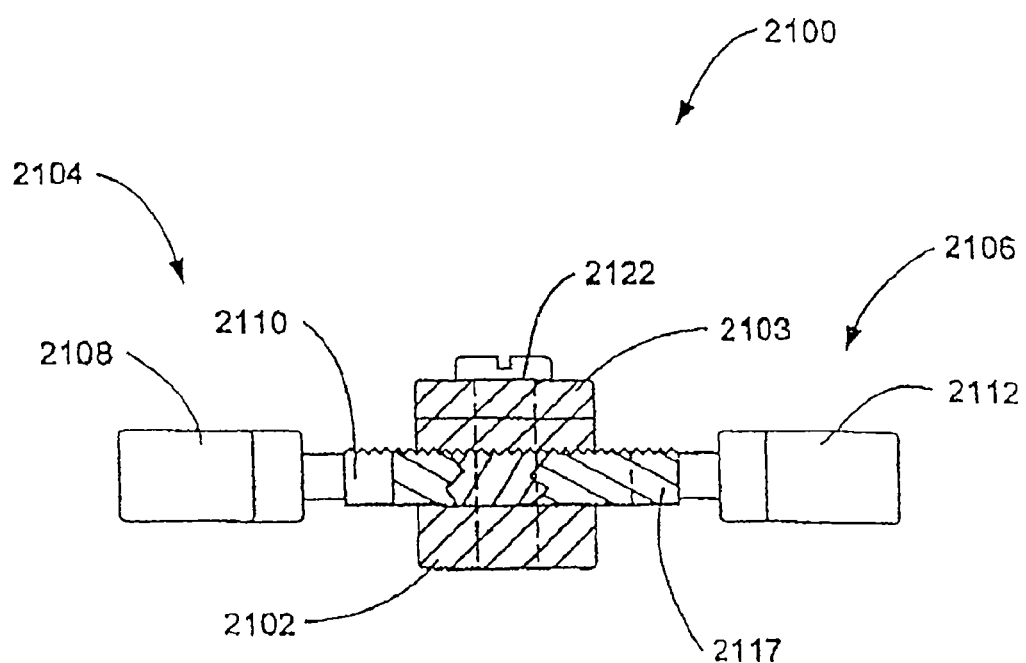
FIG. 140 is a partial section view taken through line 140-140 of FIG. 139.

Another embodiment 2100 of the invention can be seen in FIGS. 137-140. Components and features of this embodiment 2100 which are similar to components and features of the embodiment 2000 have similarly least significant digits. Thus the hub for embodiment 2100 would be 2102. The main difference between the embodiment 2100 and the previously described embodiment 2000 is directed to the hub 2102 and the shafts 2110 and 2114. In this embodiment, the shafts 2110, 2114 are substantially rectangular in cross-sections as opposed to semi-circular as in the previous embodiment of FIG. 130. As can be seen in FIG. 138, shaft 2110 is substantially rectangular in cross-section and include rack or teeth 2116. Shaft 2114 is shaped as a fork with two tines 2115 and 2117. Further, the two tines have rack or teeth 2118. The shaft 2110 of the first hook member 2104 slides between the two tines 2115 and 2117. As can be seen in FIG. 139, with the shaft 2110 slipped between the two tines 2115, 2117 and also with shafts 2110, 2114 located in the rectangular bore 2120 of the hub 2102, the top cap 2103 (which is shown both from the top side (FIG. 138) and from the bottom side (FIG. 138b)) can be placed over the hub 2102. The teeth or rack 2105 on the bottom side of the cap 2103, mesh with the teeth or rack 2116 and 2115, 2117 of the first and second hook members. Once this is accomplished, the screw 2122 can be inserted through the indicated bore so that the cap 2103 can tighten down on the hub 2102, locking the shafts 2110 and 2114 of the first and second hook members in place.

All the other features, dimensions, characteristics, materials, methods of insertion, and methods of operation of the embodiment shown in FIG. 138 are similar to or derivations from that shown in the embodiment of FIG. 130.

Figure 141:
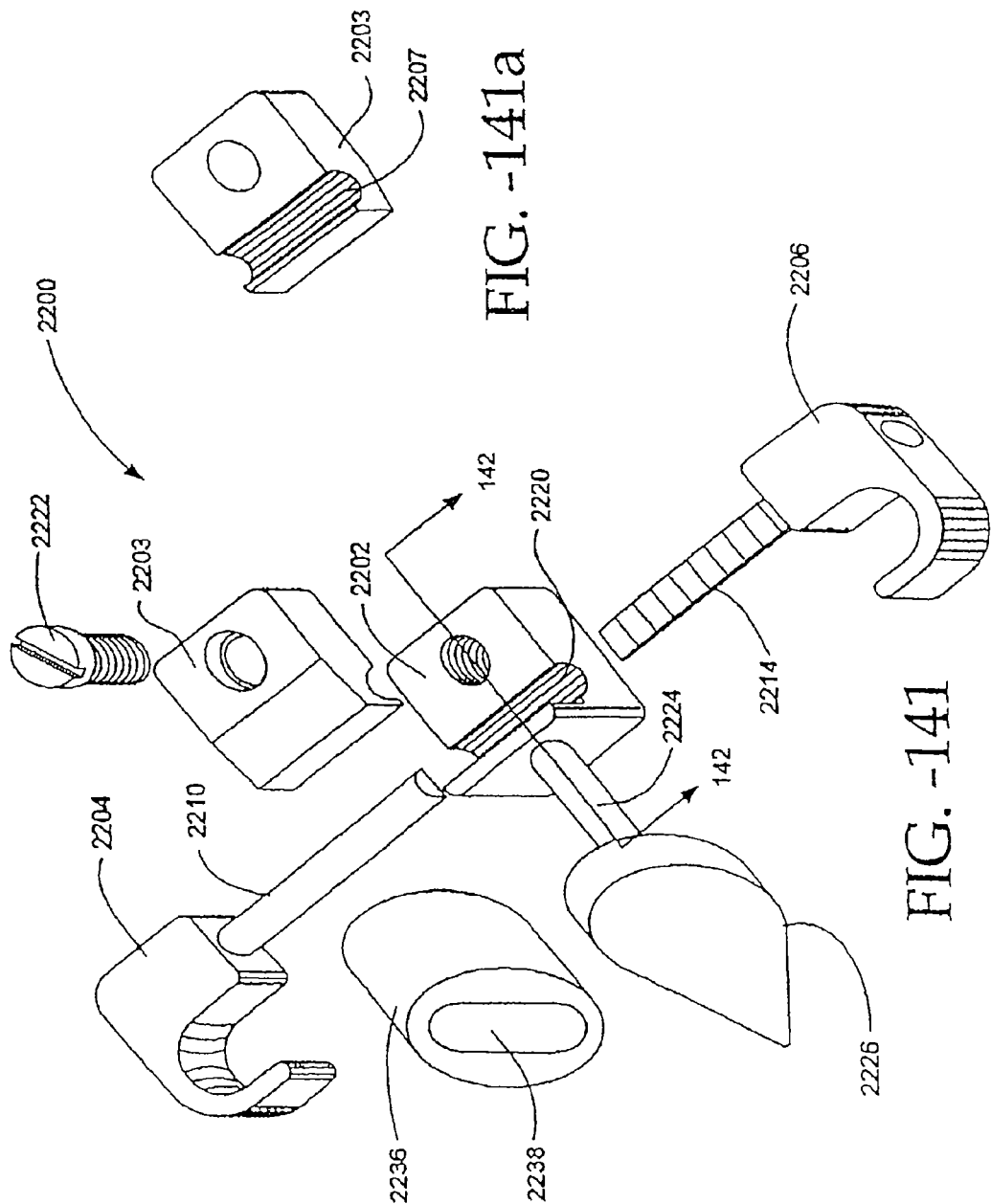
FIG. 141 is an exploded view of yet another embodiment of the invention.
Figure 142:
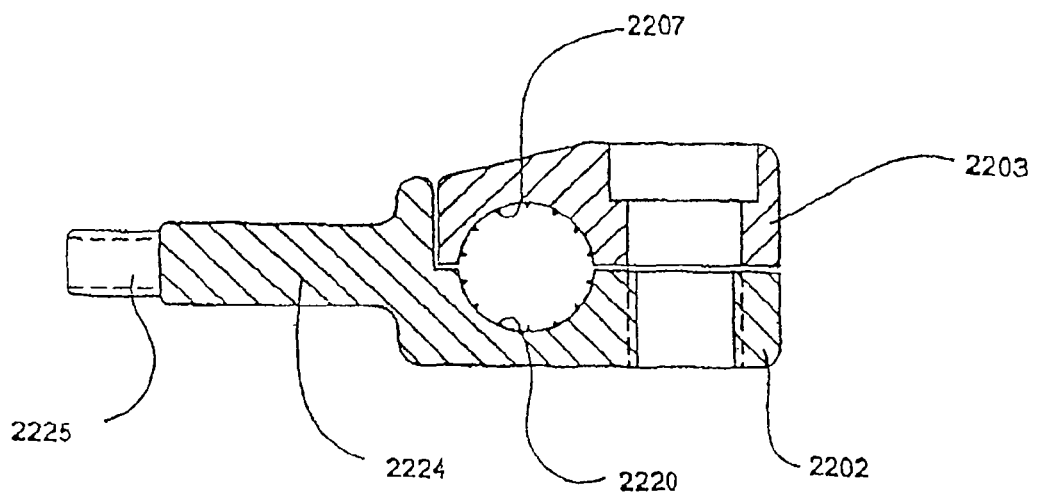
FIG. 142 is a sectional view of a body portion of the embodiment of the invention of FIG. 141 taken through line 142-142.
Figure 143:
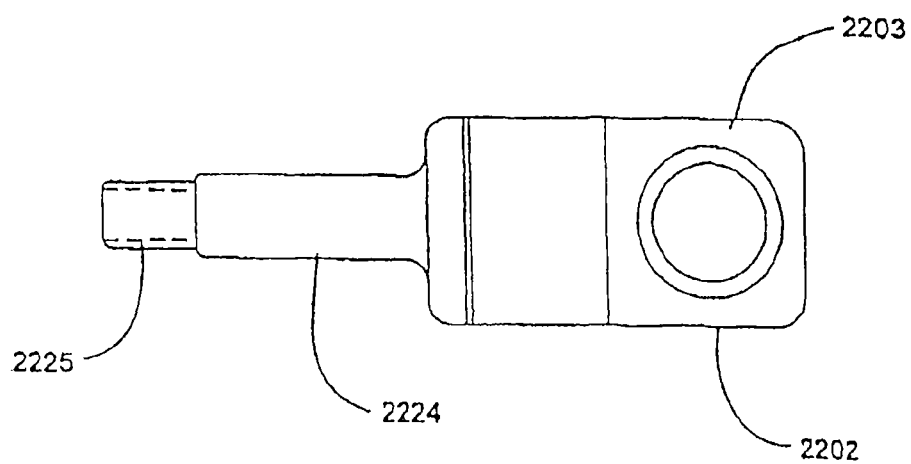
FIG. 143 is a top view of the body portion shown in FIG. 142.

Embodiments of FIGS. 141-143

Another embodiment of the invention is depicted in FIGS. 141-143. This embodiment is similar to the other embodiments 2000 and 2100. This embodiment is numbered 2200. Similar elements, features, methods and aspects have similar numerical designations with respect to the lowest two significant digits. Thus the hub of embodiment 2200 is identified as hub 2202.

In this particular embodiment, the hub has rigidly affixed thereto shaft 2224. Here shaft 2224 does not slide in a slot as happens with respect to the prior two embodiments 2000 and 2100. Shaft 2224 can be screwed into hub 2202 or integrally formed with hub 2202. Additionally, the guide 2226 can be integrally formed with the shaft 2224 or in other manners fastened to the shaft 2224 as with a thread mechanism. In this particular embodiment, as can be seen in FIG. 143, the shaft 2224 is integrally formed with the hub 2202 and the shaft 2224 includes a threaded extension 2225 onto which is screwed the guide 2226. For this particular embodiment, the sleeve or spacer 2236 includes the elongated slot 2238 in order to provide for freedom of movement between the sleeve or spacer 2236, the hub 2202, and the first and second hook members 2204 and 2206.

In this particular embodiment the shaft 2210 and 2214 are similar to those depicted with respect to the embodiment 2000. In other words each has a rack or teeth which mate with the other. Shafts 2210 and 2214 are inserted through the semi-circular bore 2220 of the hub 2202, and then the cap 2203 is mated on top of the hub 2202. The cap includes a semi-circular bore 2207 which is positioned over the upper shaft 2210. Both bores 2207 and 2220 include ribs, teeth, or threads that run along the length of the bores. These ribs, teeth, or threads are urged against the shafts in order to assist in locking the shafts in place. Alternatively, the ribs, teeth, or threads of the bores can be across the length of the bores. The shafts 2210 and 2214 can have teeth, ribs, or threads that are positioned all about the shafts so that the shafts can lock to each other, and so that the teeth, racks or threads on the bores can lock the shafts in place. Once the cap 2203 is positioned over the hub 2202, the screw 2222 is positioned in the bore of the hub 2202 in order to lockingly position the first and second hook members 2204 and 2206 relative to the hub. In particular, with respect to embodiment 2200, the degrees of freedom are attributable to (1) the slot 2238 in the spacer 2236, (2) the shafts 2210 and 2224 which can be positioned relative to each other to position the hooks 2204 and 2206 relative to the hub, and accordingly relative to the spacer, and (3) the ability of the hooks 2204 and 2206 to swivel or pivot.

As indicated above, all the other features, materials, aspects, dimensions, and so forth, of the embodiment 2200 are similar to and can be specified according to the other embodiments 2000 and 2100.

A preferred method of insertion of this embodiment 2200 into a patient is as follows. Initially through a small incision the guide, spacer and hub are inserted so that the guide is positioned between and distracts apart adjacent spinous processes, allowing the spacer to come between the spinous processes. The spacer and guide can be moved in a posterior to anterior direction, and the spacer is able to rotate and translate in order to accommodate such movement. After this is accomplished, the first and second hook members are positioned through the incision and around upper and lower spinous processes. Once that is accomplished, the spinous processes are urged towards each other and about the spacer, if this is not already the condition caused by the insertion of the spacer in order to distract the spinous processes. Then the racks of the shafts are meshed together, and the cap is placed upon the hub in order to secure the hooks firmly to the hub and thus to secure the spinous processes rigidly in position about the spinous processes.

Embodiments of FIGS. 144-146c

Figure 144:
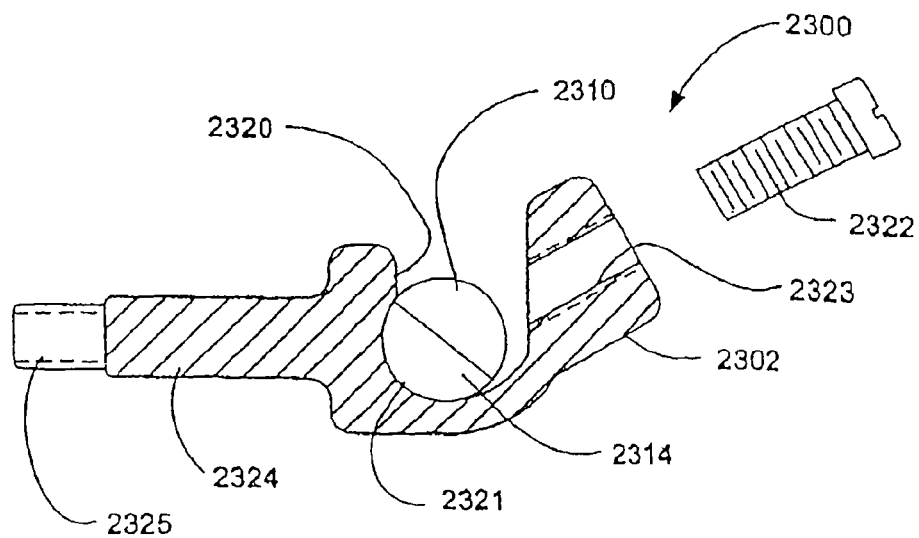
FIG. 144 is a sectional view of yet another embodiment of a body portion of the invention.

A further embodiment 2300 of the invention is depicted in FIG. 144. In FIG. 144, the hub 2302 of this embodiment is depicted. This hub could be used, for example, with the embodiment shown in FIG. 141 and similar components are similarly numbered. In this embodiment, the hub 2302 includes an integral shaft 2324 with a threaded end 2325 which can accept a guide such as guide 2226 of FIG. 141. Unlike the embodiment in FIG. 141, this hub 2203 does not have a cap. Instead hub 2302 includes an open bore 2320 which is shaped in order to receive shafts 2310 and 2314, which have mating notches or teeth. Bore 2320 has a portion 2321 which is circular and which receives the mated shaft 2310, 2324.

Once this is accomplished, a screw 2322 is received in the threaded bore 2323 in order to lockingly position the mated shafts 2310, 2324. As this embodiment has an open bore 2320 and no cap, mating of the shafts 2310, 2314 to the open bore 2320 of the hub 2302 can be done quickly and efficiently.

Figure 145:
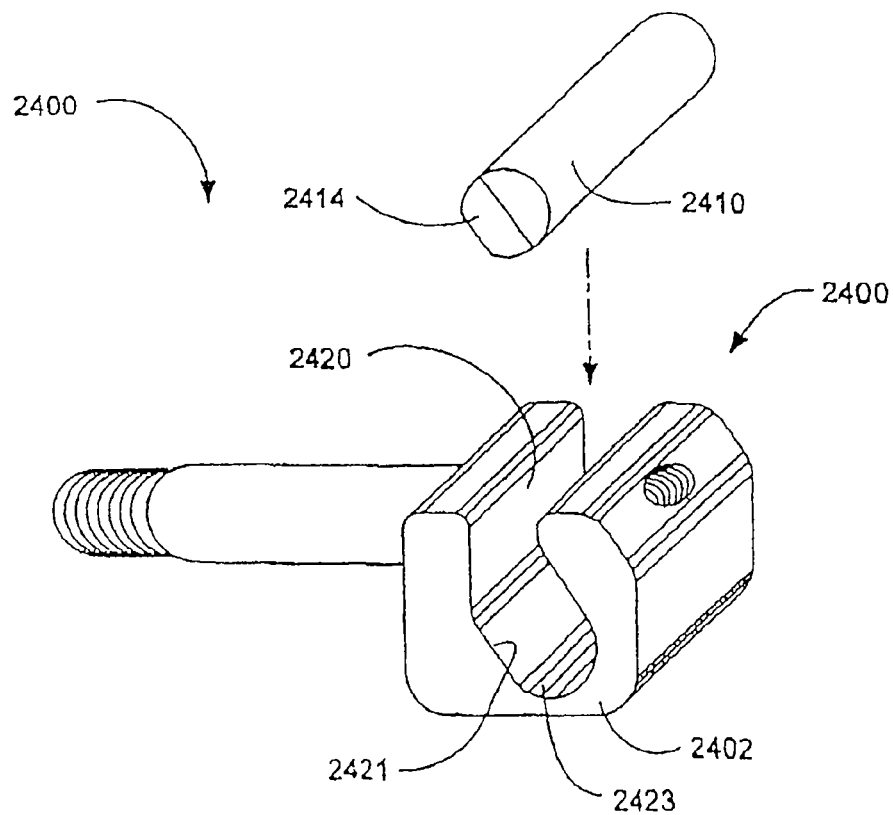
FIG. 145 is a perspective view of yet a further embodiment of the body portion of the invention.

FIG. 145 shows a hub 2402 of an embodiment 2400. This hub 2402 is similar to hub 2302, with the open bore 2420 having a shape which is different from the shape of bore 2320. In this embodiment bore 2420 includes a flat 2421 and a circular portion 2423. The shafts 2410 and 2414 when mated together would register in this open bore 2420. In particular, shaft 2414 has a flat which mates to flat 2421 and the combined shafts 2410 and 2424 have a circular portion which would mate to the circular portion 2423 of the bore 2420. Otherwise, hub 2202 would function similarly to hub 2302.

Figure 146A:
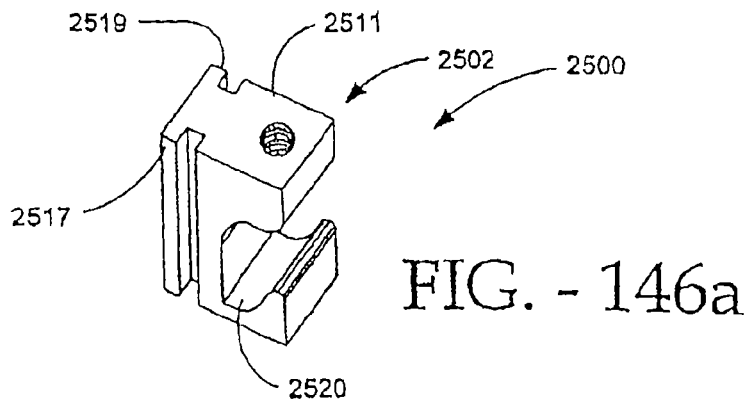
FIGS. 146a, 146b, and 146c depict yet a further embodiment of a body portion of the invention.
Figure 146B:
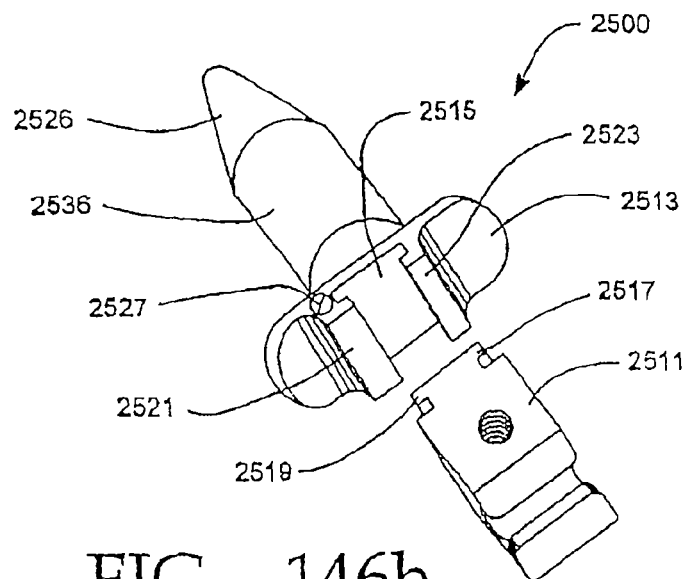
Figure 146C:
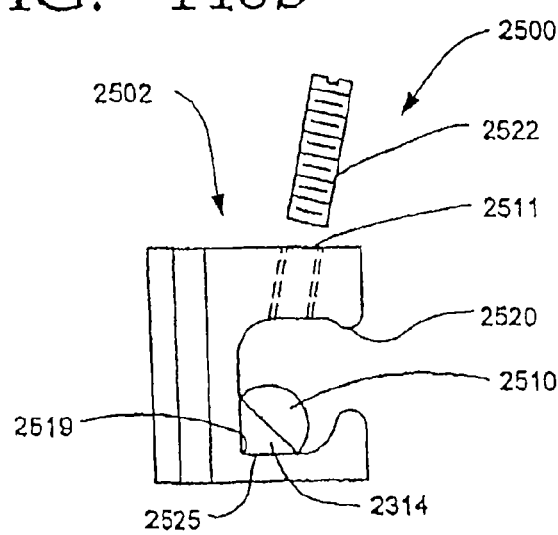

FIGS. 146a, 146b, and 146c depict a hub arrangement 2502 of an embodiment 2500 of the invention. In this embodiment, hub 2502 has two components 2511 and 2513. Component 2511 includes an open bore 2520 which is specially shaped in order to register shafts 2510, 2514 of the first and second hook members. In this particular embodiment, shaft 2510 is semi-circular in cross-section while shaft 2514 is triangular-shaped in cross-section. The triangular shape of shaft 2514 mates with the corner 2525 of the open bore 2520.

The term open bore refers to 2520 and also to bores 2320 and 2420 in FIGS. 144 and 145, and means that not only are both ends of the bore open, but there is a longitudinal slot along the length of the bore which is open, allowing access to the bore from the side of the bore. Once the shafts 2510, 2514 are inserted as shown FIG. 146c, a screw 2522 can be tightened through a bore of the hub 2502, locking the shafts in place. Once this has occurred, the first portion 2511 of the hub 2502 can be mated into the second portion 2513 of the hub 2502. In this embodiment, the second portion of the hub 2513 includes a slot 2515 into which can be slid or snapped into the first portion 2511. The first portion 2511 includes tangs 2517 and 2519 which fit under lips 2521, 2523 respectively as the first portion 2511 of the hub 2502 is slid or alternatively snapped into engagement with the second portion 2513. Once this occurs, a locking cam 2527 is turned in order to cause a cam member to be urged against this portion 2511 of the hub in order to lock 2511 to the second portion 2513. Alternatively, it is to be understood that the act of sliding or snapping hub portion 2511 into hub portion 2513 can be sufficient to lock portion 2511 into portion 2513. This embodiment further includes spacer 2536 and cone shaped guide 2526.

Other features, functions, dimensions, and so forth of this embodiment are similar to the other embodiments as, for example, the embodiment of FIG. 141.

For purposes of insertion, one insertion methodology can be to insert the second hub portion 2513 with the guide 2526 into the position between the spinous processes. After this is accomplished, the hook members can be positioned about the spinous processes and locked into the first hub portion 2511. Then the first hub portion 2511 could be slid or snapped into engagement with the second hub portion 2513. Following that, the cam 2527 can be turned in order to secure the first hub portion 2511 to the second hub portion 2513.

Embodiments of FIGS. 147a-149b

Figure 147A:
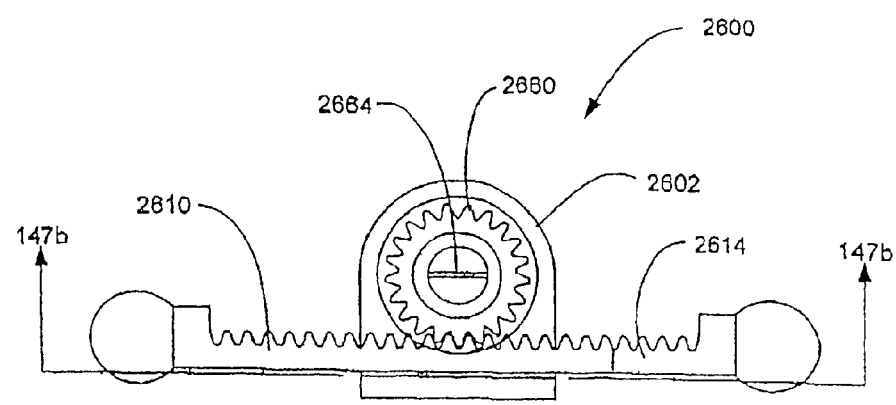
FIGS. 147a and 147b are side and top views of yet another embodiment of the invention depicting a mechanism for adjusting the positions of the hook mechanisms of, for example, the embodiment of the invention of FIGS. 130, 137, and 141.
Figure 147B:
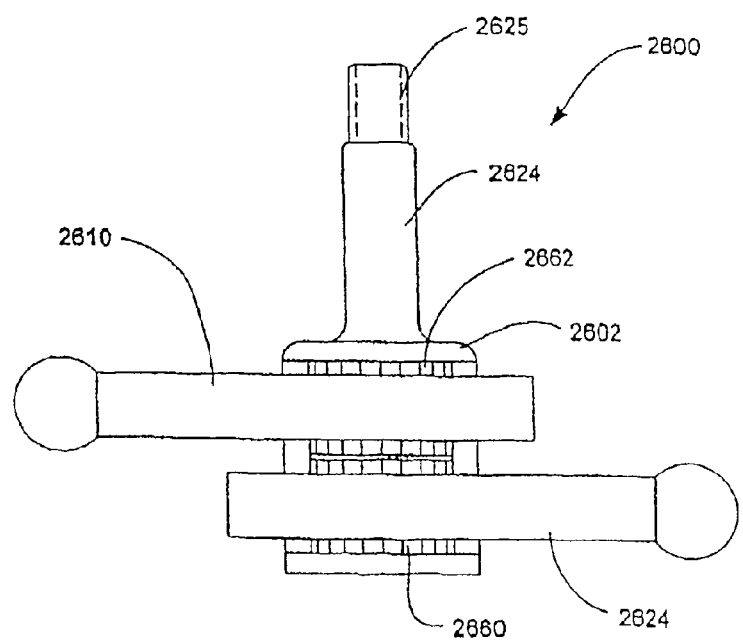

FIGS. 147a and 147b depict another embodiment 2600 of the invention. This embodiment 2600 includes a hub 2602 and a rack and pinion arrangement. The rack and pinion arrangement includes first and second pinions 2660 and 2662. These pinions engage shafts 2610 and 2614 respectively. In these embodiments, these shafts 2610 and 2614 have rounded ends to which the hook is secured as depicted in, for example, FIG. 131. For simplicity, these hooks have been left off of FIGS. 147a, 147b. The position of the shafts 2610 and 2614 can be adjusted relative to the hub. Once the shafts 2610, 2614 are appropriately positioned the pinions can be locked in position, locking the shafts in position. Pinions can be locked in position by tightening down screws such as screw 2664 against the pinion 2660. A similar screw, not shown, would tighten down pinion 2662.

Figure 148A:
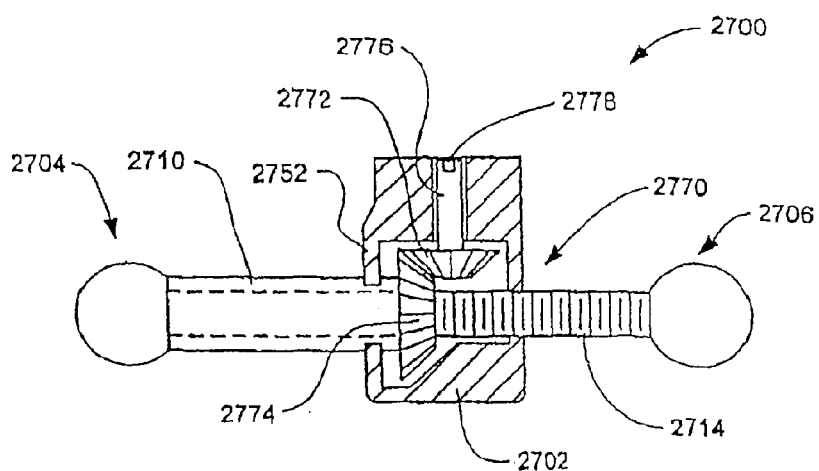
FIGS. 148a and 148b are sectional top and side views of yet another embodiment of the invention for adjusting the position of the hook mechanisms.
Figure 148B:
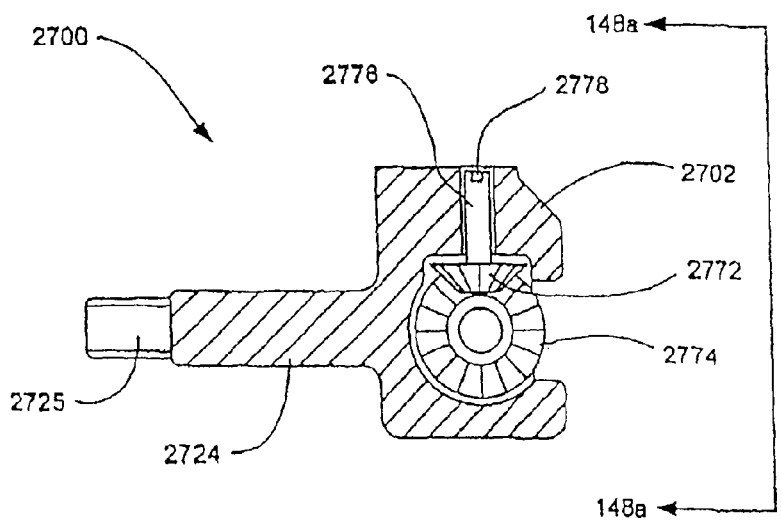

Another embodiment of the invention, embodiment 2700 is depicted in FIGS. 148a and 148b. In this embodiment a bevel gear arrangement 2770 is contained in the hub 2702. Bevel gear arrangement 2770 includes a first bevel gear 2772 and a second bevel gear 2774. Bevel gear 2772 has a shaft 2776 extending therefrom with a slot 2778. Slot 2778 can receive a tool for turning the bevel gear 2772. Bevel gear 2774 is mated to a threaded shaft 2710 of the hook member 2704. In this particular embodiment, the hook is not shown as is the case for the embodiment of FIGS. 147a and 147b. When the bevel gear 2772 is turned, it turns bevel gear 2774. The turning of bevel gear 2774 causes the threaded shaft 2714 to retreat into or extend out of the center of the other shaft 2710. With the hook members positioned around spinous processes, the bevel gear 2772 can be used to turn bevel gear 2774 in order to draw the hook member 2706 toward the hub 2702, tightening the hook members about the spinous processes.

In this embodiment 2700, a shaft 2724 extends therefrom in order to receive a spacer and a guide in the same manner that, for example, the embodiment of FIG. 144 receives a spacer and a guide.

Figure 149A:
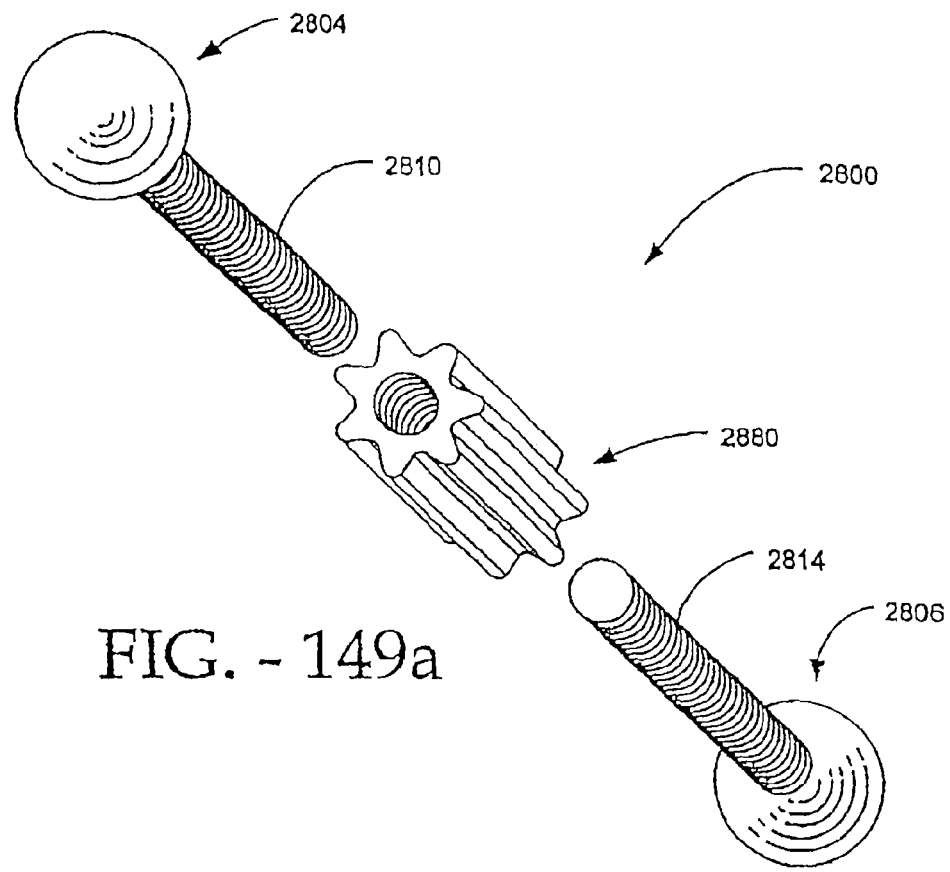
FIGS. 149a and 149b are perspective and side views of yet a further mechanism of an embodiment of the invention for adjusting the position of hook mechanisms of the invention.
Figure 149B:
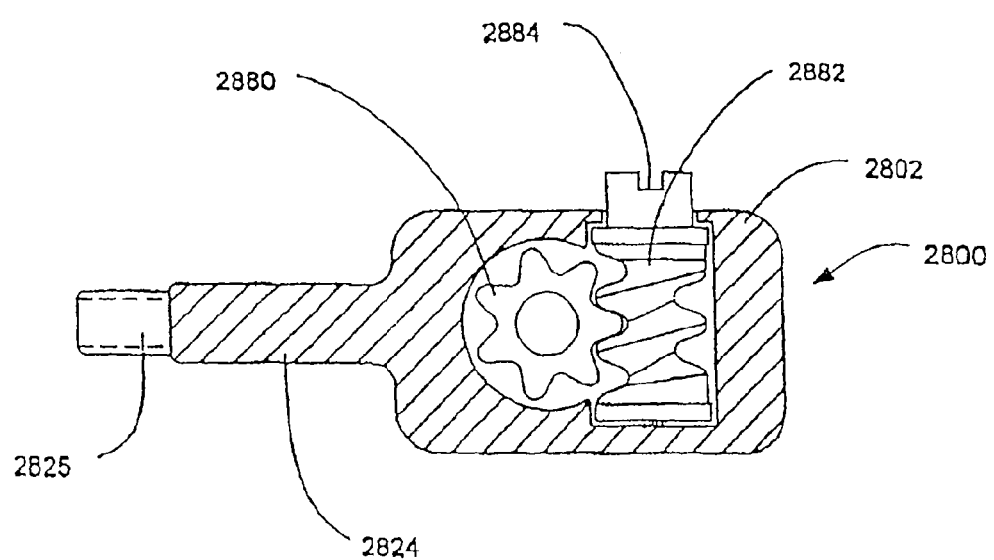

FIGS. 149a and 149b depict embodiment 2800 of the invention. Embodiment 2800 includes a hub 2802 which houses a turnbuckle arrangement 2880 which is actuated by a worm gear drive 2882. Turnbuckle 2880 receives the threaded shaft 2810 and 2814 of the hook members 2804, 2806 respectively. As with the past embodiments, the actual hooks of these hook members are not depicted in order to simplify the drawing. By turning the turnbuckle 2880, the threaded shafts 2810, 2814 are either drawn into or urged out of the turnbuckle. Thus, by turning the worm gear 2882 with a tool placed in the slot 2884, the turnbuckle turns, causing the hook members to extend out of or be urged into the hub 2802.

Extending from the hub is a shaft 2824 with a threaded end 2825. As with the other embodiments, such as the embodiment in FIG. 144, a spacer can be placed on the shaft 2824 and a guide can be placed on the threaded end 2825.

The preferred method of inserting this embodiment is to insert the embodiment as a whole, placing the guide and spacer between the spinous processes. The hooks would be initially rotated 90° from their final orientation. Once inserted adjacent to the spinous processes, the hooks would be rotated by 90°. and the spacer and the hooks would be further urged into contact with the spinous processes. Once this has occurred, the turnbuckle would be turned in order to tighten the hooks about the spinous processes.

Figure 150:
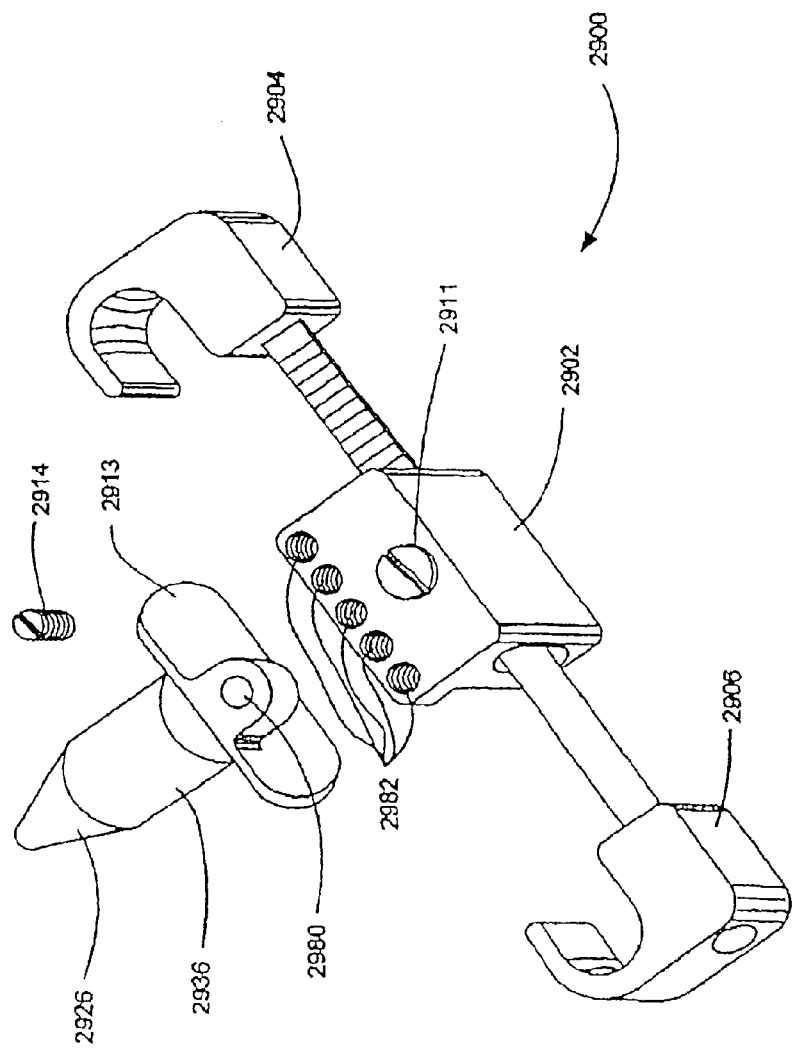
FIG. 150 is a perspective view of yet a further embodiment of the invention.

Embodiment of FIG. 150

Another embodiment 2900 of the invention is depicted in FIG. 150. This embodiment is similar to several of the other embodiments and, in particular, to the embodiment shown in FIG. 130. Accordingly, similar elements will have similar least significant numbers. By way of example, the hub is designated 2902. In this particular embodiment, the hub is comprised of two components, the first hub component 2911 and the second hub component 2913. This is somewhat similar to the hub components shown in FIG. 146b.

The two hook members are secured to the first hub component 2911 in much the same manner as the hook members of FIG. 130 are secured to the hub in FIG. 130.

The hub 2902 is divided into first hub component 2911 and second hub component 2913 in order to add flexibility in the positioning of the guide and spacer fitted to second hub component 2913 with respect to the first and second hook members 2904 and 2906 which are secured to the first hub component 2911. Thus, should the anatomy of the spine and in particular the spinous process require, the spacer 2936 and the guide 2926 can be moved relative to the first and second hook members 2904 and 2906 by selectively positioning the second hub component 2913 relative to the first hub component 2911. This can be accomplished by aligning the bore 2980 over one of the plurality of bores 2982 positioned through the first hub component 2911. After this is accomplished, a threaded screw 2984 can be inserted through smooth bore 2980 and engage one of the threaded bores 2982 in order to secure the second hub component 2913 to the first hub component 2911, thus positioning the sleeve or spacer 2936 in a desired location relative to the first and second hook members.

Figure 151:
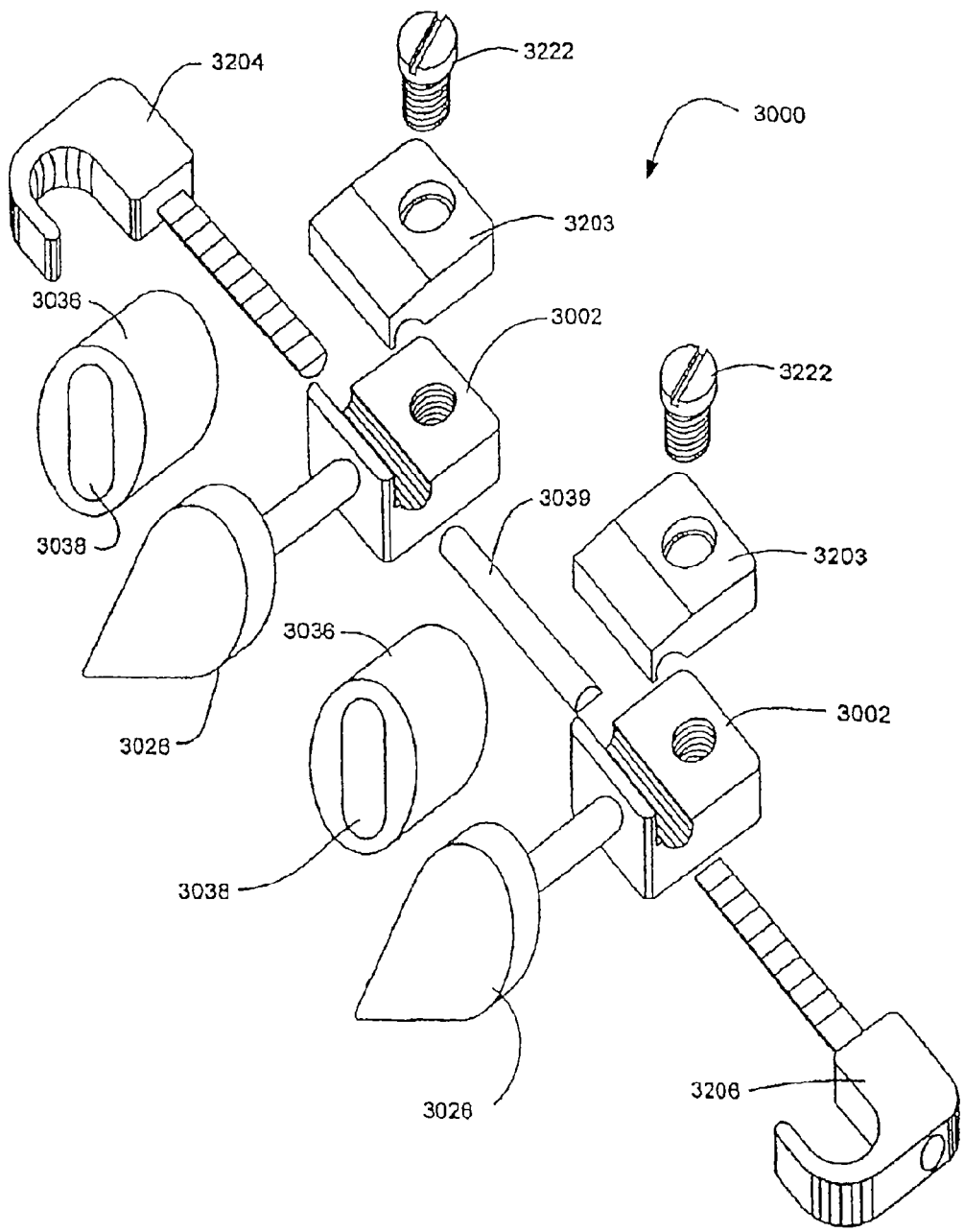
FIG. 151 is a perspective view of an embodiment of the invention which is addressable to multiple levels of spinous processes.

Embodiment of FIG. 151

Yet another embodiment of the invention 3000 is depicted in FIG. 151. Embodiment 3000 is meant for a double level spinous process fixation. That is to say that three spinous processes are engaged and rigidly fixed together. Such a situation would occur, for example, when there is a double level primary fusion. That is, three adjacent vertebral bodies are all fused together. In such a situation a double level supplemental spine fixation device 3000 would be used. This embodiment 3000 could be designed using any of the other embodiments depicted heretofore. Embodiment 3000 is in this particular instance modeled after the embodiment 2000 shown in FIG. 141. Accordingly, the elements that are similar to FIG. 141 have similarly least significant digits. By way of example, the hubs of FIG. 151 are both designated 3002 in accordance with the designation of FIG. 141. Similarly, the hub caps, sleeves, hook members, spacers, and guides are similarly numbered. In this embodiment two hubs, two spacers, and two guides are required as the first guide 3026 and the spacer 3036 would be inserted between first and second spinous processes, while the second guide 3026 and spacer 3036 would be inserted between the second and third spinous processes. The hook members 3204 and 3206 would hook about the first spinous process and the third spinous process respectively.

A preferred method of insertion of the device relative to three spinous processes would be to insert the guides and spacer between the first and second, and then the second and third spinous processes in order to distract apart the first and second spinous processes and also to distract apart the second and third spinous processes. After this is accomplished, the first hook member would be placed about the first spinous process and the second hook member would be placed about the third spinous process. The shafts of the hook members would be inserted in the respective hubs 3002. In this situation, the shafts are both up-facing racks or teeth as shown in FIG. 151. A linking shaft 3039 has downwardly facing racks or teeth. Thus the upwardly facing rack or teeth of the first hook member 3204 would be laid in the upper hub 3002 with the teeth facing up. The teeth of the member 3039 facing down would engage the rack or teeth of the first hook 3204. Once this is accomplished, the cap will be placed over the hub and the screw inserted in order to rigidly secure the hook member and the shaft 3039 relative to the upper hub 3002. Then the shaft of the second hook 3206 would be positioned in the lower hub 3002. The rack of shaft 3039 would mesh and lock with the rack of the shaft of the second hook member 3206. Once this is accomplished, the cap 3203 would be placed over the hub and the screw would be inserted through the cap into the hub in order to secure the shaft 3039 and the second hook member 3206 relative to the lower hub.

Embodiments of FIGS. 152-160

Figure 152:
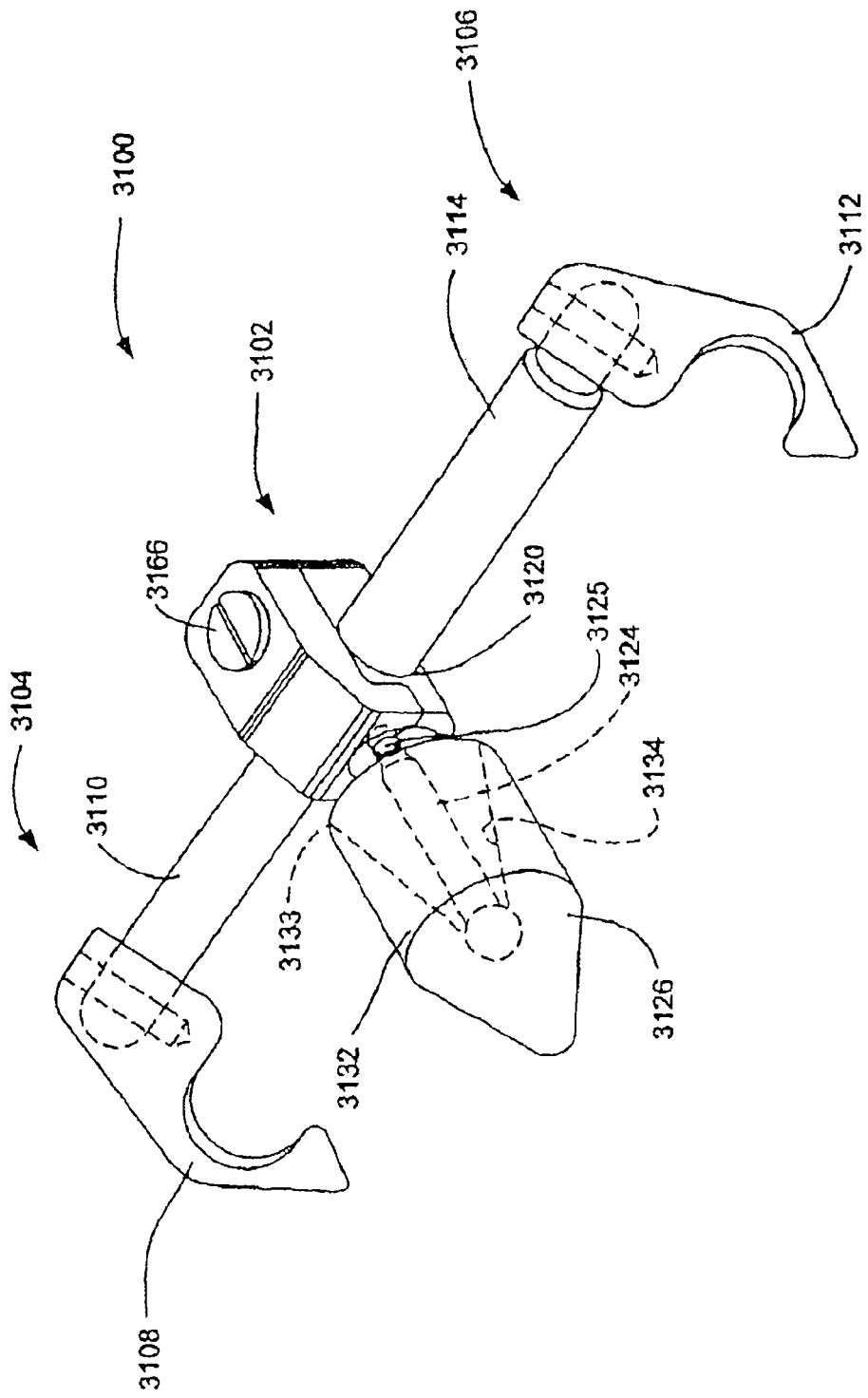
FIG. 152 is a perspective view of an alternative embodiment of the supplemental spine fixation device of the invention.

An alternate embodiment 3100 of the supplemental spine fixation device of the invention is depicted in FIG. 152. This embodiment 3100 includes a hub 3102 to which is adjustably secured a first hook member 3104 and second hook member 3106. First hook member 3104 includes a hook 3108 which is more fully described herein below, and a shaft 3110 extending therefrom. Similarly, second hook member 3106 includes a second hook 3112 and shaft 3114 extending therefrom. Shaft 3110 and 3114 are assembled together in a manner as will be described hereinbelow.

As described more fully below, hook 3108 is swively or pivotally mounted to shaft 3110. It is to be understood that the description and functionality of the first hook member 3108 applies equally well to that of the second hook member 3106. The shaft 3110, onto which hook 3108 is mounted in this embodiment, is received inside of the shaft 3114. Shaft 3110 can extend from shaft 3114 in a telescoping or sliding manner relative to shaft 3114 or alternatively shaft 3110 can be threaded into shaft 3114 and the rotation of shaft 3110 would allow it to extend from or be retracted into shaft 3114. Shafts 3110 and 3114 are received in a bore 3120 of the hub 3102. In this particular embodiment shaft 3114 can be press fit or otherwise secured in bore 3120. Shaft 3110 is thus free to move relative to the hub 3102 and the shaft 3114, until the hub 3102 is assembled, locking shaft 3110 into position in this particular embodiment. This locking arrangement will be discussed more fully below.

The hooks 3108 and 3112 are designed and shaped to fit to spinous processes. Further the hooks 3108 and 3112 are swivelly mounted to the shafts 3110 and 3114, respectively, in order to accommodate the various sizes, shapes, and positions of the spinous processes of the human population.

Swively mounted to the hub 3102 is a shaft 3124, and extending from the shaft 3124 is an inner-spinous process guide, or lead-in nose, or tissue expander 3126. The shaft 3124 at its proximal end includes a ball 3125, which is received in socket 3127 which is formed by the two portions of the hub 3102. At this ball and socket mechanism, the shaft 3124 is pivotable with respect to the hub 3102. With this arrangement, the tissue expand 3126 has some freedom of movement with respect to the hub 3102. The other end of the shaft 3124 (FIG. 154*a*) also includes a ball 3129 which fits into a socket arrangement 3131 created in the guide or tissue expander 3126. This arrangement allows the guide or tissue expander 3126 to pivot with respect to the shaft 3124. Accordingly the shaft 3124 is free to pivot relative to the hub and the guide or tissue expander 3126 is free to pivot relative to shaft 3124. This movement, as well as the ability of hooks 3108 and 3112 to swivel on the shaft 3110 and 3114, and the ability of the shaft to be positioned relative to each other allows the embodiment 3100 to conform to the spinous process anatomy.

In this particular embodiment, a sleeve or spacer 3132 is pivotally mounted on the shaft 3124 along with the guide 3126. In other embodiments as described below, the sleeve spacer 3132 is free to rotate relative to the guide 3126. Spacer 3132 includes a central bore 3134 in which the shaft 3124 extends. The spacer 3132 as well as guide 3136 are thus able to pivot and rotate about the shaft 3124. The spacer 3132 in this embodiment is cylindrical and in this particular embodiment is oval or elliptical in shape. For such shapes, the spacer can have minor diameters of 6 mm, 8 mm, 10 mm, and 12 mm. Smaller and larger diameters are within the spirit and scope of the invention. In addition, the spacer can be egg shaped as more fully described below. Further, the base of the guide 3126 is somewhat elliptical in shape in order to make a smooth transition between the guide 3126 and the spacer 3132 as the guide and spacer are inserted between the spinous processes in order to distract apart the spinous processes. As the guide 3126 and the spacer 3132 are rotatable and pivotable on the shaft 3124, and as the spacer 3132 is elliptically shaped, it can be inserted into one position and then as the entire embodiment 3100 is positioned to the final securing position, the spacer 3132 can be rotated about the shaft 3124 and pivoted relative thereto in order to accommodate the shape of the space between the spinous processes as the spacer is moved generally from a posturing position to an anterior position closer to the spine.

As can be seen in FIG. 152 and also in FIGS. 154*a* and 154*c*, the central bore 3134 of the spacer 3132 has a first end 3133 which is enlarged and in this particular embodiment substantially elliptical in shape. The second end 3135 is smaller. The reason for this arrangement is most evident in FIGS. 154*a* and 154*b* where in phantom various positions of the shaft 3124 are depicted demonstrating the pivotability of the guide 3124 and the sleeve 3132 relative to the hub 3102. As can be seen in FIGS. 154a and 154c, in this particular embodiment, the shaft 3124 is inserted into the small end 3135 of the sleeve 3132. A retainer 3137 is inserted relative to the ball 3129 of the shaft 3124. The lead-in nose or tissue expander 3126 is then inserted over the small end 3139 of the sleeve 3132 and pin 3141 is inserted into aligned slots in the guide 3126 and the sleeve 3132 in order to assemble together guide 3126, the retainer 3137 and the sleeve 3132 about the ball 3129 of the shaft 3124 to create a ball and socket arrangement, whereby the guide 3126 and sleeve 3132 are pivotable and rotatable about the ball 3129.

Figure 160:
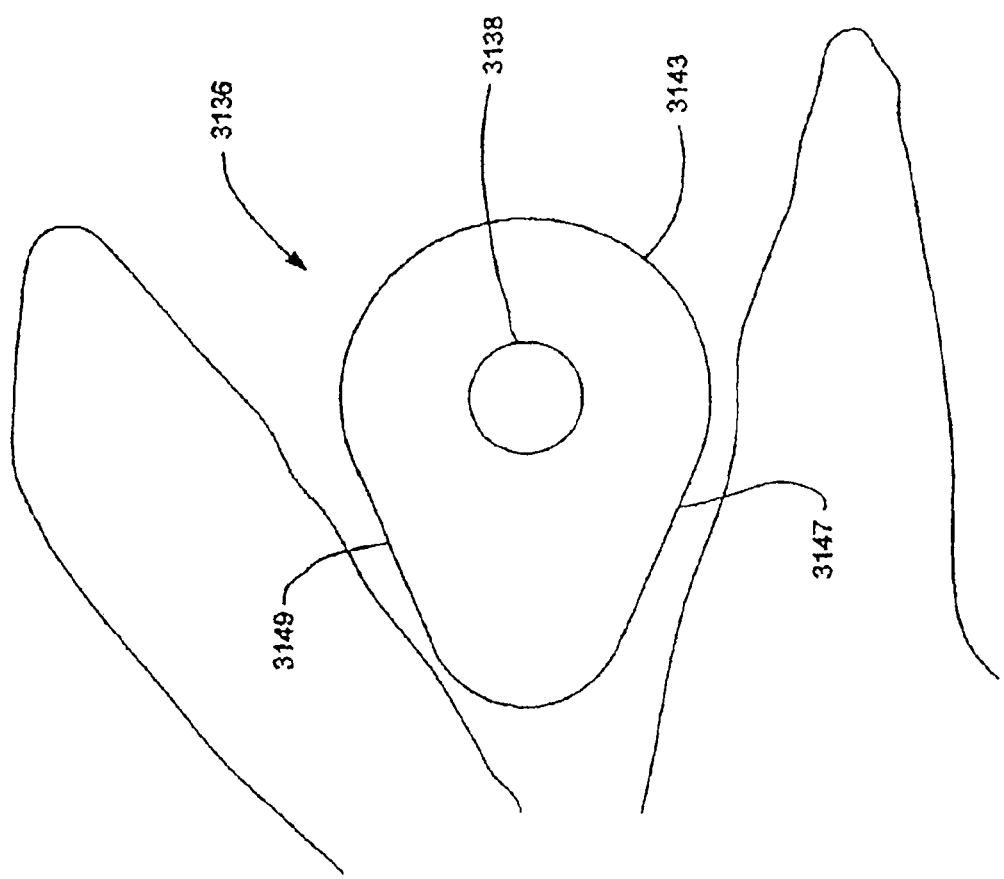
FIG. 160 is an alternate embodiment of a sleeve of the invention positioned between adjacent spinous processes.

The spacer 3132 can include an alternate embodiment spacer 3136 as shown in FIG. 160. This spacer 3136 can be substituted for spacer 3132. Spacer 3136 includes an egg-shape cross-section with a central bore 3138 upon which the shaft 3124 can be inserted so as to allow the spacer 3136 to rotate about the shaft 3124. As can be seen in FIG. 160, the egg-shaped spacer 3136 has a blunt end 3143 and a pointed end 3145. The center of the bore 3138 is off-center and more towards the front end 3134 in this preferred embodiment allowing the pointed nose end 3145 to be positionable more closely to the spine. This allows the flat sides 3147, 3149 between the blunt end 3143 and pointed end 3145 to be positioned closer to the spine and adjacent to portions of spinous processes which are generally comprised of stronger bone. In addition, these flat sides 3147 and 3149 can more easily accommodate and carry and thus spread the load placed thereupon by the adjacent spinous processes. The bore 3138 can be shaped like bore 3134 (FIG. 154c) to allow for pivoting and rotating motion. Also, in order to accommodate bore 3138 of the egg-shaped spacer 3136 being off-center, the lead-in guide 3126 would also be egg-shaped and have an off-center position where shaft 3124 is attached.

In another arrangement, the embodiment as shown in FIG. 154c could be modified to so that the small end 3139 of the spacer 3132 or of the spacer 3136 is severed from the remainder of the spacer 3132, 3136 and pinned by itself to the guide 3126 in order to capture the ball of the shaft. Thus the remainder of the spacer 3132, 3136 could rotate free of guide 3126.

Before proceeding to more specific details of this embodiment 3100, it is to be understood that the same features of the spacer, the shaft, and the lead-in guide, which are found on other embodiments such as by way of example only the embodiments of FIGS. 10, 16, 20, 22, 86, 88, 92 and 119b, and other figures can be incorporated into this embodiment. By way of example only, the implant 3100 can be comprised of stainless steel, titanium, or other biologically acceptable materials. The shape of the lead in plug can be cone shaped, pyramid shaped and other shapes with a small lead in cross-section expanding into a larger cross-section which is similar to the cross-section of the spacer 3132, in order to gradually distract apart the spinous processes to a sufficient distance so that the spacer 3132 or the spacer 3136 can conveniently fit between the spinous processes. Further, the spacer, as shown in the other embodiments, can include a spacer made of stainless steel or titanium or of a super-elastic material or of a silicone. The spacer besides being cylindrical, can be saddle-shaped along the surface which engages the spinous processes so that the high edges and the lower central portions can more fully accommodate the shape of the spinous process. This shape also aides in spreading the load across the broader contact area between the spinous processes and the spacer. For example, the spacer 3132 or 3136 could have a shape such as the saddle shape defined by the mated together components of the embodiment of FIG. 16. Further, dimensions of this embodiment as applied to the guide 3106 and the spacer 3132 can be acquired from other embodiments presented herein. By way of example only, the guides and spacers can have multiple shapes with the small diameter of the elliptical shape being on the order of 6 mm, 8 mm, 10 mm, 12 mm and 14 mm.

The shape of the guide 3126 and the spacer 3132 or the spacer 3136 is such that for purposes of insertion between the spinous processes, the spinous processes do not need to be altered or cut away in any manner in order to accommodate this implant. Further, the associated ligaments do not need to be cut away and there would be very little or no damage to the other adjacent and surrounding tissues. Similarly, the hook members 3104 and 3106 are appropriately shaped, as described below and are also pivotable so that alterations of the spinous processes is not required.

Referring to FIG. 155a through 155e, the design and shape of the hook 3108 is more fully described and depicted. As indicated above, the description will be made with respect to the first hook 3108. This description applies equally well to second hook 3112. As can be seen in FIG. 155a, the first hook 3108 includes a bore 3144 into which the shaft 3110 is received. The shaft has a rounded end which has a bore provided therethrough. This bore mates with the bore 3145 associated with the bore 3144 of the hook 3108. When the bore of the shaft 3110 and the bore 3145 of the hook are aligned, a pin or screw can be inserted in order to lock the hook 3108 onto the shaft 3110. As can be seen in FIG. 155d, the lower end 3147 of the bore 3144 is oval or ob-round in shape allowing for the shaft to be pivotally received in the bore. Thus the hook 3108 is pivotable with respect to the end of the shaft 3110. The hook thus can pivot in order to accommodate the shape of the spinous process. Turning to FIG. 155a, the lead in nose or guide or tissue expander 3150 of the hook 3108 is pointed as can be additionally seen in FIGS. 155d and 155e. This allows the guide 3150 to be easily inserted between spinous processes and spread the tissue so that the concave recess 3152 can be received over the spinous process. The hook is then locked on the spinous process in order to retain the hook 3108 in place adjacent to the spinous process. The recess 3152 has a cross-section which is convex in shape in order to accommodate the various surface shapes of the spinous process and in order to even out the load transfer between the hook and the spinous process.

Again with respect to the lead in nose 3150 in a preferred embodiment, this nose is essentially shaped in the form of a pyramid with all of its sides rounded and curved. This allows the nose 3150 to easily be inserted over and past the spinous process, until the concave recess 3152 rests over the spinous process with the hook element 3154 caught by the spinous process in order to retain the hook 3108 in place.

Figure 153:
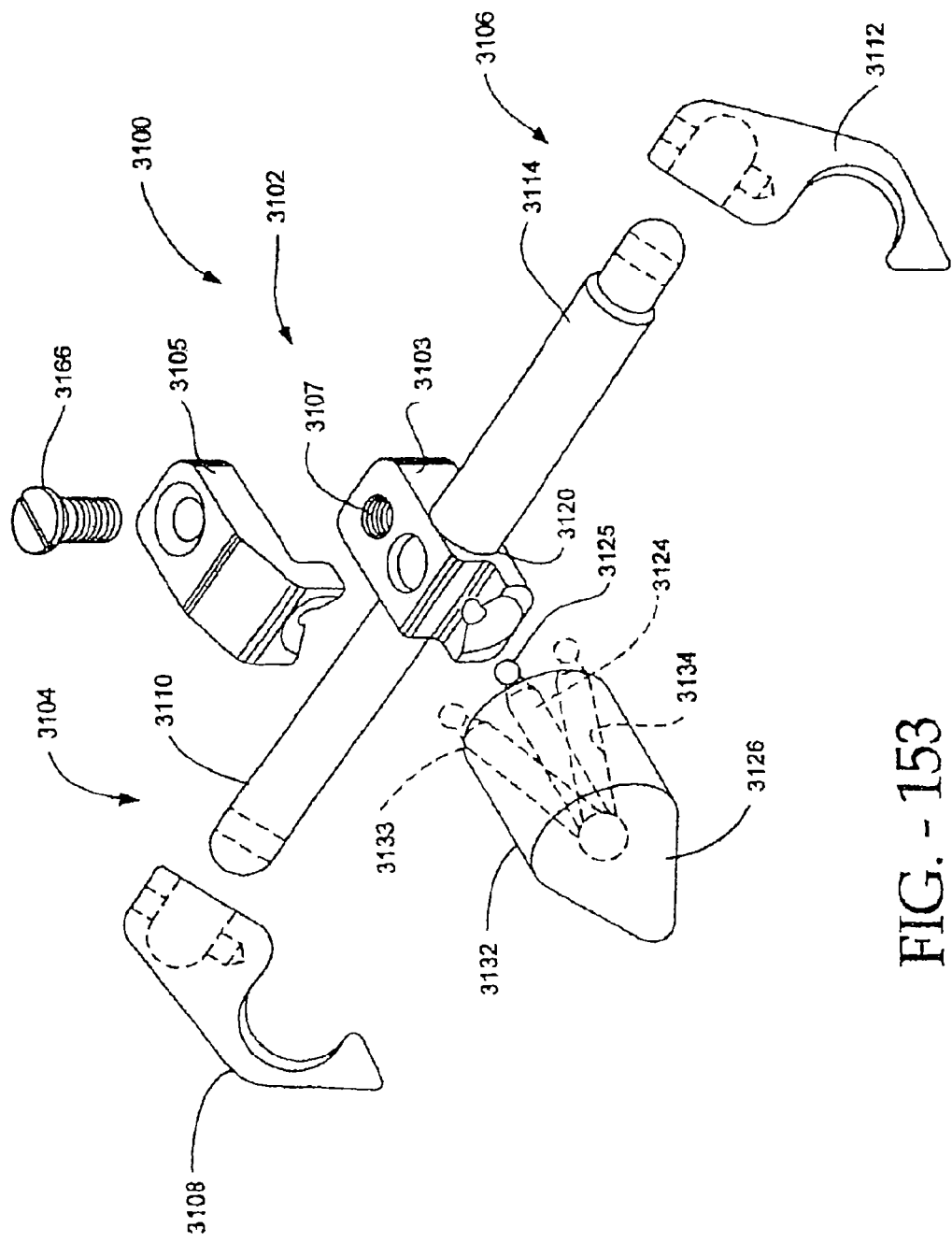
FIG. 153 is an exploded view of the embodiment of the invention of FIG. 152.
Figure 156:
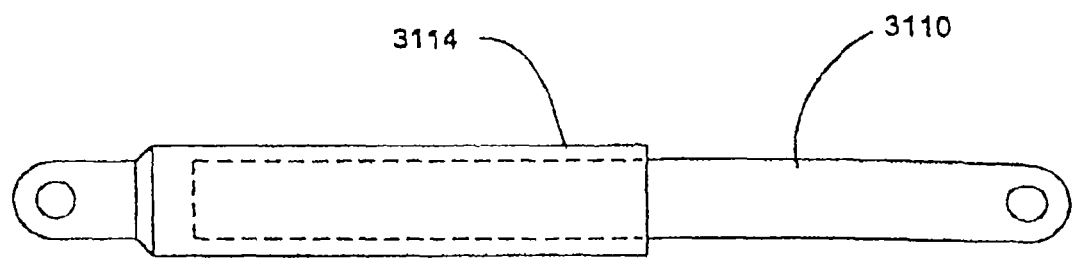
FIG. 156 is a view of an embodiment of a shaft arrangement of the invention upon which hooks can be mounted.
Figure 157:
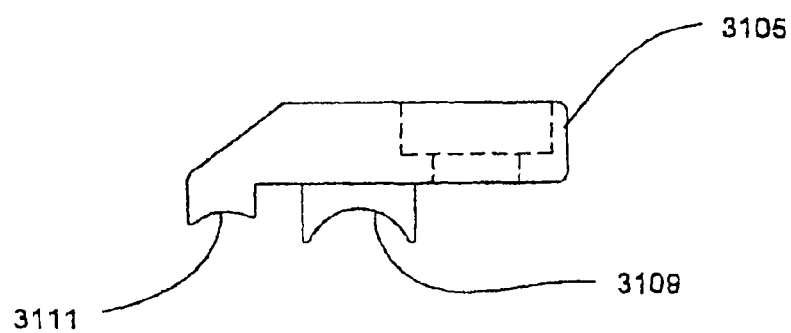
FIG. 157 is an alternate view of the top member of the hub showing the locking mechanism.

As can be seen in FIG. 153, the hub 3102 is comprised of two portions. The lower hub portion 3103 receives the shaft 3110 and 3114. The lower portion 3103 also receives the shaft 3124 upon which the nose and sleeve are mounted. The upper portion 3105 of the hub 3102 mates with a lower portion 3103 in order to lock the shaft 3110 and the shaft 3124 in place. The upper hub portion 3105 is secured to the lower portion 3103 with a screw through threaded bore 3107. As can be seen in FIG. 157, upper hub portion 3105 includes a locking projection 3109. This locking projection includes a concave surface. The locking projection 3109, with the upper hub portion 3105 is mated to lower hub portion 3107, bears down upon the shaft 3110 to lock it in position. Upper hub portion 3105 also includes a half spherical captured enclosure 3111. With the hub portions assembled, the enclosure 3111 captures the ball end of shaft 3124. It is to be understood that with respect to the embodiment of FIG. 153, that with the two halves of the hub 3102 mated together, a spherically shaped capture enclosure captures the ball end of shaft 3124.

Figure 158A:
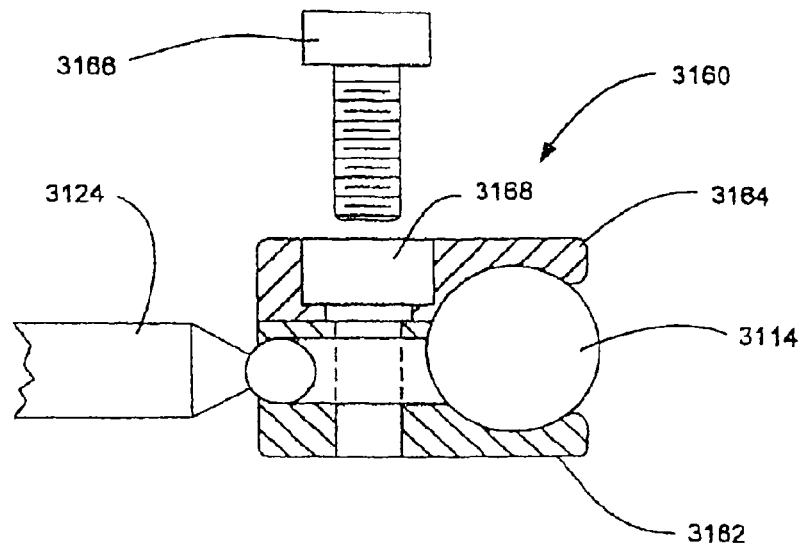
FIGS. 158a and 158b are sectioned views of an alternate embodiment of the hub mechanism of the invention.
Figure 158B:
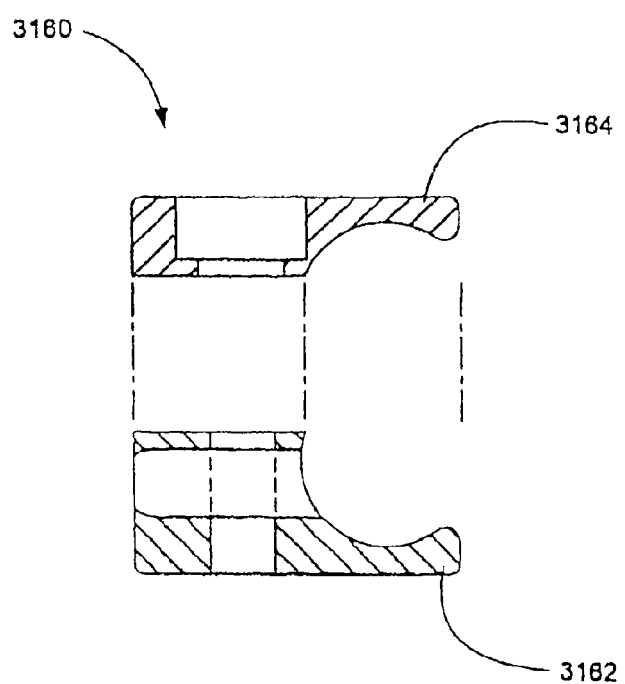

FIGS. 158a and 158b depict alternative embodiments of a hub arrangement. This alternative hub 3160 includes lower hub portion 3162 and upper hub portion 3164. In this embodiment, the ball end of the shaft 3124 is captured in the lower half of the hub 3160. The upper half 3164 of the hub is mated to the lower half with a screw 3166 which is placed through a leaf spring 3168 carried with the screw 3166. The leaf spring bias the upper hub portion 3164 towards the lower hub portion 3162 in order to trap and capture the shaft 3114. Once this is accomplished, the screw 3166 is tightened in order to complete the assembly.

Figure 159:
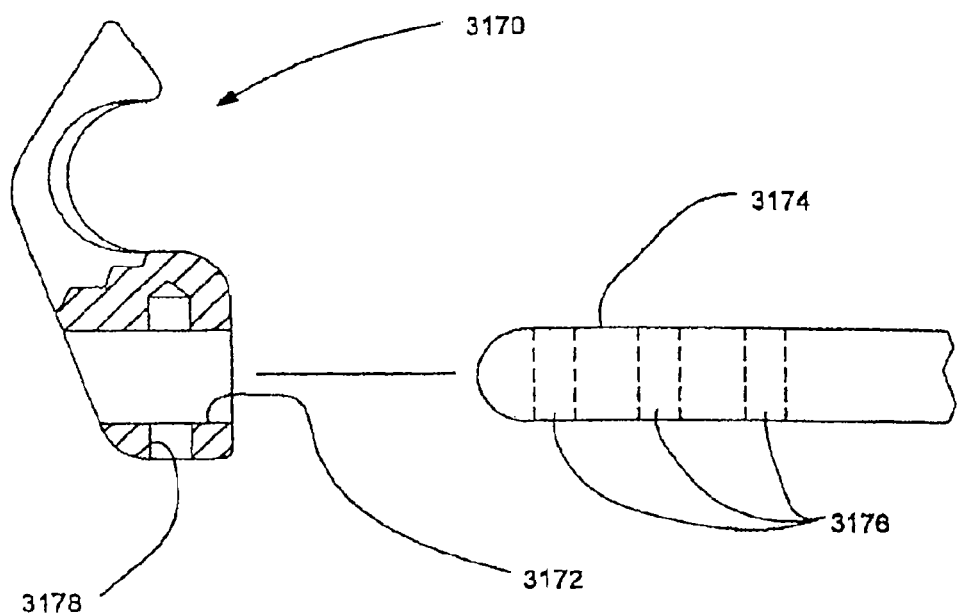
FIG. 159 is an alternate embodiment of the hook attached to a shaft of the invention.

FIG. 159 depicts yet an alternate embodiment of the hook and shaft arrangement which could be used instead of, byway of example only, hook 3108 and shaft 3110. In this arrangement the hook 3170 includes a bore 3172 which goes completely through the hook 3170. Both ends of the oval are oval or ob-round in order to allow the hook 3170 to pivot on shaft 3174. Shaft 3174 has a plurality of bores 3176 provided therethrough, any one of which can align with the bore 3178 which is provided across the bore 3172 of the hook 3170. When such an alignment is made a pin or screw can be inserted into bore 3178 in order to secure the shaft 3174 to the hub 3170. By selecting one of the several bores 3176 in the shaft 3174, the position of the hook relative to the hub can be adjusted in order to accommodate the shape and spacing of the various spinous processes.

Embodiment 3100 can be implanted in a number of methods in accordance with the teachings for the implantation of the embodiment 2000. Preferably this would occur once a spine fixation device is implanted between the vertebral bodies in order to fuse together adjacent vertebral bodies.

In one preferred embodiment of implantation, in particular with respect to the embodiment of FIG. 153, the guide and sleeve or spacer can be inserted between adjacent spinous processes. Once this is accomplished, the hooks at the end of shafts could be positioned relative to the hub 3102 so that the hooks can grab about adjacent spinous processes. Once this has occurred, the shaft 3124 can be received in the lower portion of the hub. The upper portion of the hub 3105 can be mated with the lower portion in order (1) to capture and fix shaft 3124 in place, allowing for the movement of the shaft 3124, and also (2) to capture and fix the shaft 3110 in place to rigidly position the shaft 3110 relative to the hub 3102.

It is also to be understood that in other situations the fully assembled embodiment can be inserted in place relative to the adjacent spinous processes. Once this accomplished, a screw such as the screw in FIG. 153 can be tightened in order to secure the various shafts relative to the hub 3102.

In all of the above procedures, and also in the procedures with respect to prior embodiment 2000, it is advantageous that the embodiments can address the adjacent spinous processes from one side of the spinous processes and do not require exposure to both sides of the spinous processes. Thus, this procedure is less traumatic to the surgical site.

Embodiment of FIGS. 161a-163c

The embodiments depicted in FIGS. 161a to 163c have some of the same functionalities, features, design characteristics, and materials as previously described in the embodiments depicted and described in FIGS. 1 to 129. FIGS. 1 to 129 are directed to spine distraction implants and methods used in distracting apart spinous processes in order to relieve pain associated with the spine such as, by way of example only, the pain associated with spinal stenosis. Accordingly, as appropriate, and even if not specifically mentioned in each inventive description of FIGS. 161a to 163c, many of the design characteristics, features, functionalities, materials, measurements, dimensions, purposes, aspects, and objects of the devices in FIGS. 1 to 129 are applicable to the present invention.

Figure 161A:
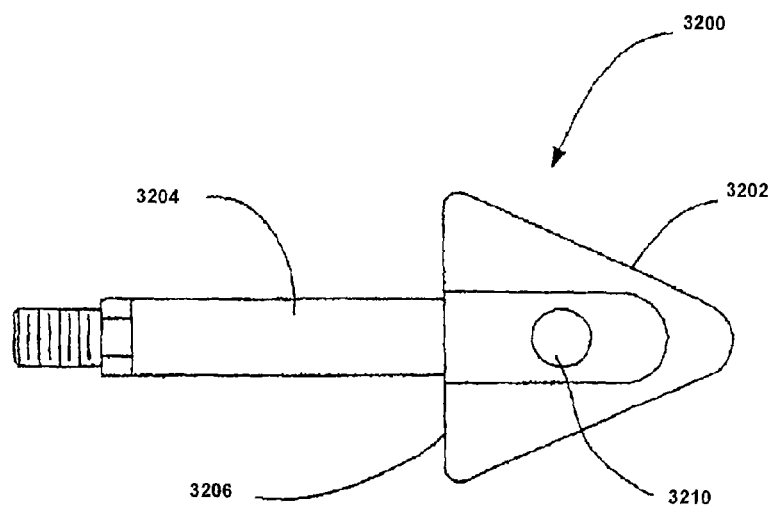
FIGS. 161a, 161b and 161c are top, side, and side sectioned views respectively of an embodiment of a lead-in nose, guide, or tissue expander of the invention.
Figure 161B:
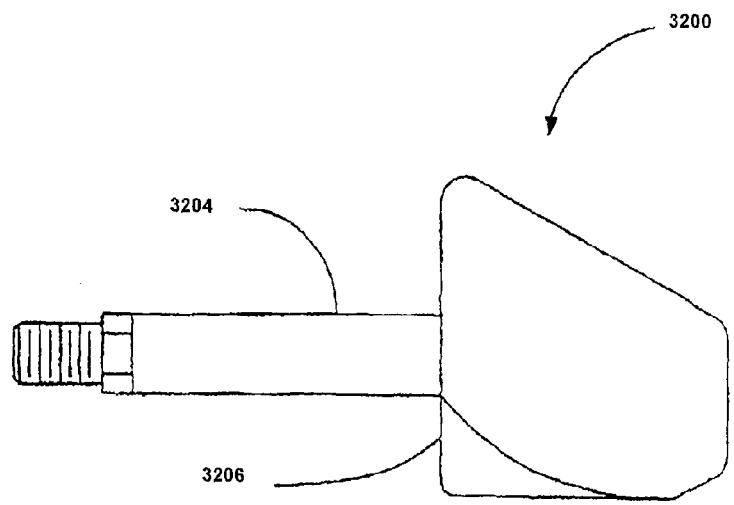
Figure 161C:
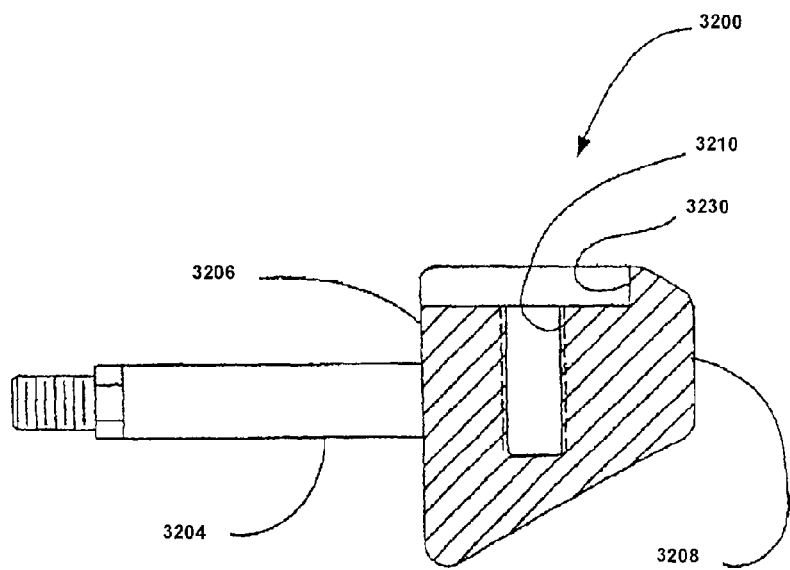

An alternate embodiment of the implant of the invention is depicted in FIGS. 161a-163c and designated implant 3200. This implant 3200 is similar to prior implant with several different features. These additional features are depicted in FIGS. 161a-163c. In particular, in FIG. 161a there is depicted a modified lead-in nose, guide or tissue expander 3202. In this particular embodiment, the guide 3202 is integrally formed with a central body 3204 and the central body 3204 is secured by a number of devices including by threads to the main body or first wing units described with respect the prior embodiments. It is to be understood, however, that the guide 3202 can be secured to the central body 3204 by a variety of mechanisms including that of a thread bore. In reviewing all of FIGS. 161a to 161e, is evident that the guide 3202 has an elliptical base 3206. The guide 3202 progressively and somewhat elliptically is reduced in cross-sectional size from the base 3206 to the tip 3208. In this particular embodiment, the tip 3208 is somewhat elongated. As can be seen in FIGS. 161a, 161c, the guide includes a threaded bore 3210 which receives a screw (not shown) which is used to affix a second wing as described in prior embodiments.

Figure 161D:
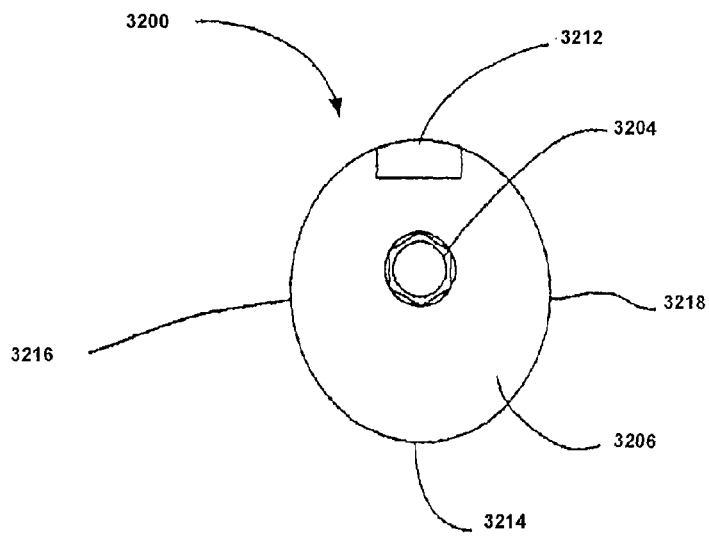
FIG. 161d is a left-end view of FIG. 161c.

With respect to FIG. 161d, it is evident that the central body 3204 extends from elliptical base 3206 from a point which is somewhat closer to end 3212 than to end 3214. The reason for this is to allow more of the flatter sides 3216, 3218 to be positioned closer to the spine and thus adjacent to the portions of the spinous process which are closer to the spine and thus are stronger than portions of the spinous processes located further from the spine. Additionally, this allows the flat surface to have more contact with the outer portions of the spinous processes in order to spread the force exerted by the implant on the spinous processes.

Elliptical spacers associated with the guide 3202 can come in a plurality of sizes. These include spacers with a minor diameter of 6 mm, 8 mm, 10 mm, and 12 mm. As appropriate, the implant can come in smaller and larger sizes.

Figure 161E:
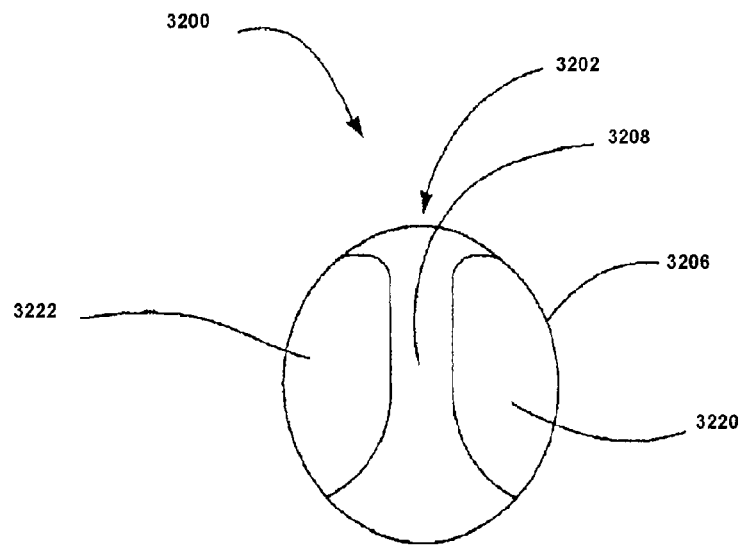
FIG. 161e is a right-end view of FIG. 161c.

With respect to FIG. 161e, in this particular embodiment, surface portion of the guide 3202 adjacent to the tip 3208 includes flat surfaces 3220 and 3222. These surfaces slant toward the elongated tip 3208 and assist in the insertion of the guide 3202 between the spinous processes by distracting and expanding the tissue between the spinous processes as the implant is positioned.

Figure 162:
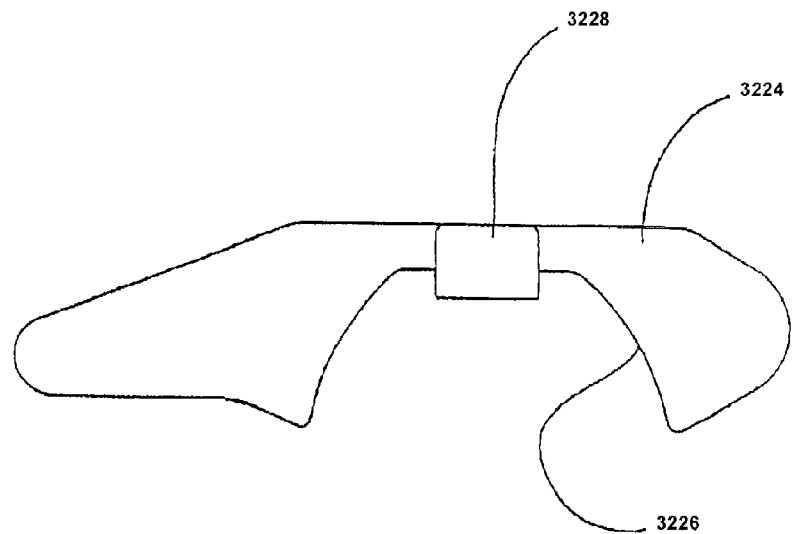
FIG. 162 is an alternate embodiment of a second wing of the invention usable with the guide or tissue expander in FIG. 161a-161e.
Figure 163C:
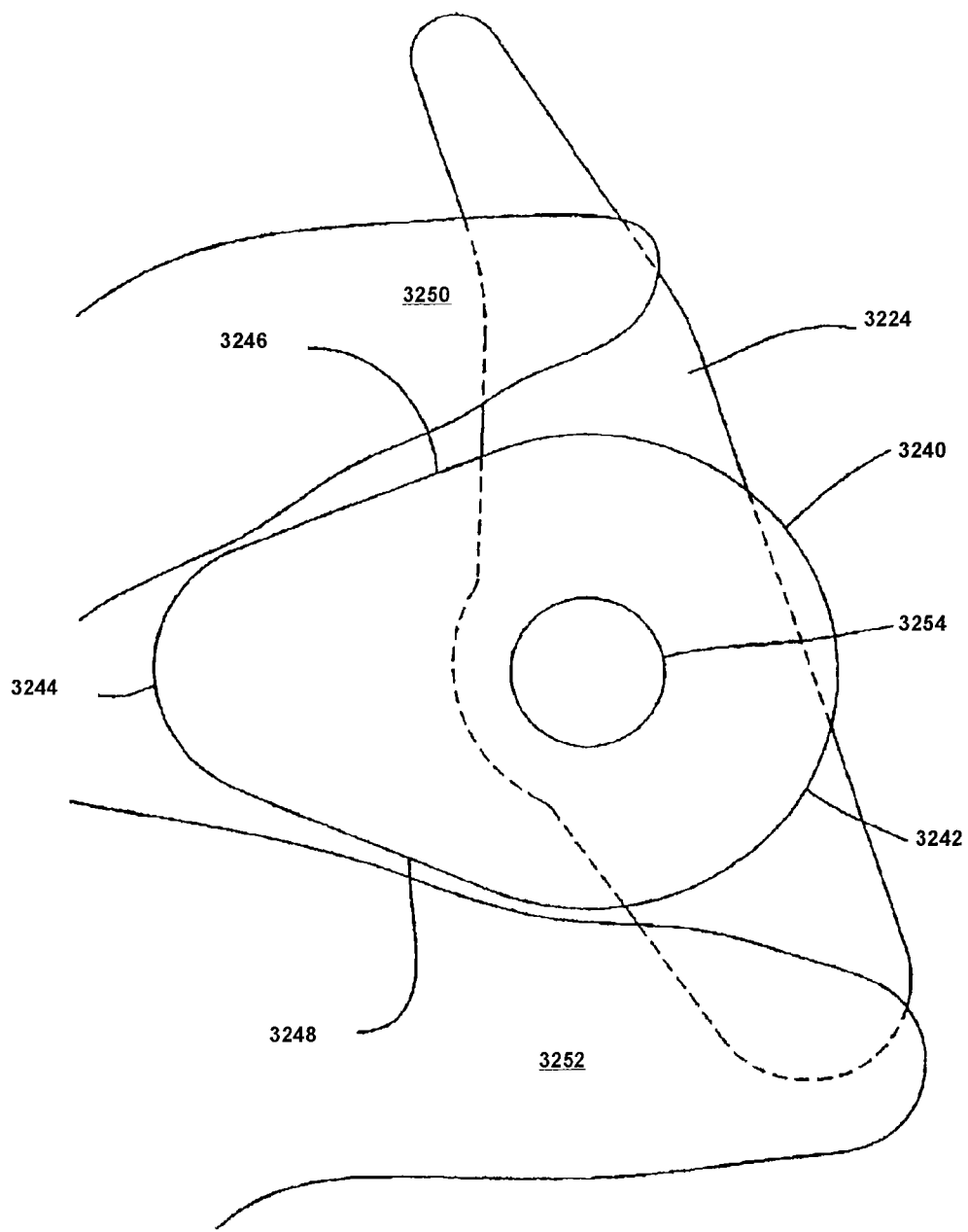
FIG. 163c is a side view of an embodiment of an implant of the invention implanted in the spine, the implant having at least a first wing.

FIG. 162 depicts an alternative embodiment of the second wing 3224 of the invention. In this embodiment, the second wing 3224 includes a concave recess 3226 which is designed to fit over the elliptically shaped nose 3202 and in this particular embodiment adjacent to the elliptical base 3206. Second wing 3224 includes a projection 3228 which fits in to the groove 3230 located above the threaded bore 3210 of the guide 3202.

A spacer or sleeve, not shown, associated with this embodiment can be elliptically shaped and about the same size as the elliptical base 3206 of the lead-in guide or tissue expander 3202. Alternatively, as shown in FIG. 163a, the spacer 3240 can be substantially egg-shaped with a blunt end 3242 and a pointed end 3244. This egg-shaped spacer 3240 also includes flat side 3246 and 3248 located between the blunt end 3242 and the pointed end 3244. As can be seen to FIG. 163a, the sleeve 3240 is positioned between spinous processes 3250,

3252. In this embodiment, the central bore 3254 upon which the sleeve 3240 rotates about the central body (shown in prior embodiments) is offset towards the blunt end 3242. This means that the pointed end 3244 can be positioned closer to the spine and adjacent to the portions of the spinous processes which are closer to the spine and which portions are stronger than more distally located portions of the spinous processes. In addition, the flat sides 3246 and 3248 of the spacer 3240 more fully conform to the sides of the spinous processes 3250, 3252 in order to spread the load transferred by the spacer 3240 onto the adjacent spinous processes 3250, 3252.

With such an arrangement, in order to have a smooth transition between the sleeve and the lead-in guide or tissue expander, the base of the lead-in guide as previously shown in FIG. 161*d* is somewhat modified to base 3256 of the guide as shown in FIG. 163*b*. In this embodiment, the base 3256 is also egg-shaped, conforming to the shape of the sleeve 3240. Further, the central body 3258 expending from the nose 3255 is off-centered toward the blunt end 3260 and away from the pointed end 3262, in order again to conform to the functionality of the sleeve 3240.

With such an arrangement, the method of implantation is similar to that of the other prior art described embodiments. However in this situation, due to the fact that the bore 3254 of the sleeve 3240 is offset, the pointed end of the sleeve 3244 can be positioned close to the spine in order to contact stronger portions of the spinous processes with the flat sides 3246 and 3248 of the spacer 3240.

Figure 164:
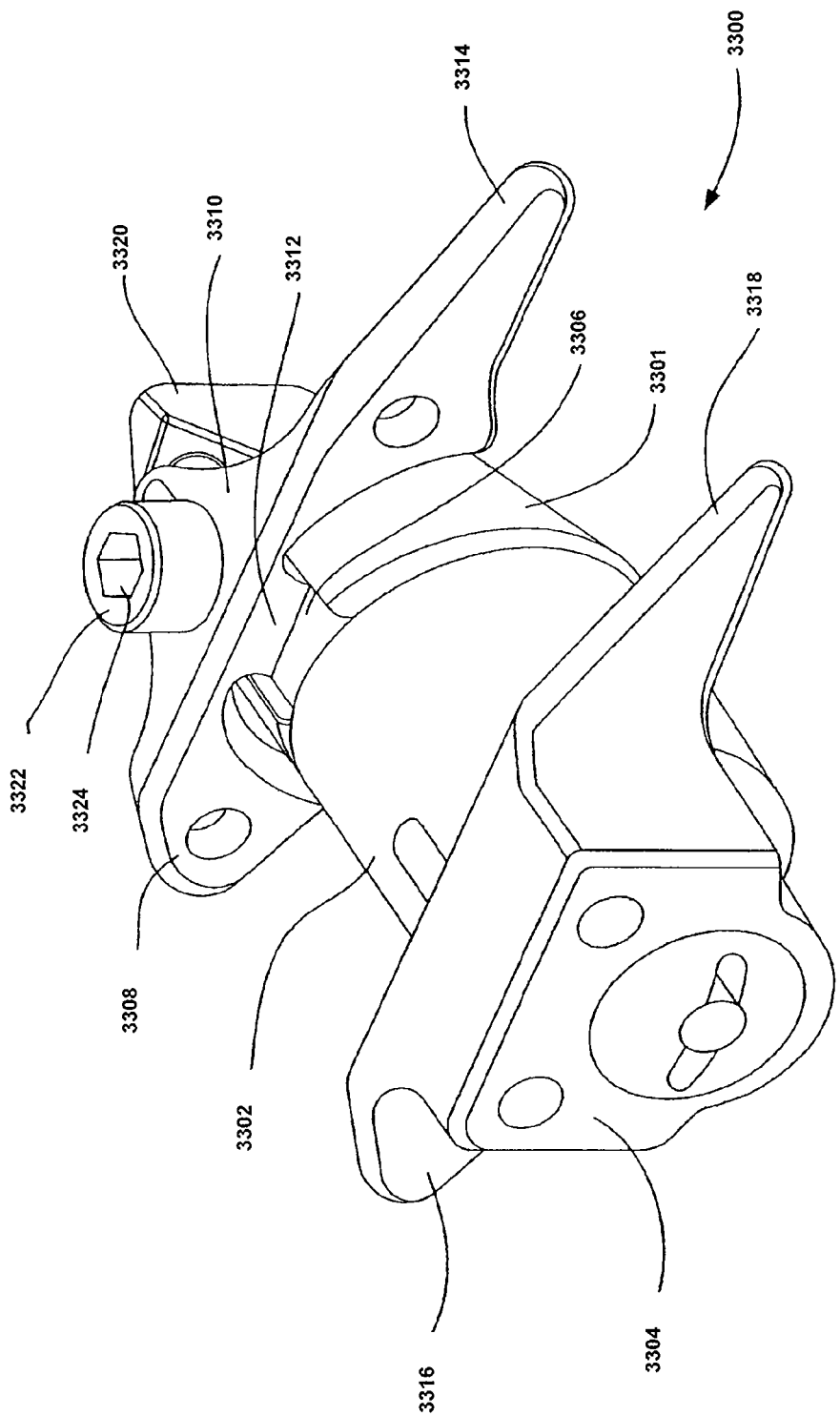
FIG. 164 is a perspective view of an embodiment of the present invention.

Referring to FIG. 164, the implant device 3300 has a main body 3301. The main body 3301 includes a spacer 3302, a first wing 3304, a tapered front end, lead-in guide or tissue expander 3320 and an alignment track 3306. The main body 3301 is inserted between adjacent spinous processes. Preferably, the main body 3301 remains safely and permanently in place without attachment to the bone or ligaments. All of the components of the implant device 3300 are made of biologically acceptable material such as, but are not limited to, high strength titanium alloy or stainless steel. Preferably the first wing 3304 is laser welded to the main body 3301.

The tip of the tissue expander 3320 has the smallest diameter, allowing the tip to be inserted into a small initial dilated opening. The diameter and/or cross-sectional areas of the tissue expander 3320 then gradually increases until it is substantially similar to the diameter of the main body 3301 and spacer 3302. The tapered front end 3320 makes it easier for a physician to urge the implant device 3300 between adjacent spinous processes. When urging the main body 3301 between adjacent spinous processes, the front end 3320 distracts the adjacent spinous processes to the diameter of the spacer 3302. As shown in FIG. 164, the tissue expander 3320 is a pyramid shape. In another embodiment the tissue expander preferably has an angle of twenty-five degrees that allows it to clear the facet. This reduces the length of the front end 3320. One will appreciate that the shape of the tissue expander 3320 can be other shapes such as, but not limited to, cone shaped, or any other shape with a small lead-in cross-section expanding into a larger cross-section. These types of shapes gradually distract the spinous processes to a sufficient distance so that the spacer 3302 can conveniently fit between the spinous processes.

The spacer 3302 can be made of stainless steel, titanium, a super-elastic material or silicone or other biologically acceptable material. The material can be rigid or resilient as desired. As shown in FIG. 164, the spacer 3302 is an elliptically shaped cylinder. One will appreciate that the spacer can consist of other shapes such as, but not limited to, egg-shaped, round-shaped or saddle-shaped. For example, the spacer 3302 can be saddle-shaped along the surface which engages the spinous processes so that the high edges and the lower central portions can more fully accommodate the shape of the spinous processes. Preferably, the spacer 3302 can swivel, allowing the spacer 3302 to self-align relative to the uneven surface of the spinous process. This ensures that compressive loads are distributed equally on the surface of the bone. By way of example only, the spacer 3302 can have diameters of six millimeters, eight millimeters, ten millimeters, twelve millimeters and fourteen millimeters. These diameters refer to the height by which the spacer distracts and maintains apart the spinous process. Thus for an elliptical spacer the above selected height would represent the small diameter measurement from the center of the ellipse. The largest diameter would be transverse to the alignment, of the spinous process, one above the other. Smaller and larger diameters are within the scope of the invention.

The shape of the spacer 3302 and for that matter the shape of the entire implant is such that for purposes of insertion between the spinous processes, the spinous processes do not need to be altered or cut away in any manner in order to accommodate the implant 3300. Additionally, the associated ligaments do not need to be cut away and there would be very little or no damage to the other adjacent or surrounding tissues other than piercing through and separating, or dilating an opening in a ligament.

The first wing 3304 has a lower portion 3316 and an upper portion 3318. The upper portion 3318 is designed to preferably accommodate, in this particular embodiment, the anatomical form or contour of the L4 (for an L4-L5 placement) or L5 (for an L5-S1 placement) vertebra. It is to be understood that the same shape or variations of this shape can be used to accommodate other vertebra. The lower portion 3316 is also rounded to accommodate, in a preferred embodiment, the vertebra. The lower portion 3316 and upper portion 3318 of the first wing 3304 will act as a stop mechanism when the implant device 3300 is inserted between adjacent spinous processes. The implant device 3300 cannot be inserted beyond the surfaces of the first wing 3304. Additionally, once the implant device 3300 is inserted, the first wing 3304 can prevent side-to-side, or posterior to anterior movement of the implant device 3300.

The implant device 3300 also has an adjustable wing 3310. The adjustable wing 3310 has a lower portion 3308 and an upper portion 3314. Similar to the first wing 3304, the adjustable wing 3310 is designed to accommodate the anatomical form or contour of the vertebra.

The adjustable wing 3310 is secured to the main body 3301 with a fastener 3322 provided through tapered cavity 3330. The adjustable wing 3310 also has an alignment tab 3312. When the adjustable wing 310 is initially placed on the main body 3301, the alignment tab 3312 engages the alignment track 3306. The alignment tab 3312 slides within the alignment track 3306 and helps to maintain the adjustable wing 3310 substantially parallel with the first wing 3304 in this preferred embodiment. When the main body 3301 is inserted into the patient and the adjustable wing 3310 has been attached, the adjustable wing 3310 also can prevent side-to-side, or posterior to anterior movement.

Figure 165:
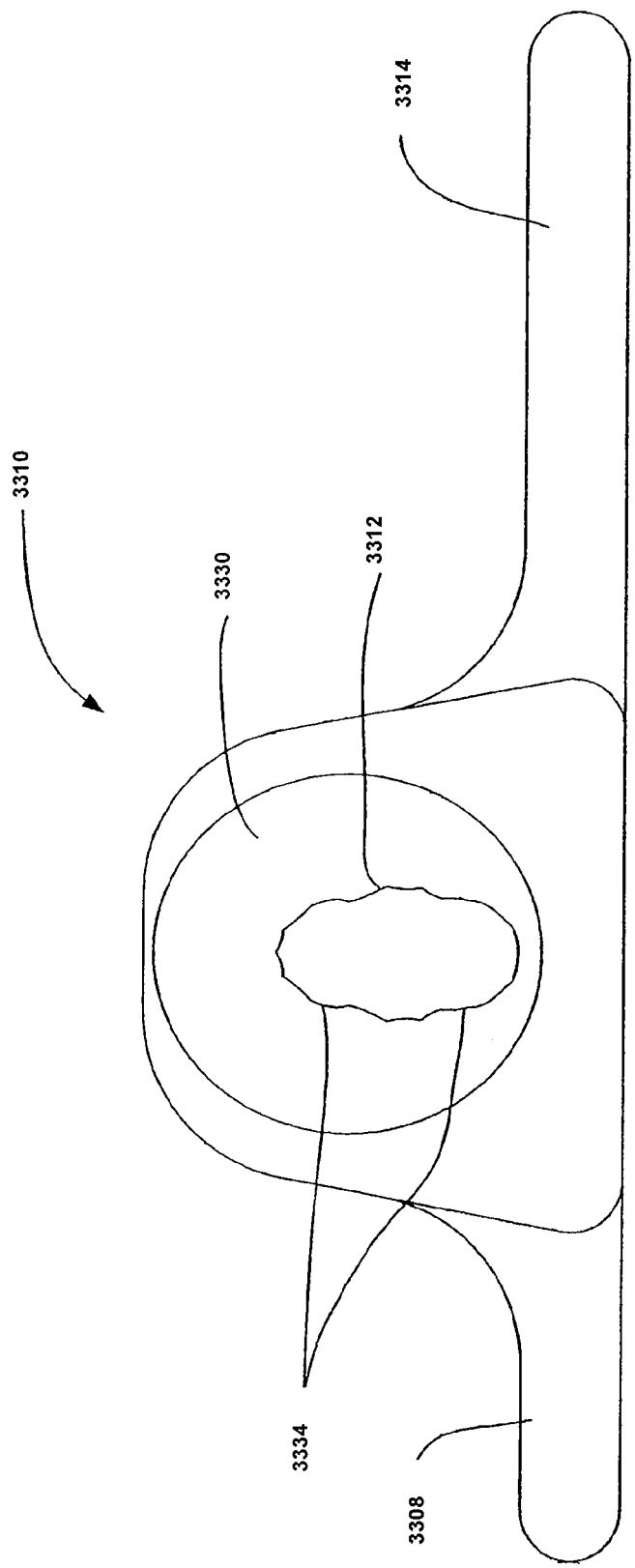
FIG. 165 is a top view of an embodiment of the adjustable wing of the present invention.

Referring now to FIG. 165, the adjustable wing 3310 includes the above mentioned tapered cavity 3330. The tapered cavity 3330 has a middle portion 3332, two end portions 3334 and a tapered wall 3331. The diameter of the middle portion 3332 is larger than the diameter of either end portion 3334. The tapered wall 3331 has a larger diameter at the top surface of the adjustable wing 3310 than at the bottom surface. Accordingly a cone-like shape is formed. When the fastener 322 engages the main body 301 and is rotated, the fastener 322 travels into the main body 301 (see FIG. 164). As the fastener 3322 travels into the main body 3301, the adjustable wing 3310 will travel along the alignment track 3306 towards the first wing 3304. The alignment tab 3312 engages the alignment track 306 and functions as a guide, keeping the adjustable wing 3310 and the first wing 3304 substantially parallel to each other.

Figure 166:
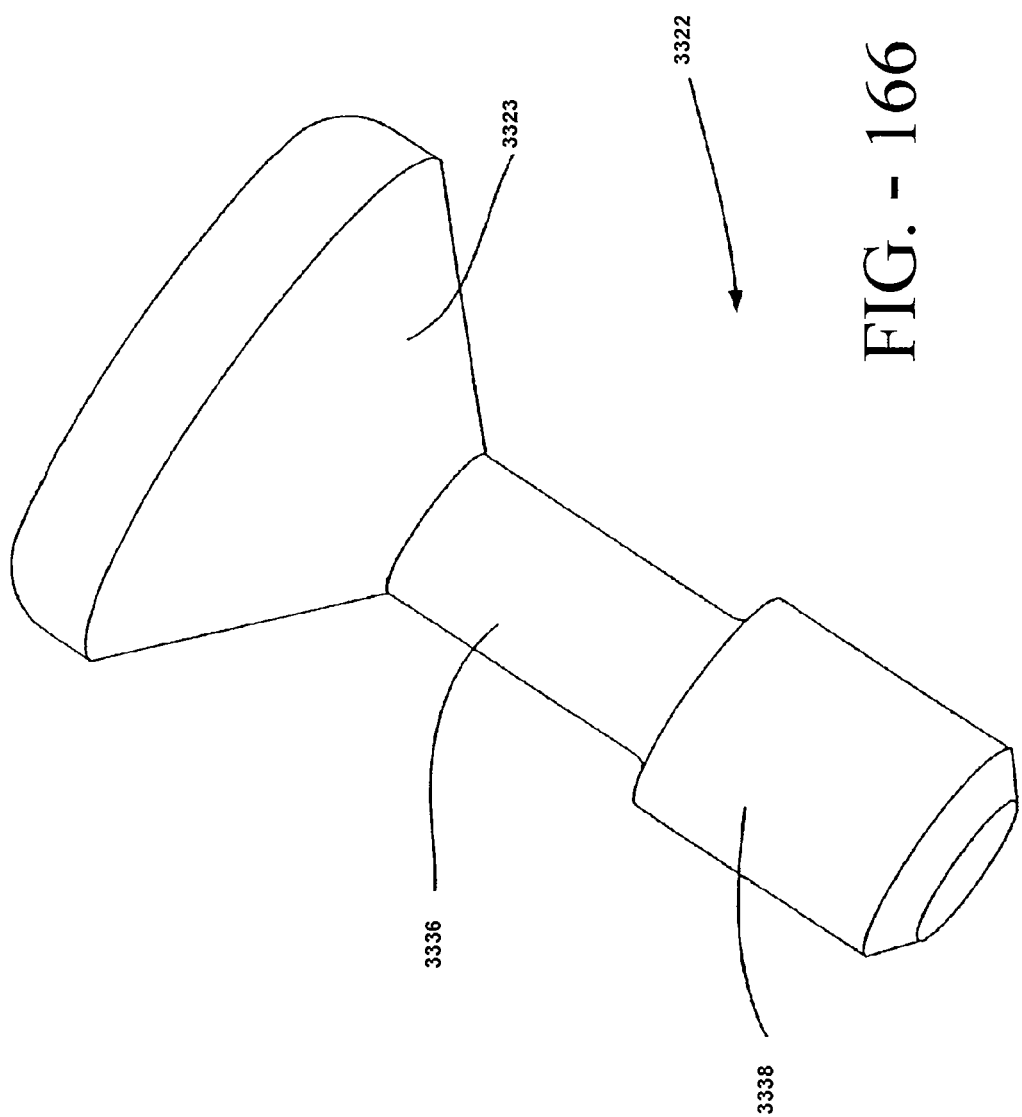
FIG. 166 is a perspective view of an embodiment of the fastener used in the present invention.

The fastener 3322 has a tapered head 3323, a middle section 3336 and threaded bottom section 3338 (see FIG. 166). The top end of the tapered head 3323 was a diameter substantially similar to the diameter of the top surface of the tapered cavity 3330. The diameter of the tapered head 3323 is reduced as the tapered head meets the middle section 3336. The slope of the tapered head 3323 is similar to the slope of the tapered cavity 3330 of the adjustable wing 3310. The middle section 3336 has a diameter substantially similar to the end portions 3334 of the adjustable wing 3310. The threaded bottom section 3338 has a slightly larger diameter than the middle section 3336 and is in one embodiment slightly smaller than the diameter of the middle portion 3332 of the adjustable wing 3310.

As the diameter of the end portions 3334 are smaller than the diameter of the bottom section 3338, the fastener 3322 cannot initially be placed through the end portions 3334 of the adjustable wing 3310. Accordingly, to fasten the adjustable wing 3310 to the main body 3301, the threaded bottom section 3338 of the fastener 3322 is placed through the middle portion 3332 of the adjustable wing 3310 and into the main body 3301. With a turn of the fastener 3322, the threaded portion of the bottom section 3338 will engage the main body 3301.

In another preferred embodiment the diameter of threaded bottom section 3338 is larger than the diameter of the middle portion of the adjustable wing 3310. For this embodiment, the fasteners 3322 is inserted into the cavity 3330 by slicing the cavity 3330 (FIG. 165) through the thinnest portion of the wall, spreading the wall open, inserting the middle section 3336 in the cavity with the threaded bottom section 3338 projection below the cavity 3330, and laser welding the wall closed. The slicing step preferably includes using a carbide slicing device.

Figure 167:
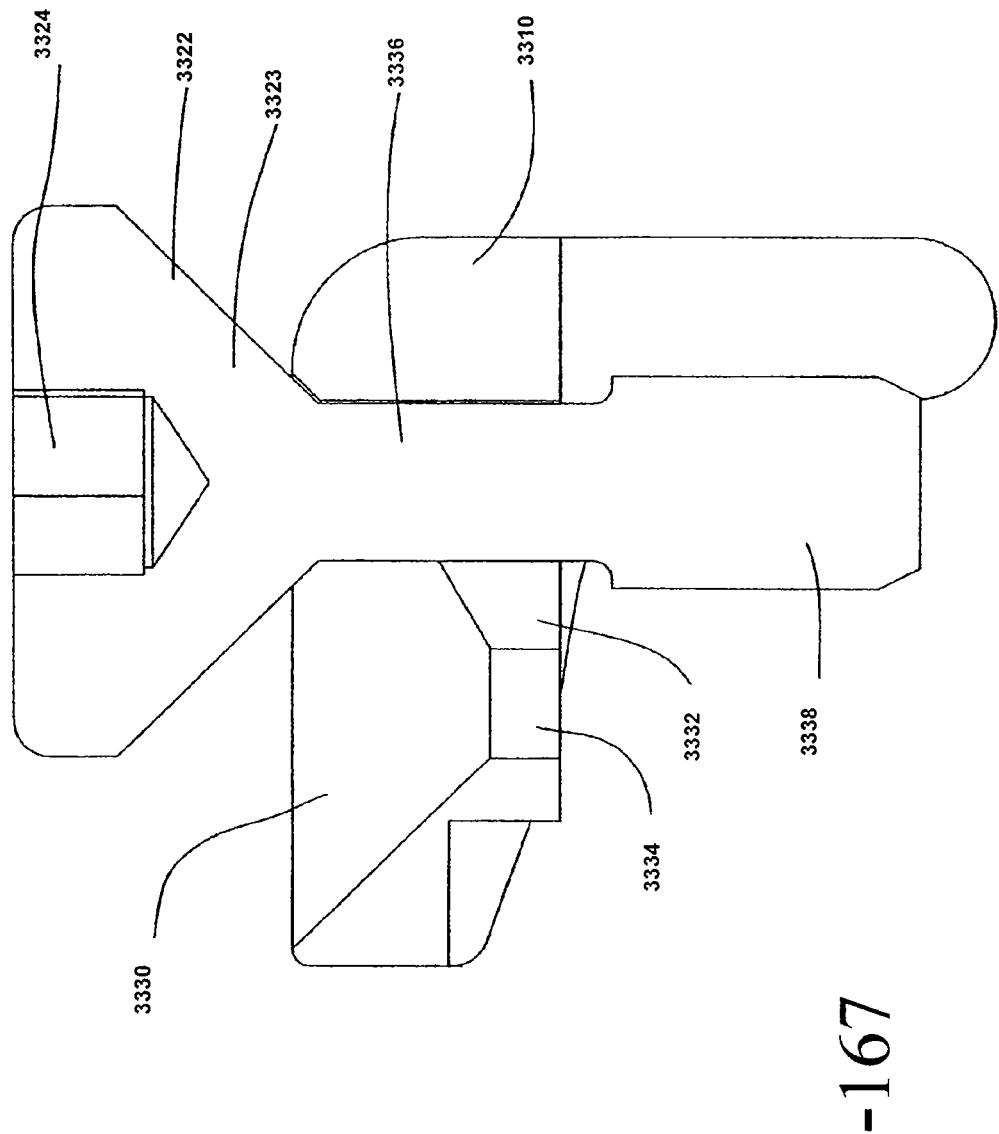
FIG. 167 is cut-away view illustrating the interaction between the fastener and the adjustable wing with the adjustable wing is in a first position.

When the adjustable wing 3310 is in the position furthest from the position of the first wing 3304, the tapered head 3323 of the fastener 3322 is substantially out of, and not engaging, the tapered cavity 3330 of the adjustable wing 3310 (See FIG. 167). As the fastener 3322 is rotated, the fastener 3322 will continue to engage, and travel further into, the main body 3301. As the fastener 3322 travels downwardly into the main body 3301, the tapered head 3323 of the fastener 3322 contacts the wall 3331 of the tapered cavity 3330. The adjustable wing 3310 can freely slide back and forth, limited by the end portions 3334 of the tapered cavity 3330. When the tapered head 3323 contacts the wall 3331 of the tapered cavity 3330, the adjustable wing 3310 moves towards the first wing 3304 guided by the alignment tab 3312 in the alignment track 3306. Therefore, the adjustable wing 3310 remains substantially parallel to the first wing 3304 in this preferred embodiment as the adjustable wing 3310 moves toward the first wing 3304 (see FIG. 168). It is to be understood that the tab 3312 and the track 3306 can be eliminated in another embodiment of the invention.

Figure 168:
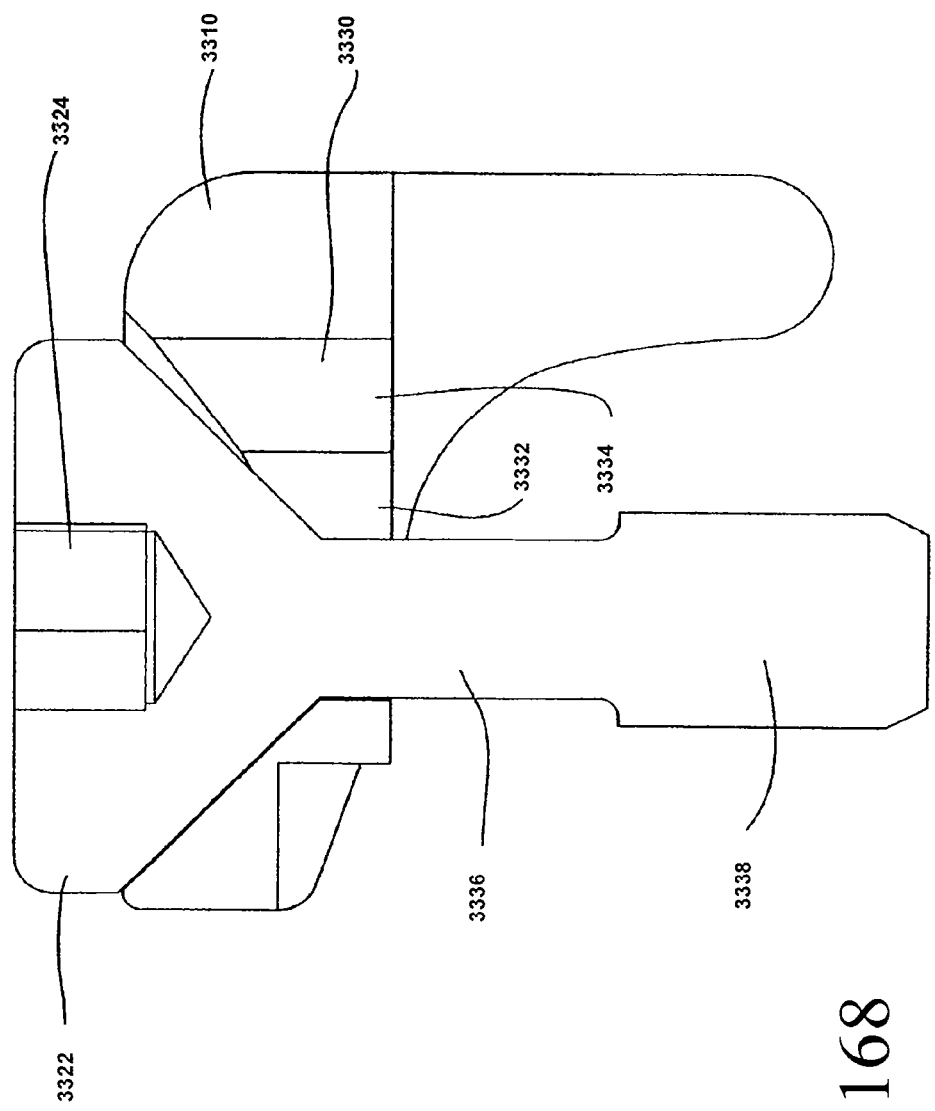
FIG. 168 is a cut-away view illustrating the fastener engaging the adjustable wing with the adjustable wing in a second position.

As shown in FIG. 168, the tapered head of 3323 of the fastener 3322 is mated in the tapered wall 3331 of the adjustable wing 3310. Accordingly, with this ramp mechanism, the adjustable wing 3310 is urged toward the spinous processes and the first wing 3304 and is locked in position at its closest approach to the first wing 3304. This arrangement allows the surgeon to loosely assemble the implant in the patient and then urge the adjustable wing closer to the first wing, by rotating fastener 3322 into body 3310 making the implanting method more tolerant to the anatomy of the patient.

The structure of the spine is of course unique for every patient. Accordingly if the width of the spinous processes is excessive, the adjustable wing can be left in a position that is between that shown in FIG. 167 and that shown in FIG. 168. The separation between the first wing 3304 and the adjustable wing 3310 can be incrementally adjusted by the number of turns of the fastener 3322.

Figure 169:
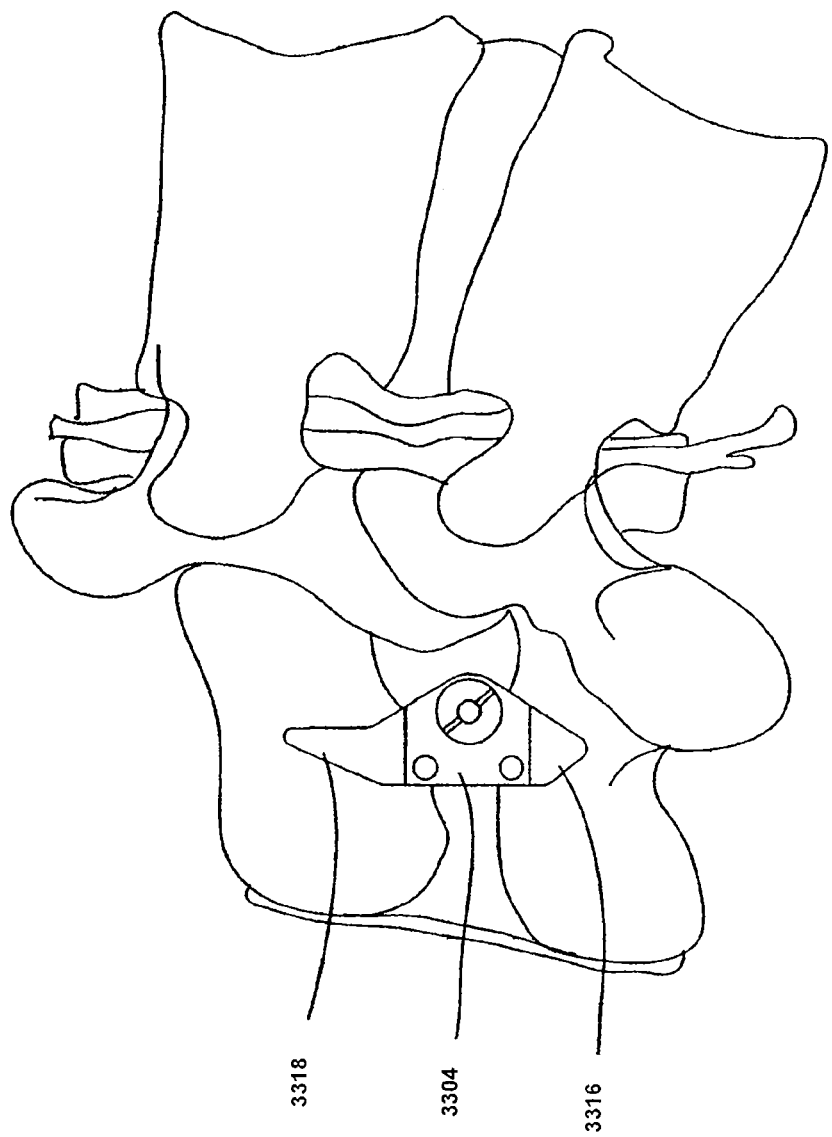
FIG. 169 is a side view illustrating an embodiment of the present invention as implanted between adjacent spinous processes.
Figure 170:
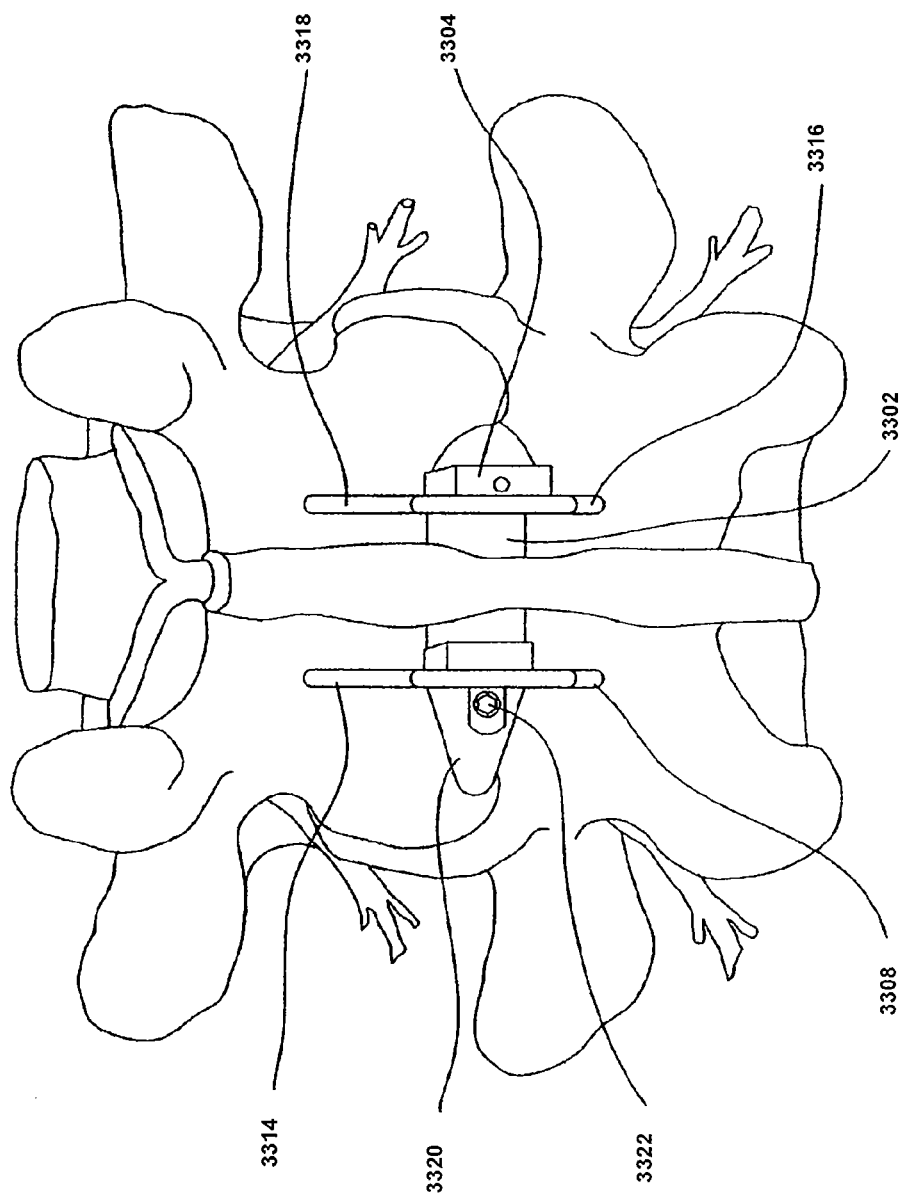
FIG. 170 is a front view of an embodiment of the present invention as implanted between adjacent spinous processes.

FIGS. 169 and 170 illustrate the position of the implant device 3300 in a patient. As shown by FIG. 169, the lower portion 3316 and upper portion 3318 of the first wing 3304 function to prevent side-to-side movement, toward and away from the vertebral body ensuring that the implant device 3300 remains in place. Similarly, the adjustable wing 3310 will also prevent excessive side-to-side movement. The wing also prevents motion in the direction of the main body into the space between the spinous processes.

Figures 171B, 171C:
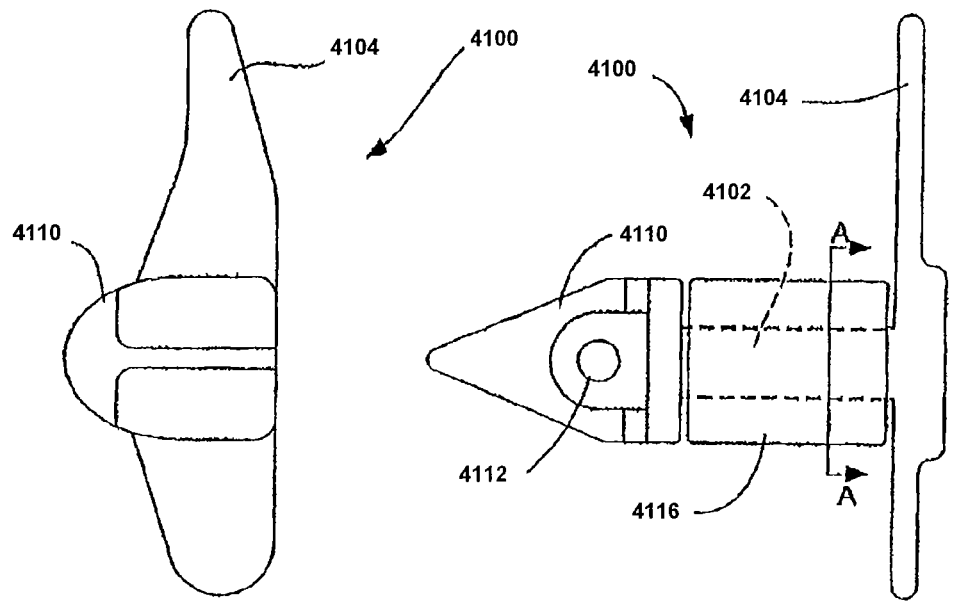
FIG. 171b is a side view of the embodiment of the invention of FIG. 171a including a spacer, a main body and a first wing.
FIG. 171c is a plane view of the embodiment of the invention in FIG. 171b.
Figures 171D, 171E:
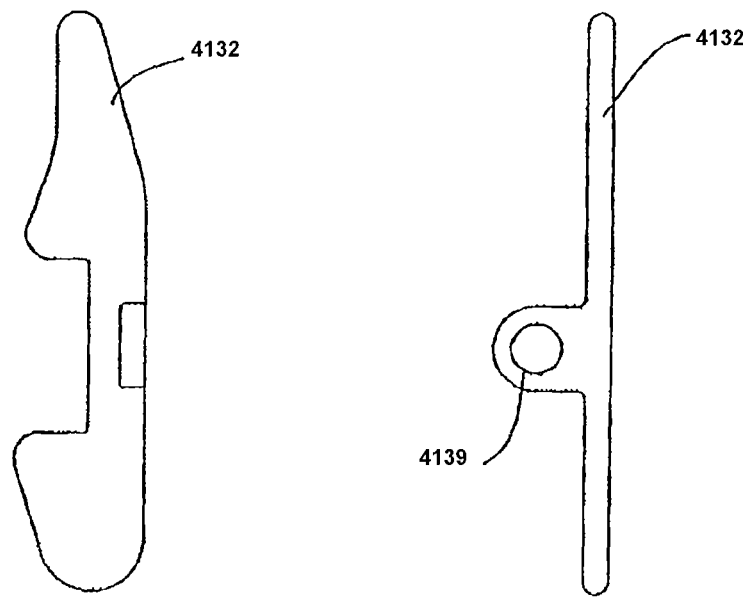

An embodiment of the implant 4100 is depicted in FIGS. 171a, 171b and 171c. This implant includes the first wing 4104 and sleeve 4116 and a lead-in and distraction guide 4110. This embodiment further includes, as required, a second wing 4132 as depicted in FIGS. 171d and 171e. As can be seen in FIG. 171a, a central body 4102 extends from the first wing 4104. Also, as can be seen in FIGS. 171a and 171b, the guide 4110 in this particular embodiment is pointed in order to allow the implant to be inserted between, and if necessary distract, adjacent spinous processes.

Figure 171F:
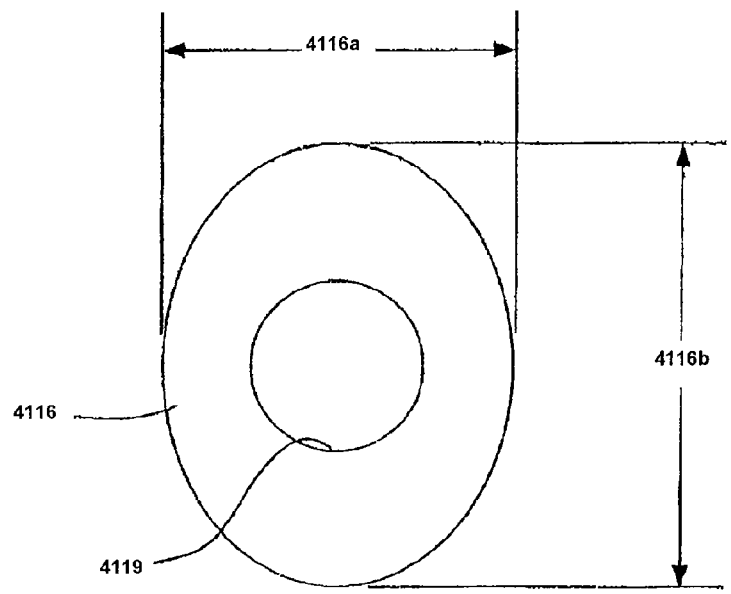
Figure 171G:
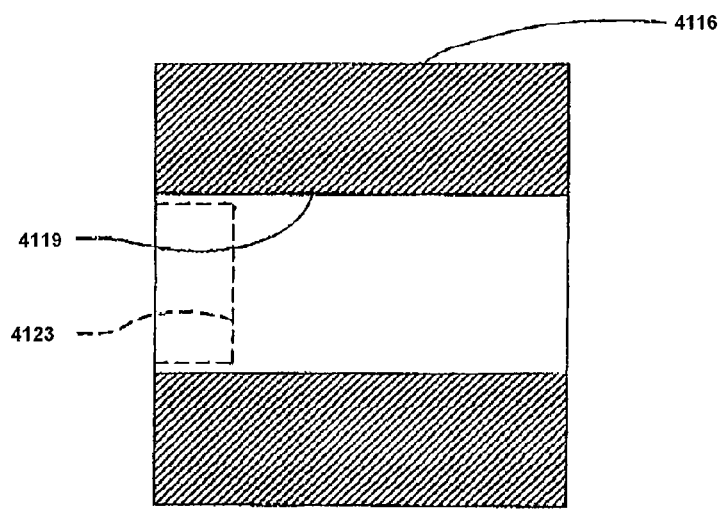

Additionally, as can be seen in FIGS. 171a, 171f and 171g, the sleeve 4116 is preferably cylindrical, and oval or elliptical in shape in cross-section. It is to be understood that sleeve 4116 can have other shapes as described throughout the specification and be within the spirit and scope of the invention. Sleeve 4116 includes a central bore 4119 which extends the length of sleeve 4116. The sleeve 4116 is received over the central body 4102 of the implant 4100 and can rotate thereon about the central body 102. In these embodiments, the spacer 4116 can preferably have minor and major dimensions as follows:

| Minor Dimension (4116a) | Major Dimension (4116b) |
| --- | --- |
| 6 mm | 10 mm |
| 8 mm | 10.75 mm |
| 12 mm | 14 mm |
| 6 mm | 12.5 mm |
| 8 mm | 12.5 mm |
| 10 mm | 12.5 mm |

In another preferred embodiment, the spacer 4116 has a cross-section with a major dimension and a minor dimension and the major dimension is greater than the minor dimension and less than about two times the minor dimension.

It is to be understood that the sleeve can be comprised of biologically acceptable material such as titanium or stainless steel. Additionally, it can be comprised of super-elastic material such as an alloy of nickel and titanium. Other structural and material variations for the sleeve are described below.

The advantage of the use of the sleeve 4116 as depicted in the embodiment of FIG. 171a is that the sleeve can be rotated and repositioned with respect to the first wing 4104, in the embodiment, in order to more optimally position the implant 4100 between spinous processes. It is to be understood that the cortical bone or the outer shell of the spinous processes is stronger at an anterior position adjacent to the vertebral bodies of the vertebra than at a posterior position distally located from the vertebral bodies. Accordingly, there is some advantage of having the implant 4100 placed as close to the vertebral bodies as is possible. In order to facilitate this and to accommodate the anatomical form of the bone structures, as the implant is inserted between the vertebral bodies and urged toward the vertebral bodies, the sleeve 4116 can be rotated relative to the wings, such as wing 4104, so that the sleeve is optimally positioned between the spinous processes, and the wing 4104 is optimally positioned relative to the spinous processes. Without this capability, depending on the anatomical form of the bones, it is possible for the wings to become somewhat less than optimally positioned relative to the spinous processes.

As required, the implant 4100 can also include a second wing 4132 which fits over the guide 4110 and is preferably secured by a bolt through apparatus 4134 of second wing 4132 to the threaded bore 4112 located in guide 4110. As implanted, the first wing 4104 is located next to the adjacent first side of the spinous processes and the second wing 4132 is located adjacent to second side of the same spinous processes.

Referring now to FIGS. 172-178, various embodiments of spacers adapted for placing between the first wing 4104 and the second wing 4132 are shown. The preferred material for the various spacers described below is titanium in combination with a deformable material such as silicone. It is within the scope of the present invention to manufacture the spacers from other biologically acceptable material such as, by way of example only, stainless steel or an alloy of nickel and titanium along with another deformable material such as another deformable polymer.

Figure 172:
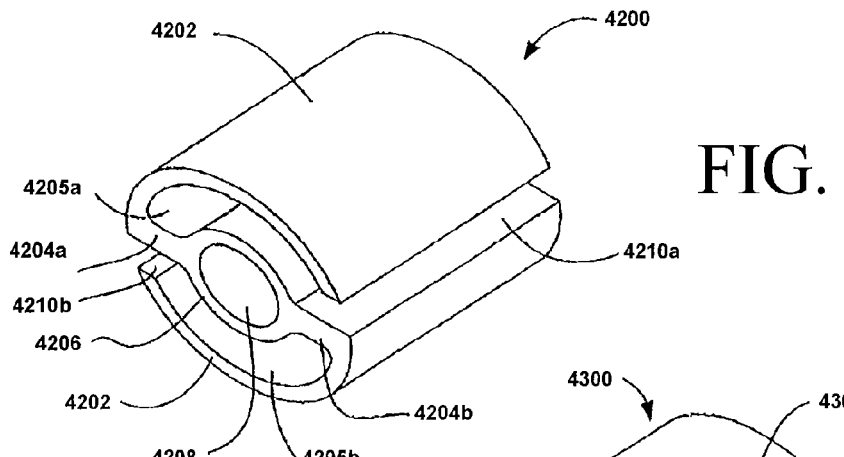
FIG. 172 is a perspective view of still another embodiment of the spacer of the invention.

Turning now to FIG. 172, the spacer 4200 includes an outer shell 4202. The outer shell 4202 is integrally formed with the center shaft 4206 by two support columns 4204. The center shaft has a bore 4208 extending through. Each support column 4204 extends substantially perpendicular from the center shaft 4206. Between the outer shell 4202 and the center shaft 4206, a cavity 4205 is created.

The shape of the outer shell 4202 as shown in FIG. 172 is elliptical in shape. It is within the scope of the invention that the outer shell 4202 may comprise other shapes such as, but not limited to, a cylindrical or egg shape. Regardless of the shape, the outer shell 4202 is not continuous in this preferred embodiment. One half of the outer shell 4202 extends from the end of one support column 4204*a* and around the center shaft 206 until the outer shell 4202 almost reaches the second support column 4204*b*. The second half of the outer shell 4202 is the same as the first half, and in this case both halves extend in a clockwise direction. Since each half of the outer shell 4202 extends from a different support column 4204, two slots 4210*a* and 4210*b* are created. Both slots 4210*a*, 4210*b* extend along the length of the spacer 4200. The slots 4210 function to lower the rigidity of the outer shell 4202 so that the outer shell 4202 is more flexible and functions as a cantilever spring. The smallest diameter of the space (circular or elliptical) can preferably range from 6 mm. to 11 mm. The thickness of the outer shell can preferably be 2 mm. The spacer can have other dimensions as identified previously.

Preferably, a compressible substance 4207 is placed into the cavities 4205*a*, 4205*b* located between the outer shell 4202 and the center shaft 4206. The compressible substance 4207 provides resistance against the outer shell 4202 traveling towards the center shaft 4206. As previously mentioned, the compressible substance in this embodiment is preferably silicone. It is within the scope of the invention that the compressible substance 4207 may comprise another medium such as, but not limited to, urethane-coated silicone and/or co-formed with silicone so that the urethane will not be attacked by the body, or another ultra-high molecular weight polymer. Another preferred material is polycarbonate-urethane, a thermoplastic elastomer formed as the reaction product of a hydroxl terminated polycarbonate, an aromatic diisocyanate, and a low molecular weight glycol used as a chain extender. A preferred polycarbonate glycol intermediate, poly(1,6-hexyl 1,2-ethyl carbonate)diol, PHECD, is the condensation product of 1,6-hexanediol with cyclic ethylene carbonate. The polycarbonate macroglycol is reacted with aromatic isocyanate, 4,4'-methylene bisphenyl diisocyanate (MDI), and chain material is preferable used at a hardness of 55 durometer. This material, as well as the other materials, can be used in the other embodiments of the invention.

The compressible medium preferably has a graduated stiffness to help gradually distribute the load when a spinous processes places a force upon the outer shell 4202. For example, the hardness of the silicone can be the lowest where the silicone contacts the outer shell 4202, and the hardness of the silicone can be the highest where the silicone contacts the center shaft 4206. Alternatively, the silicone can have a higher hardness in the center of the silicone located between the outer shell 4202 and the center shaft 4206.

The compressible medium 4207 fills the cavity between the outer shell 4202 and the center shaft 206 and is flush with the outer shell 4202. When the spacer 4200 is inserted between adjacent spinous processes, the outer shell 4202 protects the compressible substance (e.g., silicone) from directly contacting the spinous processes because the slots 4210 are along the side of the spacer 4200. Therefore, the deformable material 4207 does contact the spinous processes and wear debris is reduced or eliminated.

Figure 173:
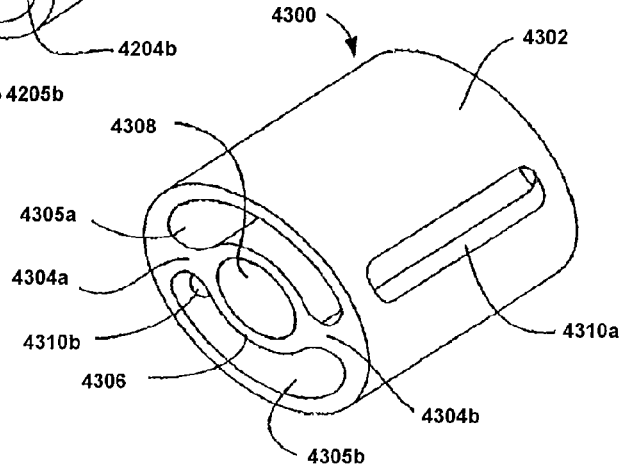
FIG. 173 is a perspective view of yet another embodiment of the spacer of the invention.
Figure 174:
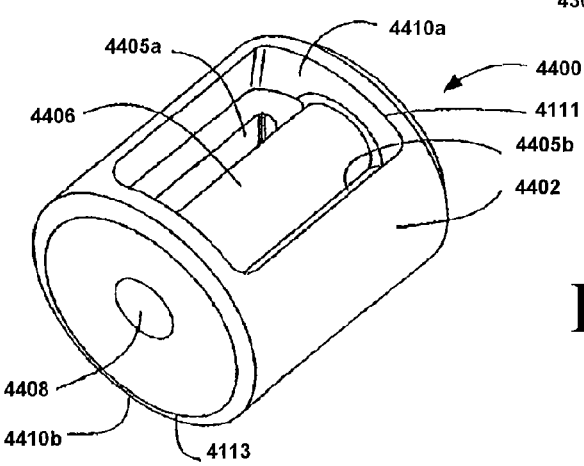
FIG. 174 is a perspective view of still another embodiment of the spacer of the invention.
Figure 175A:
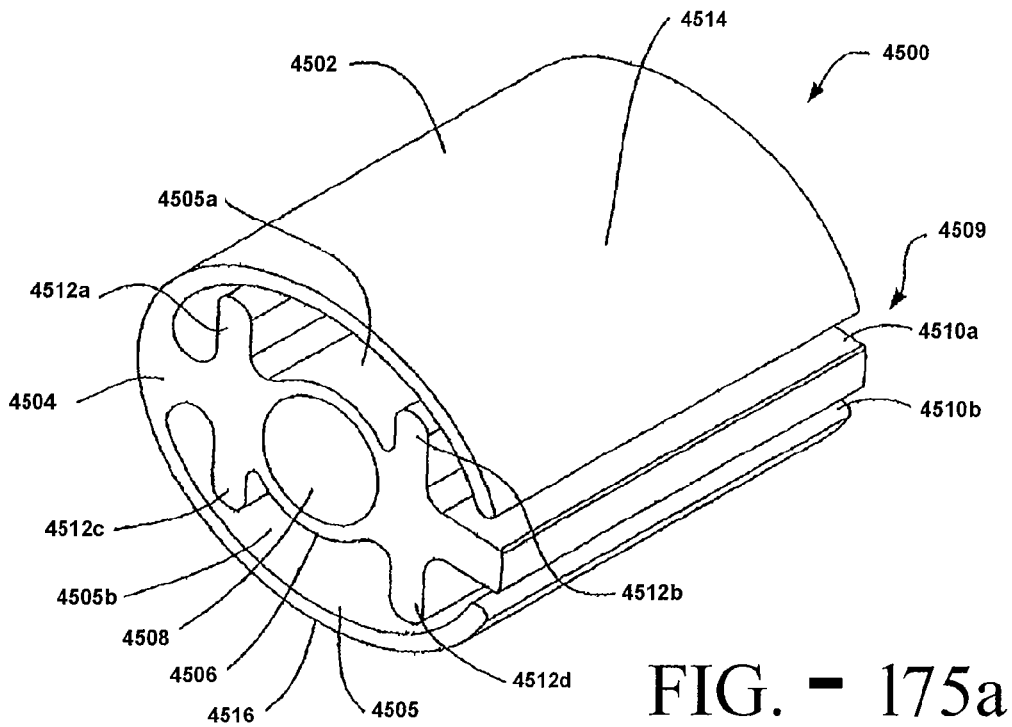
FIG. 175a is a perspective view of yet another embodiment of the spacer of the invention.
Figure 175B:
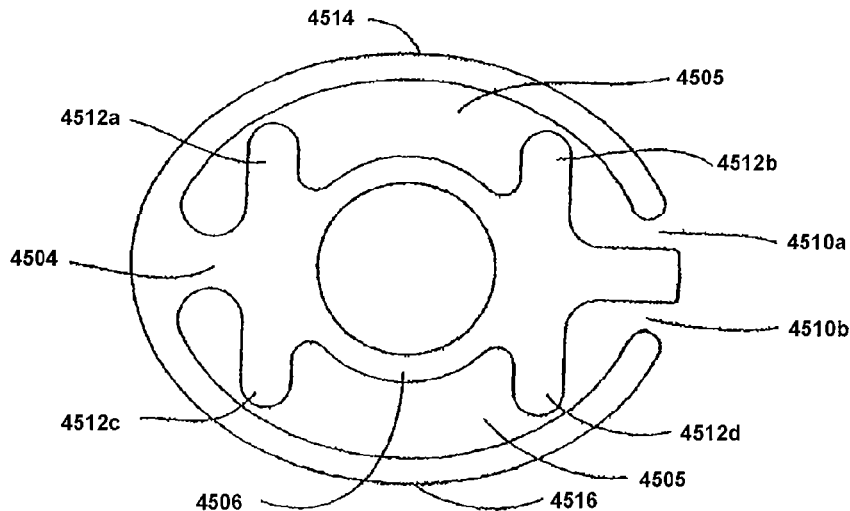

It is to be understood that for this and also in the embodiments in FIGS. 173, 175*a* and 175*b*, the embodiment can be constructed without a compressible material, with the outer shell solely providing the flexibility of the spacer. It is also to be understood that the embodiments shown in FIGS. 173-178 can have the dimensions and be made of the materials similar to those of FIG. 172. It is additionally to be understood that the metal components of any of the embodiments hereof can be comprised of a suitable plastic or composite material including fibers for strength.

Now referring to FIG. 173, the spacer 4300 has an outer shell 4302 and a center shaft 4306. The center shaft 4306 has a bore 4308 extending through. The center shaft 4306 is connected with the outer shell 4302 by two support columns 4304*a,b*, with each support column 4304*a,b* located on opposite sides of the center shaft 306. Similar to the embodiment of the present invention as illustrated in FIG. 172, the outer shell 4302 is elliptical, yet may comprise other shapes such as, but not limited to, a cylindrical or egg shape.

The outer shell 4302 has two slots 4310*a,b*. The slots 4310*a,b* extend through the wall of the outer shell 4302 to form a rectangular-like opening. It is within the scope of the invention for the spacer 4300 to have more than two slots 4310 and with different shapes. The slots 4310*a,b* are used to make the outer shell 4302 more flexible. It is preferred that the slots 4310*a,b* are located on the sides of the spacer 4300 so that none of the slots 4310*a,b* contact a spinous process.

Between the outer shell 4302 and the center shaft 4306 are two cavities 4305*a,b*. These cavities are separated by the support columns 4304*a,b*. The two cavities created between the outer shell 4302 and the center shaft 4306 preferably have a compressible substance therein. As previously mentioned, the compressible substance is preferably silicone. To improve the load distribution upon the outer shell 4302 and ease the load on the spinous processes, the silicone can have a graduated stiffness. For example, the hardness of the silicone can be the lowest where the outer shell 4302 contacts the silicone, and the hardness of the silicone can be the highest where the center shaft 4306 and the support column 4304 contacts the silicone. Alternatively, the silicone can have a higher hardness in the center of the silicone riding between the outer shell 4302 and the center shaft 4306.

The silicone is placed between the outer shell 4302 and the center shaft 4306 so that the silicone extends into the slots 4310 and is flush with the outer shell 4302. Since the spinous processes do not directly contact the silicone, this embodiment of the present invention also helps prevent wear debris.

Referring now to FIG. 174, yet another embodiment of the present invention includes spacer 4400. The spacer 4400 has an outer shell 4402 and a center shaft 4406. The center shaft 4406 has a bore 4408 extending through. The spacer 4400 has two openings 4410a,b that are substantially along the top 4111 and bottom 4113 portions of the outer shell 4402. Between the outer shell 4402 and the center shaft 4406, cavities 4405a,b are created which connects the two openings 4410a,b.

Similar to the previous embodiments, a compressible medium such as silicone is placed into the cavity 4405a,b and openings 4410a,b until the silicone becomes flush with the outer shell 4402. Preferably, the silicone also has a graduated stiffness. For example, the hardness of the silicone can be the lowest where it is flush with the outer shell 4402, and can be the highest where the silicone contacts the center shaft 4406. Unlike the previous embodiments, the exposed silicone will directly contact the spinous processes.

Referring now to FIGS. 175a-175b, another embodiment of the invention is spacer 4500. The spacer 4500 has an outer shell 4502 and a center shaft 4506. The outer shell 4502 forms a "C"-like shape. The center shaft 4506 has a bore 4508 extending through. The center shaft 4506 is attached to the outer shell 4502 by a support 4504. The support 4504 is substantially horizontal extending from the vertical center of the "C" to the middle of the open end 4509. The outer shell 4502 defines two slots 4510a,b along the length of the open end 4509. Both slots 4510a,b are defined by the space between the support 4504 and each end portion of the outer shell 4502. Since the outer shell 4502 is fixed at one end only, the outer shell 4502 functions like a cantilever-type spring. The outer shell 4502 is shown as elliptical in shape. It is within the scope of the present invention that the spacer 4500 may comprise other shapes such as, but not limited to, a cylindrical or egg shape.

The support 4504 has preferably at least two protrusions such as protrusions selected from protrusions 4512a,b,c,d. For example, the spacer 4500 in FIGS. 175a,b has four protrusions 4512a,b,c,d. Each protrusion 4512a,b,c,d extends substantially and preferably perpendicular in this embodiment from the support 4504 towards the inner surface of the outer shell 4502. While the spacer 4500 is in anon-compressed state, there is a gap between each protrusion 4512a,b,c,d and the outer shell 4502. When the spacer 4500 is compressed, the protrusions 4512a,b,c,d function to restrict the deflection of the outer shell 4502. When a spinous process exerts a force upon the outer shell 4502, the outer shell 4502 will deflect toward the center shaft 4506 until the outer shell 4502 contacts the protrusion 4512a,b,c,d. Essentially, the protrusions 4512a,b,c,d, function as a stop mechanism preventing the outer shell 4502 from deflecting too much, and thus limiting the motion of the spinous processes.

Similar to the previous embodiments, cavities 4505a,b are formed between the center shaft 4506 and the outer shell 4502. A compressible substance such as silicone is placed within the cavity 4505. It is preferable that the silicone have a graduated stiffness to help distribute the load placed upon the outer shell 4502. For example, the hardness of the silicone can be the lowest where the silicone contacts the inner surface of the outer shell 4502, and the hardness of the silicone can be the highest where the silicone contacts the center support shaft 4506, and the support 4504 and the protrusions 4512a, b,c,d. Alternatively, the silicone can have a higher hardness in the center of the silicone rising between the outer shell 4502 and the center shaft 4506.

The silicone fills the cavities 4505a,b until the silicone is flush with the outer shell 4502. When the spacer 4500 is inserted between adjacent spinous processes, the top and bottom portions 4514, 4516 of the spacer 4500 contact the spinous process. Therefore, the silicone will not directly contact the spinous processes which aids in the prevention of wear debris.

Figure 176A:
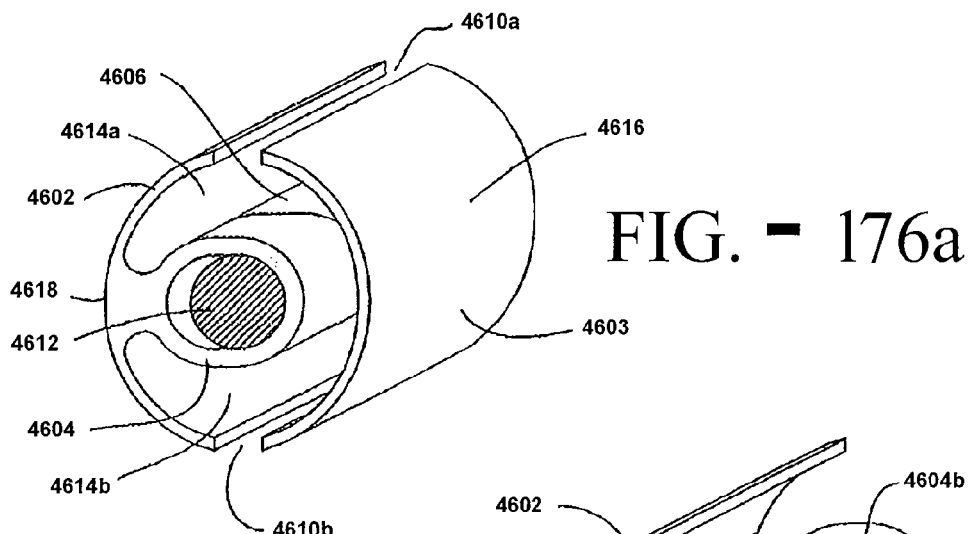
Figure 176B:
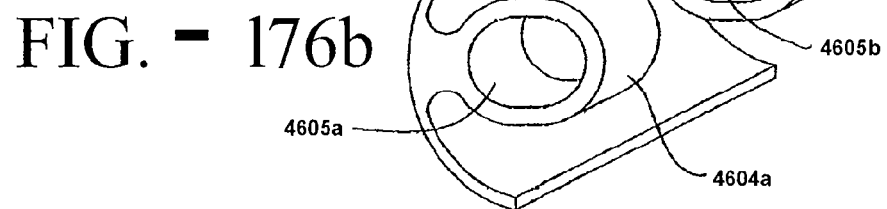
Figure 176C:
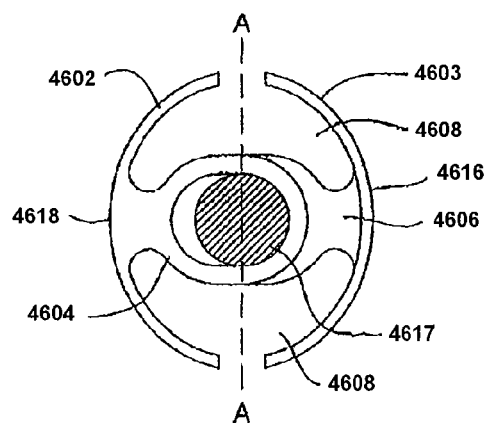

Referring now to FIGS. 176a-176c, another embodiment of the present invention is spacer 4600. The spacer 4600 has a first outer shell 4602 and a second outer shell 4603. The first outer shell 4602 has at least two support elements 4604a,b. Each support element 4604a,b has a bore 4605a,b extending therethrough. The support elements 4604a,b are located substantially at either end of the first outer shell 4602 along a single horizontal axis. The bores 4605a,b are oval in a preferred embodiment. This shape allows the spacer 4600 to move relative to the central shaft or axis (FIG. 117) upon which the spacer is mounted. The second outer shell 4603 has a single support element 4606, located substantially in the center of the second outer shell 4603 and along the same horizontal axis as the two support elements 4604a,b. The support element 4606 also has a bore extending through which is similar to bore 4605. Support element 4606 is located between support element 4604a,b in FIG. 176a. A central shaft 4612 (shaft 4102 in FIG. 171c) is placed through the support elements 4604a,b, 4606 to form a hinge-type connection between the first outer shell 4602 and the second outer shell 4603 (see FIG. 176a). The hinge-type connection allows the first outer shell 4602 and the second outer shell 4603 to move independently of each other.

When the first outer shell 4602 and the second outer shell 603 are connected by shaft 4612, slots 4610a,b are created along the side edges of the spacer 4600. Two cavities 4614a,b are also created, defined by the hinge-type connection between the first outer shell 4602 and the second outer shell 4603. Similar to the previous embodiments, a compressible substance (e.g., silicone) can fill each cavity and extend into the slots 4610a,b until the silicone is flush with the first outer shell 4602 and the second outer shell 4603. Additionally, it is preferred that the silicone have a graduate hardness similar to the previous embodiments. In one embodiment, the hardness of the silicone can be the highest along view line A-A, and can be the lowest where the silicone contacts the first and second outer shell 4602, 4603. Alternatively, the silicone can have the highest hardness where it contacts the support elements 4604a,b, 4606, and can have the lowest hardness where the silicone fills the slots 4610a,b.

When the spacer 4600 is inserted between adjacent spinous process, only the top and bottom portions 4616, 4618 of the spacer 4600 will directly contact each spinous process. Therefore, the first outer shell 4602 and the second outer shell 4603 prevent direct contact between the silicone and the spinous process. Accordingly, the spacer 4600 helps prevent wear debris from being formed.

Figure 177:
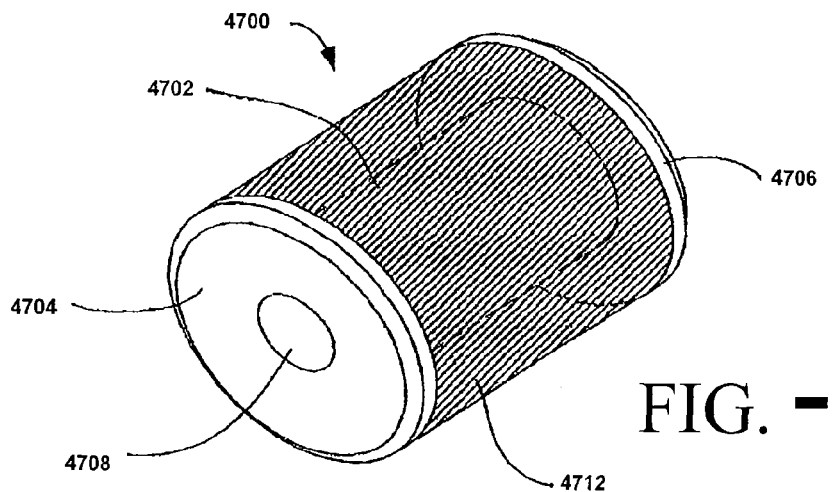

Now referring to FIG. 177, still yet another embodiment of the present invention is spacer 4700. Spacer 4700 includes preferably a component in the shape of an elliptical or oval or cylindrical spool 4710. Alternatively, the component 4700 can be formed for method or suitable plastic material or composites including, by way of example only, fibers for strength. The spacer 4700 has a center shaft 4702 with a bore 4708 extending through. As in other embodiments, the bore 4708 can be, by way of example only, circular, oval or elliptical. A first end 4704 and a second end 4706 are integrally formed with the center shaft 4702 in this preferred embodiment. Both the first end 4704 and the second end 4706 extend outward from the center shaft 4702 and form a circular rim around each end of the center shaft 4702. It is within the scope of the present invention for the first end 4704 and second end 4706 to comprise other shapes such as, but not limited to, elliptical, circular, oval or egg-shaped.

A compressible medium 4712 surrounds the center shaft 4702. As previously mentioned, the compressible substance is preferably silicone. The silicone extends out from the center shaft 4702 until it is flush with the outer rim of both the first end 4704 and the second end 4706. With the silicone around the center shaft 4702, the spacer 4700 will look like an elliptical cylinder in this embodiment. The spacer 4700 does not have an outer shell surrounding the silicone. When the spacer 4700 is inserted between adjacent spinous process, the silicone will directly contact the spinous process. A preferred embodiment of the spacer 4700 will have silicone with a graduated stiffness to help distribute the load placed upon the spacer 4700. For example, the hardness of the silicone can be the lowest at the outermost surface that contacts the spinous process, and the hardness of the silicone can be the highest where the silicone surrounds and contacts the center shaft 4702. Alternatively the hardness can be greater where the silicone contacts the spinous process and then less hard adjacent to the center shaft 4702.

Figure 178A:
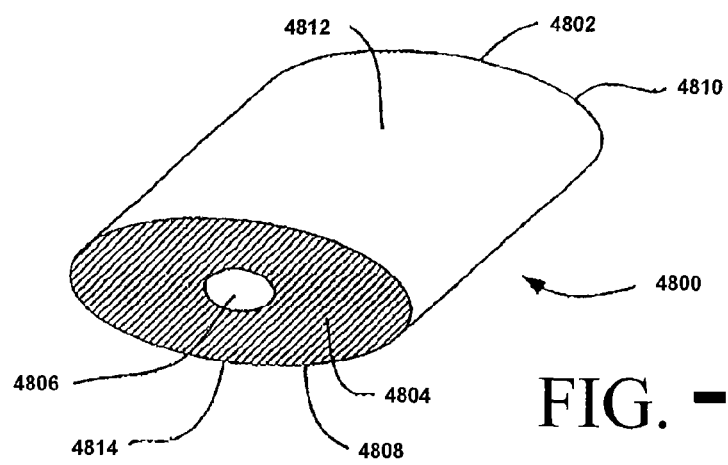

Now turning to FIG. 178a, another embodiment of the present invention is spacer 4800. The spacer 4800 has an outer shell 4802 which can be metallic or plastic. The outer shell 4802 is preferably elliptical in shape. It is within the scope of the present invention that the outer shell 4802 can be a shape such as, but not limited to, a cylindrical or egg shape. Regardless of the shape, the outer shell 4802 is open on both ends 4808, 4810.

A compressible substance 4804 is placed within the outer shell 4802 and is flush with both ends 4808, 4810 of the outer shell 4802. A bore 4806 extends through the compressible substance 4804. If desired the bore can be defined by a metallic or plastic sleeve held on the compressible substance 4804. Similar to the previous embodiments, the compressible substance 4804 is preferably silicone. A preferred embodiment of the spacer 4800 has silicone with a graduated stiffness. In an embodiment, the hardness of the silicone can be the highest at the bore 4806, and the hardness of the silicone can be the lowest where the silicone contacts the inner surface of the outer shell 4802. Alternatively, the hardness of the silicone can be the highest adjacent shell and lowest about bore 4806.

When the spacer 4800 is inserted between adjacent spinous processes, only the top and bottom portions 4812, 4814 will directly contact each spinous process. Therefore, the outer shell 4802 prevents direct contact between the silicone and the spinous processes. Accordingly, the spacer 4800 helps prevent wear debris from being formed.

By way of example only, the thickness of the outer shell can be about 0.010 inches with the hardness of the compressible medium being about 50 durometer. By way of example only, the outer shell can be about 0.010 inches with the hardness of the compressible medium being about 70 durometer.

Figure 178B:
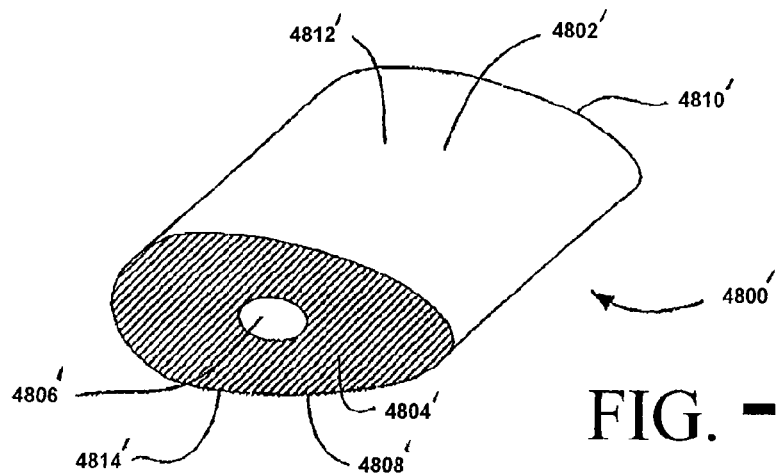

It is also to be understood that the spacer 4800 can include any of the compressible medium 4804 discussed herein and/or compatible with the body, with a bore hole provided therethrough. That is to say that the outer shell 4802 can be eliminated in this embodiment. Preferably the spacer is comprised of silicone, however, other materials are within the spirit and scope of the invention. FIG. 178b depicts an egg-shaped spacer 4800' with a bore 4806'. The spacer 4800' is comprised of a compressible medium.

Figure 179A:
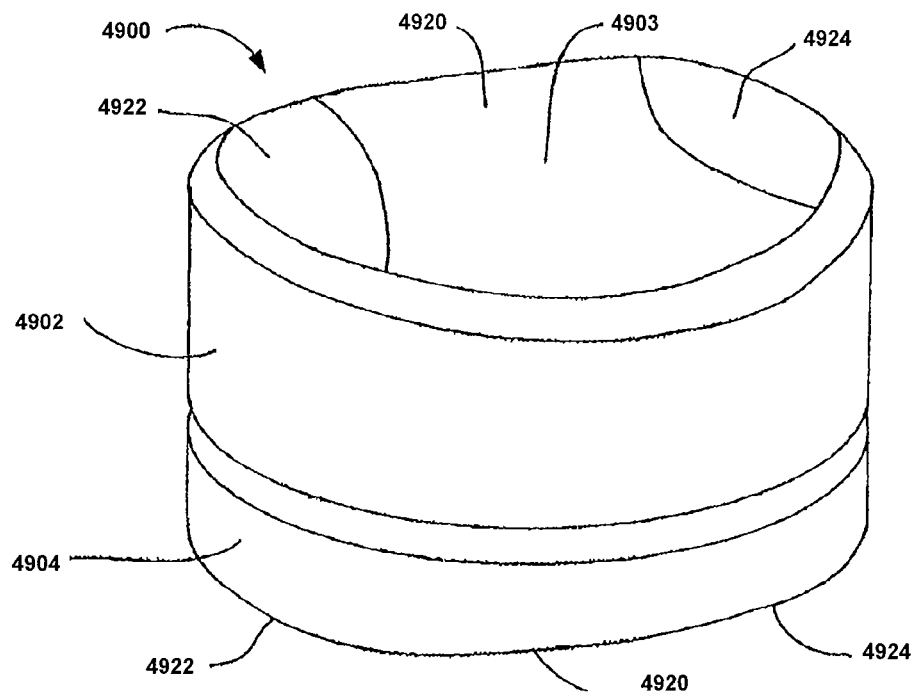
Figure 179B:
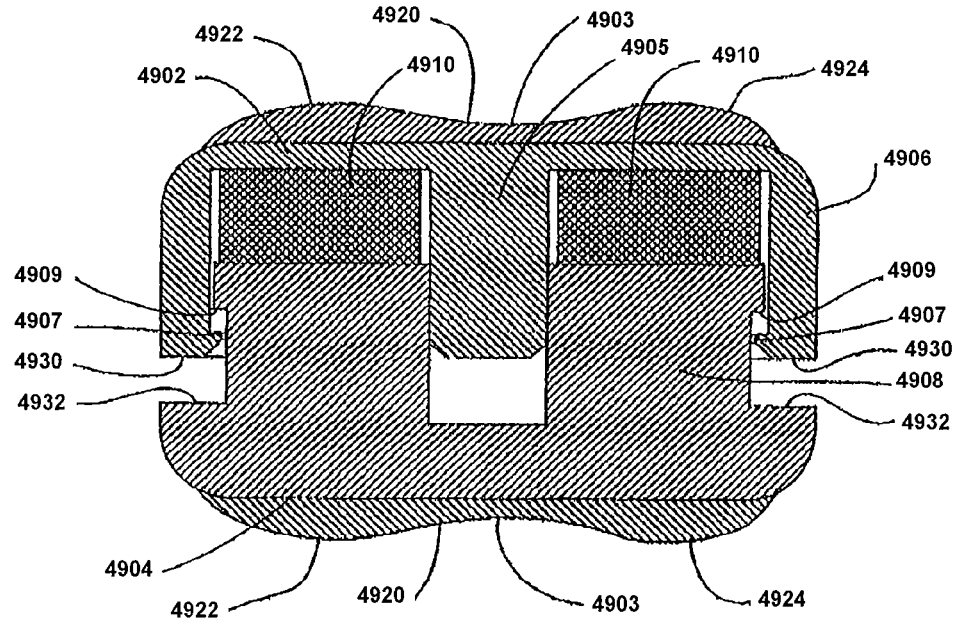

Referring now to FIGS. 179a-179b, the interspinous process device on implant 4900 has a first support 4902 and a second support 4904. The first support 4902 and the second support 4904 directly contact the spinous process and can be made of a suitable metal or a suitable plastic. Both the first support 4902 and the second support 4904 have a contour 4903. The contour 4903 allows the device 4900 to be contoured to and to engage each spinous process so, preferably, that the device 4900 does not move laterally. Each contour 4903 includes a concave portion 4920 and upstanding ridges 4922, 4924. It is to be understood that the ridges can be higher than shown in FIG. 179a in order to define a deeper contour. Additionally, ridges 4924, especially when higher, of supports 4903, 4904 together can define a first wing and ridges 4922, especially when higher, of support 4903, 4904 define a second wing. Such wings can function in much the same way as the wings described in other embodiments of the invention.

During the method of implanting device 4900, both spinous processes are exposed using appropriate surgical techniques, and thereafter the device 4900 is positioned so that the saddles 4903 of both the first support 4902 and the second support 4904 engage the respective spinous process. The concave shape of the saddle 903 distributes the forces between the saddle 4903 and the respective spinous process. This ensures that the bone is not reabsorbed due to the placement of the device 4900 and that the structural integrity of the bone is maintained.

Referring now to FIG. 179b, the first support 4902 has a female receiving mechanism 4906 and the second support 4904 has a male engaging mechanism 4908. The width of the female receiving mechanism 906 and the male engaging mechanism 4908 are substantially similar. The female receiving mechanism 4906 further has an alignment column 4905 to assist in the movement of the supports 4902, 4904 relative to each other.

The first support 4902 and the second support 4904 are interlocked so that the first support 4902 and the second support 4904 cannot be independently separated. The first support 4902 has a ledge 4907 that extends around the inner circumference of the first support 4902. Similarly, the second support 4904 has a ledge 4909 extending around the circumference of the male engaging mechanism 4908. If the first support 4902 and the second support 4904 travel in opposite directions, the ledges 4907 and 4909 will eventually engage and prevent the first support 4902 and the second support 4904 from separating. Preventing the first support 9402 and the second support 4904 from separating also contains the compressible medium 4910, as described below, within the device 4900.

Placed within the female receiving mechanism 4906 is a compressible medium 4910. As previously mentioned the compressible medium 4910 provides resistance, limiting the possible range of motion of the spinous process. By way of example only, the compressible medium 4910 can be silicone. It is within the scope of the present invention that the compressible medium can include, by way of example only, a spring mechanism, a synthetic gel or a hydrogel. The compressible or deformable material can also include material which offers, for example, increased resistance to compression the more the material is compressed. For example, as compression and deformation occur, the material can offer a steady resistive force or a resistance force that increases, either linearly or non-linearly, the more the implant is compressed.

With respect to an embodiment with a graduated stiffness, the hardness of the silicone can be the lowest where the first support 4902 contacts the silicone, and the hardness of the silicone 4910 can be the highest where the second support 4904 contacts the silicone. Alternatively, the silicone can have a higher hardness in the center of the silicone riding between the supports 4902, 4904.

In this and with the other embodiments, the medium 4910 can also be designed to vary resistance to movement according to the speed or rate of deformation. For example, when an individual leans back slowly, the adjacent spinous processes place a force onto the first support 4902 and the second support 4904. With slow backward bending the force is small and gradual until the limit of compression of the material is reached. However, if the individual attempts a rapid activity that can result in a severe first compression of the device 4900, the medium 4910 can offer higher stiffness, preventing the spinous processes from making excessive motion and causing pain.

Preferably, the height of the device 4900 is slightly larger than the undistracted distance between the adjacent spinous processes. When the device 4900 is then inserted between the spinous process, the contours 4903 will press against each spinous process and assist to keep the device 4900 in place. During a daily routine, an individual will perform functions that will translate into vertical movement of each spinous process. It is important that the individual be able to retain some of his normal range of motion. To retain a normal range of motion, the device 4900 can preferably be compressed when the spinous processes place a force upon the first support 4902 and the second support 4904. Thus, when the device 4900 is in a normal state the outer peripheral edge 4930, 4932 of first and second support 4902, 4904 respectively do not contact each other. However, ridges 4930, 4932 act as a limit to the amount device 4900 can be compressed. Such an arrangement reduces potential resorption of the bone adjacent to the implant and to more gradually limit extension or backward bending of the spinal column.

The embodiment of this implant as well as the several other implants described herein act to limit extension. These implants, however, do not inhibit the flexion of the spinal column when the spinal column is bent forward.

This invention includes instruments and methods for inserting spinal implants in the vertebral columns of patients and to spinal implants themselves. In one embodiment, instruments are provided for inserting a main body assembly between spinous processes of adjacent vertebrae. These instruments, termed herein "main body insertion instruments" generally comprise an elongated body portion having a handle at one end, an insertion shaft and an insertion tip. The insertion tip engages with the main body assembly and holds the assembly in fixed relation to the instrument. The surgeon prepares the site for implantation, and uses the instrument to urge the assembly between spinous processes of adjacent vertebrae.

In other embodiments of this invention, different instruments can be used to insert universal wings on to the main body assembly of the spinal implant. These other instruments are termed herein "wing insertion instruments." A wing insertion instrument generally comprises a handle, an insertion shaft and an insertion tip. The insertion tip of a wing insertion instrument engages with the universal wing and holds it fixed relative to the instrument. The surgeon then grasps the handle portion of the instrument and uses it to urge the wing implant portion into proximity with a main body assembly which has been inserted between spinous processes of the spine.

I. Main Body Insertion Instrument

Figure 180:
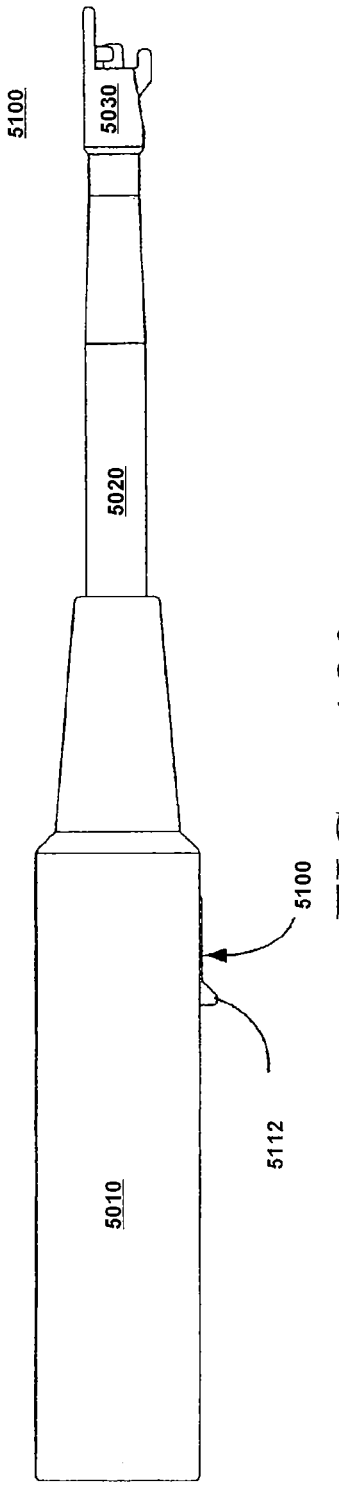
Figure 181:
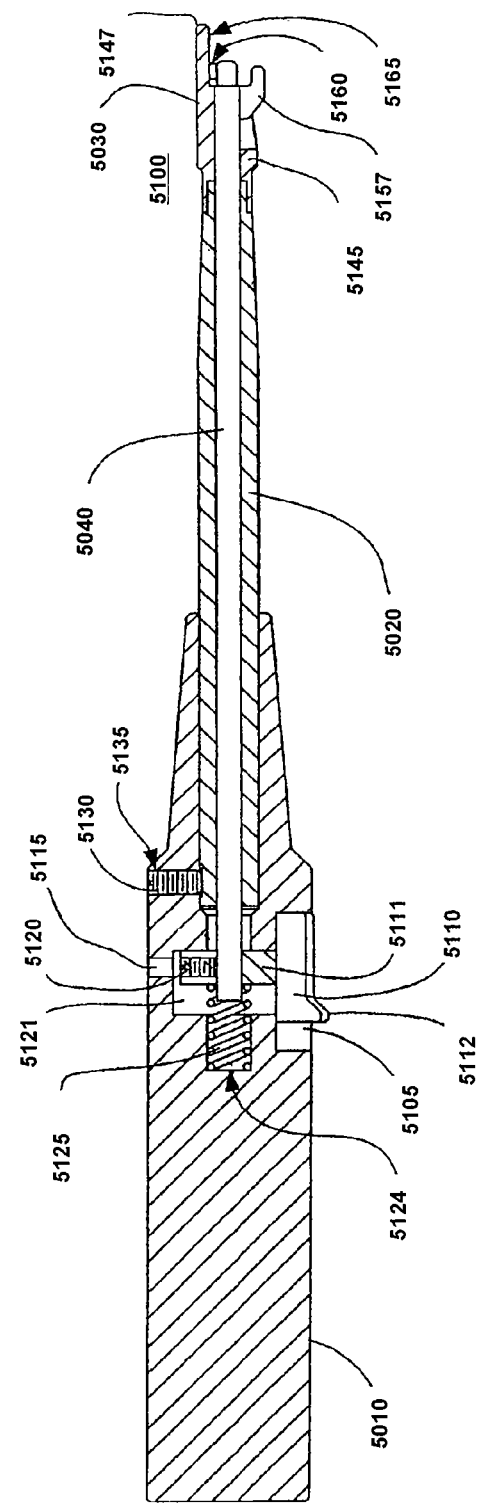

Main body insertion instrument of this invention is illustrated, by way of example only, in FIGS. 180-182. FIG. 180 depicts an exterior view of a main body insertion instrument 5100 of this invention having a handle 5010, an insertion shaft 5020 and an insertion tip 5030. Handle 5010 can be made of any suitable material, such as by way of example only, Gray ULTEM™, a polyetherimide resin. Insertion shaft 5020 can be made of any suitable, strong material, such as 304 stainless steel. Insertion shaft 5020 has a central bore extending through its length. The proximal end of insertion shaft 5020 is adapted to fit within the distal end of handle 5010, and can be held in place with a set screw, made of, by way of example only, 304 or 455 stainless steel. A main body insertion tip 5030 is attached to the distal end of the insertion shaft. Insertion tip 5030 can be made of, by way of example only, 17-4 stainless steel. A bore extends longitudinally through the insertion tip 5030 and is contiguous with the bore through the insertion shaft 5020. An insertion rod 5040, having a distal end with a spacer engagement pin and a locking pin, extends through the length of the bore in insertion shaft 5020. Insertion rod 5040 extends into the handle 5010 of the main body insertion instrument 5100. On one side of handle 5010, insertion knob 5110, having a raised portion 5112, is for manipulation of a locking pin and spacer engagement pin in insertion tip 5030. The insertion knob 5110 can be made of, by way of example only, 304 stainless steel. The stainless steel components of the instruments of this invention can desirably meet ASTM Standard F899-95: Standard Specifications for Stainless Steel Billet, Bar, and Wire for Surgical Instruments.

FIG. 181 depicts a longitudinal cross-sectional view of a main body insertion instrument 5100 as depicted in FIG. 180, and shows details of this embodiment of the invention. Handle 5010 has an insertion knob groove 5105 on a lateral surface, within which insertion knob 5110 is provided. Insertion knob 5110 and groove 5105 are sized so that insertion knob 5110 can move in a proximal/distal path along the handle 5010. Insertion knob 5110 has said raised portion 5112 used for applying force to move insertion knob 5110 proximally and distally along handle 5010. Insertion knob 5110 is attached to rod 5111, which is located within cavity 5121 of the cavity 5121. When placed within cavity 5121, the rod 5111 engages spring 5125, which is located within an interior space 5124 of handle 5010. Spring 5125 is urged against insertion rod 5040. The spring 5125 provides a force that urges rod 5111 and also rod 5040 toward the distal portion of the instrument 5100. Spring 5125 is compressed by manual movement of insertion knob 5110 in a proximal direction, acting via rod 5111. Because insertion rod 5040 is engaged with rod 5111, insertion rod 5040 is drawn proximally by proximal movement of insertion knob 5110. When manual force on insertion knob 5110 is relaxed, as for example, after alignment of a main body implant in relation to insertion tip 5030, spring 5125 urges rod 5111, insertion rod 5040 and insertion knob 5110 in a distal direction. As insertion rod 5040 is urged distally, locking pin 5155 and spacer engagement pin 5157 are urged toward the distal end of insertion instrument 5100 as well, where pins 5155, 5157 can engage the main body assembly of the spinal implant. FIG. 181 depicts insertion shaft 5020 having a proximal end that is adapted to fit within the distal portion of handle 5010. When so placed, set screw 5130 engages with insertion shaft 5020 to keep insertion shaft 5020 engaged in handle 5010. Set screw 5130 can be made of any convenient material, such as, by way of example only, stainless steel. It can be especially desirable for set screws 5120 and 5130 to be completely removable from handle 5010, to provide open access to the interior of handle 5010 for cleaning and sterilization Insertion tip 5030 is adapted to fit onto the distal end of insertion shaft 5020, byway of example only, with an interference fit. FIG. 181 depicts such an interference fit engagement of insertion tip 5030 with the distal end of insertion shaft 5020. However, other ways of attaching insertion tip 5030 to insertion shaft 5020 are contemplated and are considered to be part of this invention.

FIG. 181 depicts components of insertion tip 5030, which include a proximal portion 5145, which can act as a position stop for spacer engagement pin 5157. Spacer engagement pin 5157 protrudes laterally from the portion of the insertion rod 5040, and is adapted to engage a spacer engagement hole of a main body assembly. When so engaged, spacer engagement pin 5157 can position a spacer relative to the remainder of the main body wing and tissue expander, making insertion of the implant between spinous processes convenient. At the distal end of insertion rod 5040, locking pin 5155 is positioned to engage a hole in the main body assembly. Thus, when so engaged, locking pin 5155 and spacer engagement pin 5157 can hold the main body, tissue expander and spacer in position relative to one another for convenient insertion. At the distal end of the insertion tip 5030, portion 5147, having a flat medial surface 5165, can support the main body. In some embodiments, one or more alignment pins 5160 can be provided to engage with a main body to provide additional support during surgery.

In general, the construction of main body insertion instrument 5100 desirably is sufficiently robust to provide firm support of the main body assembly during surgery. For example, in certain situations, it can be desirable for the surgeon to exert relatively large forces on the main body assembly to urge the tissue expander between spinous processes. Generally, the connective tissue, including ligaments, can be strong and tough, tending to resist stretching. However, during surgery using the spinal implants and insertion instruments of this invention, it may be desirable to deflect, distract and/or stretch the ligaments to permit passage and proper location of spinal implants. In these situations, the instruments are strong and rigid.

It also can be desirable for the surfaces to be smooth and have relatively simple geometrical shape. Simple shape and relatively open construction can provide for easy access to the interior of the parts of the instrument, and can permit easy and convenient cleaning and sterilization.

FIG. 182*a*-182*c* depict the insertion tip 5030 of main body implant insertion instrument 5100 in additional detail. FIG. 182*a* depicts a side view of insertion tip 5030 fitted into the distal end of insertion shaft 5020. Bore 5150 of insertion shaft 5020 is shown in dashed lines. Locking pin 5155 of insertion rod 5040 is shown in the distal-most extension, as urged by spring 5125 of FIG. 181. Portion 5147 is shown having alignment pin 5160 with an axis aligned substantially perpendicularly to the plane of portion 5147. Spacer engagement pin or catch 5157 is shown above locking pin 5155. At its distal-most extension, locking pin 5155 crosses the axis of alignment pin 5160. When alignment pin 5160 and spacer engagement pin 5157 have engaged their respective portions of a main body assembly, the assembly can be firmly held by the insertion tip 5030.

FIG. 182*b* depicts an insertion tip as shown in FIG. 182*a* in which the insertion rod 5040 has been moved to a proximal position. In the embodiment depicted in FIG. 182*b*, locking pin 5155 and spacer engagement pin 5157 have been retracted sufficiently to be proximal to surface 5156 of insertion tip 5030. When so positioned, the main body assembly can be disengaged from insertion tip 5030 and the instrument can be withdrawn from the patient's body, leaving the main body assembly in place.

FIG. 182*c* depicts a top view of insertion tip 5030. Insertion rod 5040 is shown in the retracted position, with locking pin 5155 and spacer engagement pin 5157 being located proximally to surface 5156 of insertion tip 5030. Two alignment pins 5160 are shown. When engaged with a main body assembly, flat surfaces 5156 and 5165, alignment pins 5160, and locking pin 5155 and spacer engagement pin 5157 of the instrument 5100 can hold the main body assembly firmly to the insertion instrument.

FIGS. 183*a*-183*c* depict the method of engagement of a main body insertion instrument of the invention with a main body assembly of the invention.

FIG. 183*a* depicts a main body assembly 5400 of the invention for use with the instrument 5100 of this invention. Main body assembly 5400 has a main body wing 5401 having a cephalad wing member 5402 and a caudal wing member 5402*a*. Cephalad wing member 5402, after insertion, is aligned toward the head of the subject along the right side of a dorsal spinous process. Member 5402*a* is also positioned along the side of a spinous process. Main body wing 5401 also can have one or more holes 5403 adapted to receive alignment pins 5160 of main body insertion instrument 5100. Main body wing 5401 also has locking pin hole 5404 adapted to receive locking pin 5155 of main body insertion instrument 5100. Main body wing 5401 is attached to spacer 5405, which has spacer engagement hole 5406 adapted to receive spacer engagement pin 5157 of insertion instrument 5100. On the other end of spacer 5405, tissue expander 5407 is shown, having a threaded hole 5408 adapted to receive a bolt of a universal wing implant (described below). Tissue expander 5407 has a tapered left end to ease insertion of the main body assembly between spinous processes.

FIG. 183*b* depicts a lateral view showing the points of engagement between a main body assembly and main body insertion instrument. Insertion rod 5040 of insertion instrument is shown in a retracted, or proximal position. Locking pin 5155 and spacer engagement pin 5157 are shown aligned proximally to plane 5156 of insertion tip 5030. Spacer engagement pin 5157 is adapted to engage with spacer engagement hole 406, locking pin 5155 is adapted to engage with locking pin hole 5404, and alignment pin 5160 is adapted to engage with alignment hole 5403.

FIG. 183*c* depicts main body insertion instrument engaged with main body assembly. While insertion rod 5040, locking pin 5155 and spacer engagement pin 5157 are in the retracted position, a main body assembly has been positioned with alignment pin 5160 received into alignment pin hole 5403. Thereafter, insertion rod 5040 has been urged distally by the spring 5125 of FIG. 181, thereby engaging locking pin 5155 with locking pin hole 5404 and spacer engagement pin 5157 with spacer engagement hole 5406. The engagement of spacer engagement pin 157 with spacer 5405 keeps spacer 5405 from rotating about its axis, and thereby keeps the spacer 5405 in position relative to the tissue expander 5407 and to the main body implant insertion instrument 5100.

II. Wing Insertion Instrument

A wing insertion instrument of this invention is depicted in FIG. 184-186. FIG. 184 depicts an exterior, lateral view of a wing insertion instrument 5500, having a handle 5010, and insertion shaft 5020, an insertion tip 5030 and a driver knob 5050. As with the main body insertion instrument 5100 depicted in FIGS. 180 and 181, on a lateral surface, insertion knob 5110, having raised portion 5112 is provided to actuate a locking mechanism at the distal end of the instrument.

FIG. 184 depicts a cross-sectional longitudinal view through the wing insertion instrument 5500 of this invention. Handle 5010 has an insertion knob groove 5505 on a lateral surface, within which insertion knob 5110 is provided. Insertion knob 5110 and groove 5505 are sized so that insertion knob 5110 can move in a proximal/distal path along the handle 5010. Insertion knob 5110 has a raised portion 5112 used for applying force to move insertion knob 5110 proximally and distally along handle 5010. Insertion knob 5110 is attached to rod 5511, which is located within interior space 5521 of the handle 5010. Rod 5511 engages insertion rod 5541 byway of set screw 5520 which is accessible through hole 5515. Hole 5515 is desirably of sufficient size to permit complete removal of set screw 5520 from the instrument, permitting insertion knob 5110 to be removed from handle 5010 and the instrument to be cleaned and sterilized.

Insertion shaft 5540 has a proximal end that fits within the distal portion of the bore of handle 5010. Set screw 5530 is inserted through hole 5535, and engages insertion shaft 5540 with handle 5010. It is desirable for hole 5535 to be of sufficient size for set screw 5530 to be completely removed, permitting cleaning and sterilization of the component parts of instrument 5500.

Insertion rod 5541 extends through the full length of the bore of instrument 5500, and has a proximal portion sized to accommodate spring 5525. When installed in handle 5010, insertion rod 5541 compresses spring 5525. The distal end of spring 5525 is held in place by handle end cap 5501, which, along with handle 5010 can be made of, by way of example, Gray ULTEM™. Handle end cap 5501 is engaged with handle 5010 by means of threads. Thus, for disassembly, handle end cap 5501 can be disengaged from handle 5010, and spring 5525 and insertion rod 5541 can be removed from the proximal end of handle 5010. When assembled, rod 5511 and insertion knob 5110 are urged by spring 5525 in a distal direction. The distal motion is stopped when insertion knob 5110 or rod 5511 reach the distal wall of space 5521. Spring 5525 is further compressed by manual movement of insertion knob 5110 in a proximal direction, acting via insertion rod 5511. Because insertion rod 5541 is engaged with rod 5511, insertion rod 5541 is drawn proximally by proximal movement of insertion knob 5110. When manual force on insertion knob 5110 is relaxed, as for example, after alignment of a universal wing in relation to insertion tip 5030, spring 5525 urges insertion rod 5541 and insertion knob 5110 in a distal direction. As insertion rod 5541 is urged distally, driver 5555 is urged toward the distal end of insertion instrument 5500 as well.

Driver knob 5502 is provided at the proximal end of instrument 5500. Driver knob 5502 can be made of, by way of example, Gray ULTEM™. Driver knob 5502 has a bore into which the proximal most extension of insertion rod 5541 is placed. Insertion rod 5541 is held within driver knob 5502 by means of set screw 5504 within hole 5503. It can be desirable for hole 5503 to be sufficiently large so that set screw 5504 can be completely removed from driver knob 5502 for cleaning and sterilization. Insertion rod 5541 desirably is free to rotate about its longitudinal axis, so that when driver knob 5504 is rotated, driver 5555 is rotated.

In summary and referring to FIGS. 181 and 185, set screws 5120, 5130 of main body insertion instrument 5100, and set screws 5520, 5530, and 5504 of universal wing insertion instrument 5500 can be removed using a hex screw driver, having a hexagonal driver head made of, by way of example, 5455 tainless steel. Such removal can be used to disassemble the instruments 5100 and 500 for cleaning.

FIGS. 186*a*-186*c* depict details of insertion tip 5030 of wing insertion instrument 5500 of this invention. FIG. 186*a* is an end-view of the distal end of insertion tip 5030, showing driver 5555, alignment pins 5560, and surfaces 5547 and 5565. An edge of universal wing 5800 can abut surface 5547 to provide support during the insertion of universal wing 5800. A surface of universal wing 5800 can abut surface 5565 to provide additional support of universal wing 5800.

FIG. 186*b* depicts a bottom view of insertion tip 5030 of wing insertion instrument 5500. Insertion rod 5541 is depicted in a distal position, within insertion shaft 5540. Driver 5555 is shown extending into space 5567 of insertion tip 5030. FIG. 186*c* depicts a bottom view of the insertion tip 5030 as shown in FIG. 186*b* with the driver 5555 and insertion rod 5541 in a proximal position, with the distal-most end of driver 5555 retracted from the space 5567. In this position, mounting ring 5816 of FIG. 187 (below) of a universal wing can be received in space 5567.

FIGS. 187*a*-187*c* depict a universal wing 5800 of the invention for use with the wing insertion instrument 5500 of the invention. FIG. 187*a* is a lateral view of universal wing 5800, having caudad portion 5801 and cephalad portion 5802. Alignment holes 5806 are adapted to receive alignment pins 5560 of wing insertion instrument 5500. Although two alignment holes 5806 are depicted, additional or fewer alignment holes can be provided. Between caudad portion 5801 and cephalad portion 5802, mounting ring 5816 is provided having an oblong bore therethrough to receive shaft 5814 of bolt 5812. Bolt 5812 has a proximal end with a recess 5813 adapted to receive driver 5555 of instrument 5500. The distal end of bolt 5812 is threaded to engage with hole 5408 of a tissue expander 5407 depicted in FIGS. 183*a*-184*c*. The oblong bore has partial threads that allow a bolt to be screwed through the bore with the smooth shaft of the bolt then trapped in the bore.

FIG. 187*b* is a side view of universal wing 5800 without bolt 5812, depicting mounting ring 5816 with oblong bore 5817 therethrough. Alignment holes 5806 are shown as dashed lines. FIG. 187*c* depicts a similar view of universal with 5800 with bolt 5812 provided. Hex recess 5813, adapted to receive driver 5555 of instrument 5500 is shown. Hole 5817 is oblong to provide a choice of positions of bolt 5812 within bore 5817. By providing a choice of bolt positions, the surgeon can install universal wing with a desired spacing between universal wing 5800 and main body wing 5401.

FIGS. 188*a*-188*c* depict the relationships between wing insertion instrument 5500 of this invention and the universal wing 5800 of the invention. FIG. 188*a* depicts a lateral view of the insertion tip 5030, with driver 5555 in space 5567 and alignment pin 5560. Insertion rod 5541 is shown within insertion shaft 5540. Also depicted is universal wing 5800, having bolt 5812 with recess 5813, mounting ring 5816, alignment hole 5806, and caudad wing portion 5801. The axes of driver 5555 and alignment pin 5560, which in this embodiment cross each other and can be substantially perpendicular if desired, are shown in relation to recess 5813 and alignment hole 5806, respectively.

FIG. 188*b* depicts a lateral view of insertion tip 5030 engaged with universal wing 5800. Driver 5555 is received by recess 5813 in bolt 5812 and alignment pin 5560 is received by alignment hole 5806. Bolt 5812 is received within recess 5567 of insertion tip 5030, and when insertion shaft 5541 is rotated, bolt 5812 can rotate.

FIG. 188c depicts a bottom view of insertion tip 5030 and universal wing 5800, engaged as in FIG. 188b. Cephalad portion 5802 and caudad portion 5801 of the universal wing are shown engaged by alignment pins 5560 received through alignment holes 5806. Edge 5807 of wing 5800 is shown abutted against surface 5547 of insertion tip 5030.

III. Trial Implant Instruments

Spinal implant surgery can be carried out by using specially designed instruments to determine the correct size of an implant to be used and to predistract the spinous process. The instruments incorporating trial implants comprise a handle, made of a convenient material, for example, Gray ULTEM™. FIGS. 189a-189d depict four embodiments of trial implant instruments of the invention. FIG. 189a-189d depict instruments 6000, 6001, 6002, and 6003 of this invention, each having handle 6006 and insertion shaft 6007. The instruments differ in the size of the trial implant for each. Trial implant 6010 is the smallest, implant 6011, 6012, and 6013 become progressively larger, corresponding to instruments 6000, 6001, 6002 and 6003, respectively. These trial implants in the embodiment are cylindrical in shape with diameters of 6 mm, 8 mm, 10 mm, and 12 mm, respectively. The trial implants have a lead-in nose, guide, or tissue expander that is cone shaped. Other shapes such as elliptical shapes, oval shapes, and egg-shapes are within the scope of the invention. Further, the nose can be of other shapes such as pyramid shaped. In use, these trial implant instruments are used one after the other to size the implant location and to progressively distract the implant location in preparation for insertion of the implant, which is left in the patient.

IV. Methods of Insertion of Spinal Implants

To use the instruments of this invention to insert spinal implants of the invention, a patient is placed, desirably in a lateral decubitus position with maximum flexion of the lumbar spine. Lateral decubitus position permits easy orientation of the main body assembly during surgery. Generally, the implant can be inserted between the spinous processes from the bottom or right side of the spinous processes to the top or left side of the spinous processes. Such orientation permits easy visualization of the main body assembly when the universal wing is attached. The wings should be oriented properly, with cephalad portions 5402 and 5802 oriented in a cephalad direction, and caudad portions 5402a and 5801 oriented in a caudal direction. The field is prepared for sterile surgery, and local anesthesia of the area is provided. Once the entry point is determined, local anaesthetic is applied to the skin and the underlying musculature.

To insert a spinal implant in one affected vertebral area for a single level implant process, a midline incision about 1.5 inches long is made at the entry point, exposing the supraspinous ligament overlying the spinous processes at the symptomatic level. The fascia may be incised on either side of the spinous processes and supraspinous ligament. The paraspinous musculature can be elevated laterally from both sides of the midline. The supraspinous ligament is desirably preserved. The interspinous ligament may be separated to permit insertion of main body assembly 5400.

To insert spinal implants in adjacent portions of the spine for a double level implant process, a midline incision about 3 inches long is made at the entry point, exposing the supraspinous ligament overlying the spinous processes at the appropriate segments. The fascia is incised if necessary on either side of the spinous processes and supraspinous ligament. The paraspinous musculature can be elevated laterally from both sides of the midline.

The first implant 5400 can be inserted at the inferior level, and the second implant 5400 of the same or different size, can be inserted at the superior, adjacent level after the first implant has been completely secured. If the supraspinous ligament is compromised during the procedure, it can be desirable to suture the excision in the ligament closed after insertion of the spinal implant.

Before installing the spinal implant 5400, the intraspinous space is prepared using trial implants. Generally, the surgeon can first select the smallest trial implant, for example, trial implant 6000. The trial implant 6000 is urged between the spinous processes of the patient, and if little resistance is encountered, the surgeon can select a larger sized trial implant, such as trial implant 6001. If insufficient resistance is encountered, the surgeon can use progressively larger trial implants to distract the spinous process. When the correct trial implant is found, the spinal implant 5400 is then chosen for insertion. Additionally, the surgeon may choose to use a trial implant instrument that is larger than the implant to be used in order to further distract the spinous process to make the insertion of the implant easier.

To insert the main body assembly, a surgeon or assistant engages such assembly with main body insertion instrument 5100 of this invention. The leading edge of tissue expander 5407 of the main body assembly is advanced through the interspinous ligament. If significant resistance is encountered during the insertion of the implant, the next smallest size main body assembly can be used. Once the correct sized implant has been selected, the main body implant is inserted as shown in FIGS. 190a and 190b.

FIG. 190a depicts a right lateral view of a portion of a spine of a patient. L4 and L5 refer to lumbar vertebrae 4 and 5, respectively. For purposes of illustration only, these lumbar segments are depicted. However, any spinal segments can be the sites of insertion of the implants by use of the instruments of this invention. L4-5D refers to the intravertebral disk. L4D and L5D refer to the dorsal spinous processes of L4 and L5, respectively. Main body insertion instrument 5100 having insertion tip 5030 attached to main body assembly 5400 is shown in position. Cephalad portion 5402 and caudad portion 5402a of a main body wing are shown. It can be desirable to urge main body assembly 5400 ventrally within intraspinous space 6005.

FIG. 190b depicts a dorsal view of an inserted main body assembly 5400. Spacer 5405 is shown between dorsal spinous processes L4D and L5D. Main body wing 5401 is shown near the right lateral surfaces of spinous processes L4D and L5D.

FIG. 191 depicts a left lateral view of the L4-L5 area of a patient. The main body assembly 5400 has been inserted, and the tissue expander 5407 is shown, urged ventrally in intraspinous space 6005. Main body wing portions 5402 and 5402a are shown in dashed lines, being located behind (i.e., the right of) the spinous process L4D and L5D, respectively. Threaded hole 5408 in tissue expander 5407 is shown, and axis (dashed lines) is shown to depict the insertion of threaded portion 5815 of bolt 5812 of universal wing 800. Insertion tip 5030 of wing insertion instrument 5500 is shown, with a universal wing engaged 5800, as depicted in FIGS. 188b and 188c. The engaged wing is shown from the top view, in contrast to the view of FIG. 188c, which is from the bottom. While grasping main body insertion instrument 5100, the surgeon inserts the universal wing with wing insertion instrument 5500. When the universal wing is brought into the correct position relative to the main body assembly, bolt 5812 can be inserted into hole

5408 of the tissue expander 5407, and by rotation of the driver knob 5050 of FIG. 184 in a clockwise direction, driver 5555 can rotate bolt 5812 thereby engaging threads of the threaded end 815 with the threads of hole 5408. Alternatively, if the threaded portions 5815 of bolt 5812 and hole 5408 have left-handed threads, then driver knob 5050 should be rotated in a counter-clockwise direction to engage bolt 5812 with threaded hole 5408. Before tightening bolt 5812, it can be desirable to urge universal wing 5800 medially or closer to main body wing 5401 to provide a desired degree of support of spinous processes L1D and L2D. Once in the proper position, bolt 5812 can be tightened, and the insertion instrument 5100 and 5500 are removed, the incisions sutured and closed.

FIG. 192 depicts a dorsal view of the spine of a patient, depicting an installed main body assembly 5400 with universal wing 5800 attached thereto. Universal wing portion 5802 is shown oriented in the cephalad direction, as is main body wing portion 5402. Caudad wing portions 5801 and 5402*a* are shown oriented in the caudal direction. Wing element 5400, 5402*a* are shown near the right lateral surface of the spinous process. Universal wing 5800 is shown placed near the left lateral surfaces of the spinous process. Adjustment of the spacing between universal wing 5800 and the spinous process is accomplished by urging the wing medially before tightening bolt 5812 in oblong mounting ring 5817.

V. Alternative Insertion Instrument Sets

FIGS. 193 through 196 depict alternative instrument sets of the invention. The aspects of these instrument sets, that are similar to the above described inventive instrument sets, are similarly numbered. Further, the description of the previously described instrument sets applies equally well to these alternative embodiments of the present invention.

In FIG. 193 the main body insertion instrument 5100 is shown nested to the wing insertion instrument 5500. Both instruments together hold an implant 5400. With respect to the main body insertion instrument 5100 in this embodiment, this insertion instrument 5100 is essentially identical to that shown in FIG. 1. The wing insertion instrument 5500 has been modified to include an elongated concave recess 5580 (FIG. 194) which extends, in this preferred embodiment, for substantially the length of the handle 5010. This elongated concave recess 5580 is shaped to conform to the outer surface of the handle 5010 of the main body insertion instrument 5100. Accordingly the handle 5010 of the main body insertion instrument 5100 can be nested in this recess 5580 so that the main body insertion instrument can be mated and nested to the wing insertion instrument 5500. (FIGS. 193, 194). This nesting affords the ability of the handles to align with each other so that the wing carried by the wing insertion instrument 5500 can be slid into place relative to and aligned with the main body carried by the main body insertion instrument 5100, as the instrument 5500 is slid along the handle of instrument 5100.

FIGS. 195 and 196 depict yet a further alternative embodiment of the instrument set including a main body insertion instrument 5100, and a wing insertion instrument 5500. The main body insertion element 5100 in this embodiment includes an offset handle 5010 which is depicted as offset from the shaft by about 45 degrees. It has been understood that greater and lesser offsets can be accomplished and be within the spirit and scope of the invention. The offsets servers two functions. The first function is that it gives the surgeon greater leverage in manipulating and positioning the main body of the implant through the ligaments associated with the spinous processes and eventually the spinous processes themselves. This additional leverage allows the physician to urge the main body of the implant into position.

Also it can be seen in FIG. 195, the main body insertion instrument 5100 includes a flange 5101. This flange 5101 is an additional enhancement to the insertion tool 5100. It is then to be understood that the instrument set in FIGS. 195 and 196 can be fabricated without the flange 5101 and the mating groove 5501 of the wing insertion instrument 5500 and still be within the spirit scope of the invention. As seen in FIG. 196, the mating groove 5501 of the wing insertion instrument 5050 is located in the recess 5580.

It is to be understood that without the flange 5100 and the mating groove 5501, the embodiment of the insertion instrument 5100 of FIG. 195 can be received in the recess 5580 of the wing insertion instrument 5500 of FIG. 196 as the wing insertion instrument 5500 is moved relative to the main body insertion element 5100 in order to align the wing relative to the main body at the surgical site.

With the flange 5101 and the mating groove 5501 and with the embodiment of the insertion element 5100 of FIG. 195 positioned so that the main body is inserted through the spinous processes, the wing insertion instrument 5500 can be mated over the main body insertion instrument 5100 with the flange received in the mating groove 5501. After this is accomplished, the wing insertion instrument 5500 can be slid relative to the main body insertion instrument 5100 in order to bring the wing into contact with and aligned with the main body. After this has occurred, the wing can be fastened to the main body.

It is to be understood that the wing insertion instrument 5500 can also have an offset handle like the offset handle of main body insertion instrument 5100 of FIG. 196.

It is to be understood that other devices and methods for mating and aligning insertion instrument 5100 with the wing insertion instrument 5500 can be envisioned and be within the spirit and scope of the invention.

INDUSTRIAL APPLICABILITY

From the above, it is evident that the present invention can be used to relieve pain caused by spinal stenosis in the form of, by way of example only, central canal stenosis or foraminal (lateral) stenosis. These implants have the ability to flatten the natural curvature of the spine and open the neural foramen and the spacing between adjacent vertebra to relieve problems associated with the above-mentioned lateral and central stenosis. Additionally, the invention can be used to relieve pain associated with facet arthropathy. The present invention is minimally invasive and can be used on an outpatient basis.

Additional aspects, objects and advantages of the invention can be obtained through a review of the appendant claims and figures.

It is to be understood that other embodiments can be fabricated and come within the spirit and scope of the claims.

The foregoing description of preferred embodiments of the present invention has been provided for the purposes of illustration and description. It is not intended to be exhaustive or to limit the invention to the precise forms disclosed. Obviously, many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An apparatus, comprising:
a first elongate member having a first longitudinal axis;
a second elongate member configured to move relative to the first elongate member and extending along a second longitudinal axis;
an engagement portion of the first elongate member configured to removably engage a first surface of an interspinous-process implant; the engagement portion of the first elongate member comprising at least one post protruding from the first elongate member transverse to the first longitudinal axis so as to cross the first and second longitudinal axes when the first elongate member is viewed from the side;
an engagement portion of the second elongate member configured to removably engage a second surface of the interspinous-process implant angularly offset from the first surface;
wherein the second elongate member is configured to translate within the first elongate member along a longitudinal axis of the first elongate member.

2. An apparatus, comprising:
an insertion tool having a first elongate member defining a longitudinal axis and a second elongate member;
the first elongate member having an engagement portion configured to removably engage an interspinous-process implant having a longitudinal axis that includes a proximal end and a distal end of the interspinous-process implant and that is non-parallel to the longitudinal axis of the insertion tool;
the engagement portion of the first elongate member comprising at least one post protruding from the first elongate member along a post axis; the post axis transverse to the first longitudinal axis and oriented to cross the first and second longitudinal axes when the first elongate member is viewed from the side;
the second elongate member moveable longitudinally relative to the first elongate member between a retracted position and a deployed position;
a biasing member configured to bias the second elongate member toward the deployed position.

3. The apparatus of claim 2 wherein:
an engagement portion of the first elongate member is configured to engage a first portion of the interspinous-process implant from a first direction;
an engagement portion of the second elongate member is configured to engage a second portion of the interspinous-process implant from a second direction different than the first direction while the engagement portion of the first elongate member is engaging the first portion of the interspinous-process implant from the first direction.

4. The apparatus of claim 2 wherein:
an engagement portion of the first elongate member is configured to be received within a first opening defined by the interspinous-process implant;
an engagement portion of the second elongate member is configured to be received within a second opening defined by the interspinous-process implant when the second elongate member is disposed within the first elongate member while the engagement portion of the first elongate member is received in the first opening defined by the interspinous-process implant; a longitudinal axis of the first opening being non-parallel to a longitudinal axis of the second opening.

5. The apparatus of claim 2 wherein:
at least a portion of an engagement portion of the second elongate member is disposed within the first elongate member when the second elongate member is in the retracted position; and
the portion of the engagement portion of the second elongate member is disposed outside of the first elongate member when the second elongate member is in the deployed position.

6. An apparatus, comprising:
an insertion tool defining a longitudinal axis and having an engagement portion configured to releasably grip an interspinous-process implant having a longitudinal axis that includes a proximal end and a distal end of the interspinous-process implant; wherein the insertion tool is configured to releasably grip the implant from a first direction that is non-parallel to the longitudinal axis of the insertion tool;
wherein the insertion tool has a first elongate member and a second elongate member; the second elongate member disposed at least partially in the first elongate member and moveable relative to the first elongate member in a direction along a first longitudinal axis of the first elongate member;
a biasing member coupled to the first elongate member and the second elongate member, the biasing member configured to maintain the second elongate member in at least one of a first position or a second position; a distal portion of the second elongate member being disposed within the first elongate member when in the first position; the distal portion of the second elongate member being disposed outside the first elongate member when in the second position;
a distal portion of the first elongate member defining the engagement portion and comprising at least one post protruding from the first elongate member along a post axis; the post axis transverse to the first longitudinal axis and oriented to intersect the first longitudinal axis when the insertion tool is viewed from the side;
wherein the first direction is non-parallel to the first longitudinal axis.

7. The apparatus of claim 2 wherein the post axis is perpendicular to the first longitudinal axis.

8. The apparatus of claim 2 wherein the second elongate member further comprises a catch having a surface facing the post and spaced therefrom; wherein the surface, when the insertion tool is viewed from the side with the second elongate member in the deployed position, overlaps the post.

* * * * *